US012741062B2

(12) United States Patent
Vacanti et al.

(10) Patent No.: US 12,741,062 B2
(45) Date of Patent: Sep. 22, 2026

(54) CELL SCAFFOLD DEVICE HAVING THREE-DIMENSIONAL STRUCTURE WITH INTERWOVEN CHANNELS

(71) Applicant: The General Hospital Corporation, Boston, MA (US)

(72) Inventors: Joseph P. Vacanti, Winchester, MA (US); Matthew J. Hancock, Needham, MA (US); Mark S. Oliver, Boston, MA (US); Andrew P. Spann, Needham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 18/045,751

(22) Filed: Oct. 11, 2022

(65) Prior Publication Data

US 2023/0065127 A1 Mar. 2, 2023

Related U.S. Application Data

(62) Division of application No. 16/424,374, filed on May 28, 2019, now abandoned.

(Continued)

(51) Int. Cl.

*A61F 2/00* (2006.01)
*A61L 27/38* (2006.01)

(Continued)

(52) U.S. Cl.

CPC ........... *A61L 27/56* (2013.01); *A61L 27/3834* (2013.01); *A61L 27/52* (2013.01); *A61L 31/16* (2013.01);

(Continued)

(58) Field of Classification Search

CPC ........................................................ A61F 2/06

See application file for complete search history.

(56) References Cited

U.S. PATENT DOCUMENTS 6,143,293 A * 11/2000 Weiss .................. A61L 27/3625 435/395
6,455,311 B1 9/2002 Vacanti (Continued)

FOREIGN PATENT DOCUMENTS

CN 202129066 U 2/2012
WO 2014052835 A1 4/2014

OTHER PUBLICATIONS

Griffith et al., In Vitro Organogenesis of Liver Tissue, Annals of the New York Academy of Sciences, 1997, 831 (1):382-397.

(Continued)

*Primary Examiner* — Jacqueline Woznicki

(74) *Attorney, Agent, or Firm* — QUARLES & BRADY LLP

(57) ABSTRACT

A cell-scaffold device includes at least one channel network including an inlet, a plurality of channels include a parent channel having an end portion communicating with the inlet and another end portion communicating with a first bifurcation, forming two child channels. Each child channel has an end portion communicating with a respective end portion of the first bifurcation and another end portion communicating with a second bifurcation, forming two grand-child channels from each child channel. Each grand-child channel has an end portion communicating with a respective end portion of the second bifurcation and another end portion. The other end portion of the grand-child channel either forms an outlet or a third child channel in communication with the grand-child channel. Each forming of grand-child channels defines a generation of the fractal structure. The (Continued)

devices are of use as scaffolds for seeding, growing, and maintaining cells implanted in and/or on the device.

17 Claims, 94 Drawing Sheets

Related U.S. Application Data

(60) Provisional application No. 62/676,602, filed on May 25, 2018.

(51) Int. Cl.

| | |
|---|---|
| ***A61L 27/52*** | (2006.01) |
| ***A61L 27/56*** | (2006.01) |
| ***A61L 31/16*** | (2006.01) |
| ***B33Y 10/00*** | (2015.01) |
| ***C12N 5/00*** | (2006.01) |
| *A61F 2/02* | (2006.01) |
| *A61F 2/04* | (2013.01) |
| *A61L 27/54* | (2006.01) |
| *A61L 31/14* | (2006.01) |
| *B33Y 80/00* | (2015.01) |
| *C12M 1/12* | (2006.01) |

(52) U.S. Cl.

CPC ............ *B33Y 10/00* (2014.12); *C12N 5/0068* (2013.01); *A61F 2/0077* (2013.01); *A61F 2/02* (2013.01); *A61F 2/04* (2013.01); *A61F 2210/0076* (2013.01); *A61F 2310/00982* (2013.01); *A61L 27/54* (2013.01); *A61L 31/148* (2013.01); *A61L 2300/414* (2013.01); *B33Y 80/00* (2014.12); *C12M 25/14* (2013.01)

(56) References Cited

U.S. PATENT DOCUMENTS

| | | | | |
|---|---|---|---|---|
| 8,357,528 | B2 * | 1/2013 | Vacanti | C12N 5/0062 435/395 |
| 8,591,597 | B2 * | 11/2013 | Hoganson | A61F 2/04 623/1.42 |
| 9,506,024 | B2 * | 11/2016 | Marx | C12M 25/14 |
| 2002/0182241 | A1 | 12/2002 | Borenstein et al. | |
| 2006/0019326 | A1 | 1/2006 | Vacanti et al. | |
| 2006/0136182 | A1 | 6/2006 | Vacanti et al. | |
| 2007/0281353 | A1 | 12/2007 | Vacanti | |
| 2009/0069904 | A1 * | 3/2009 | Picha | A61L 27/14 623/23.72 |
| 2010/0098742 | A1 | 4/2010 | Vacanti et al. | |
| 2010/0234678 | A1 * | 9/2010 | Pryor | A61F 2/062 435/395 |
| 2011/0024346 | A1 | 2/2011 | Weinberg et al. | |
| 2011/0250585 | A1 | 10/2011 | Ingber et al. | |
| 2013/0030548 | A1 | 1/2013 | Ling | |
| 2013/0196438 | A1 | 8/2013 | Chun et al. | |
| 2014/0234953 | A1 | 8/2014 | Vacanti et al. | |
| 2014/0243995 | A1 * | 8/2014 | Kolewe | A61L 27/3804 623/23.72 |
| 2015/0050686 | A1 | 2/2015 | Sheth et al. | |
| 2015/0376595 | A1 * | 12/2015 | LeDuc | B29C 49/071 435/177 |
| 2016/0129440 | A1 * | 5/2016 | Borenstein | B81C 99/0085 156/245 |
| 2016/0271610 | A1 | 9/2016 | Foulds et al. | |
| 2016/0303283 | A1 * | 10/2016 | Gagnon | A61L 27/54 |
| 2017/0240854 | A1 * | 8/2017 | Machluf | C12M 25/14 |
| 2017/0252701 | A1 | 9/2017 | Nosrati | |
| 2018/0236134 | A1 | 8/2018 | Vacanti | |
| 2018/0327702 | A1 * | 11/2018 | Gannon | C12M 23/16 |
| 2019/0358367 | A1 | 11/2019 | Vacanti et al. | |

OTHER PUBLICATIONS

Hasan et al., A Multilayered Microfluidic Blood Vessel-Like Structure, Biomed Microdevices, 2015, 17(5):88, 23 pages.

Lu et al., Techniques for Fabrication and Construction of Three-Dimensional Scaffolds for Tissue Engineering, International Journal of Nanomedicine, 2013, 8:337-350.

Murphy et al., 3D Bioprinting of Tissues and Organs, Nature Biotechnology, 2014, 32(8):773-785.

Sadovoy et al., Cellular Matrices (Scaffolds) for Bone Regeneration: State of the Art, Spinal Surgery, 2014, 2:79-86 [Includes English Language Abstract].

Xiong et al., Jet-Based 3D Printing of Biological Constructs, Solid Freeform Fabrication Symposium 2014 Proceedings, pp. 1069-1075.

China National Intellectual Property Administration, First Office Action and Search Report, Application No. 201980049231.2, May 7, 2022, 19 pages.

Colombia Patent Office, Office Action, Application No. NC2018/0002590, Jan. 22, 2020, 9 pages.

European Patent Office, Supplementary Partial European Search Report, Application No. 16/37473, Mar. 1, 2019, 13 pages.

European Patent Office, Extended European Search Report, Application No. 16837473, Jun. 17, 2019, 10 pages.

European Patent Office, Extended European Search Report, Application No. 19808365, Mar. 4, 2022, 10 pages.

International Searching Authority, International Search Report and Written Opinion, PCT/US2016/044435, Nov. 29, 2016, 14 pages.

International Searching Authority, International Search Report and Written Opinion, PCT/US2019/034219, Aug. 16, 2019, 12 pages.

Intellectual Property of India, Examination Report, Application No. 202047055097, Sep. 20, 2022, 5 bages.

Israel Patent Office, Office Action, Application No. 257528, Mar. 5, 2019, 5 pages.

Patent Office of the Russian Federation, Search Report, Application No. 2018108802, Jan. 24, 2020, 4 pages.

Patent Office of the Russian Federation, Official Action, Application No. 2018108802, Jan. 24, 2020, 9 pages.

Intellectual Property Office of Singapore, Search Report and Written Opinion, Application No. 11201801218R, Apr. 2, 2019, 11 pages.

Intellectual Property Office of Singapore, Search Report and Written Opinion, Application No. 11202011590Y, Jul. 27, 2022, 13 pages.

Australian Government—IP Australia, Examination Report No. 1, Application No. 2019273040, Apr. 23, 2024, 3 pages.

Brazilian Patent and Trademark Office, Search Report and Written Opinion, Application No. BR112020023989-5, Mar. 21, 2023, 7 pages.

Japan Patent Office, Notification of Reasons for Refusal, Application No. 2020-565741, Mar. 9, 2023, 9 pages.

Brazilian Patent and Trademark Office, Written Opinion, Application No. BR112020023989-5, Jan. 9, 2024, 13 pages.

Intellectual Property Office of Singapore, Examination Report, Application No. 11202011590Y, Jan. 16, 2024, 4 pages.

* cited by examiner

10

CELL SCAFFOLD DEVICE HAVING THREE-DIMENSIONAL STRUCTURE WITH INTERWOVEN CHANNELS

CROSS REFERENCE TO RELATED APPLICATIONS

The present application is a divisional of U.S. application Ser. No. 16/424,374, filed May 28, 2019, which relates to and claims priority to U.S. Provisional Patent Application No. 62/676,602, filed on May 25, 2018. Each of the preceding patent applications are incorporated herein by reference in their entireties for all purposes.

BACKGROUND OF THE INVENTION

Field of the Invention

The present disclosure relates to implantable cell scaffold devices. More particularly, the present disclosure relates to implantable cell scaffold devices formed by additive manufacturing.

Description of Related Art

Generally, an implant is a device configured to restore, maintain, improve, or a combination thereof, a biological structure or mechanism. Typical implant devices are disposed in vivo. However, such devices can also be disposed in vitro for various uses including pharmaceutical testing and biological system analysis.

According to the Organ Procurement and Transportation Network (accessed December 2017), from 2005 to 2015 a number of patients on an organ donation waiting list increased from 90,500 to 122,000 total patients. Simultaneously, a total number of received organ donors each year held constant at 15,000 donors. Of these 15,000 received donors, approximately 5,600 donors were living persons while the remaining 9,400 donors were deceased. Since 1998, the total number of deceased donors has increased due to improved organ harvest and transportation protocols for the deceased donor. However, the number of patients on the organ donation waiting list remains greater than the number of organ donors in the United States and throughout the world. Thus, to satisfy the needs of all current and future patients requiring a transplant, whole organ fabrication is required.

Such approaches to whole organ fabrication include engineered tissue(s). Engineered tissues have been designed in labs, and include engineered skin, cartilage, and vascular grafts. Despite these advances in the field of engineered tissues, whole organ fabrication has yet to be realized as there are fundamental limitations to overcome when scaling from engineered tissues to whole organ fabrication.

Implant and tissue manufacturing methods fail to recapitulate the geometry, complexity, and life span of human tissues. A major limitation in engineering whole organs arises from various mass transport mechanisms and biological properties within an organ. In organ systems, such as aerobic respiration and waste disposal systems, diffusion is a leading mass transport mechanism. For instance, regarding aerobic respiration, most cells are within 100 microns (μm) to 200 μm from a capillary lumen. An oxygen diffusion distance limit, which is a minimum distance between a cell and an oxygen source, is dependent upon a rate of cellular oxygen consumption and a diffusion rate of oxygen through a given tissue. Additionally, a given cellular concentration in a tissue ([Cell]) and a diffusion distance to a center of a tissue (d) hold an inverse square relation ($[Cell] \propto 1/d^2$). When a characteristic dimension of an engineered tissue construct, such as a characteristic length of a blood vessel, is scaled by a factor of n, the theoretical limit of cellular density is decreased by a factor of $n^2$. Thus, an intrinsic vascular network is required to increase sizes of engineered tissues while maintaining required minimum oxygen diffusion distances.

Conventional engineered tissue designs contain two-dimensional microchannel arrays. The two-dimensional arrays can theoretically be applied to whole organs, however, these organs are inherently three-dimensional and their respective vascular organization must reflect this. When cells, including hepatocytes, are developed in a three-dimensional scaffold and disposed in a body near a capillary bed, only cells in close proximity to a blood vessel will thrive. As time elapses, new blood vessels may grow into the implanted cells, however, cells that are far from existing blood vessels will not flourish without immediate blood supply.

Thus, prior to the present disclosure there existed a need for a diverse cell scaffolding device capable of growing complex cells in three dimensions.

The information disclosed in this Background of the Invention is only for enhancement of understanding of the general background of the invention and should not be taken as an acknowledgement or any form of suggestion that this information forms the prior art already known to a person skilled in the art.

BRIEF SUMMARY

Advantageously, the cell scaffold devices detailed in the present disclosure address the shortcomings in the prior art detailed above.

Various aspects of the present disclosure are directed to providing a cell scaffold device having a plurality of branching channel networks. In some embodiments, the device includes a first branching channel network. In some embodiments, the first branching channel network is configured to distribute a first fluid at a first height of the cell scaffold device. In some embodiments, the device further includes a second branching channel network. In some embodiments, the second branching channel network is configured to distribute a second fluid. In some embodiments, the second fluid may be different from the first fluid. In some embodiments, the second branching channel network distributes the second fluid at a second height of the cell scaffold device. In some embodiments, the second height is interposed between the first height of the scaffold device and a third height of the scaffold device. In some embodiments, the device further includes a third branching channel network. In some embodiments, the third branching channel network is configured to collect the first fluid at a fourth height of the cell scaffold device. In some embodiments, the first branching channel network comprises a plurality of first channels. In some embodiments, the plurality of first channels is formed by at least three generations of branching. In some embodiments, the plurality of first channels includes a first-generation first channel and a plurality of final-generation first channels. In some embodiments, each respective channel in the plurality of first channels comprises a coplanar surface at the first height of the cell scaffold device. In some embodiments, the second branching channel network includes a plurality of second channels. In some embodiments, the plurality of second channels is formed by branching and recursive recombination. In some embodiments, the plurality of second channels further includes an inlet second channel, an outlet second channel and a plurality of intermediate second channels branched from the inlet second channel and recursively recombined to the outlet second channel. In some embodiments, one or more second channels in the plurality of second channels comprises a coplanar surface at the second height of the cell scaffold device. In some embodiments, one or more other second channels in the plurality of second channels comprises a coplanar surface at the third height of the cell scaffold device. In some embodiments, the third branching channel network further includes a plurality of third channels. In some embodiments, the plurality of third channels is formed by at least three generations of branching. In some embodiments, the plurality of third channels includes a first-generation third channel and a plurality of final-generation third channels. In some embodiments, each respective channel in the plurality of third channels comprises a coplanar surface at the fourth height of the cell scaffold device. In some embodiments, the plurality of final-generation first channels of the first branching channel network is disposed adjacent to the second height of the second branching channel network. In some embodiments, the plurality of final-generation third channels of the third branching channel network is disposed adjacent to the third height of the second branching channel network. In some embodiments, each respective final-generation first channel in the plurality of final-generation first channels of the first branching channel network is in direct fluid communication with a corresponding final-generation third channel in the plurality of final-generation third channels by a corresponding bypass channel in a plurality of bypass channels. In some embodiments, each respective bypass channel of the plurality of bypass channels extends from the first height to the fourth height of the cell scaffold device, bypasses direct fluid communication with the second branching channel network, thereby producing a compact three-dimensional structure with channels.

In some embodiments, the device includes a lower end portion of one or more first channels of the branching channel network disposed adjacent to an upper end portion of the one or more second channels located at the second height of the second branching channel network.

In some embodiments, the device further comprises a first master inlet. In some embodiments, the first master inlet is configured to distribute the first fluid by direct fluid communication to the first-generation first channel. In some embodiments, the first master inlet is further configured to collect the first fluid by direct fluid communication from the first-generation third channel. In some embodiments, the device further comprises a second master inlet. In some embodiments, the second master inlet is configured to distribute the second fluid by direct fluid communication to the inlet second channel. In some embodiments, the second master outlet is further configured to collect the second fluid by direct fluid communication to the outlet second channel.

In some embodiments, the plurality of branching channel networks further comprises a fourth branching channel network. In some embodiments, the fourth branching channel network is connected to the second master inlet and second master outlet and in indirect fluid communication with the third branching channel network.

In some embodiments, diameters of channels in the plurality of first, second, or third channels formed by branching obey Murray's Law.

In some embodiments, for a respective channel in the plurality of first, second, or third channels, a ratio of a diameter to a length of the respective channel is fixed along the length of the respective channel.

In some embodiments, a film of collagen is disposed on the cell scaffold device.

In some embodiments, the plurality of branching channel networks comprises an even number of branching channel networks greater than or equal to four.

In some embodiments, each channel of a respective branching channel network in the plurality of branching channel networks comprises a cross-sectional aspect ratio of one.

In some embodiments, the device further comprises a polyhedron exterior surface. In some embodiments, the polyhedron exterior surface is configured to encompass the plurality of branching channel networks.

In some embodiments, the plurality of branching channel networks form a monolithic portion of the cell scaffold device.

In some embodiments, each branch of a respective branching channel network in the plurality of branching channel networks is in plane with a corresponding height of the respective branching channel.

In some embodiments, the device includes a first centerline of at least one channel in the plurality of first channels. In some embodiments, the first centerline is oriented at an angle of greater than or equal to 90 degrees relative to a second centerline of the first-generation first channel.

In some embodiments, the device includes a first surface of each channel in the plurality of first channels. In some embodiments, the first surface is coplanar at the first height of the cell scaffold device. In some embodiments, the device includes a second surface, opposite the first surface, of each channel in the plurality of first channels. In some embodiments, the second surface comprises a linear ramp extending from a fifth height of the cell scaffold device to a sixth height of the cell scaffold device.

In some embodiments, the third branching channel network is a mirror image of the first branching channel network across a plane extending through the cell scaffold device.

In some embodiments, a length of the cell scaffold device is a distance extending between a first end portion of an inlet of the first-generation first channel and a first end portion of the inlet of the second channel. In some embodiments, the first end portion of the inlet of the first-generation first channel and the first end portion of the inlet of the second channel are on opposite side portions of the cell scaffold device.

In some embodiments, the second branching channel network forms a looped channel segment for distributing and collecting the second fluid.

The cell scaffold device of the present invention has other features and advantages that will be apparent from, or are set forth in more detail in, the accompanying drawings, which are incorporated herein, and the following Detailed Description, which together serve to explain certain principles of exemplary embodiments of the present invention.

Figure 1:
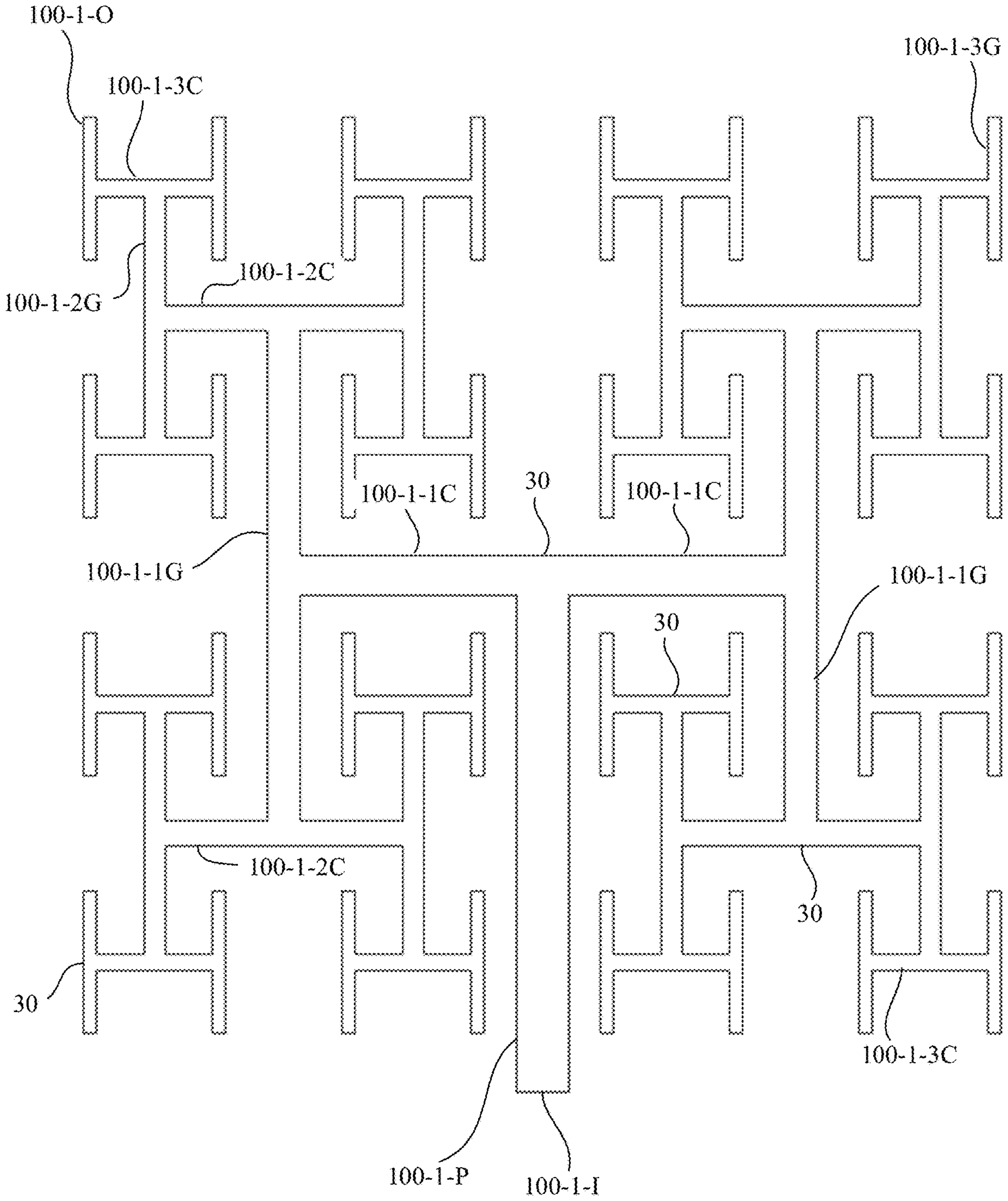
FIG. 1 illustrates a schematic view of an exemplary single layer of a scaffold device in accordance with embodiments of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing. Furthermore, in the figures, arrows depict a flow of material unless otherwise stated.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention (s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

In the interest of clarity, not all of the routine features of the implementations described herein are shown and described. It will be appreciated that, in the development of any such actual implementation, numerous implementation-specific decisions are made in order to achieve the specific goals of a design, such as compliance with use case- and business-related constraints, and that these specific goals will vary from one implementation to another and from one design to another. Moreover, it will be appreciated that such a design effort might be complex and time-consuming, but nevertheless be a routine undertaking of engineering for those of ordinary skill in the art having the benefit of the present disclosure.

It will also be understood that, although the terms first, second, etc. may be used herein to describe various elements, these elements should not be limited by these terms. These terms are only used to distinguish one element from another. For example, a first channel network could be termed a second channel network, and, similarly, a second channel network could be termed a first channel network, without departing from the scope of the present disclosure. The first channel network and the second channel network are both channel networks, but they are not the same channel network.

Additionally, it will be understood that, though the terms inlet and outlet may be used herein to describe various elements, these elements should not be limited by these terms. For example, an inlet could be termed an outlet, and similarly an outlet could be termed an inlet, without departing from the scope of the present disclosure. The inlet and the outlet are both points of drawing flow, but they are not the same points of drawing flow.

By "biodegradeable," as used herein, is meant materials that are bioresorbable and/or degrade and/or break down by mechanical degradation (e.g., dissolve, resorb, etc.) upon interaction with a physiological environment into components that are metabolizable or excretable, over a period of time from minutes to three years, preferably less than one year, while maintaining the requisite structural integrity.

By "exchange mechanism," as used herein, is meant a material or structure configured to substantially allow or inhibit a flow of material from a first element to a second element including fenestrated walls, permeable membranes, permeable walls, porous walls, porous membranes, perforations, and the like.

By "diameter," as used herein, is meant to be inclusive of equivalent characteristic lengths including hydraulic diameters of non-circular structures.

By "flush," as used herein, is meant as a surface of a first element and a coplanar surface of a second element to have a distance, or level, separating the first element and the second element to be within a tolerance of 0 μm, within a tolerance of 5 μm, within a tolerance of 10 μm, within a tolerance of 20 μm, or within a tolerance of 100 μm.

By "direct flow," as used herein, is meant as a transfer or a flow of at least one substance or material from a first element to at least a second element.

By "indirect flow," as used herein, is meant as an exchange or flow of at least one substance or material from a first element to at least a second element which is mediated by an exchange mechanism.

By "generation," as used herein, is meant a complete series of a child channel and grand-child channel generation. A "generation" thus means a T-shaped branch.

By "natural manner," as used herein, is meant a process or development as found in a nature.

By "polymer," as used herein, is meant to include polymers and monomers that can be polymerized or adhered to form an integral unit. The polymer can be non-biodegradable or biodegradable, typically via hydrolysis or enzymatic cleavage.

By "subsequent channel," as used herein, is meant, for a given channel, a channel which material flows therefrom. Accordingly, by "preceding channel," as used herein, is meant, for the given channel, a channel which material flows thereto.

By "rigid," as used herein, is meant a material that is stiff and does not deform easily. By "elastomeric," as used herein, is meant a material or a composite material that is not rigid as defined herein.

By "$i^{th}$" or "i," as used herein, is meant a generic element in a series of elements for each integer i in the set {1, . . . , i, . . . , k}, where k is a positive integer greater than or equal to two.

Furthermore, the term "channel" or "vessel" or other similar terms, as used herein, is inclusive of equivalent structures in general including a capillary, a conduit, a cylinder, a duct, a hose, a passage, a pipe, a pipeline, a siphon, a tube, and the like.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, useful methods and materials are described below. In addition, the materials, methods, and examples are illustrative only and not intended to be limiting.

Throughout the specification, channels of the present disclosure will be reference X00-Y-Z {C,G,I,O, or P}. Hereinafter, the X00 series (100, 200, . . . , i00, . . . , k00) refers to a specific channel network of the device. Hereinafter, the Y series (1, 2, . . . , i, . . . , k) refers to a level or layer of a channel network of the device. Hereinafter, the Z {C, G, I, O, or P} series {I, 1P, 1C, 1G, 2C, 2G, 3C, . . . , iC, iC, . . . , kC, kG, kO, O} refers to a generation and channel type of a level or layer. "Z" refers to the generation of the channel. "C" refers to a child channel. "G" refers to a grand-child channel. "I" refers to an inlet. "O" refers to an outlet. Furthermore, "P" refers to a parent channel.

Embodiments of the present disclosure are described in the context of cell scaffold devices. In some embodiments, the device has a volume of at least 1 cubic centimeter ($cm^3$), 10 $cm^3$, 100 $cm^3$, 1,000 $cm^3$, 5,000 $cm^3$, 27,000 $cm^3$, or 125,000 $cm^3$, and of various shapes including but not limited to squares and rectangles. In some embodiments, a gross morphology of the device is an implantable shape. Implantable shapes externally resemble organ and/or members to be replicated. Furthermore, in some embodiments the device has an overall length (e.g., from a first side surface of the device to an opposing side surface of the device) in a range of from 0.1 cm to 1 meter (m), from 0.1 cm to 75 cm, from 0.1 cm to 50 cm, from 0.1 cm to 40 cm, or from 0.1 cm to 30 cm.

Devices of the present disclosure can be utilized for a variety of applications including in vivo implants such as a liver implant, a lung implant, a heart implant, and the like, or used in vitro to test various pharmaceuticals or biological system functions. For instance, in a liver implant embodiment, a first channel network can be a portal venous network that distributes blood flow across the device to enable oxygen transport and cell nourishment in various networks, while a second channel network can be a hepatobiliary network that provides an outflow of bile. In general, a second channel network can be configured for system specific outflows such as an outflow of air in a lung implant, an outflow of blood in a heart implant, or the like. Additionally, in some embodiments a first channel network can be configured to distribute fluid or material and a second channel network can be configured to collect fluid or material distributed by the first channel network. Accordingly, in some embodiments the devices of the present disclosure mimic physiological systems in vivo (e.g., a liver, a heart, a bone, a kidney, a lung, etc.) to provide a controlled and physiological relevant cell culture within the device. Furthermore, in some embodiments the devices of the present disclosure mimic physiological systems in vitro, such as an "organ-on-a-chip," to provide a mechanism for testing pharmacokinetics of pharmaceutical compositions, pharmaceutical composition clearance, pharmaceutical composition sensitivity, pharmaceutical composition toxicity, or a combination thereof.

The devices of the present disclosure can include various materials. In many cases, the device is formed from a resorbable or biodegradable material. In some embodiments, the resorbable or biodegradable material is consumed, deteriorates, dissolves, erodes, resorbs, or a combination thereof after a predetermined time period. In such embodiments, the predetermined time is typically a function of cell population maturity, cell density, a photocatalyst reaction, a chemical reaction or equilibrium, or a combination thereof. However, the present disclosure is not limited thereto. Manufacturing the device from resorbable or biodegradable materials is particularly useful in vivo, which forms a semi-permanent shell of the device. As the device degrades, fresh blood vessels can form from the resulting structure without requiring additional modification to the device (e.g., additional surgery to a subject with the device implanted in vivo). In some embodiments, the channels of the device are formed with a predetermined cross-section. However, as the device is worn away the cross-section transforms. In general, such transformations include a rounding of internal and/or external edge portions (e.g., corners) of the channels. The rounding is further induced by cells newly formed at locations where channel walls previously were.

The device of the present disclosure is not limited to resorbable or biodegradable materials. For instance, in some embodiments the device includes a non-resorbable material, or a combination of resorbable, biodegradable, and non-resorbable materials. As such, the device can be formed of synthetic polymers, natural polymers, or a combination thereof. Suitable materials for the device include poly-dimethyl-siloxane (PDMS), poly-glycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, TeflonO, nylon silicon, and shape memory materials including poly(styrene-block-butadiene), polynorbornene, hydrogels, metallic alloys, and oligo (ε-caprolactone)diol as switching segment/oligo (p-dioxyanone) diol as physical crosslink. In some embodiments, the device includes glass filled nylon, thermoplastic polyurethane, acrylonitrile butadiene, and/or polycarbonate acrylonitrile butadiene. Furthermore, in some embodiments the device includes medical polyurethane (MPU), such as MPU 100. Other suitable polymers can be obtained by reference to The Polymer Handbook, 3rd edition (Wiley, N.Y., 1989), which is hereby incorporated by reference. In some embodiments, a combination of these polymers is used forming the device. In some embodiments, at least a portion of the device is formed from a porous material. The porous material allows nutrients, wastes, and other particles (e.g., pharmaceutical compositions) to exchange across the channel networks of the device. Furthermore, in some embodiments, (e.g., in vitro embodiments) at least a portion of the device is formed from an optically transparent or translucent material (e.g., a hybrid polymer including an epoxy acrylic polymer). An optically transparent or translucent material allows for external observation of a flow of material (e.g., medium) and cell viability within the device. Furthermore, in some embodiments, the scaffold device is formed from a rigid material, an elastomeric material, or a combination thereof. For instance, in some embodiments a membrane of the device is formed from an elastomeric material while the channel networks are formed from a rigid material.

Additionally, in some embodiments the devices of the present disclosure are fabricated or manufactured through an additive manufacturing method. These additive manufacturing methods include binder jetting methods, material extrusion methods, material jetting methods, polyjet methods, powder bed methods, sheet lamination methods, VAT photopolymerization methods, injection molding methods, layered fabrication methods such as selective laser sintering and stereolithography, or a combination thereof. In some embodiments, the device is formed as a positive mold, meaning the walls of the channels themselves, shown as black solid lines in the appended figures, are produced by a given manufacturing device. In some embodiments, the device is formed as a negative mold where the gaps in between the plurality of channels, shown as white voids in the appended figures, are produced by a given manufacturing device. Throughout the description of the devices of the present invention, exemplary embodiments of negative molds will be described for clarity. However, the present disclosure is not limited thereto.

In general, a scaffold device of the present disclosure includes at least one channel network. Each channel network includes an inlet and a plurality of subsequent channels. The plurality of channels is formed in a series of branching (e.g., bifurcating) channels, with each branch producing a channel of a smaller size. In some embodiments, each bifurcation produces a channel of a same size or a similar size (e.g., within a range of ±2% a size of a preceeding channel, ±5%, ±10%, or ±15%). In some embodiments, once the series of branching channels have achieved a predetermined size (e.g., a predetermined smallest size channel), the plurality of channels recombine in a recursive manner to form an outlet. In some embodiments, the devices includes more than one channel network (e.g., a first channel network and a second channel network) that are in fluidic communication with one another. In some embodiments, branching of the channels occurs in a linear tree. In some embodiments, branching occurs in a radial tree.

Channels of the present invention can be formed in a variety of shapes and corresponding cross-sections including, but not limited to, a circular cross-section, a rectangular cross-section, or a corresponding cross-section of a platonic solid. In some embodiments, an aspect ratio of a cross-section of each channel in a channel network is uniform (e.g., a uniform aspect ratio of 1:1). In some embodiments, an aspect ratio of a cross-section of each channel in a channel network is uniform except at a portion of a connector. In some embodiments, the cross-section of each channel is determined by a minimum thickness of a wall of the channel and a desired rigidity (e.g., bending stiffness) of the channels. The wall thickness of the channels is configured to balance various design requirements for flexural rigidity and mass transport across the walls of the channels. For instance, in some embodiments a stiffness of the walls of the channels is modified by altering a cross-section of the channels. Furthermore, in some embodiments each channel network is designed (e.g., a desired thickness, a number of generations, etc.) to account for a desired dead volume between the channels of the device. In some embodiments, a wall thickness (e.g., thickness t of FIG. 4E) of each surface of a channel is the same thickness. In some embodiments, a wall thickness of each surface of a channel is in a range of from 5 μm to 10 millimeters (mm), from 5 μm to 1,000 μm, from 5 μm to 500 μm, or from 10 μm to 500 μm. Furthermore, in some embodiments a distance between a surface of a channel and a nearest adjacent channel surface (e.g., a void, a dead volume) is in a range of from 5 μm to 5 cm, from 5 μm to 4 cm, from 10 μm to 4 cm, from 10 μm to 1 cm, from 10 μm to 1 cm, or from 10 μm to 1,000 μm.

Figure 2:
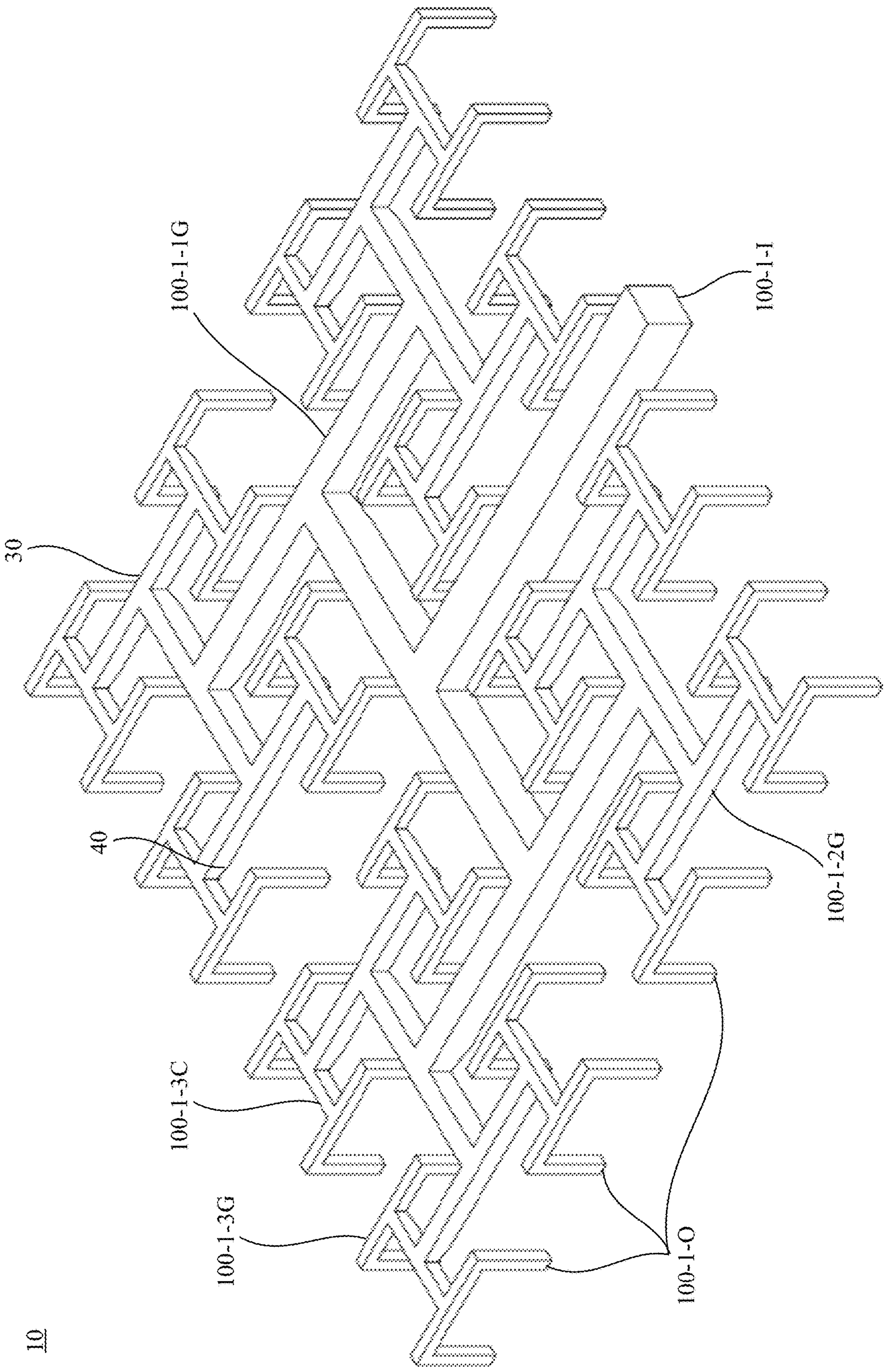
FIG. 2 illustrates an isometric schematic view of the scaffold device of FIG. 1.

Referring now to FIG. 1 and FIG. 2, there is depicted an exemplary channel network in accordance with various embodiments of the present disclosure. As shown, the device 10 includes inlet 100-1-I which in communication with parent channel 100-1-1P. Accordingly, parent channels 100-1-1P bifurcates (e.g., bifurcation 30) into child channels 100-1-1C, which in turn each bifurcate into grand-child channels 100-1-1G. Each grand-child channel ends a generation. Thus immediately subsequent channels of a grand-child channel are child channels which define a new generation. Accordingly, grand-child channels 100-1-1G bifurcate into second generation child channels 100-1-2C. The series of bifurcations can repeat until kth grand-child channels 100-1-kG are formed. Once a final desired channel generation is acquired, the final channels form outlets 100-1-O. In some embodiments, a surface of each channel in the channel network is flush with a common coplanar surface (e.g., coplanar surface (S1) of FIG. 2). As further illustrated in FIG. 1, a first centerline C1 may extend along a longitudinal axis of at least one channel in the plurality of first channels, while a second centerline C2 may extend along a longitudinal axis of the first-generation first channel. In some embodiments, the first centerline C1 may be oriented at an angle of greater than or equal to 90 degrees relative to the second centerline C2.

Figure 3:
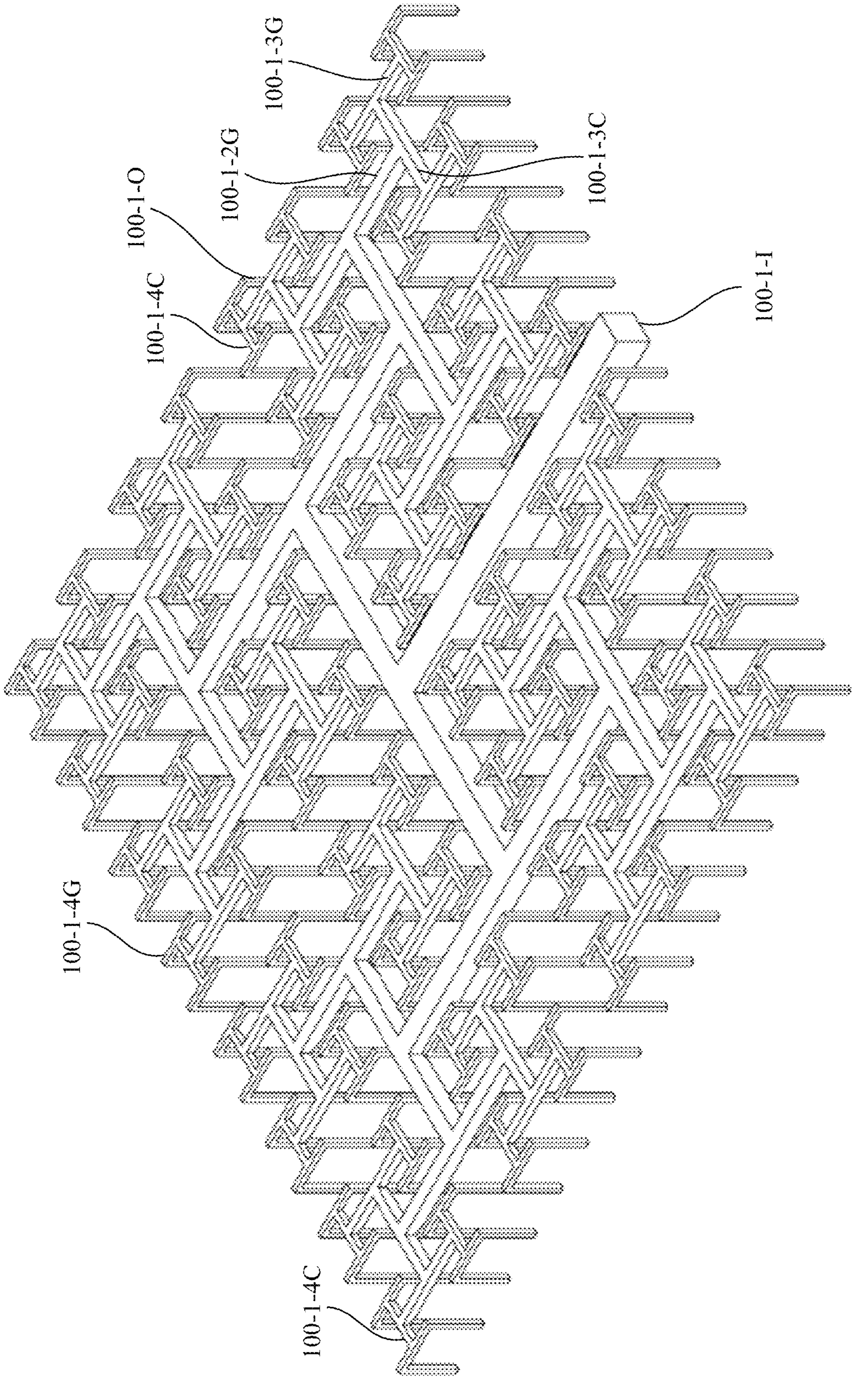
FIG. 3 illustrates an isometric schematic view of an exemplary scaffold device in accordance with embodiments of the present disclosure.

FIG. 1 and FIG. 2 depict an embodiment of the device including three generations of channels. However, there can exist k total generations in another embodiment of the present disclosure. As such, FIG. 3 depicts an embodiment of a channel network including four generations of channels. In some embodiments, a generation is interrupted such that the child channel is the end of a generation. Furthermore, in another embodiment, the inlet bifurcates leading to the parent channel can be integral with the inlet.

In some embodiments, medium (e.g., a fluid) flowing within the channels of the device exhibit laminar flow. Exhibiting laminar flow is a vital function of some embodiments of the present disclosure, since laminar flow reduces a risk of choked flow and material blockage in the channels. Further, ensuring laminar flow also maintains an optimal distribution of cells and molecules (e.g., nutrients, waste material, etc.) within the channels of the device. Thus, in some embodiments a connection exists prior to each bifurcation to ease the flow of fluid or material (e.g., prevent turbulence) and maintain physiological relevant levels of shear rate generated by the flow of fluid or material through the channels. Typically, a sharp edge portion within a channel and/or a discrete transition between varying channel diameters (e.g., an immediate transition from a first diameter to a second diameter as exemplified by connector 40 of FIG. 4B) forms localized regions of high shear rate or low shear rate. In regions that experience high shear rate, platelet activation occurs. Sharp edges at an inner side portion of a bifurcation or connection will experience a high shear rates since the flow therein forms singularities. Similarly, in regions that experience low shear rate stasis occurs leading to thrombus formation. Another consideration in designing a connection between channels of the present disclosure is dissipating flow recirculation. A sharp step (e.g., connector 40 of FIG. 4B) or a smooth, albeit steep, ramp (e.g., connector 40 of FIG. 4A) will induce recirculation, preventing distribution of cells and molecules at this connection.

Figure 31:
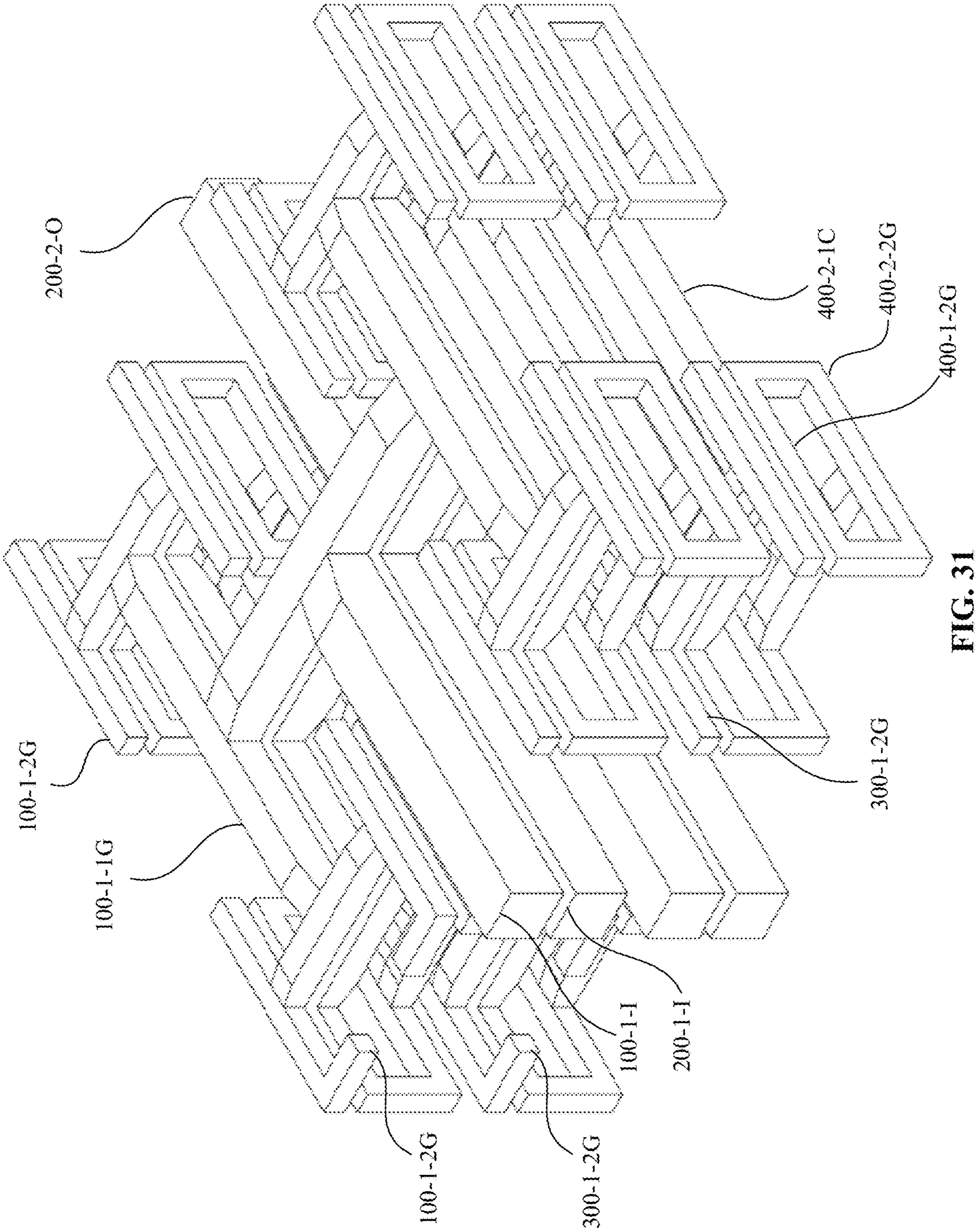
Figure 32:
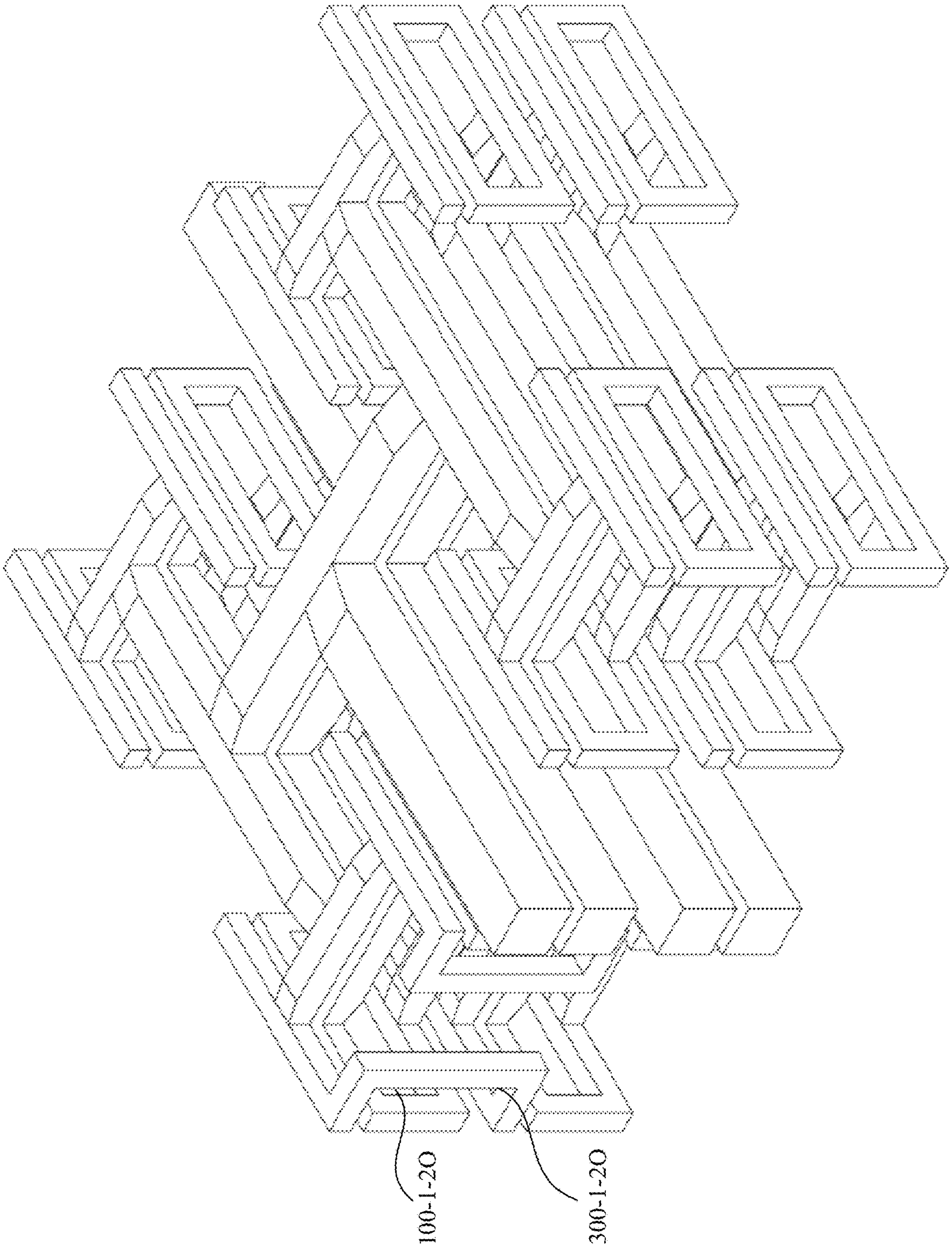
Figure 33:
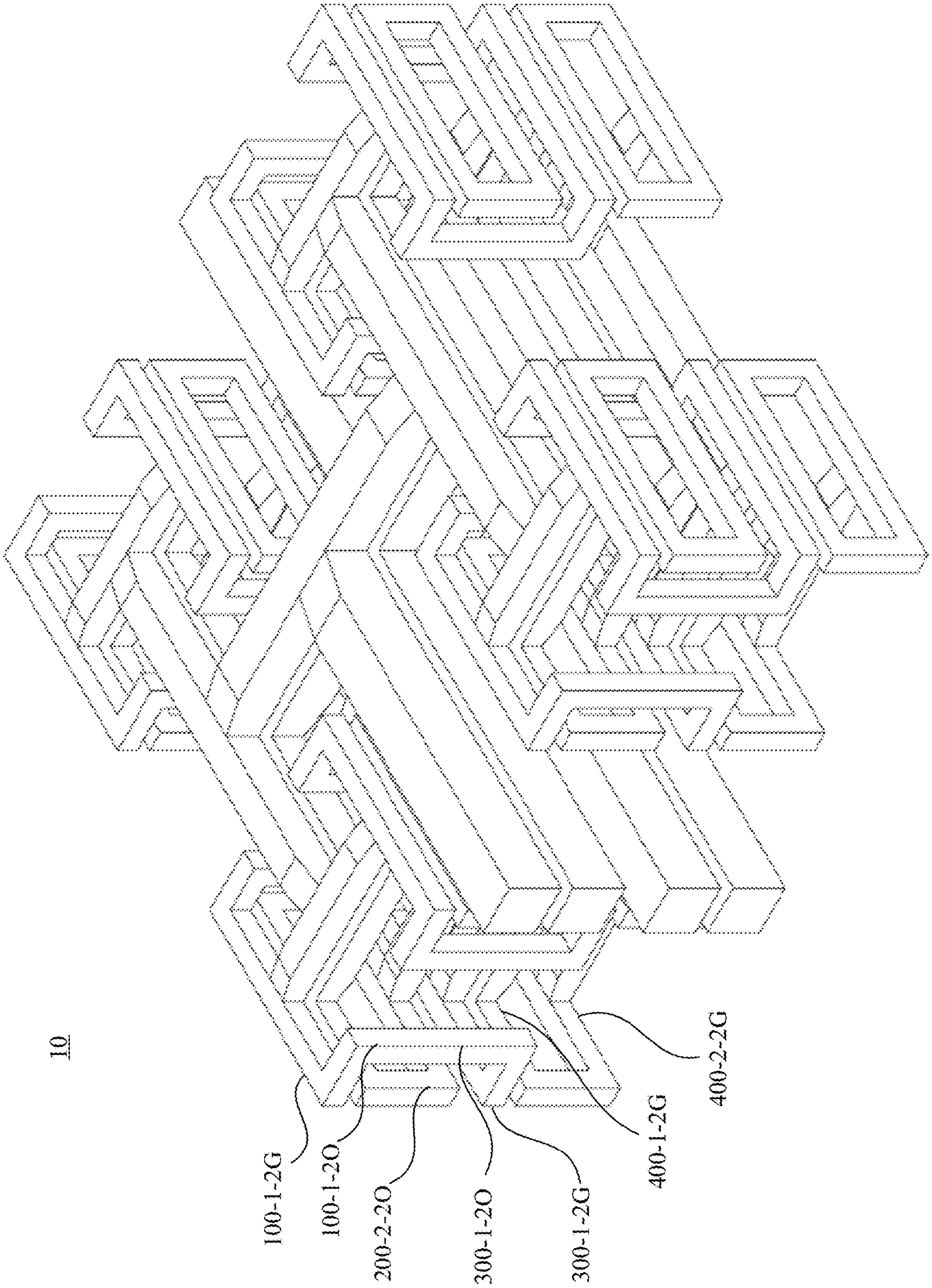

In addition to mitigating high shear rates, the connections also allow a surface of a channel in a channel network to be flush with a coplanar surface of another channel in the same channel network. In some embodiments, the connections are configured to allow each channel in a channel network to have a surface (e.g., an exterior wall of the channel) flush with a single coplanar surface located at a common height of the cell scaffold device (e.g., first height (H1) of FIG. 31, second height (H2) of FIG. 31, . . . , etc.). This flush layout allows the device to maintain a compact configuration and allow for a thickness of an exchange mechanism to have a higher degree of variability and control. Additionally, the connections aid in the dissipation of flow recirculation while allowing reducing a distance between channel networks of the device, which increases a potential maximum cell density within the device.

Figure 4A:
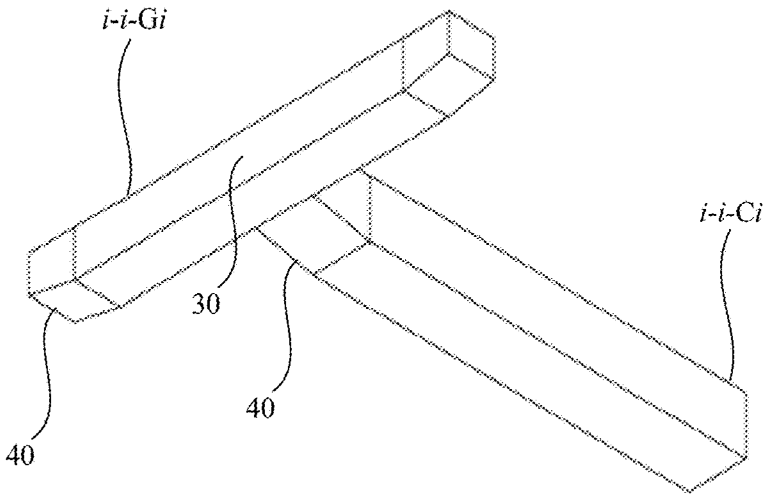
FIG. 4A and FIG. 4B are illustrations of exemplary connection types between channels in accordance with embodiments of the present disclosure.
Figure 4B:
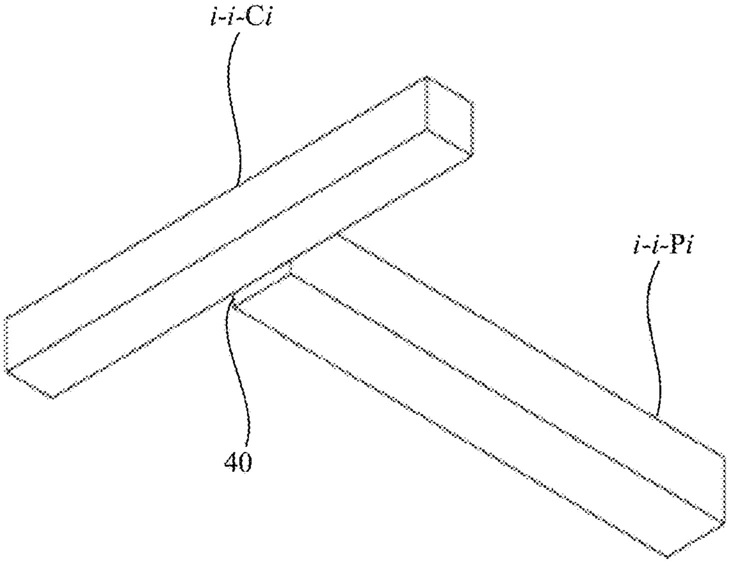

FIG. 4A and FIG. 4B illustrate various types of connections 40. The connection of FIG. 4A is a ramped connection. In an exemplary embodiment, the ramp is a linear slope; however, the ramp can also include a smooth concave ramp, a smooth convex ramp, or a reducer. FIG. 4B illustrates a stepped embodiment of connector 40. In the present embodiment, connector 40 intersects a diameter or a side portion of a subsequent channel at a rear end portion thereof. The connector can also intersect a front end portion or an intermediate portion of the subsequent channel. In additional to the singular step described and shown, the connections can include a plurality of steps.

Figure 4E:
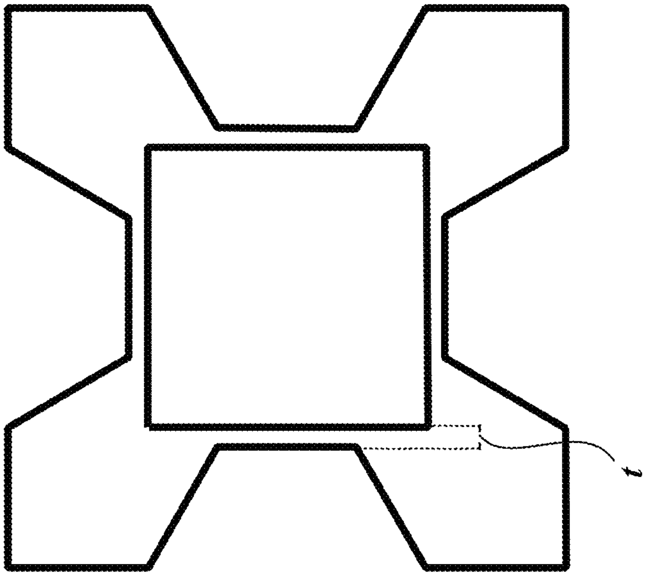
FIG. 4C, FIG. 4D, and FIG. 4E are illustrations of exemplary channel cross-sections in accordance with embodiments of the present disclosure.
Figure 4D:
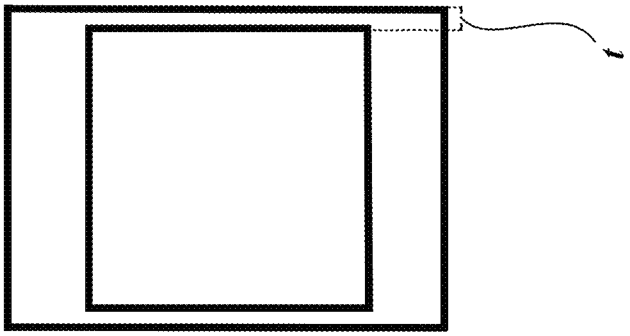
Figure 4C:
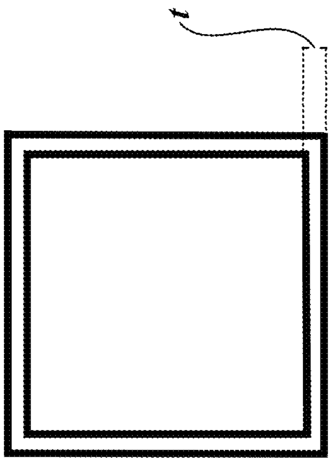

FIG. 4C through FIG. 4E illustrate exemplary channel cross-sections in accordance with embodiments of the present disclosure. Each cross-section illustrated in FIG. 4C through FIG. 4E has the same minimum wall thickness but different bending stiffnesses.

In accordance with the connections, the bifurcations of the present disclosure limit shear rate in the device while optimizing internal cross-section, volume, and packing efficiency of the channels as well as mass flow rates, pressures, and viscous drag forces experienced by medium within the channels. To maximize a number of plausible generations within a device before channels intersect and enable a higher ration of channel area to planned area of the channel network, an orthogonal bifurcation angle of approximately 90° was determined to be optimal since. However, the present disclosure is not limited thereto. For instance, in some embodiments the bifurcation angle is in a range of from 70° to 105°.

Figure 5A:
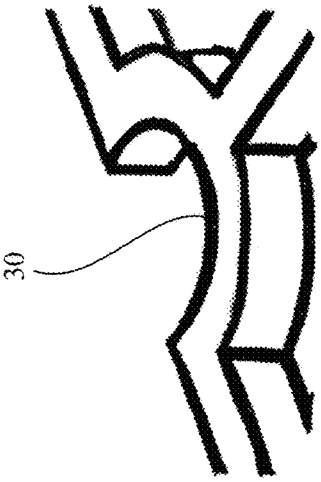
FIG. 5A, FIG. 5B, FIG. 5C, FIG. 5D, FIG. 5E, FIG. 5F, FIG. 5G, FIG. 5H, FIG. 5I, FIG. 5J, and FIG. 5K are illustrations of exemplary bifurcation types in accordance with embodiments of the present disclosure.
Figure 5B:
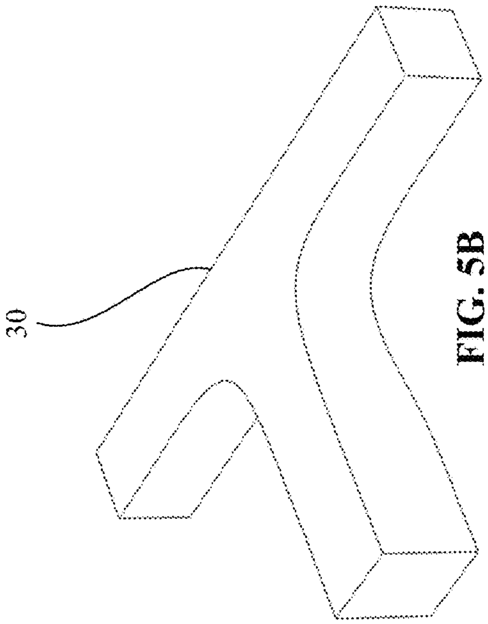
Figure 5C:
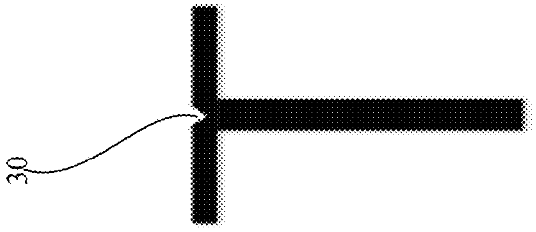
Figure 5D:
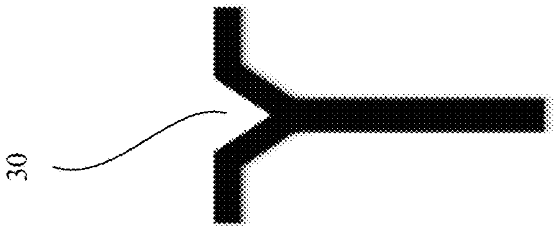
Figure 5E:
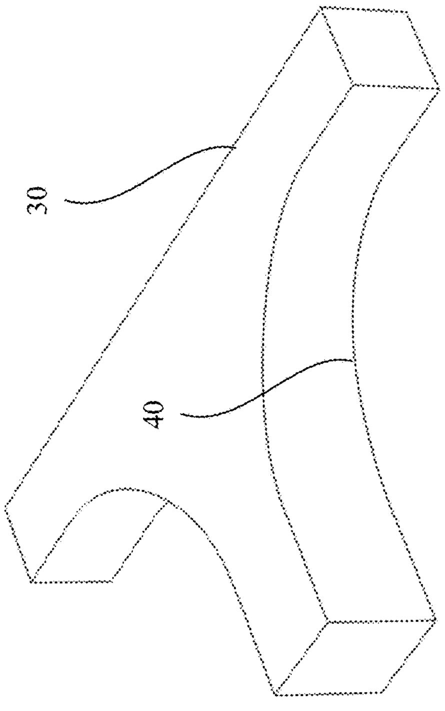
Figure 5F:
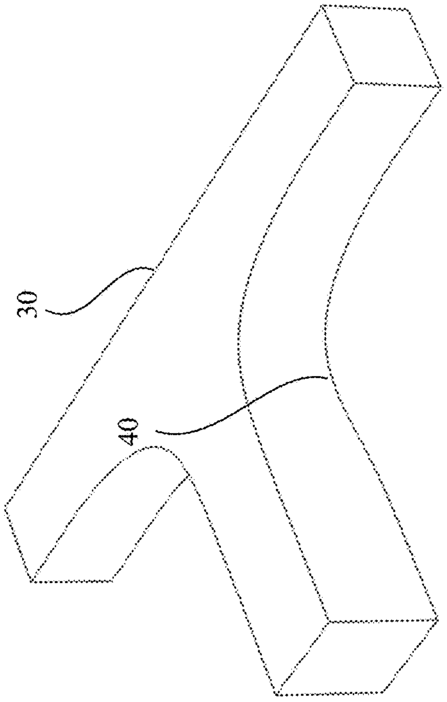
Figure 5G:
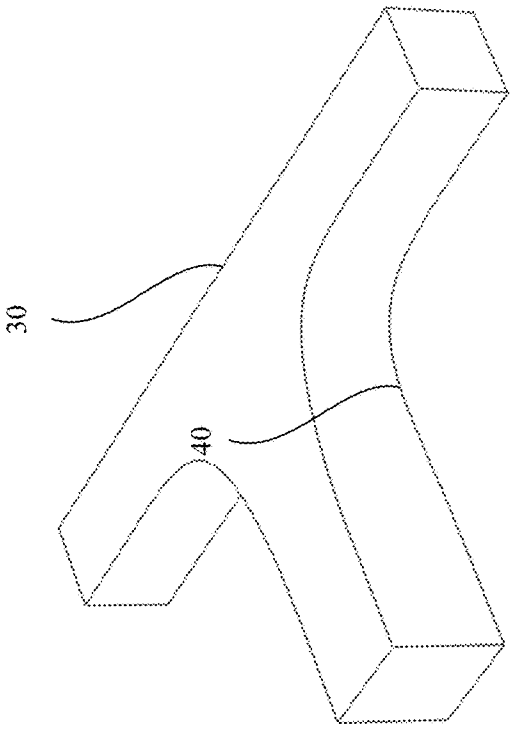
Figure 5H:
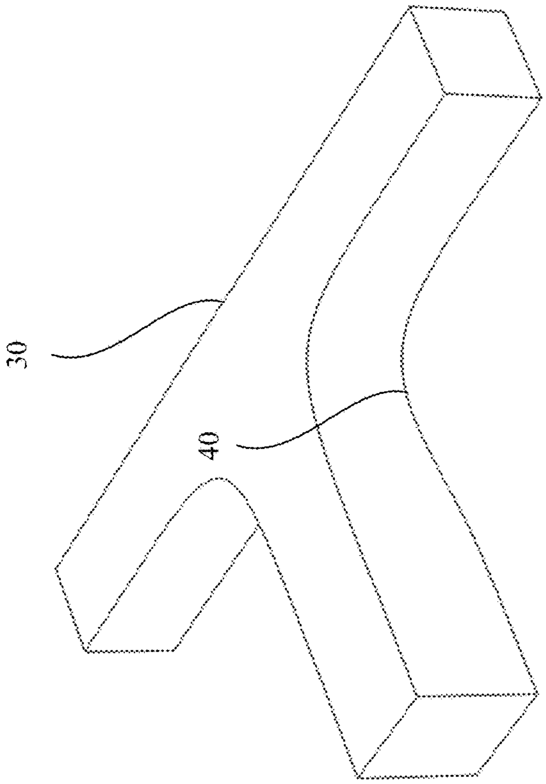
Figure 5J:
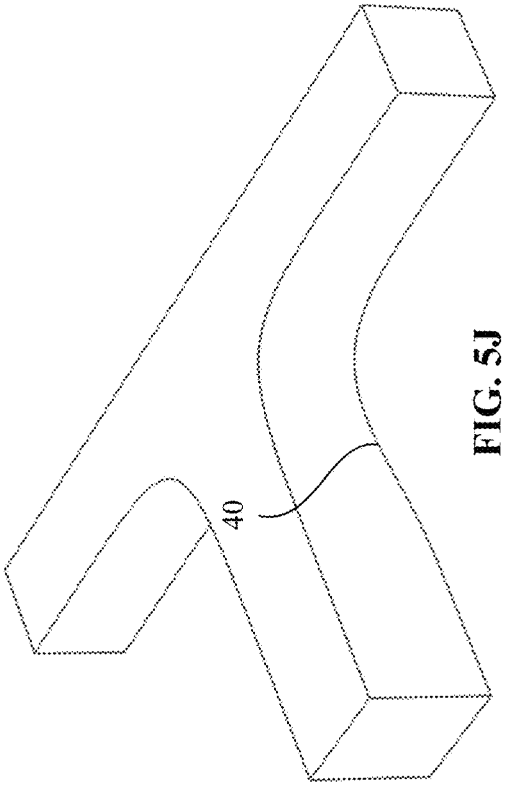
Figure 5K:
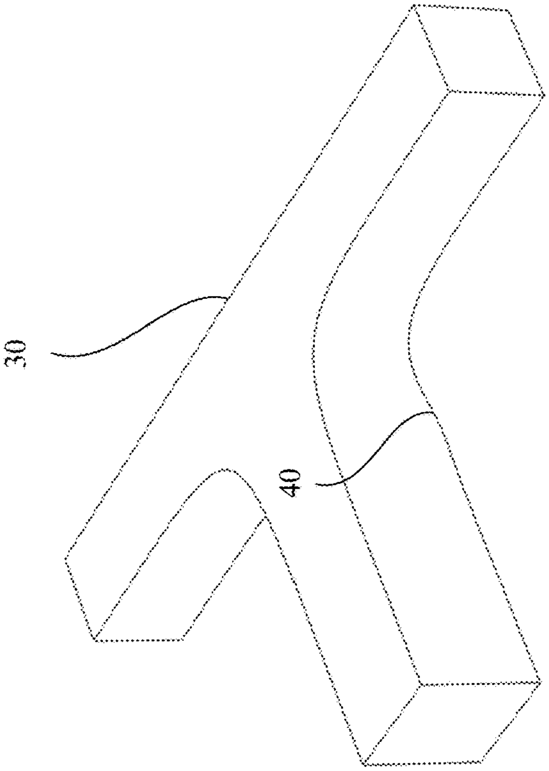
Figure 5I:
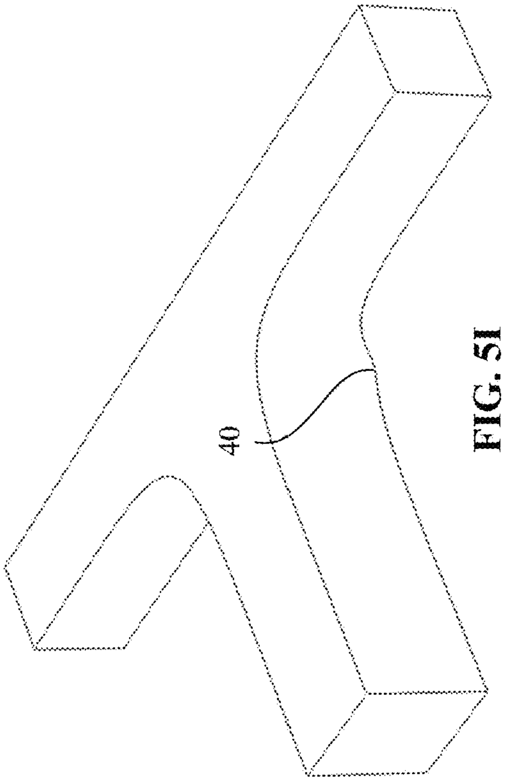
Figure 5L:
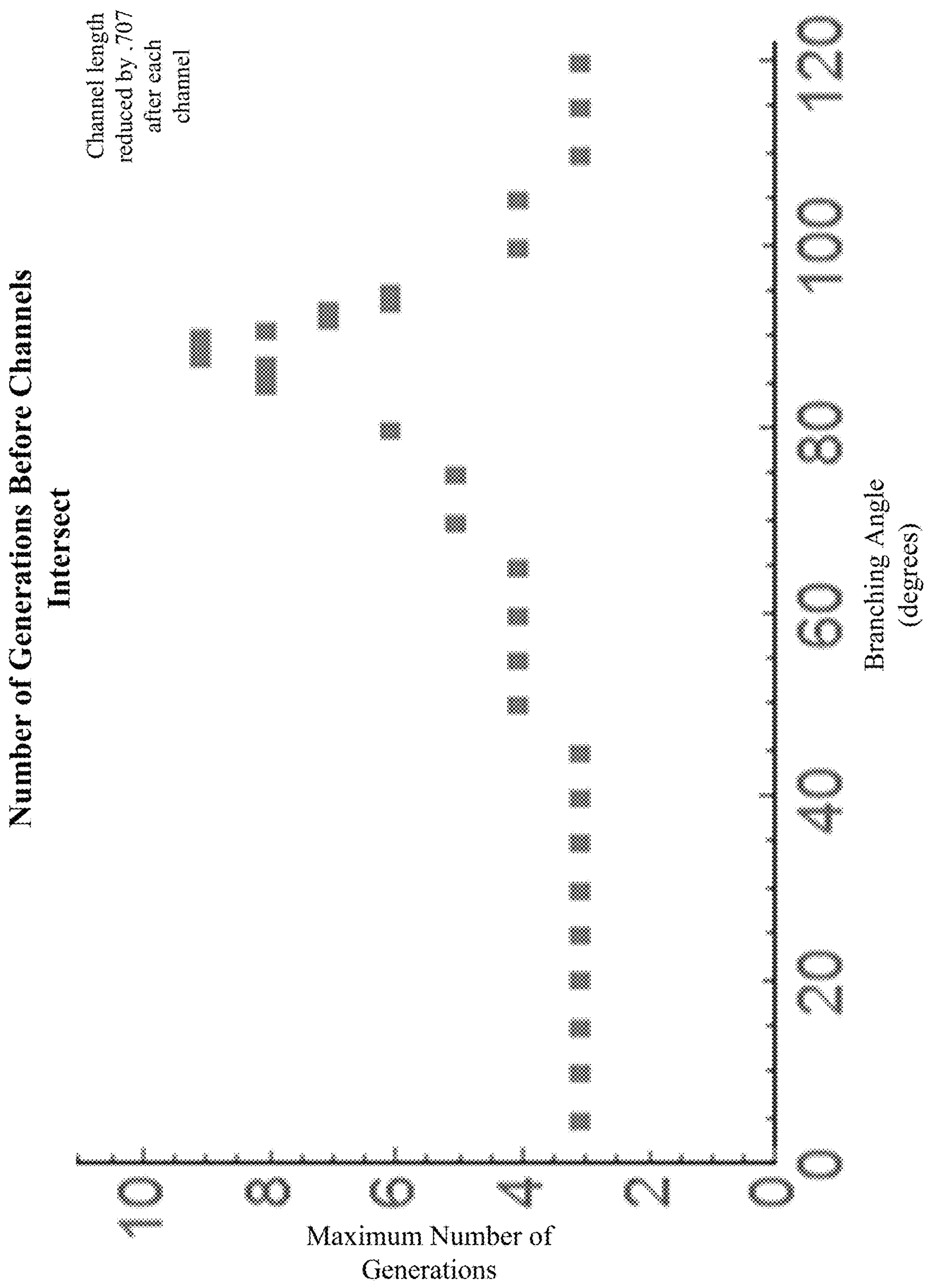
FIG. 5L and FIG. 5M illustrate exemplary plots for determining a maximum number of bifurcations before a channel intersection occurs in accordance with embodiments of the present disclosure.
Figure 5M:
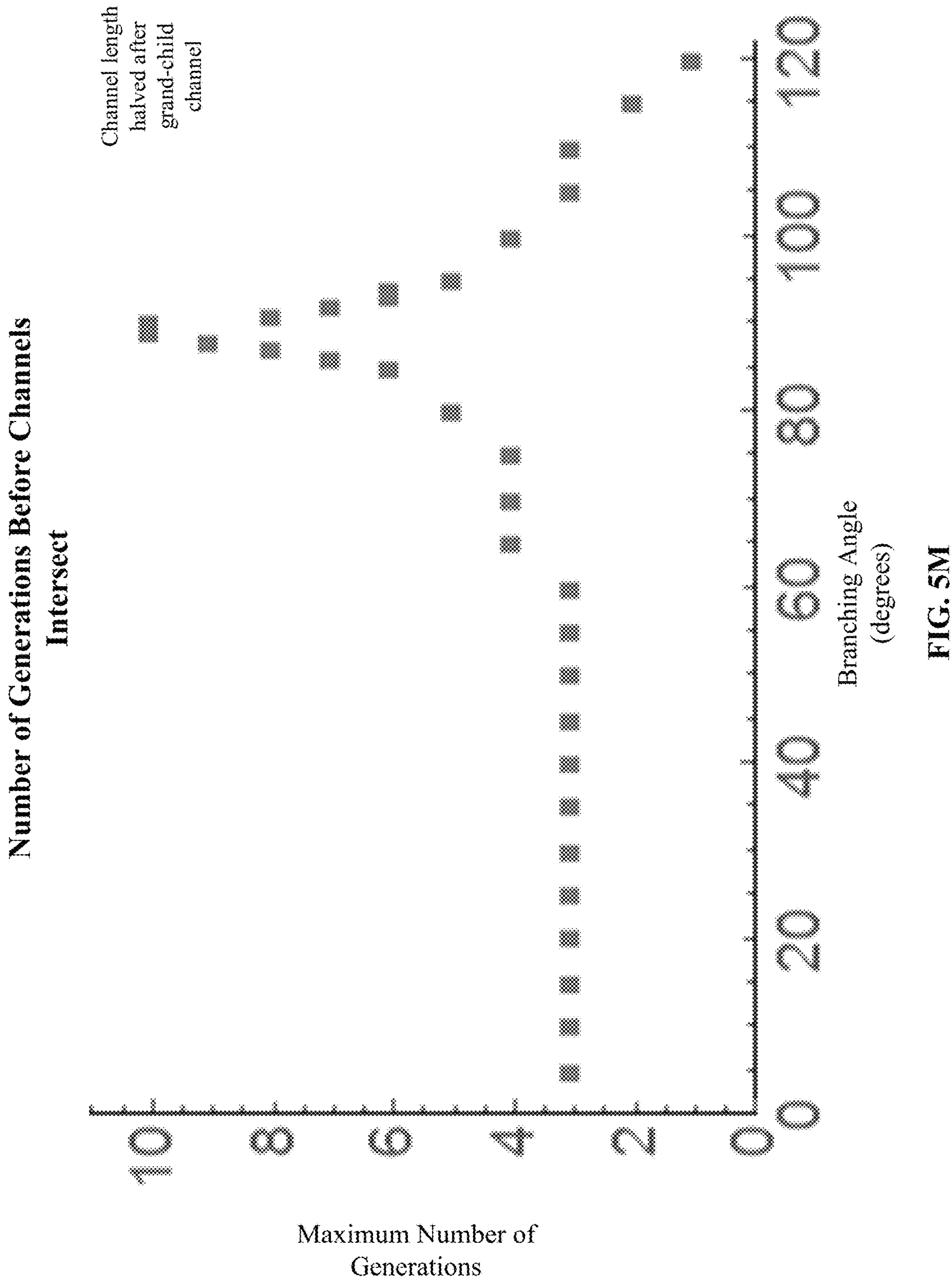
Figure 5N:
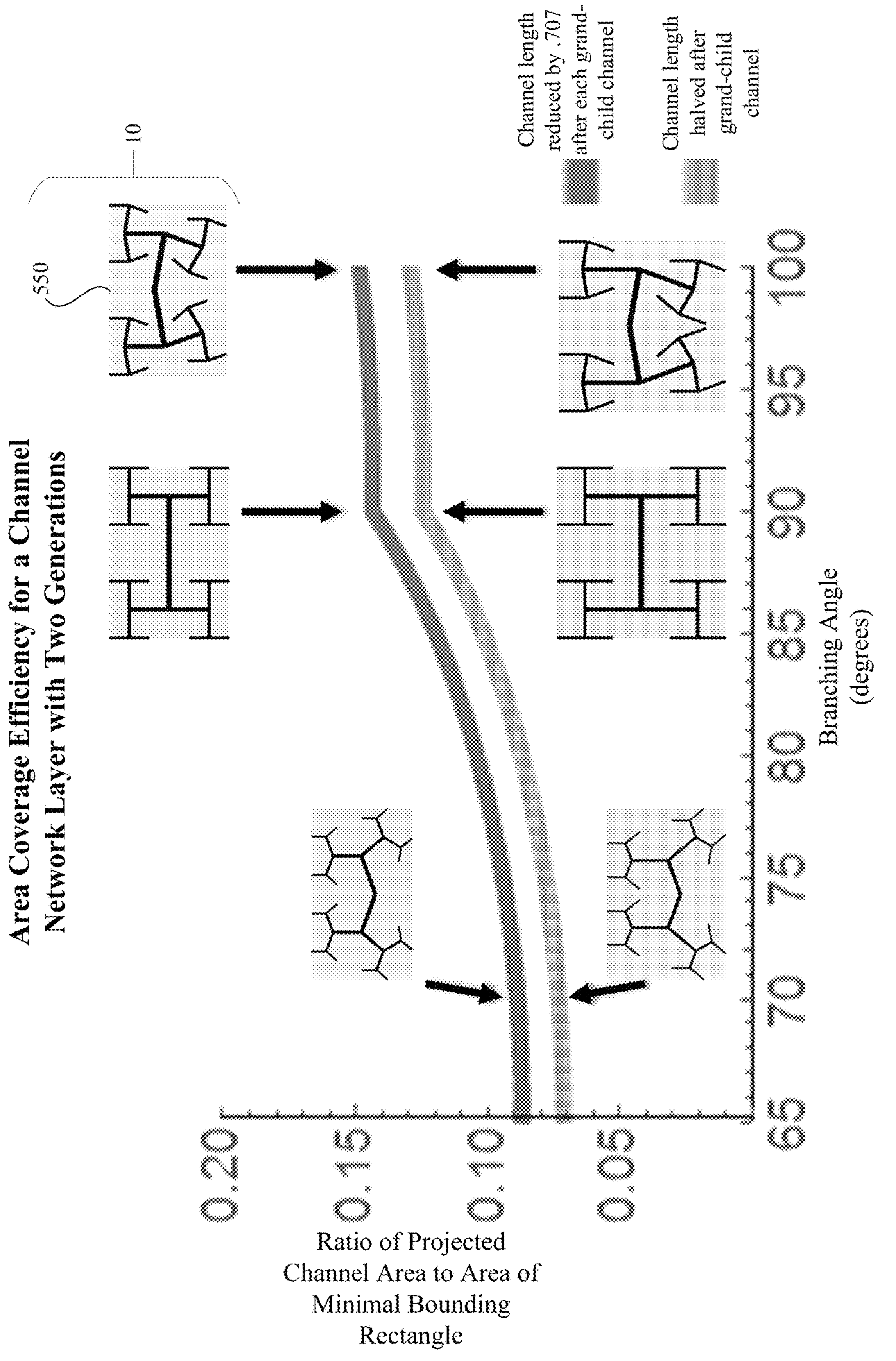
FIG. 5N illustrates an exemplary plot for determining an area coverage efficiency by branching angle and length reduction in accordance with embodiments of the present disclosure.

Referring briefly to FIG. 5L and FIG. 5M, exemplary plots for determining a maximum number of generations (e.g., bifurcations or branches) as a function of branching angle and reduction of length of subsequent channels for a planar channel network, in which a ratio of a length to a diameter of a parent channel is 10. FIG. 5L illustrates a plot in which a length of a subsequent channel is reduced by $1/\sqrt{2}$ each channel, while FIG. 5M illustrates a plot in which a length of a subsequent channel is reduced by ½ after each grand-child channel. Both plots yield a maximum number of generates at an angle of 90°. Further, as illustrated by the plots, in some embodiments if a branch angle is either smaller than 75° or larger than 105°, few (e.g., less than or equal to five) generations occur in two-dimensions before an intersection occurs. Referring to FIG. 5N, an exemplary plot is illustrated for determining a covering area efficiency (e.g., maximizing channel surface area in a fixed two-dimensional area). In FIG. 5N, a ratio of a projected area of the channel network (e.g., projected area 500) to an area of a smallest bounding rectangle (e.g., shell 550) is calculated for a fixed number of generations in which a ratio of a length to a diameter of a parent channel is 10. As illustrated by FIG. 5N, as the branching angle increases from 65° to 90°, the area coverage metric also improves. Below an angle of 65°, the channel surface area may increase, but devices include only a very small number (e.g., less than or equal to 5) of generations before channel intersection occurs. Above 90°, diminishing returns occur for improving the channel surface area since the areas of both the channels and the shell are the same, but a maximum number of allowed generations diminishes. Thus, a branching angle of 90° optimizes filling shell 550. Furthermore, a branching angle of 90° with symmetric branching evenly distributes fluid across the area efficiently and incorporates channel diameters that obey Murray's Law.

Furthermore, in some embodiments a length of a parent channel of a channel network is predetermined. Accordingly, a length of each subsequent channel (e.g., a child channel after bifurcation of the parent channel) is reduced by a predetermined factor relative to a length of an immediately preceding channel (e.g., the length of the parent channel). In some embodiments, this predetermined factor of length reduction is a constant less than or equal to 1 (e.g., 0.5). Furthermore, in some embodiments a ratio of a diameter to a length of a channel is fixed along the length of the channel. In some embodiments, the ratio of the diameter to the length is in a range of from 1:4 to 1:25 (e.g., 1:10).

Figure 10:
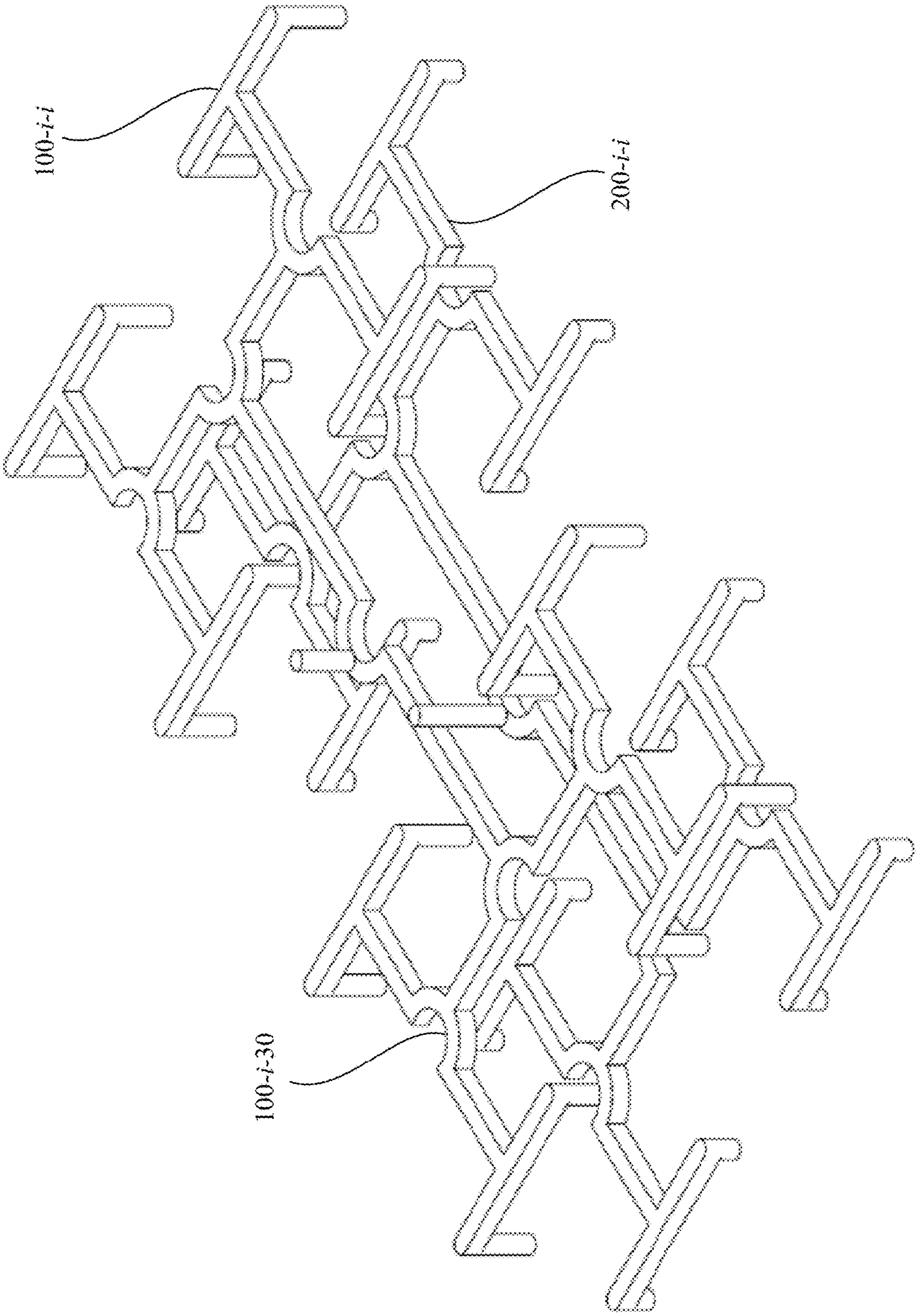
FIG. 10 illustrates an exemplary layout of a portion of a first layer and a portion of a second layer of a scaffold device utilizing the bifurcations of FIG. 5A in accordance with embodiments of the present disclosure.

Embodiments of the present disclosure include a wide variety of bifurcation shapes, including the shapes depicted in FIG. 5A through FIG. 5K. In some embodiments, the bifurcations are circular jogs (e.g., bifurcation 30 of FIG. 5A and FIG. 10). In such embodiments, bifurcation 30 provides a spatial region for a different channel to bypass a channel network without intersection, such as to supply fluid to a lower layer (e.g., a layer at a lower elevation) or channel network without intersecting an intermediate layer or channel network. For instance, referring briefly to FIG. 34, in some embodiments a first channel network includes outlets that bypass a second channel network and are in communication with corresponding outlets of a third channel network (e.g., outlets 100-1-2O are in communication with outlets 300-1-2O). Additional bifurcation shapes include a semi-circular shape, a C-shape, a T-shape, a U-shape, a V-shape, a convex wedge shape, a concave wedge shape, a chamfer shape, a fillet shape, or a Bézier curve shape. In some embodiments, the bifurcations include a protrusion (e.g., a protrusion at an internal surface of the bifurcation), an indentation, or similarly formed shapes that are configured to prevent occurrence of jet impinging in a flow. In FIG. 5E through FIG. 5H, a length of a connector is fixed while two weighted curve values of a cubic Bézier curve are varied. Typically, the Bézier curve includes four parameters. However, two of these four parameters are selected in some embodiments of the present disclosure in order to ensure continuous curvature while enabling the other two parameters to be chosen freely and/or optimized accordingly. In the present analysis of FIG. 5E through FIG. 5H, weight values range from 0 to 1 in increments of 0.1. However, in some embodiments these weight values are reduced to finer increments (e.g., 0 to 1 in increments of 0.001) in order to produce more accurate and precise results. Specifically, FIG. 5E depicts weight values of $wt_{1,2}$=0.2, FIG. 5F depicts weight values of $wt_1$=1 and $wt_2$=0.2, FIG. 5G depicts weight values of $wt_1$=0.2 and $wt_2$=1, and FIG. 5H depicts weight values of $wt_{1,2}$=1. In FIG. 5I through FIG. 5K, a length of the connector is varied while the weights are fixed (e.g., $wt_{1,2}$=1). Specifically, FIG. 5I depicts a dimensionless length of a smooth ramp connector as 0.2, FIG. 5J depicts a dimensionless length of a smooth ramp connector as 1, and FIG. 5K depicts a dimensionless length of a smooth ramp connector to be 0.5.

Figure 6A:
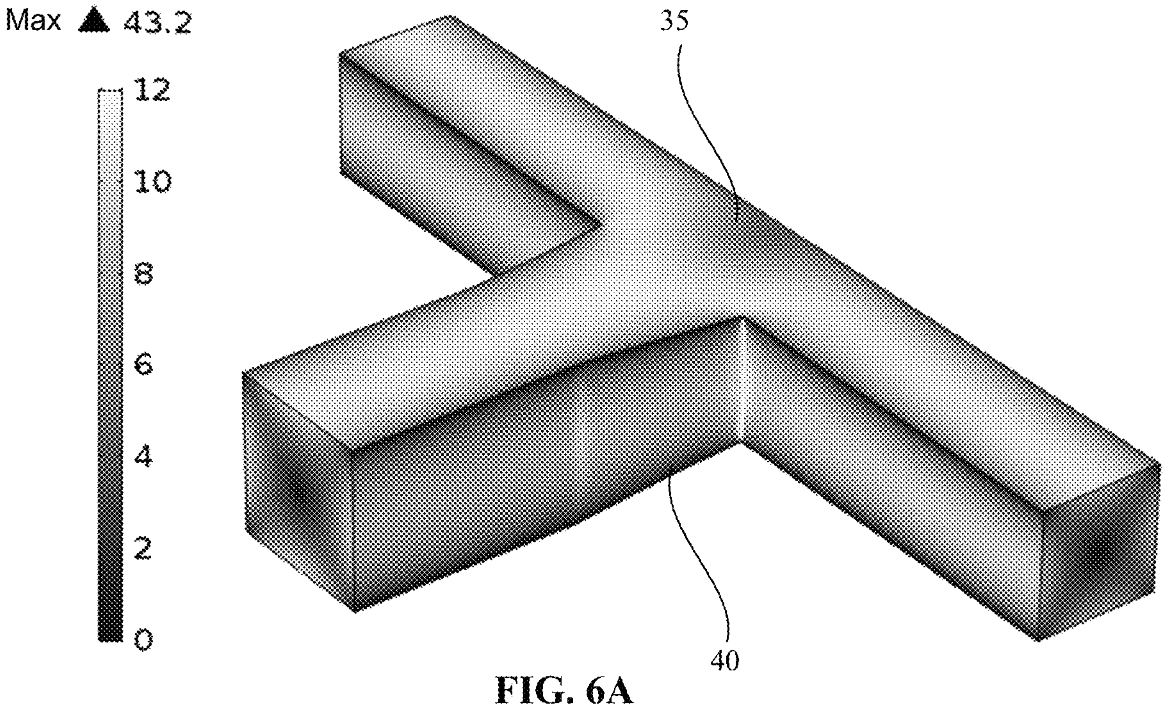
FIG. 6A, FIG. 6B, FIG. 6C, and FIG. 6D are illustrations of an exemplary dimensionless shear rate analysis in accordance with embodiments of the present disclosure.
Figure 6B:
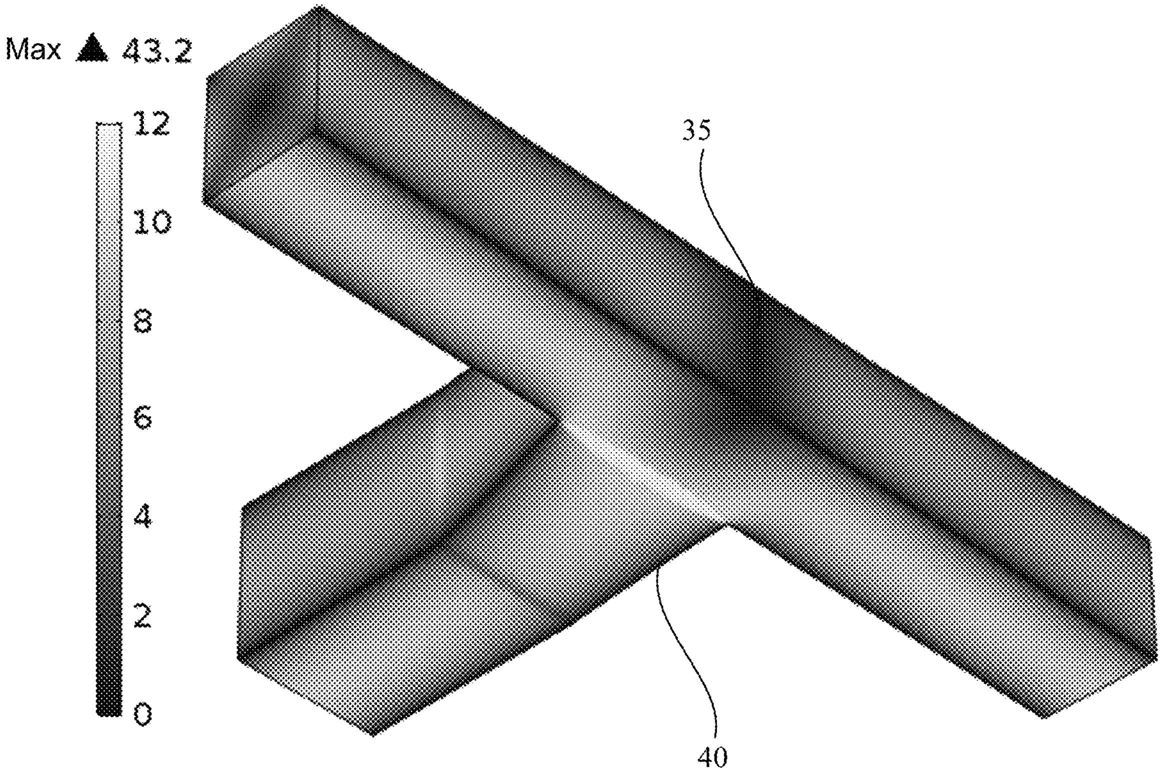
Figure 6C:
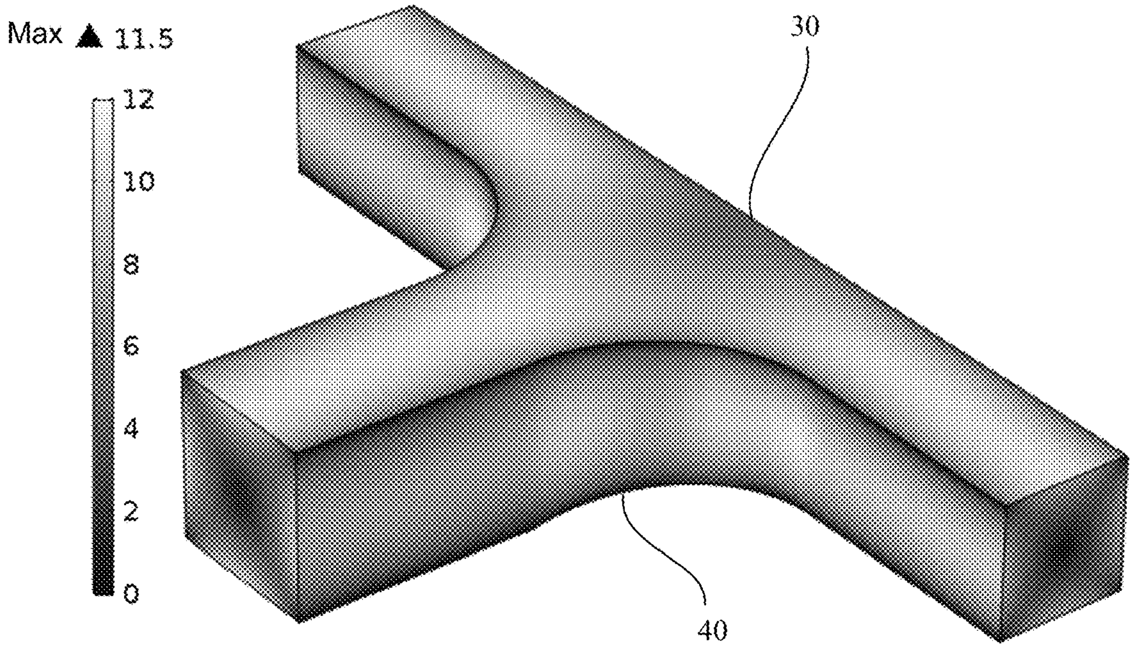
Figure 6D:
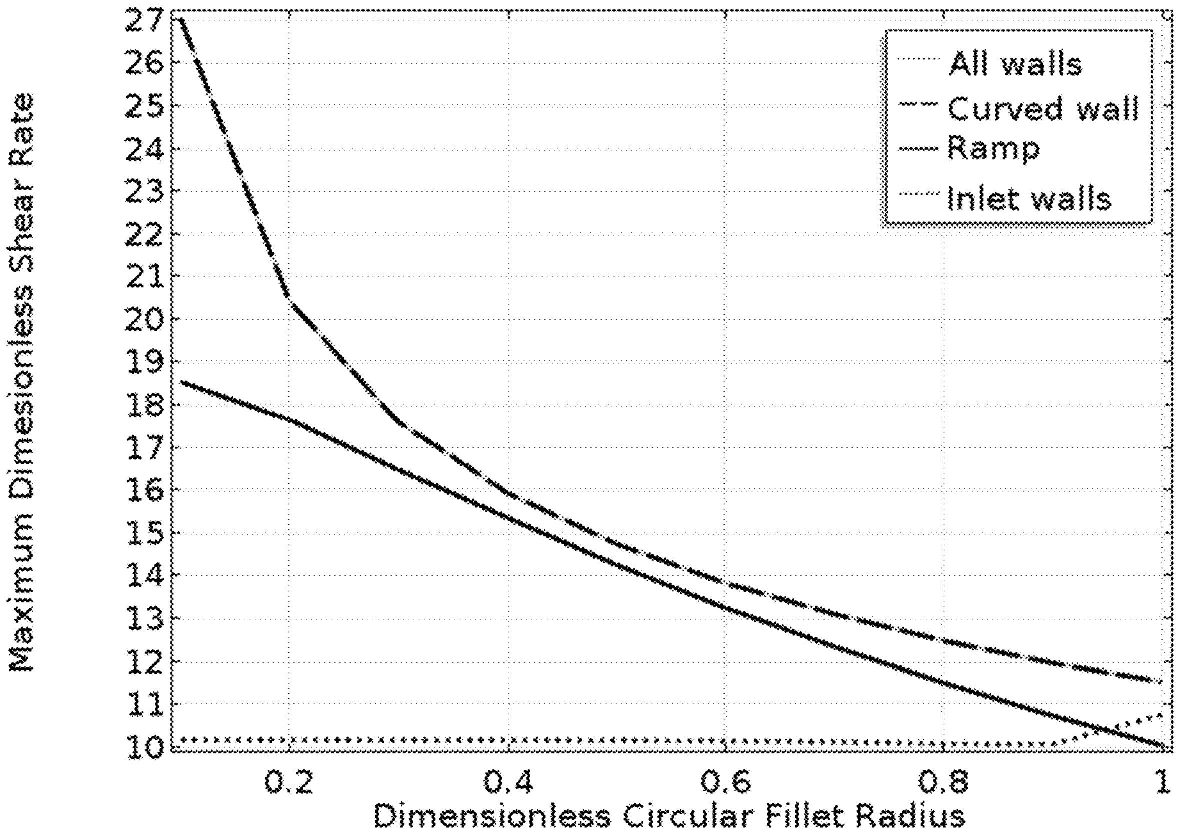

As previously described, minimizing increases in shear rate as well as a volume of low-velocity regions (e.g., zero velocity regions such as a stagnant region) at bifurcations within the device is highly preferred in embodiments of the present disclosure. FIG. 6A through FIG. 6D illustrate an analysis of dimensionless shear rates generated within various bifurcation designs. FIG. 6A and FIG. 6B illustrate a bifurcation (e.g., bifurcation 30) and a connector (e.g., connector 40) with sharp edge portions and corners. This design causes local maximums in shear rate, represented by brighter or white regions. Further, a stagnant region (e.g., stagnant region 35), representing a low velocity, is formed at a rear end portion of the bifurcation as well as along edge portions of the channel. In the present embodiment, a predicted maximum dimensionless shear rate is 43.2, while a predicted dimensionless shear rate along a center of the walls of the channel is 9.61. FIG. 6C illustrates an embodiment of a bifurcation including circular fillets designed to mitigate generated increases in shear rate. Smoothing the connector with circular fillets reduces the maximum generated dimensionless shear rate in comparison to a sharp-edged connector. However, even with a substantially large radius fillet, as shown in FIG. 6C, discontinuities in curvatures between straight portions of the channel (i.e., zero curvature) and the fillet (i.e., non-zero curvature) results in local maximums of shear rate. FIG. 6D illustrates a maximum dimensionless shear rate on a variety of channel boundaries for a bifurcation and a connector including a circular fillet at Reynolds number of 1 (Re=1). As depicted in FIG. 6D, maximum shear rates at the connector and the bifurcation are approximately 15-20% above those of the straight channel. Thus, in order to minimize the increases in shear rate at connectors and bifurcations, the shapes of the bifurcations are preferred to have no sharp edge portions, have continuous curvature, and have a smooth ramp with a gentle slope. In some embodiments, if the shapes of the bifurcations are configured according to cubic Bézier curves the curvature varies continuously from zero along an upstream straight section to positive along the curve and back to zero at a downstream straight section. In some embodiments, a smoothed step function ramp of a length (e.g., a predetermined length) leads from a first channel to a narrower second channel (e.g., from a parent channel to a child channel, from the child channel to a grandchild channel, etc.).

As illustrated in FIGS. 6A-6C, a channel of the scaffold device may include a first surface 600 and a second surface 601 opposite the first surface. In some embodiments, the first surface 600 defines a surface of the channel that is coplanar with corresponding first surfaces of other channels at a height of the cell scaffold device (e.g., first height (H1) of FIG. 31, second height (H2) of FIG. 31, . . . , etc.). The second surface 601 may define an opposite surface of the channel that comprises a linear ramp extending between different heights of the cell scaffold device.

Furthermore, as previously described, ensuring each channel and each bifurcation exhibits laminar flow within is highly preferred. If analyzing flow conditions in a channel and subsequent bifurcation, a variety of flow physics and boundary condition assumptions must be made. These assumptions are associated with a desired laminar flow having varying ratios of inertial effects and viscous effects. Furthermore, to ensure analysis results are applicable to a wide variety of connectors, bifurcations, channel dimensions (e.g., length, width, height such as first height (H1) of FIG. 31, second height (H2) of FIG. 31, . . . , etc.), flow rates, and fluid types (e.g., a culture media, blood, collagen, water, etc.), this analysis is conducted in dimensionless variables. Specifically, all spatial coordinates are scaled by an inlet diameter d, all velocity components are scaled by an average velocity at the inlet U=(flow rate)/$d^2$, a pressure is scaled by density×$U^2$, and scaling for time is d/U. Accordingly, the average dimensionless velocity at an inlet is 1 in the dimensionless variables. The analysis presented herein is in the steady-state, and thusly does not explicitly involve time. The dimensionless Navier-Stokes equations governing fluid flow in connectors and bifurcations depend on the Reynolds number, Re=(U×d)/v, where v is a kinematic viscosity of a fluid and d includes dimensionless geometrical parameters such as curve and connector shapes as well as channel aspect ratios. To ensure analysis results are applicable to a wide variety of flow rates, channel sizes, and fluids, the present disclosure considers the Reynolds number (Re) in a range of from Re=0.1 to approximately 2300, and the analysis presented herein includes Re in a range of from 0.1 through 100. For instance, FIG. 7A through FIG. 7G includes a Re of 1, while FIG. 8A through FIG. 8F include a Re of 100. A symmetry condition is imposed at a symmetry plane of y=0, an exit pressure is specified as 0 at an outlet, and the no-slip condition is imposed at the walls of the channels. In the following analysis, channels have a square cross-section (i.e., an aspect ratio of 1). Additionally, inner curved boundaries defined by the Bézier curve include two predetermined weighting parameters to maintain continuous curvature at side portions of the channels. The inner curved boundaries defined by the Bézier curve also includes two configurable weighting parameters $wt_{1,2}$ that are in a range of from 0.01 to 1. For instance, FIG. 7A through FIG. 8F, the two configurable weighting parameters are $wt_{1,2}$=1. Additionally, the exemplary smooth ramp connector has dimensionless length in a range of 0.01 to 1. In FIG. 7A through FIG. 7F and FIG. 8A through FIG. 8E, the exemplary smooth ramp connector has a dimensionless length of 1. In FIG. 7G and FIG. 8E, the exemplary smooth ramp connector has a dimensionless length of 0.1.

Figure 7A:
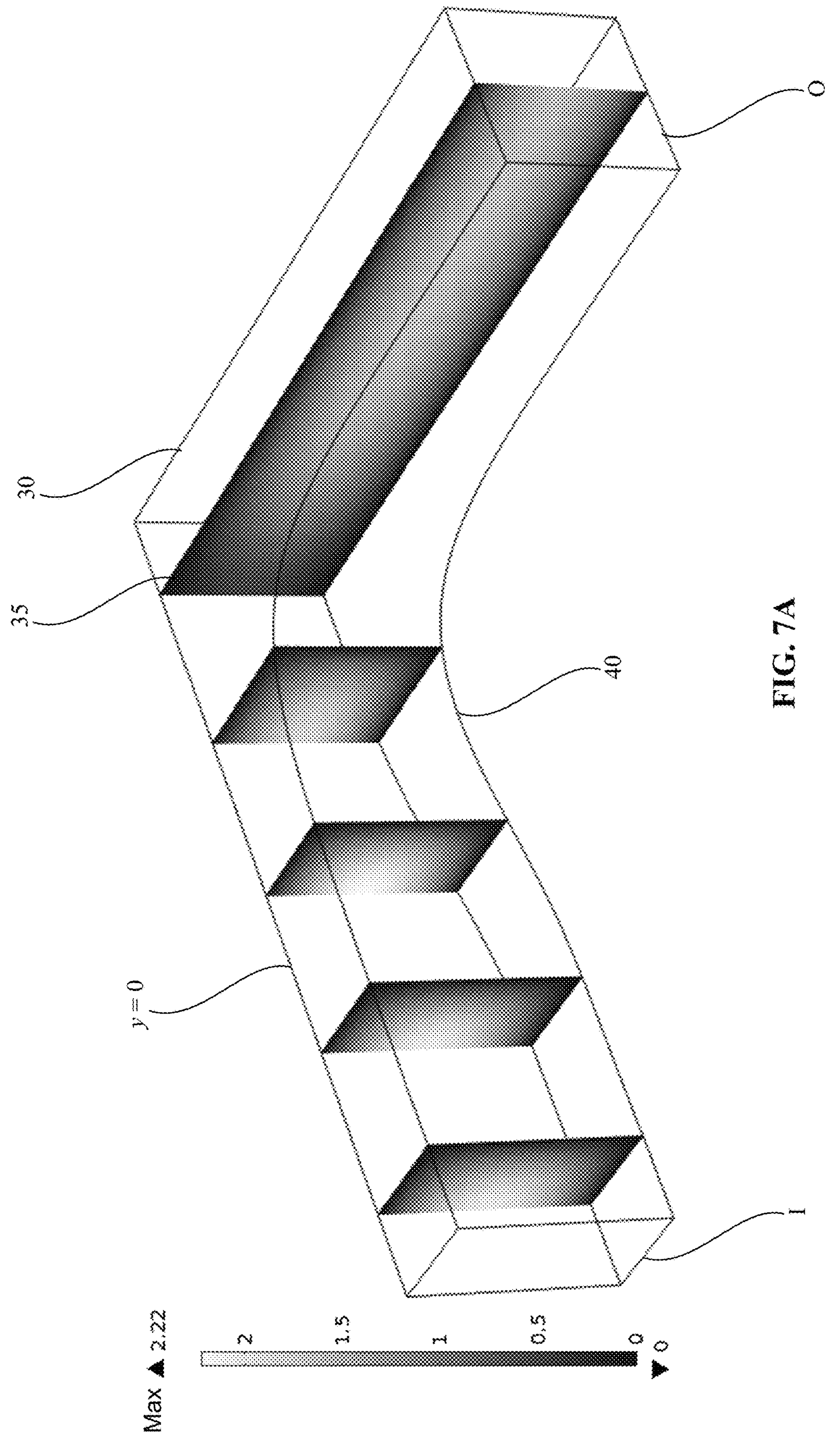
FIG. 7A, FIG. 7B, FIG. 7C, FIG. 7D, FIG. 7E, FIG. 7F, and FIG. 7G are illustrations of an exemplary dimensionless velocity, streamline, pressure, and shear rate analysis in accordance with embodiments of the present disclosure.
Figure 7B:
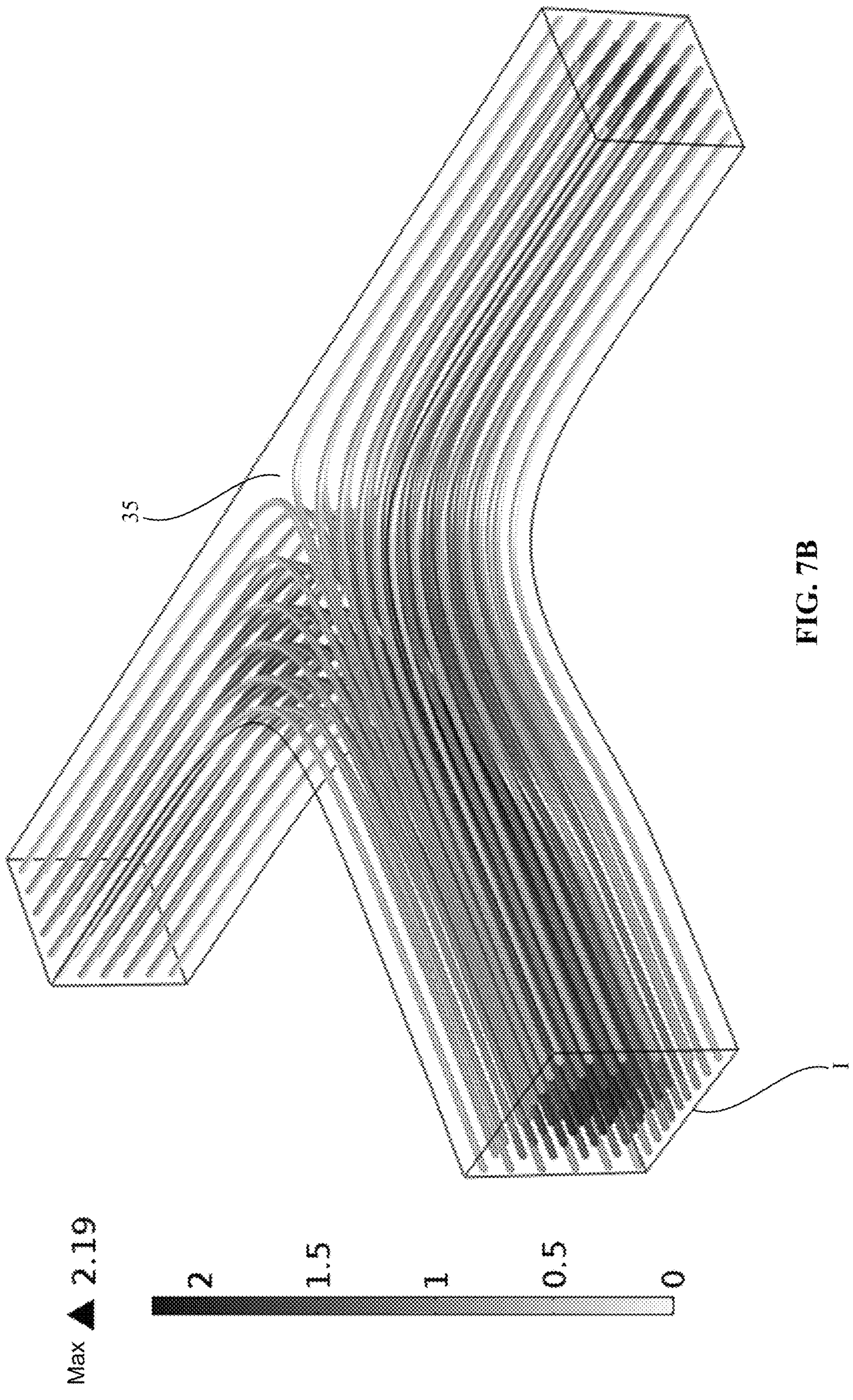
Figure 7C:
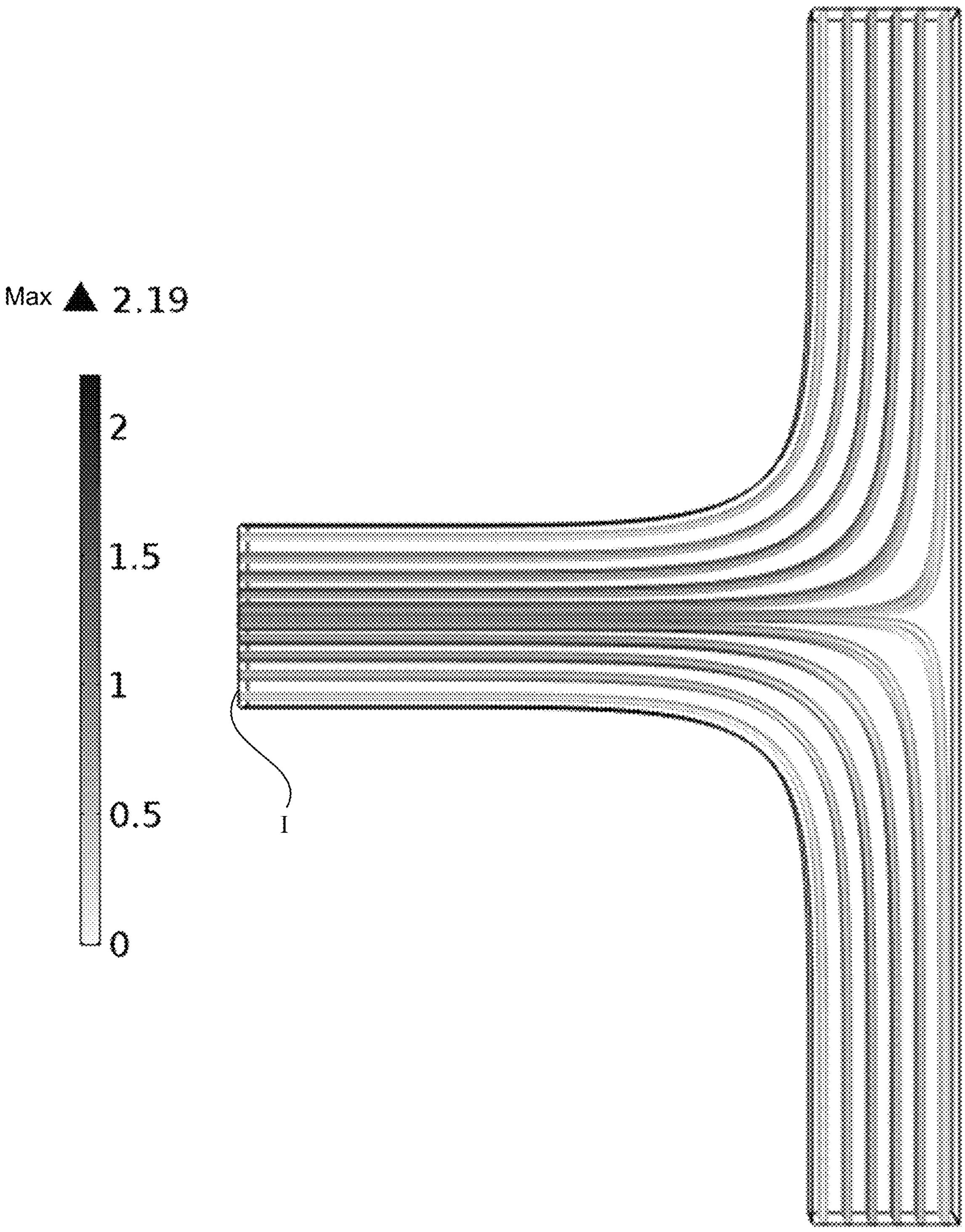
Figure 7D:
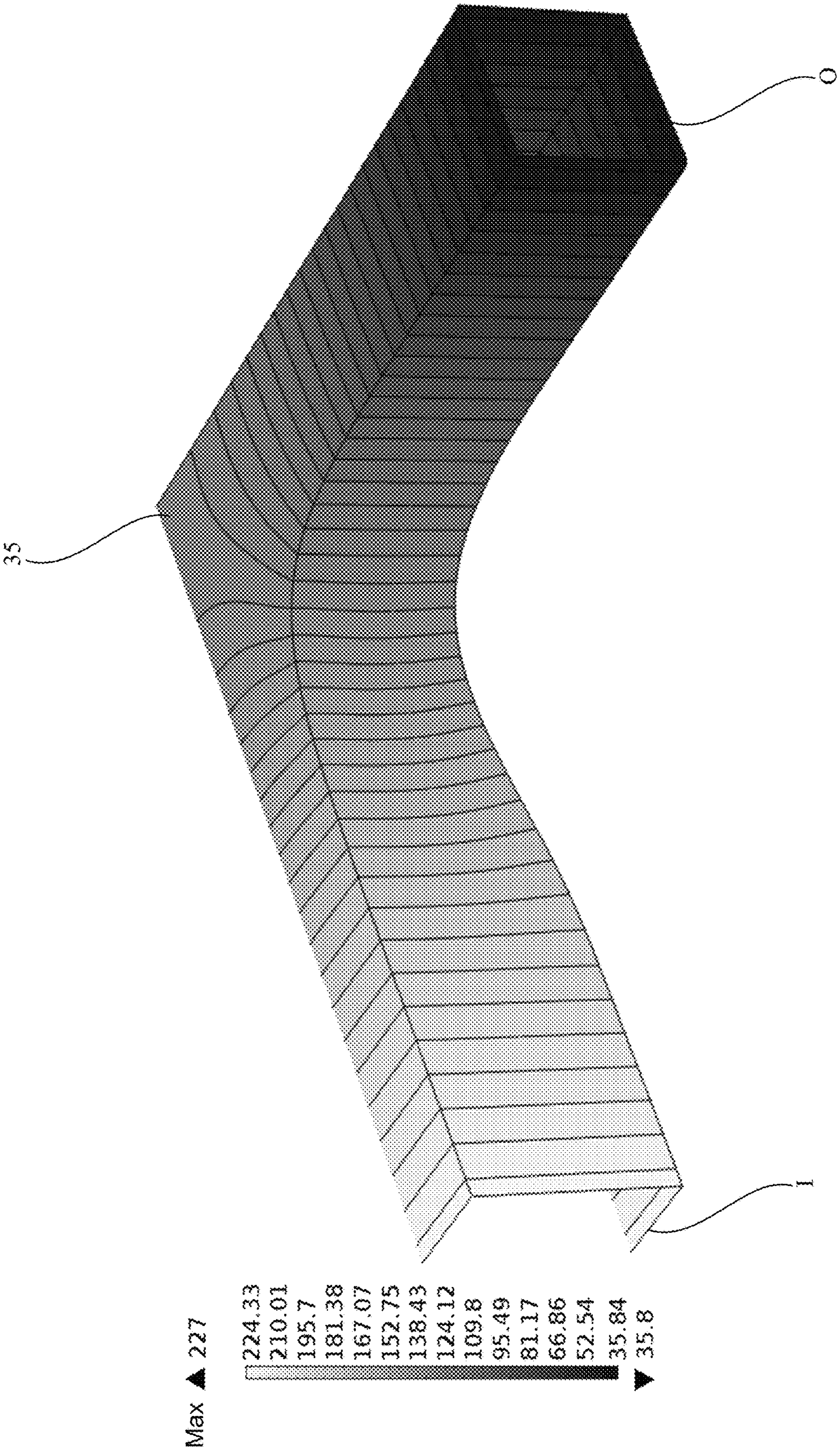
Figure 7E:
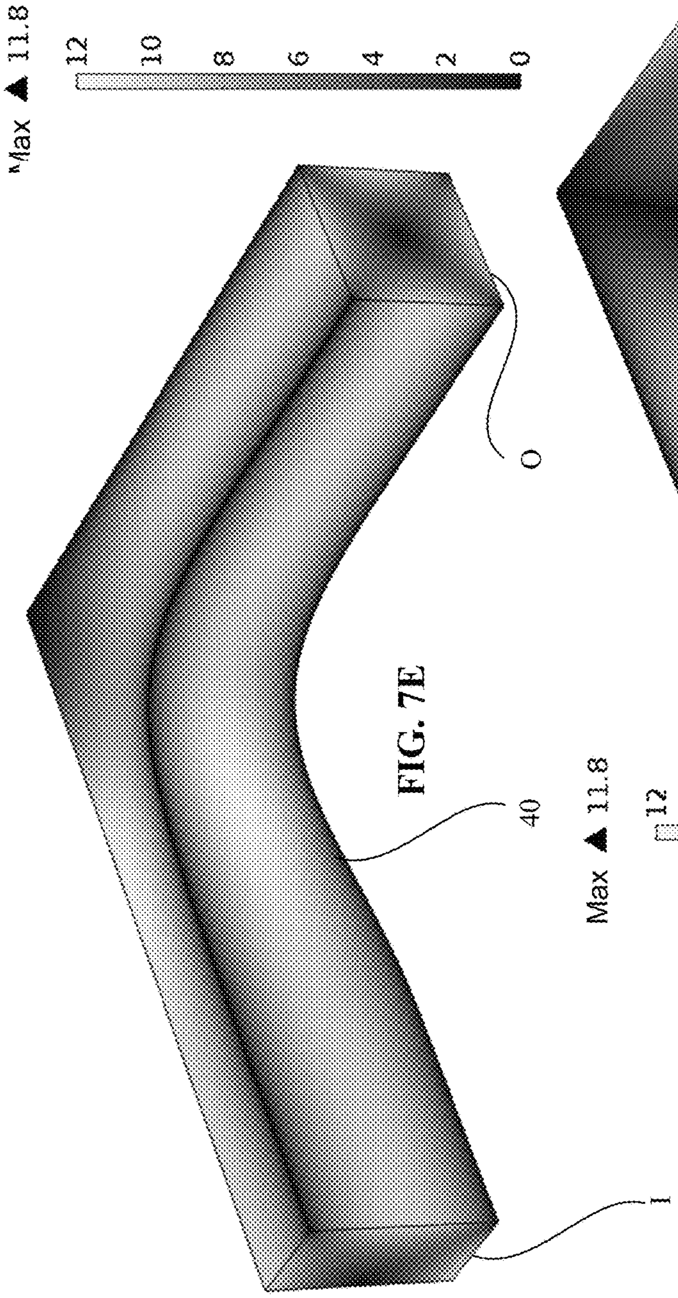
Figure 7F:
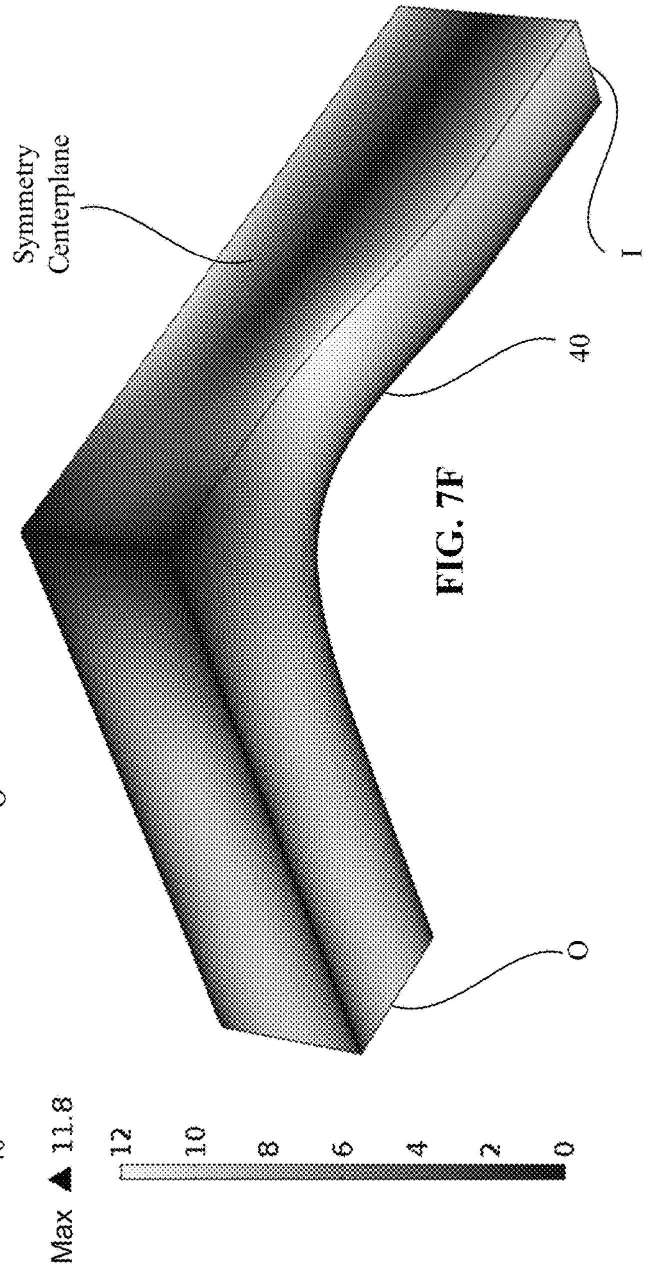
Figure 7G:
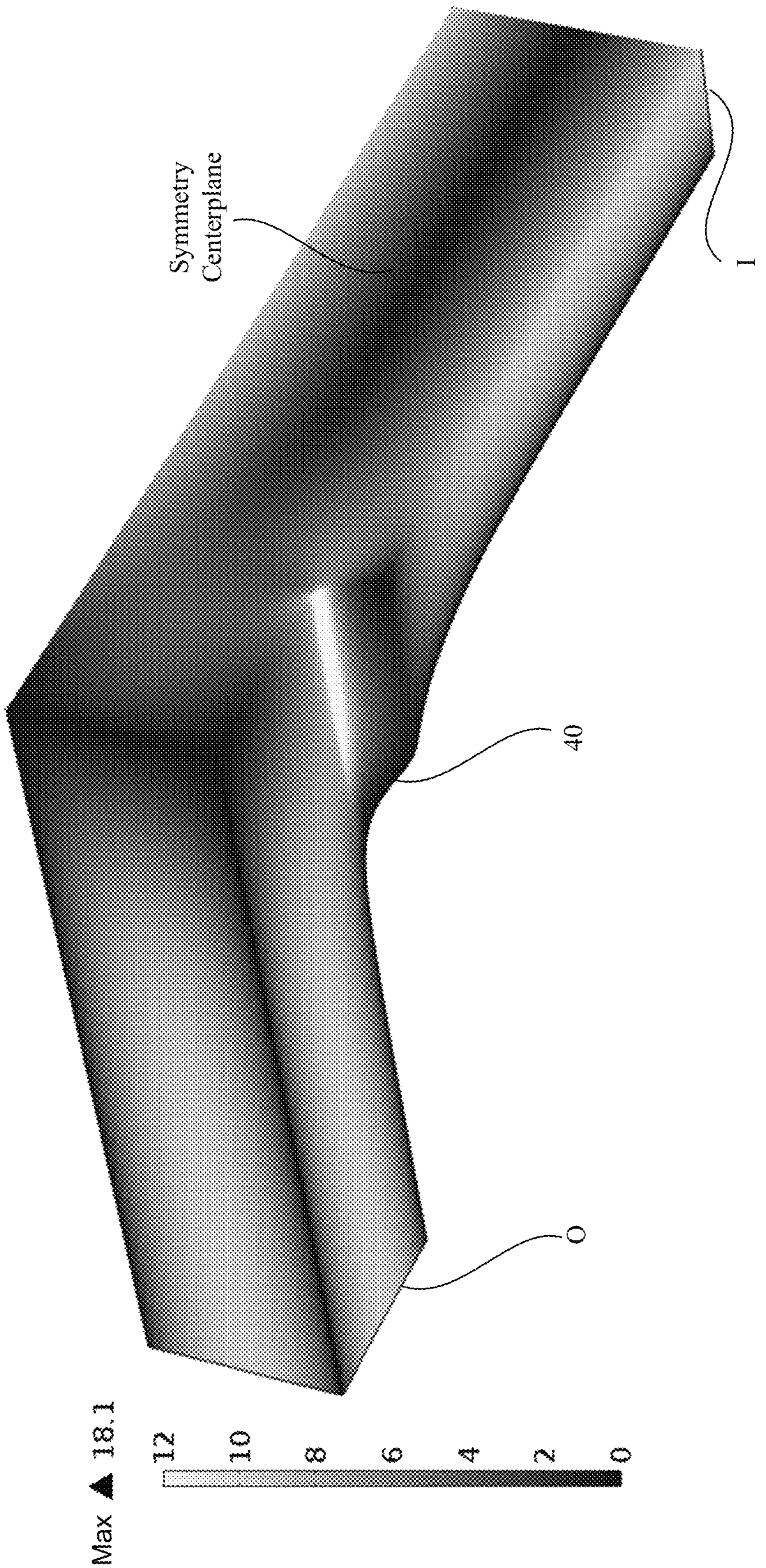

Referring to FIG. 7A through FIG. 7E, an analysis of the previously described embodiments is conducted. In the figures, a flow of medium from inlet (I) to outlet (O). Referring to FIG. 7A, dimensionless velocity magnitude is illustrated in the right symmetric half of connector 40 and bifurcation 30. As previously described, the dimensionless average velocity is 1 at the inlet. Velocities are higher (e.g., a number further from zero) at a center of the channel and 0 at the walls. Similarly, stagnant regions 35 exist at rear end portions of the bifurcation. Referring to FIG. 7B and FIG. 7D, streamlines are illustrated to visualize a flow of fluid. In the figure, a color of the streamline (e.g., a level of darkness) indicates dimensionless velocity magnitude. No recirculation is observed in these streamlines. However, a stagnant region still exists in the rear end portions of the bifurcation. Referring to FIG. 7D, dimensionless pressure contours are illustrated. Contours that are evenly spaced indicate a gradual change in a flow profile across the bifurcation. However, an exception is a large (e.g., a greater distance between adjacent contours) contour spacing near stagnant region 35. In the present embodiment, a laminar flow boundary condition is imposed at an outlet (i.e., where an exit pressure is 0). Referring to FIG. 7E and FIG. 7F, dimensionless shear rate, which is equal to dimensionless shear stress, is illustrated. In the present embodiment, a maximum shear rate is at a center of the walls, which correlates to a dimensionless shear rate of approximately 9.7, and 0 at the corners or edge portions (e.g., a region where the walls intersect). In the present embodiment, the maximum shear rate occurs at connector 40. However, in some embodiments, the maximum shear rate can occur downstream of connector 40 (e.g., at the bifurcation). Referring to FIG. 7G, an embodiment including a steep ramp (e.g., a dimensionless length of connector 40 is 0.1), the maximum shear rate occurs at the connector. No recirculation is observed in the present embodiment, as well as embodiments analyzed with Re=0.1, Re=1, and Re=10.

Biologically relevant ranges for Reynolds numbers, where $Re=(U\times d)/v=4Q/(\Pi\times d\times v)$ if an average inlet velocity is $U=Q/((\pi\times d^2)/4)$, were determined for a bio-reactor as well as a mouse liver. Human liver equivalents may also be determined. In determining, an approximate blood flow rate entering a liver is Q, and a diameter of a cylindrical inlet channel is d in meters (m).

TABLE 1

Estimated Ranges of Biologically Relevant Reynolds Numbers

| | d | Q | U | Blood at 37° C. | | Culture Media at 37° C. | |
|---|---|---|---|---|---|---|---|
| Subject | (m) | ($m^3$/s) | (m/s) | v ($m^2$/s) | Re | v ($m^2$/s) | Re |
| Bio-reactor | 1.00E−03 | 5.00E−08 | 6.37E−02 | 3.30E−06 | 1.93E+01 | 7.80E−07 | 8.16E+01 |
| Mouse liver | 6.40E−04 | 5.00E−08 | 1.55E−01 | 3.30E−06 | 3.01E+01 | 7.80E−07 | 1.28E+02 |

In some embodiments, recirculation can be observed when the connectors are substantially steep (e.g., a dimensionless length of a connector is approximately 0) or a high Reynolds number (e.g., Re is greater than 100). In these embodiments, the maximum shear rate occurs where a flow jet forms downstream of the connector, which in turn impacts the rear end portion of the bifurcation. These jet formations and impacts change the qualitative nature of a flow. Thus, as previously described, protrusions and/or indentations may be formed in and/or on the bifurcations. The protrusions and/or indentations direct a flow of medium and inhibit jet formation, reduce impacts against materials (e.g., cells) and channel walls at the bifurcation, and reduce a maximum shear rate.

Figure 8A:
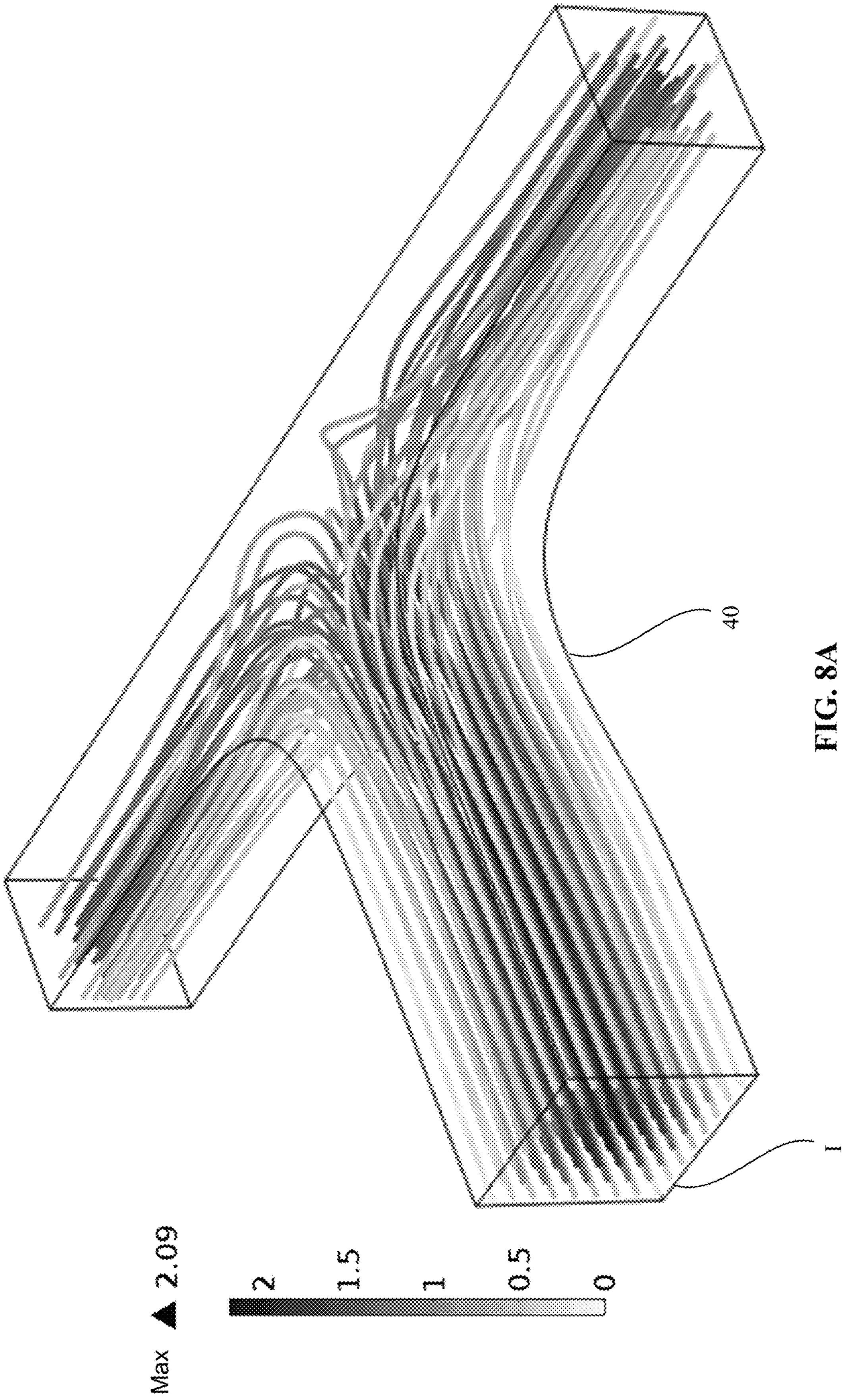
FIG. 8A, FIG. 8B, FIG. 8C, FIG. 8D, FIG. 8E, and FIG. 8F are illustrations of an exemplary dimensionless velocity, streamline, pressure, and shear rate analysis at a Reynolds number equal to 100 in accordance with embodiments of the present disclosure.
Figure 8B:
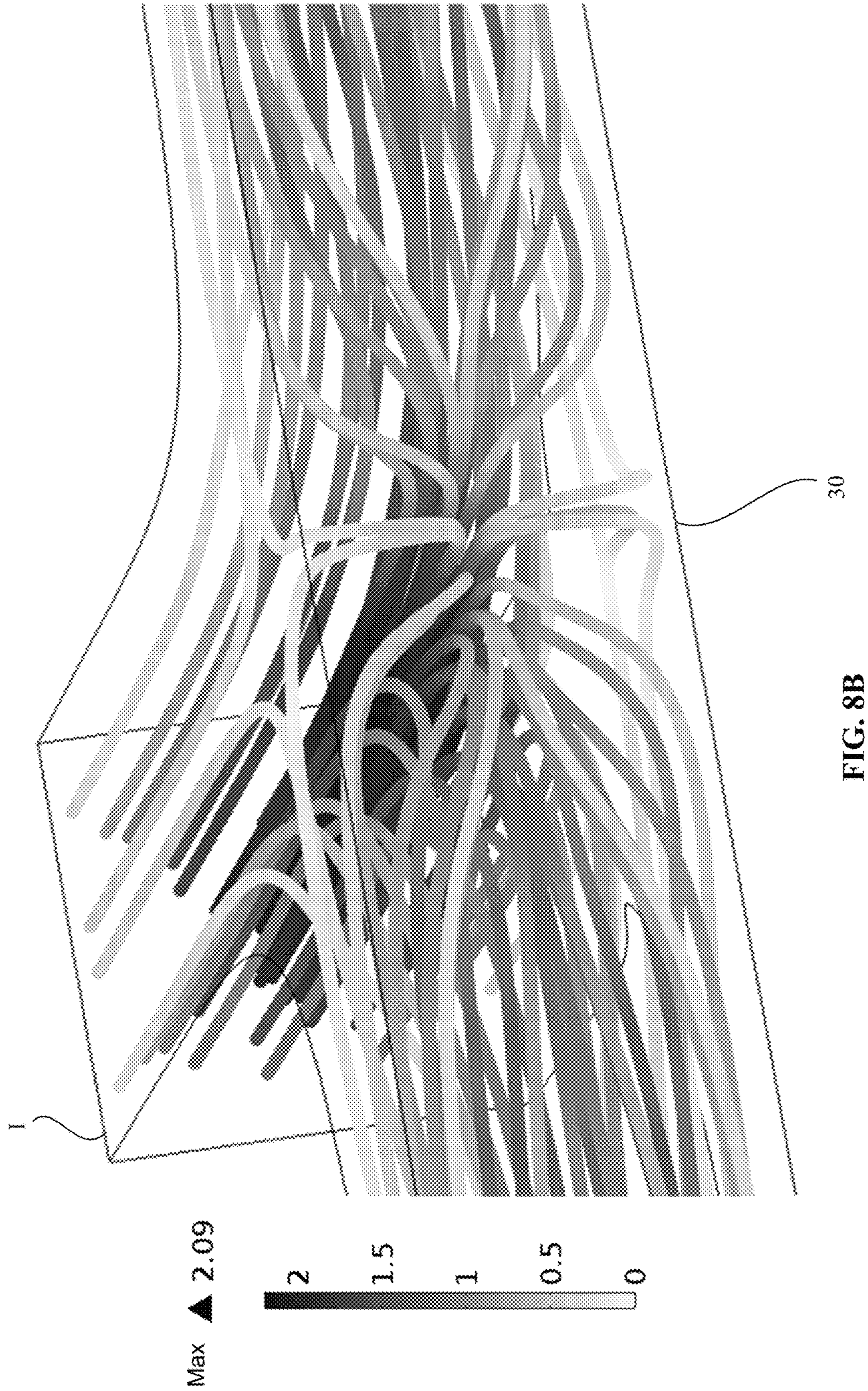
Figure 8C:
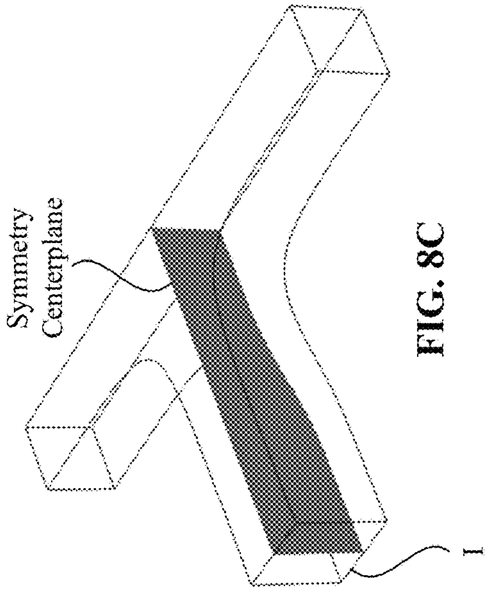
Figure 8D:
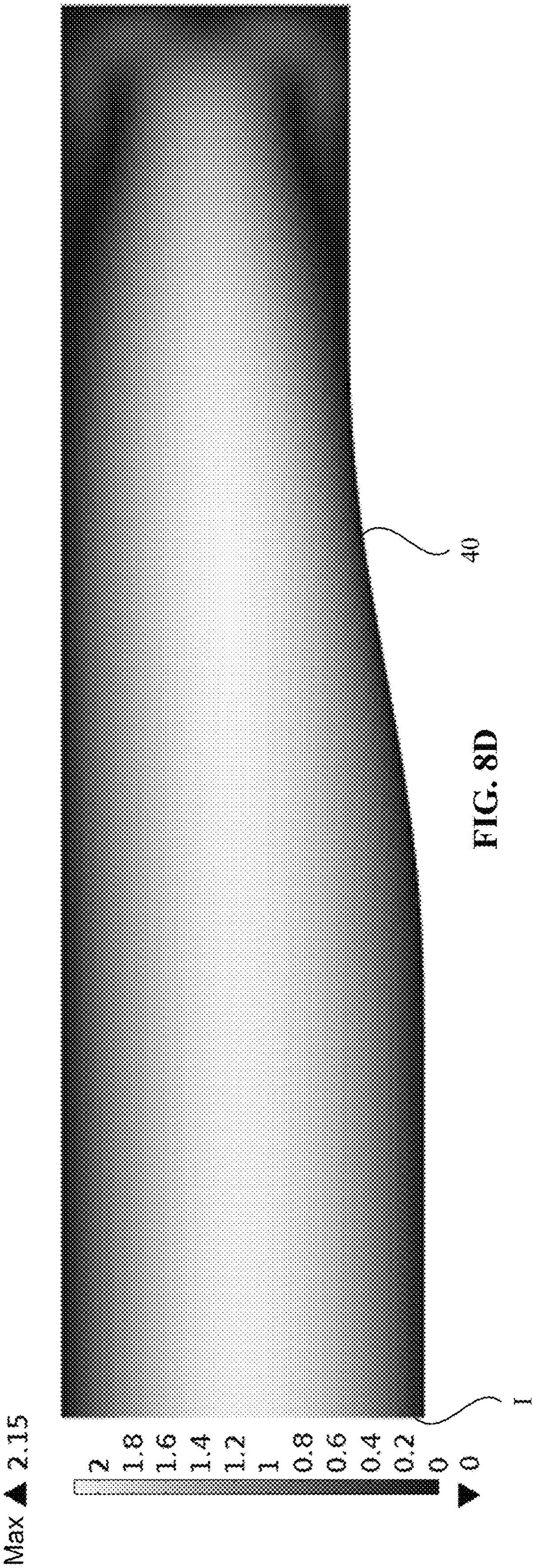
Figure 8E:
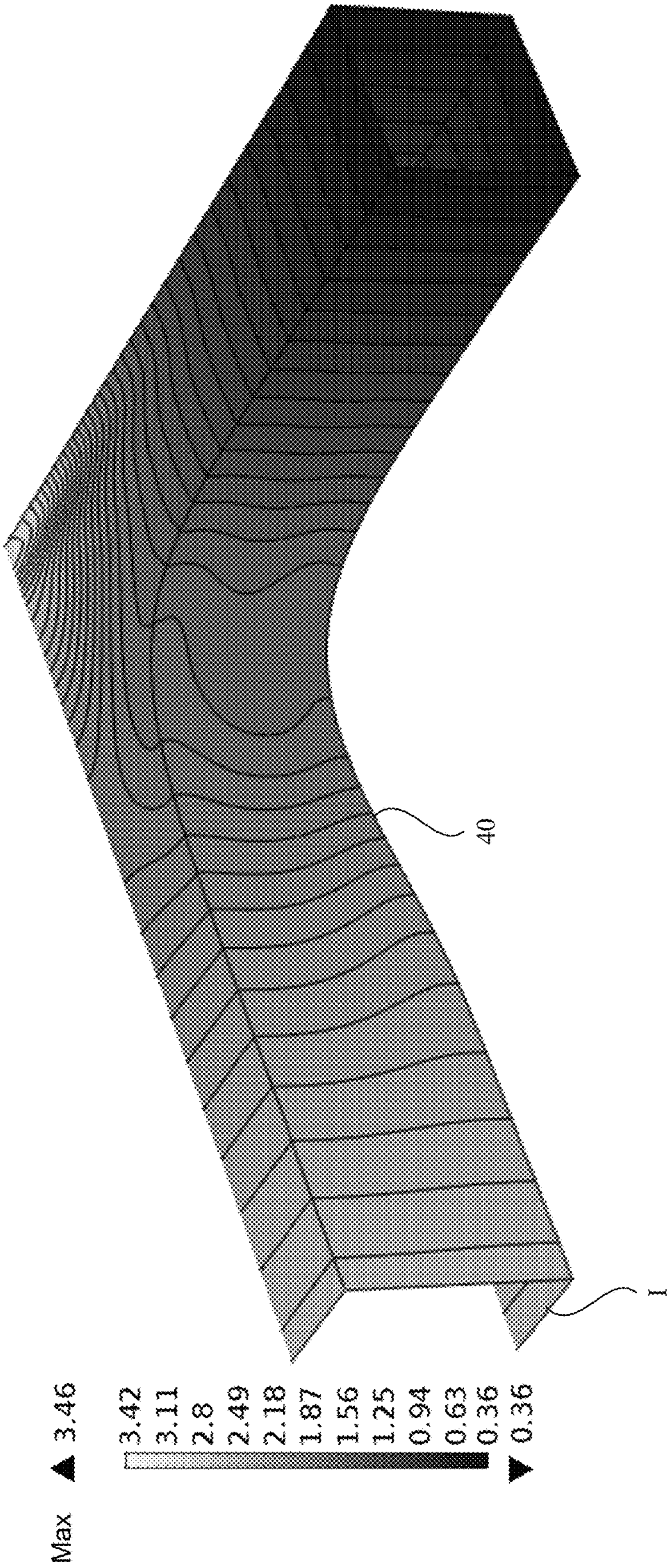
Figure 8F:
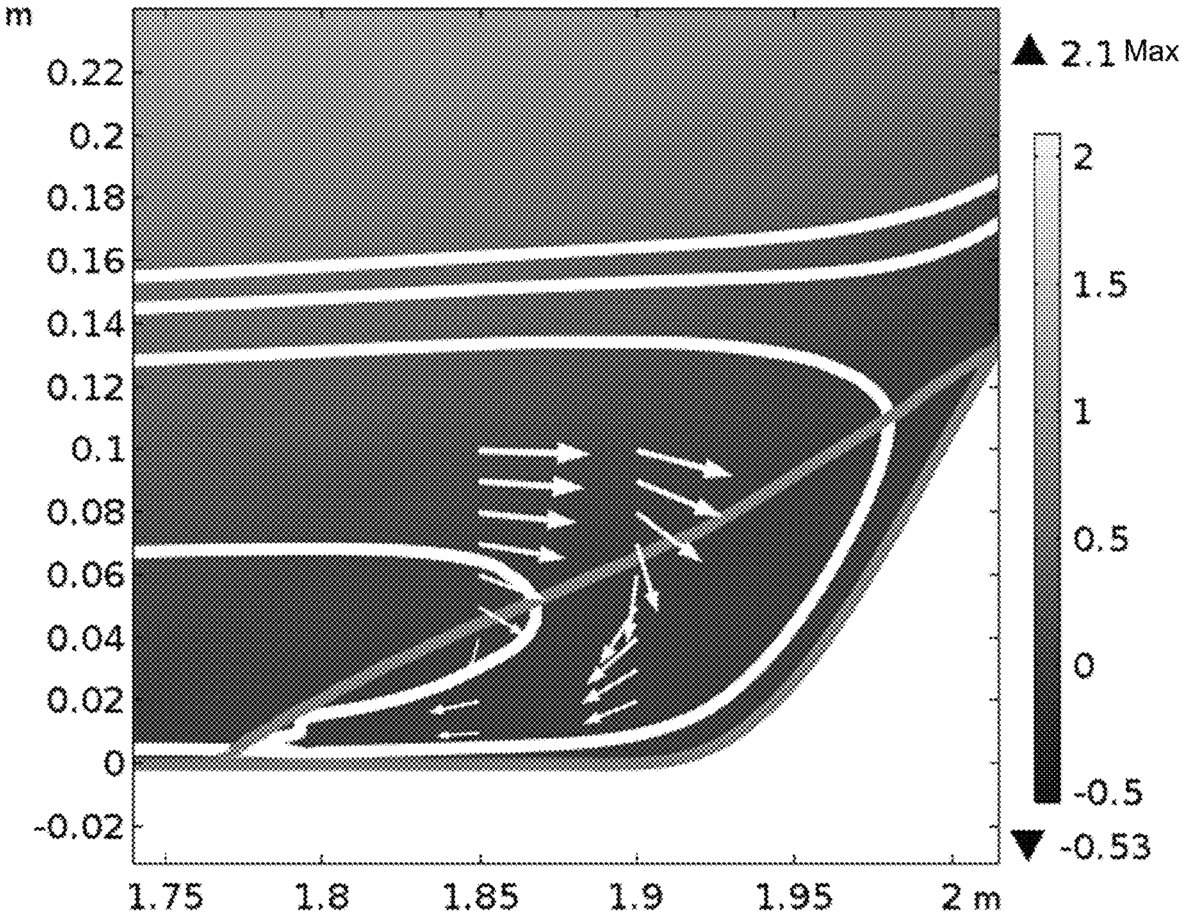

Referring to FIG. 8A through FIG. 8F, the aforementioned analysis was re-conducted. However, in conducting the analysis only the parameter Re=100 was altered. In the present embodiment, a total dimensionless pressure drop across the bifurcation is approximately a hundred times lower in comparison to the previous embodiment of Re=1. This hundred times pressure drop can occur for a plurality of reasons. For instance, when the Re is increased from 1 to 100 by reducing the viscosity by a hundred times, a flow resistance would similarity decrease by a hundred times which is consistent with a hundred times decrease in the dimensionless pressure. When the Re is increased from 1 to 100 by increasing the inflow velocity a hundred time, the physical pressure increases by a hundred times. One skilled in the art would recognized this pressure drop is only predictive, and actual pressure drops may be greater or lower in various embodiments. Furthermore, this pressure drop enables material flow from a relatively high-pressure region to a relatively low-pressure region. Referring to FIG. 8A and FIG. 8B, streamlines illustrate a jet forming at (e.g., over) the connector and impacting a rear end portion of the internal surface (e.g., wall) of the bifurcation, indicative of a higher Reynolds number laminar flow. This jet and impact are also illustrated in FIG. 8C and FIG. 8D from a plot of velocity magnitude in which higher velocities are illustrated in a lighter shade compared to lower velocities. Referring to FIG. 8E, a low density of pressure contours at the smooth curved portion indicate that a high velocity jet forms at (e.g., over) the connector and relatively maintains an initial trajectory. Accordingly, the jet does not expand or traverse with a curved portion of the channel. Furthermore, a high density of pressure contours at a rear end portion of the bifurcation indicate jet impact (e.g., a flow impacts the rear end portion of the bifurcation). Referring to FIG. 8F, an x-component of the dimensionless velocity at a bottom end portion of a connector having a dimensionless length of 0.1 is illustrated to observe recirculation. In FIG. 8F, arrows depict a direction of the velocity, a white lines illustrates a streamline, and a solid grey line illustrates a velocity of 0.

Figure 9A:
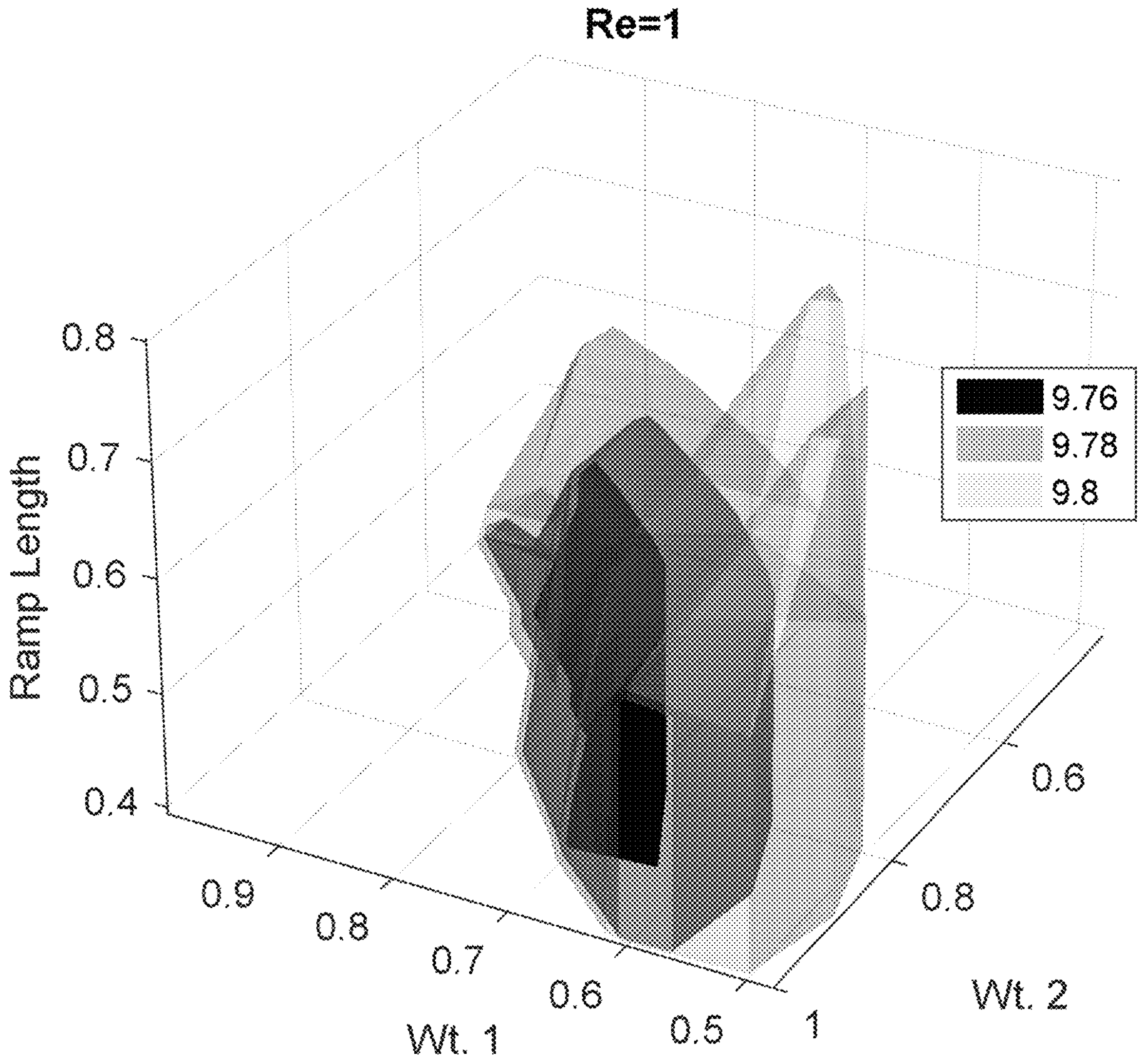
FIG. 9A, FIG. 9B, and FIG. 9C are illustrations of exemplary parametric iso-surfaces of dimensionless shear rate in terms of two inner curve weights and a dimensionless length of a smooth connector in accordance with embodiments of the present disclosure.
Figure 9B:
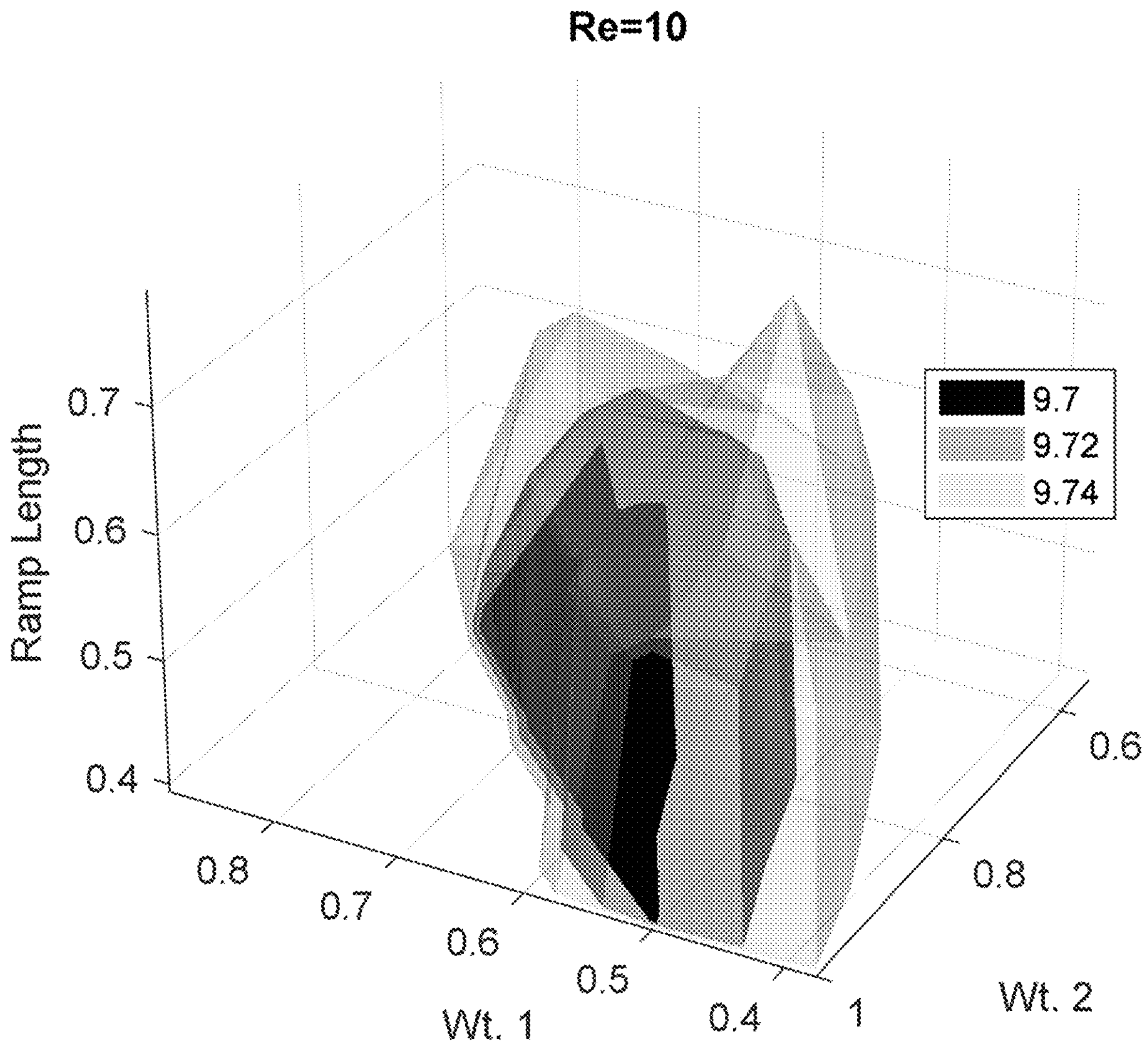
Figure 9C:
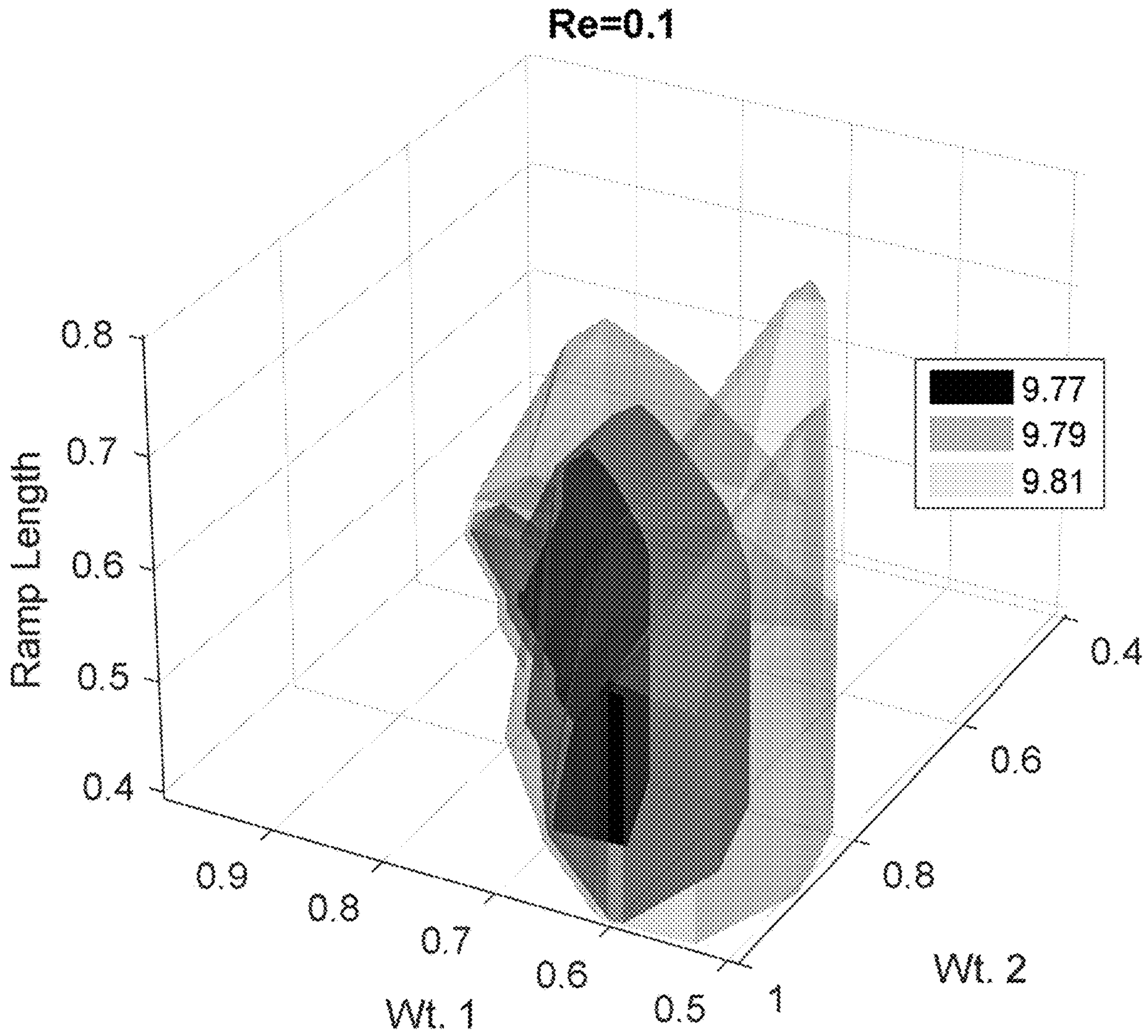

FIG. 9A through FIG. 9C illustrate a broad parameter (e.g., design space) for varying a ramped connector length and curve weights. Lengths and curve weights are optimized to minimize the additional shear rate caused by a flow division and re-direction. Similarly, to obey Murray's law, a diameter of a parent channel is larger than that of the children channels. Further, a smoothed ramp at a bottom end portion of the connection forms a transition region between the different channel diameters. The length of the ramp or, alternatively, the slope is parameterized and optimized to avoid, or reduce, a jump in shear rate. Iso-surfaces illustrated in these three-dimensional parameter domain bound shear rates within approximately 0.2 dimensionless units of a maximum shear rate in a straight portion of a channel (e.g., 9.61) at the same Reynolds number. Furthermore, the iso-surfaces illustrate a minimum shear rate increase beyond that observed in a straight portion of a channel. Referring to FIG. 7F and FIG. 7G, the previously predicted maximum shear rates of 11.8 and 18.1, respectively, are outside an optimal region illustrated by FIG. 9A. As previously described, in order to form a smoother (e.g., less course, finer grain) iso-surface increments of the weights and the ramp length should be further refined (e.g., from increments of 0.2 to 0.00001).

Figure 11:
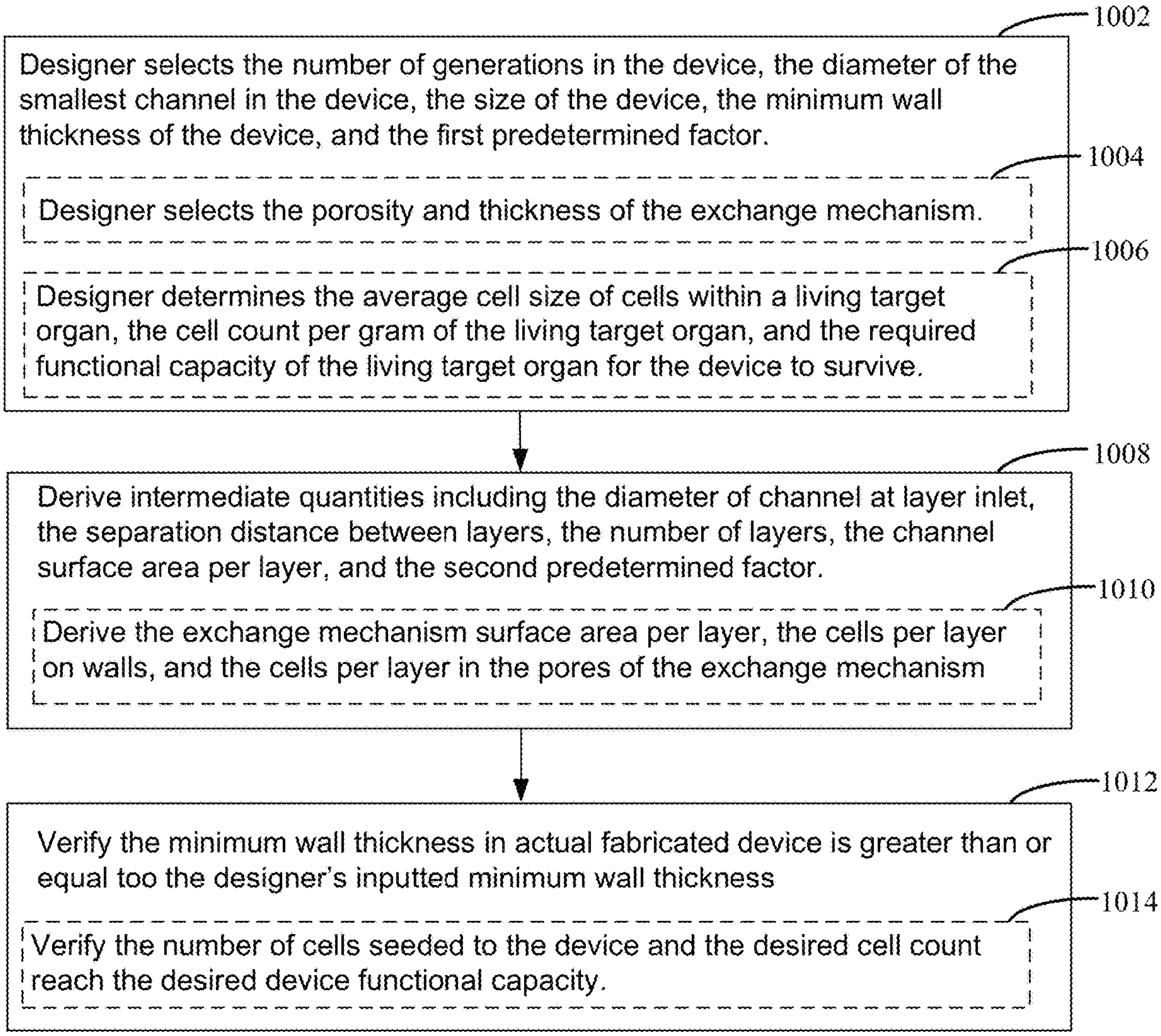
FIG. 11 illustrates a flow chart of an exemplary design process for generating a scaffold device in accordance with embodiments of the present disclosure, in which optional steps or embodiments are indicated by dashed boxes.
Figure 12:
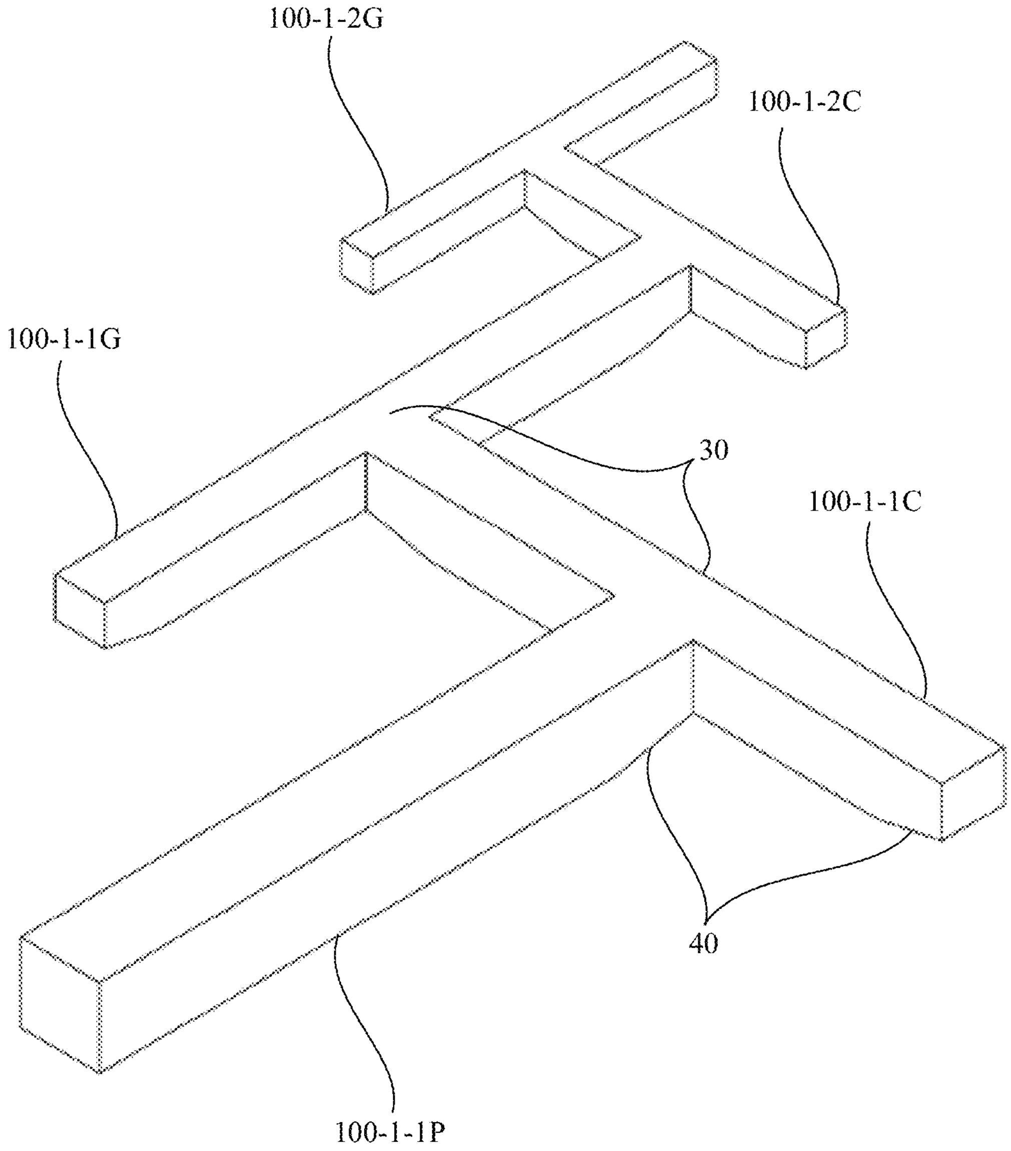
FIG. 12, FIG. 13, and FIG. 14, collectively illustrate an exemplary process for generating a single channel network layer scaffold device in accordance with embodiments of the present disclosure.
Figure 13:
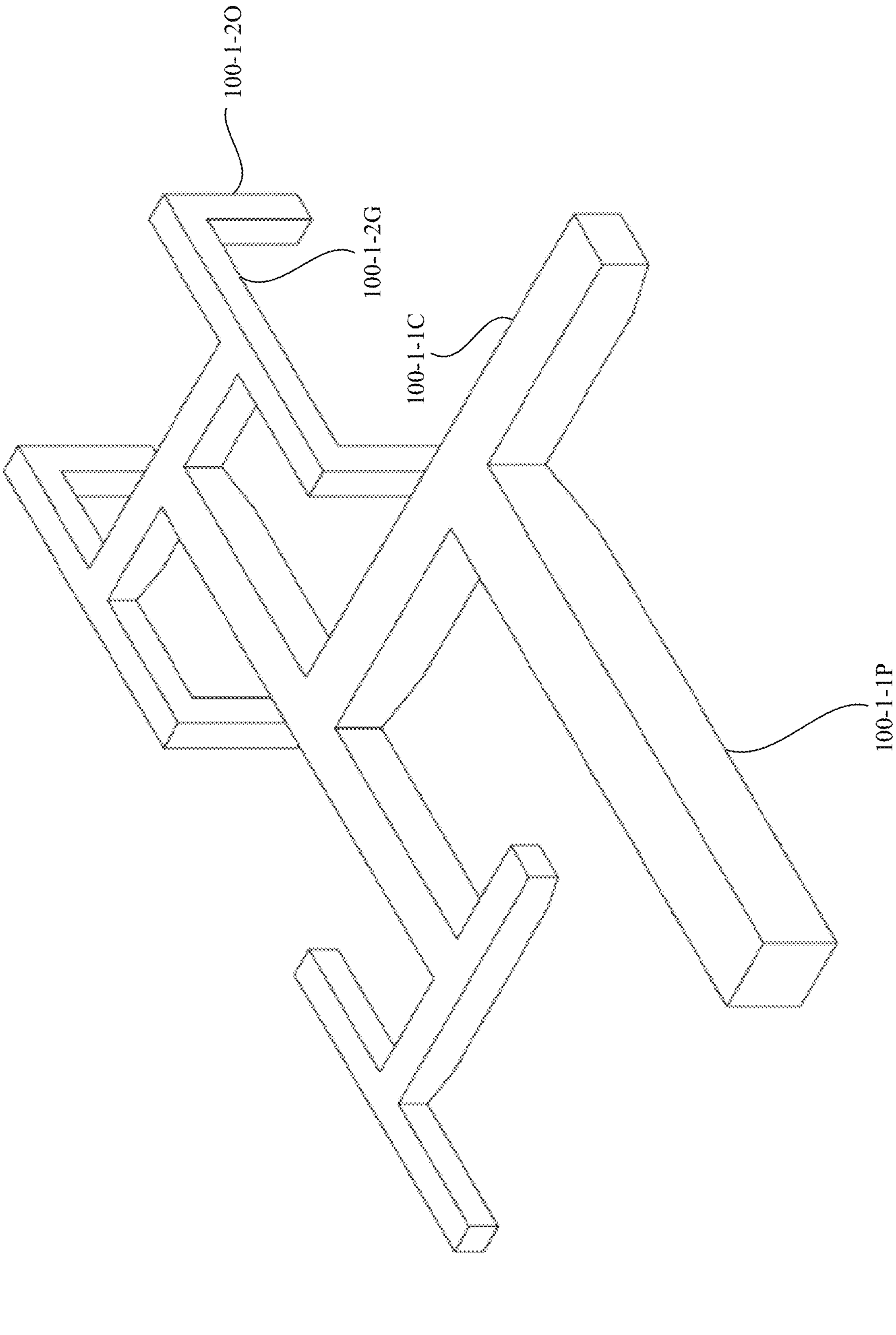

FIG. 11 illustrates a flow chart of an exemplary design process for generating a scaffold device in accordance with embodiments of the present disclosure. In the flow chart, the preferred parts of the design process are in solid line boxes whereas optional variants of the processes, or optional equipment used by the processes, are in dashed line boxed. As such, FIG. 11 illustrates processes for designing and fabricating a scaffold device.

In designing and engineering a scaffold device of the present disclosure, there are various core parameters that a designer manipulates and optimizes. Initially, a design for a scaffold device should consider an overall size, or active area (e.g., shell 550), of the scaffold device. In some embodiments, the device is formed in a square shape to optimize packing efficiency of the channels and cell density within the device. Accordingly, a length of the device is a distance between endpoints of corresponding channels on opposite side portions of the device. In some embodiments, a diameter of a smallest channel (e.g., final generation) is an essential parameter of the device as well as a total number of generations to include within the device. In some embodiments, the diameter of the smallest channel is restricted by an effective fabrication device resolution, a material of the device, or the like. One skilled in the art will recognize that as manufacturing technologies improve so will the resolution of components of the present disclosure. In some embodiments, a diameter of a smallest channel is in a range of from 5 μm to 2 mm, from 5 μm to 1 mm, from 5 μm to 750 μm, from 5 μm to 650 μm, from 10 μm to 650 μm, from 10 μm to 500 μm, or from 100 μm to 300 μm. In some embodiments, a design for a scaffold device considers a minimum wall thickness and a ratio of diameter growth or reduction with in the device. Since some embodiments of the present disclosure rely on material diffusion through the walls of the channels, or similarly a membrane, ensuring a proper wall thickness for molecular diffusivity is preferred. In some embodiments a minimum wall thickness of each channel in the one or more channel networks is in a range of from 5 μm to 500 μm, from 5 μm to 400 μm, from 10 μm to 500 μm, from 10 μm to 400 μm, or from 10 μm to 300 μm.

In some embodiments, and the exemplary embodiments described hereinafter, the device is formed as a negative mold. As such, the minimum wall thickness occurs near an inlet and end generation channel or outlet. In other embodiments, (e.g., the device is formed as a positive mold) the minimum wall thickness occurs at the smallest diameter channel. Murray's Law has proven an essential tool in optimizing a diameter of branching channels. For instance, each preceding channel before the smallest channel has a diameter that is increased by a predetermined factor derived from Murray's Law, which is based on biological observation of a ratio of inflow and outflow diameters. Murray's Law determines that $$D_o^3 = \sum_{i=1}^{n} D_i^3,$$

where $D_o$ is a diameter of a parent channel, n is a number of child channels, and Di is a diameter of an $i^{th}$ child channel. Thus, in some embodiments, the diameter of the child channel is reduced by a factor of $2^{-1/3}$. However, the present disclosure is not limited thereto. For instance, in some embodiments the diameter of the child channel is reduced by a factor in a range of from of numbers less than 1 but greater than zero (e.g., 0.5).

In some embodiments, obeying Murray's law for a first channel network but not a second channel network. For instance, in some embodiments providing or simulating a liver device, obeying Murray's law is required for a portal venous (PV) channel network that has a flow of blood, but not for a hepatobiliary (HB) channel network that has a flow of bile. In some embodiments, having each channel in the HB network is disposed at the same height (e.g., flush) for all generations, while also maintaining a width equal to that of an adjacent PV channel (e.g., a device of FIG. 47 through FIG. 53) (1002).

In some embodiments, an exchange mechanism is disposed between adjacent layers and/or channels of the device. In considering the exchange mechanism, a design for a scaffold device should determine a porosity or a pore density as a fraction of an exchange mechanism area as well as a thickness of the exchange mechanism. In some embodiments, approximating a shape of the pores as a square shape while conducting design calculations is appropriate to simplify optimizing the device (1004).

Cells of various organs often differentiate in size, cell count, and functional capacity for the organ. In some embodiments, such as designing the device as a liver implant, hepatocyte cells are a primary cell. As described above regarding a shape of the pores, in some embodiments approximating a shape of a cell as a cube while conducting design calculations is appropriate to simplify the system. Thus, in some embodiments, a design for a scaffold device considers a characteristic length of a cell, a count of cells per gram of a living target organ, and a fraction of the target organs capacity needed to function. For instance, a liver implant can produce only 30% of a capacity of a living liver yet still thrive in vivo (1006).

Once the above parameters have been determined, a non-transitory computer readable storage medium including instruction for execution by one or more processes to perform a device fabrication regimen derives a plurality of intermediate quantities that are useful to a design architect (1008, 1010).

In some embodiments, the device is mathematically modeled (e.g., modeled through a computer-aided design tool such as Autodesk®, nTopology®, Creo®, SolidWorks®, etc., modeled through a mathematical software tool such as MATLAB®, Mathematica®, etc., modeled through a physics simulation software tool such as COMSOL Multiphysics®, ANSYS Fluent®, etc., or modeled through a spreadsheet and/or a combination of the aforementioned computer software tools) to verify a number of end parameters (e.g., outlet pressure, outlet flow rate, etc.) and outputs of the device. In some embodiments, an important verification is an actual minimum wall thickness of the device, as the present value must be greater than or equal to an input value of the design. If such a value is determined to be less than the input value of the design, this indicates that the geometry of the device is incorrect. To remedy such a problem a design can reduce the diameter of the smallest channel or reduce the number of generations in the device (1012 and 1014).

Figure 14:
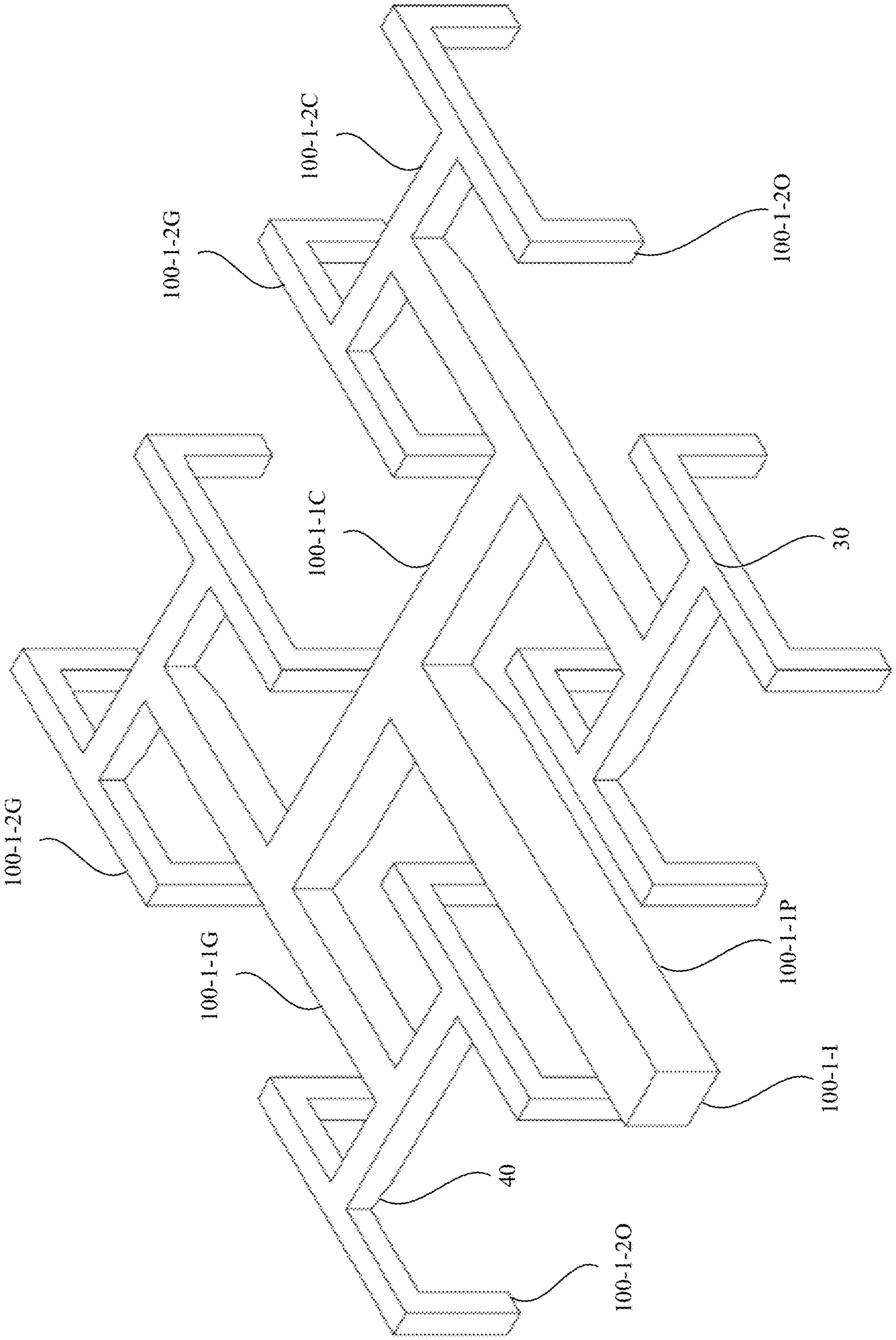
Figure 15:
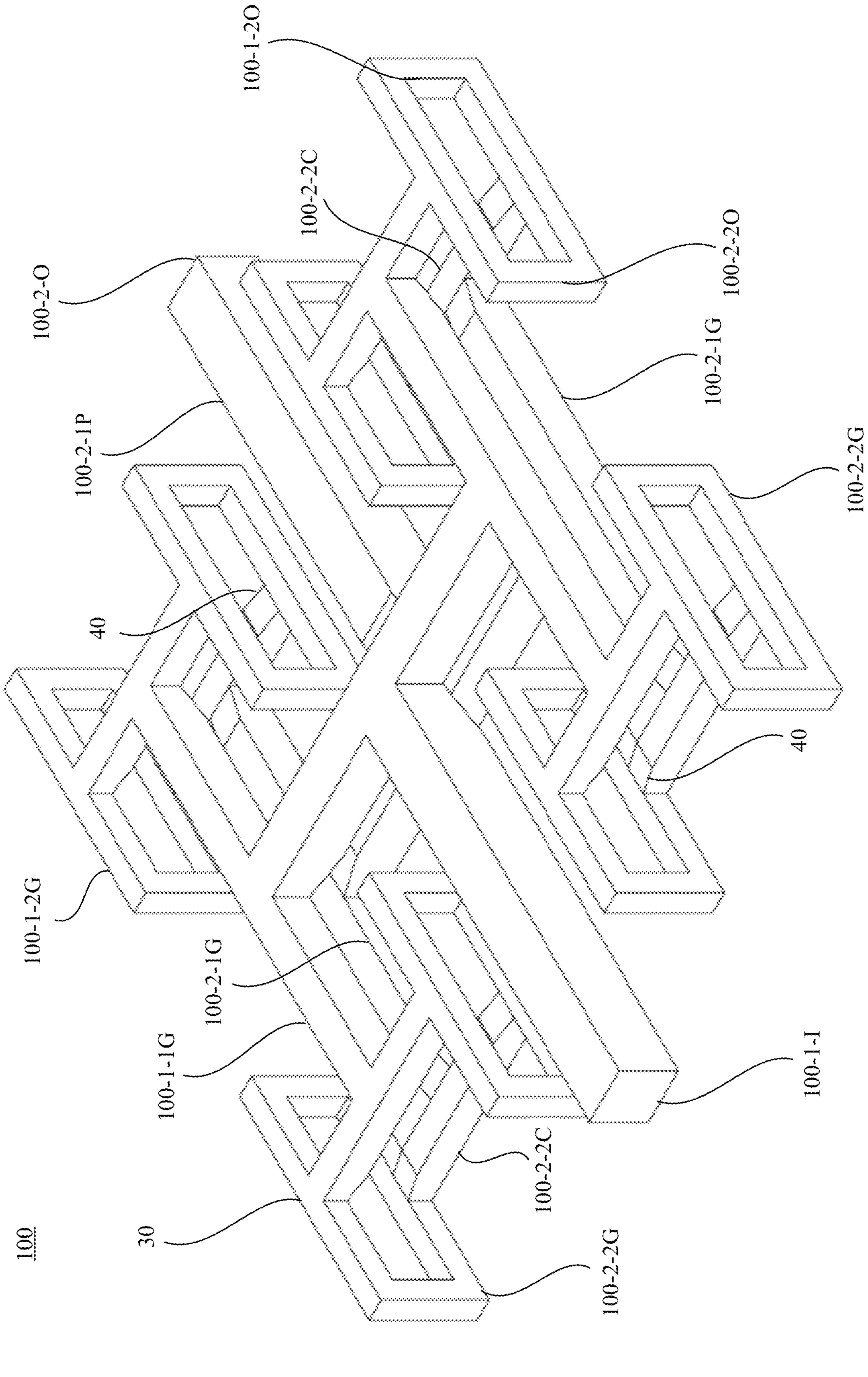
FIG. 15 illustrates an exemplary recursion of the process of FIG. 12, FIG. 13, and FIG. 14 to form a paired channel network layer in accordance with embodiments of the present disclosure.
Figure 16:
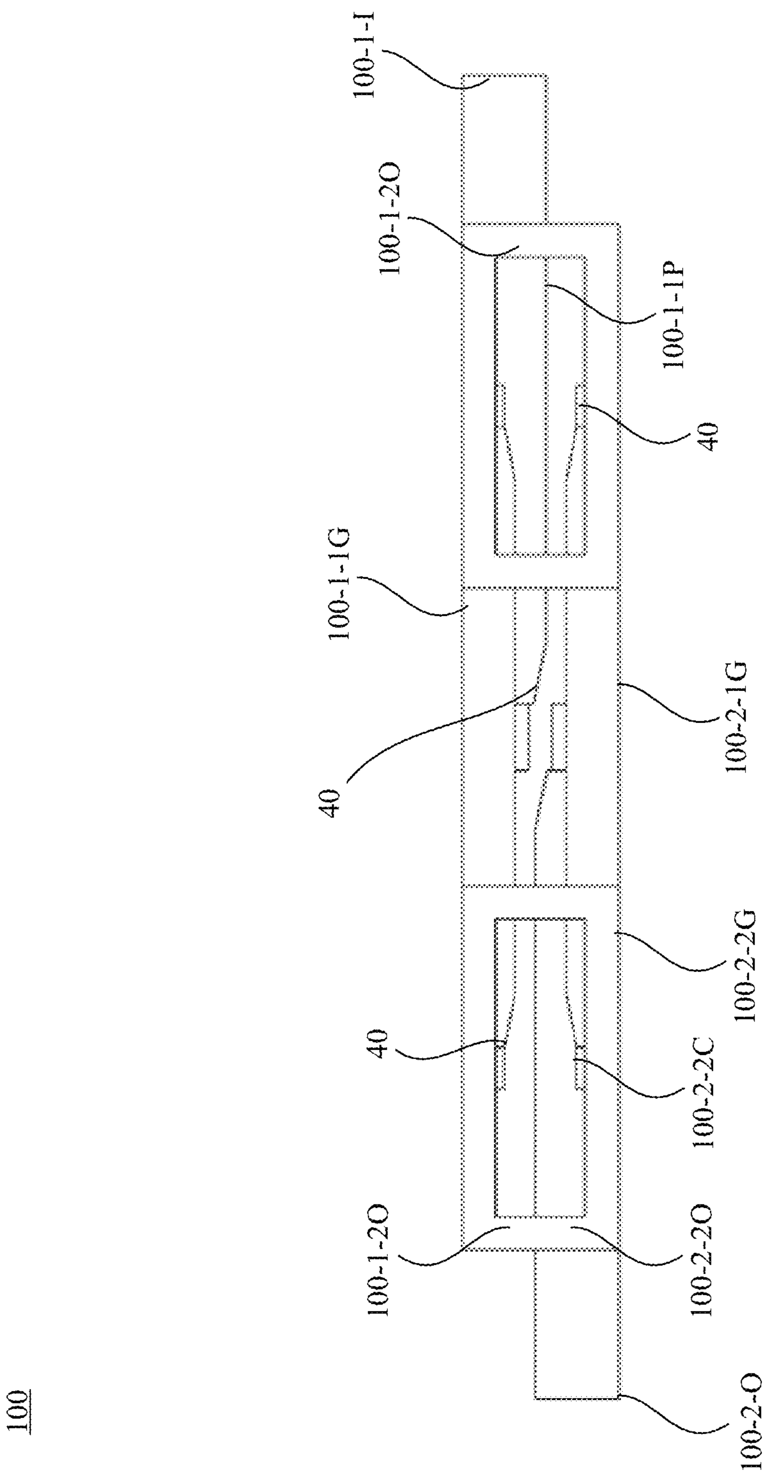
FIG. 16 illustrates a side schematic view of the paired channel network layer of FIG. 15.
Figure 17:
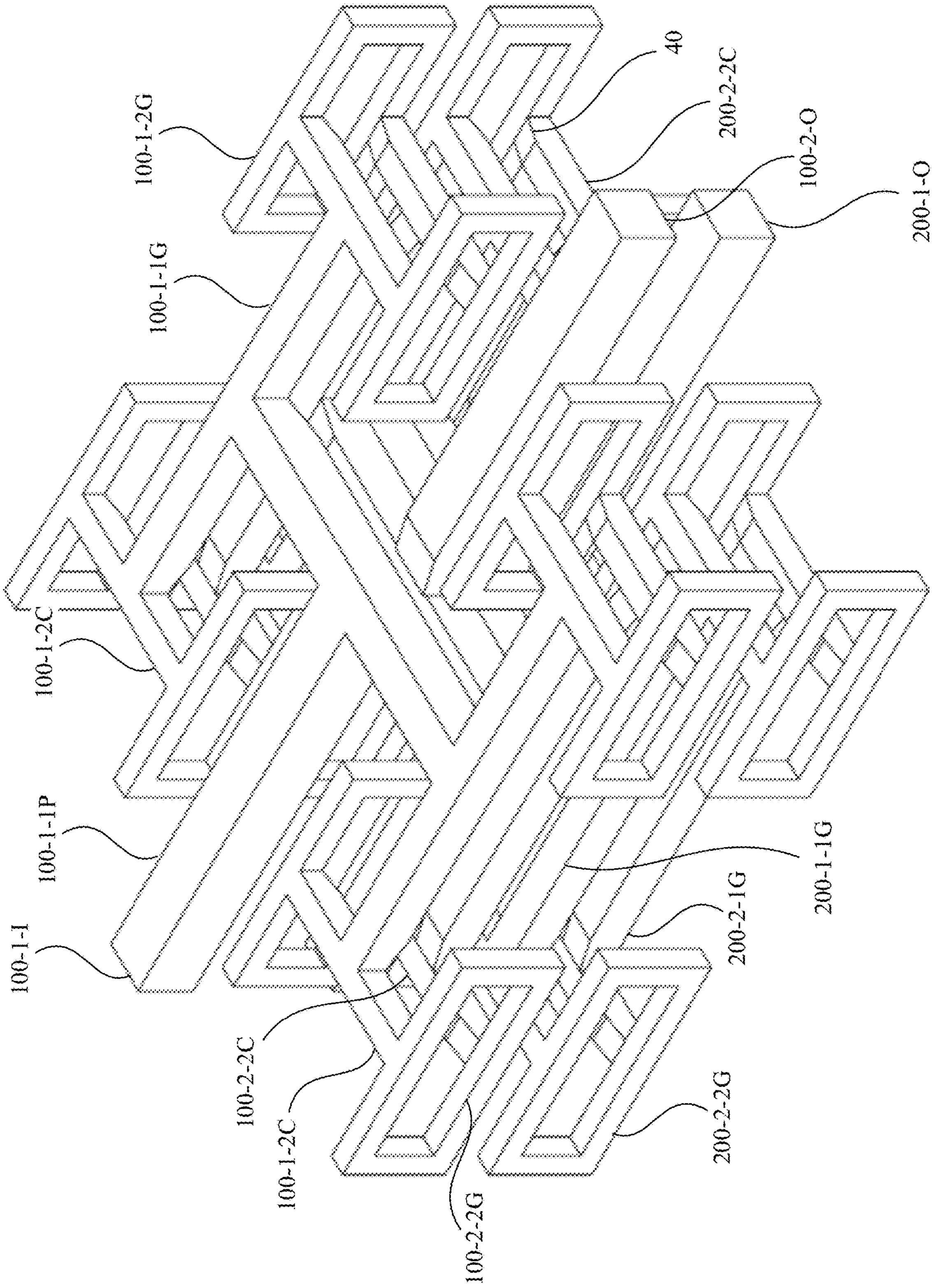
FIG. 17 illustrates an isometric schematic view of an exemplary dual paired channel network layer in accordance with embodiments of the present disclosure.
Figure 18:
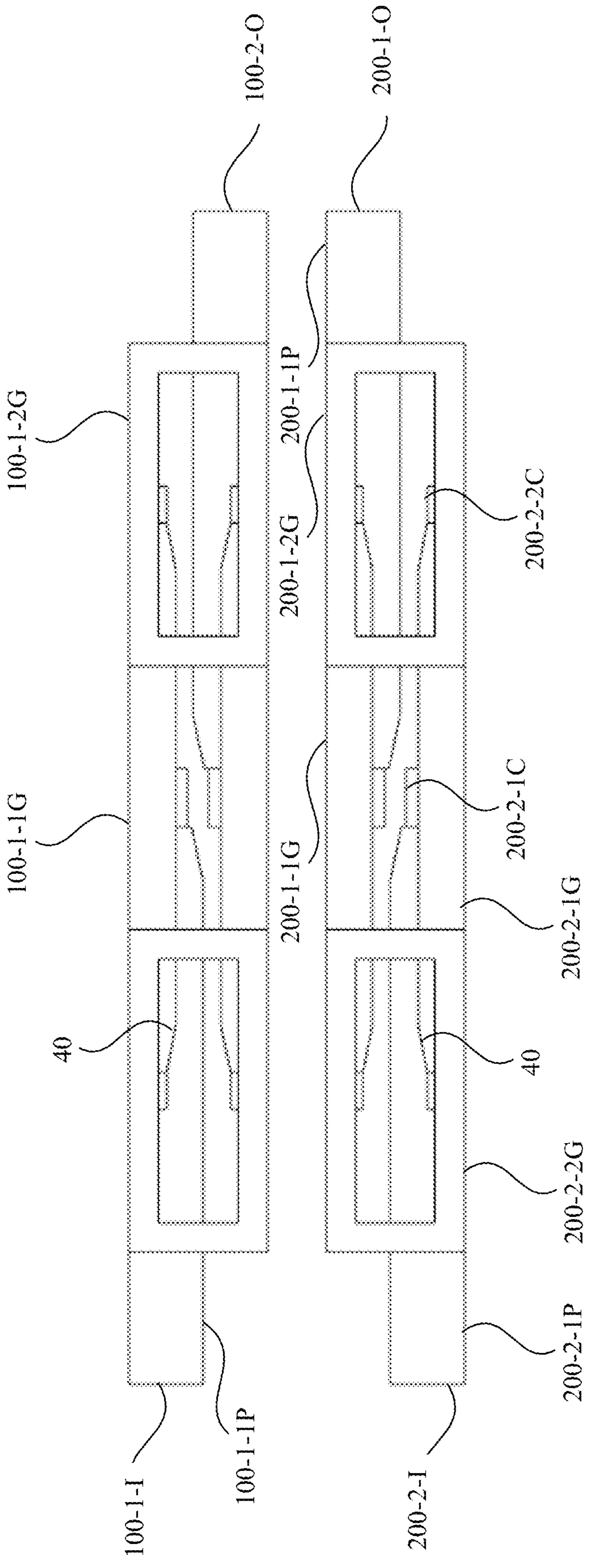
FIG. 18 illustrates a side schematic view of the dual paired channel network layer of FIG. 17.
Figure 19:
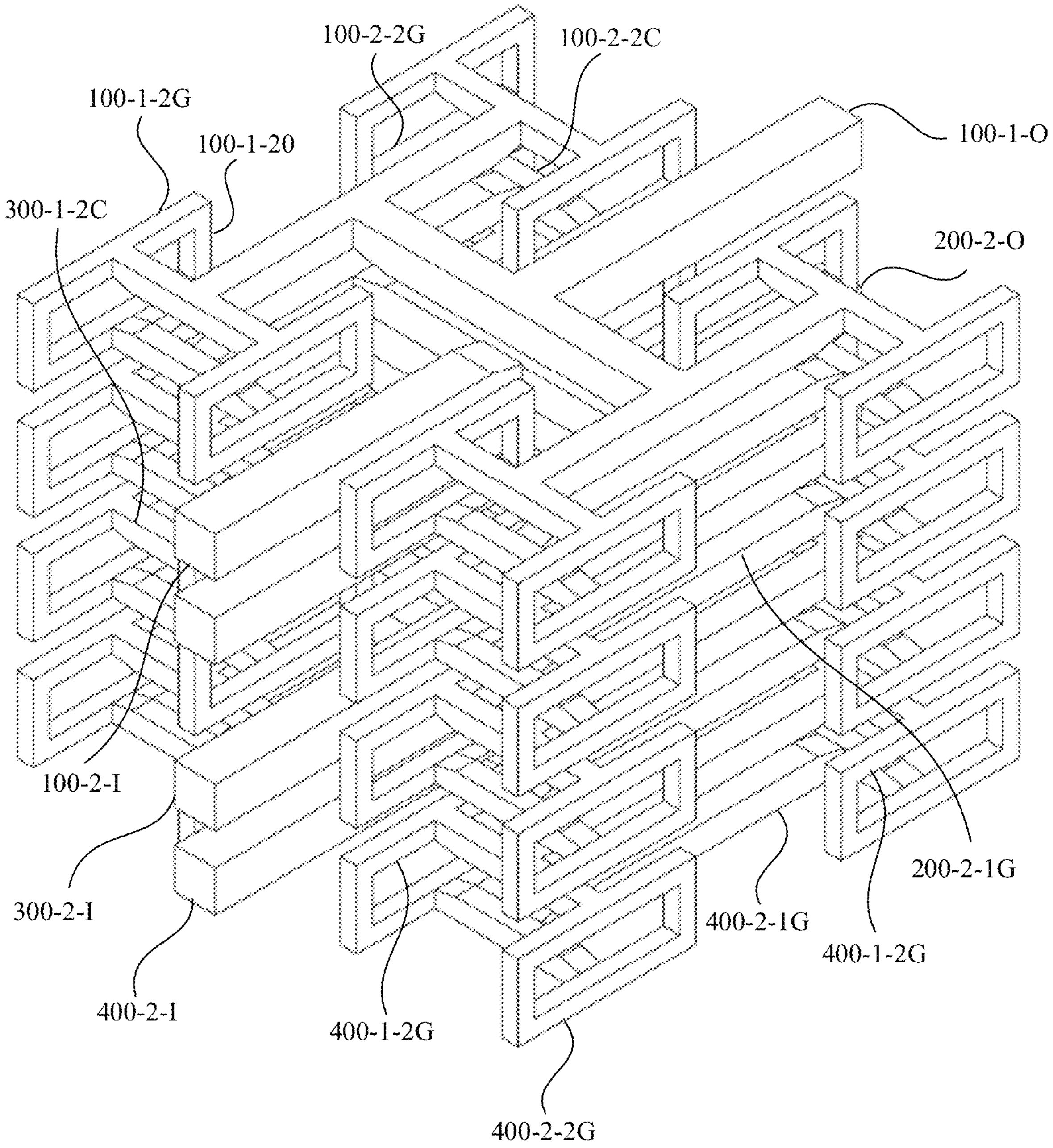
FIG. 19 illustrates an isometric schematic view of an exemplary stacked dual paired channel network layers in accordance with embodiments of the present disclosure.
Figure 20:
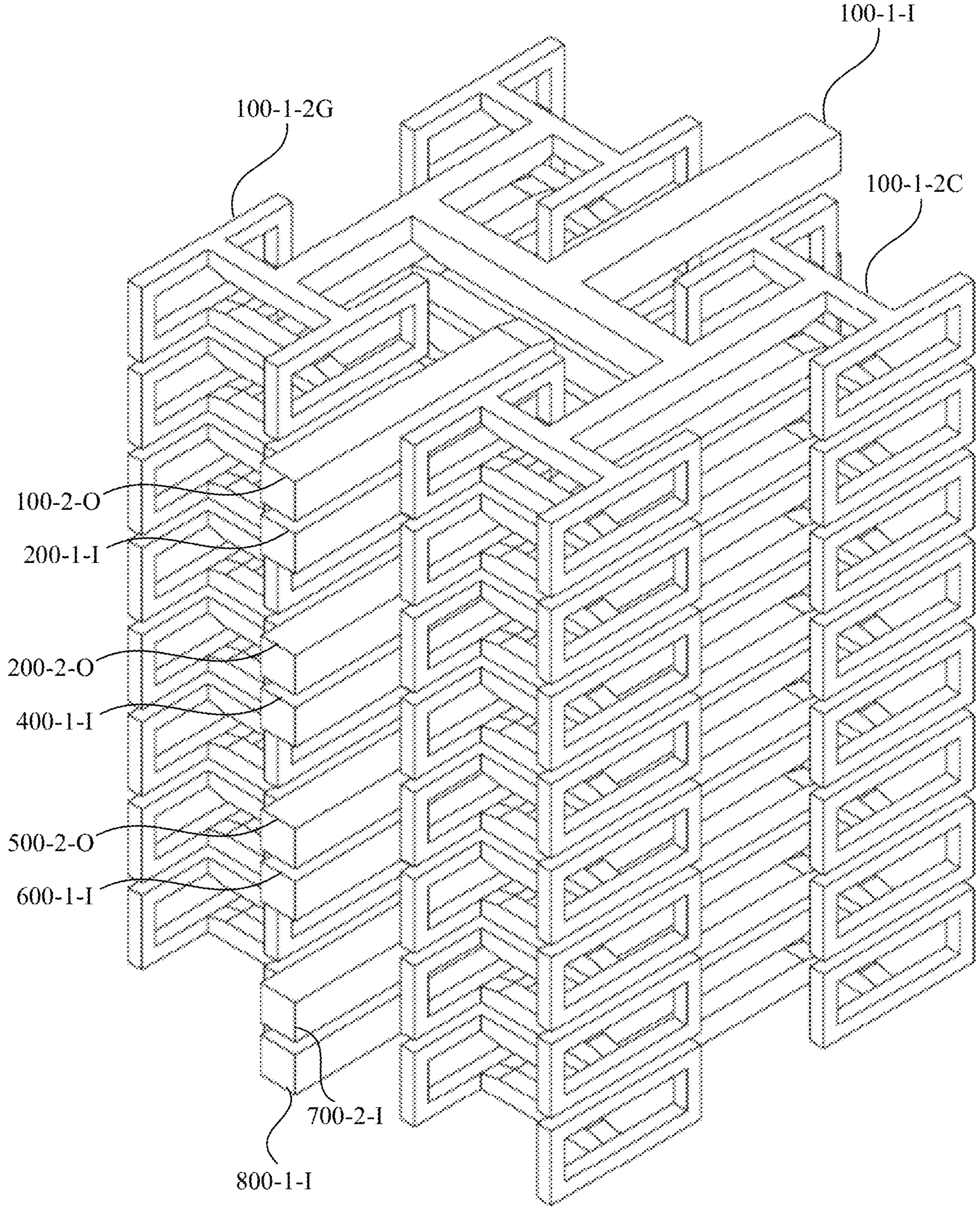
FIG. 20 illustrates an isometric schematic view of an exemplary stacked dual paired channel network layers in accordance with embodiments of the present disclosure.
Figure 21:
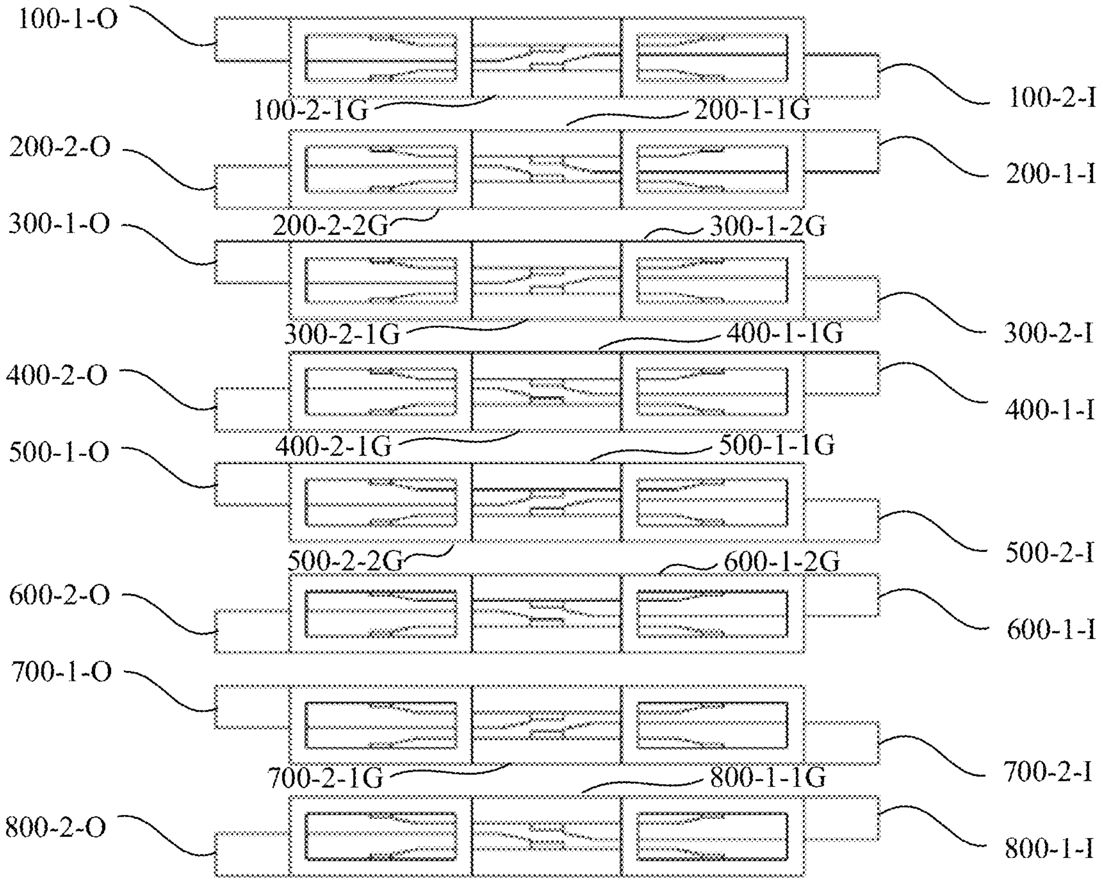
FIG. 21 illustrates a side schematic view the stacked dual paired channel network layers of FIG. 20.
Figure 22:
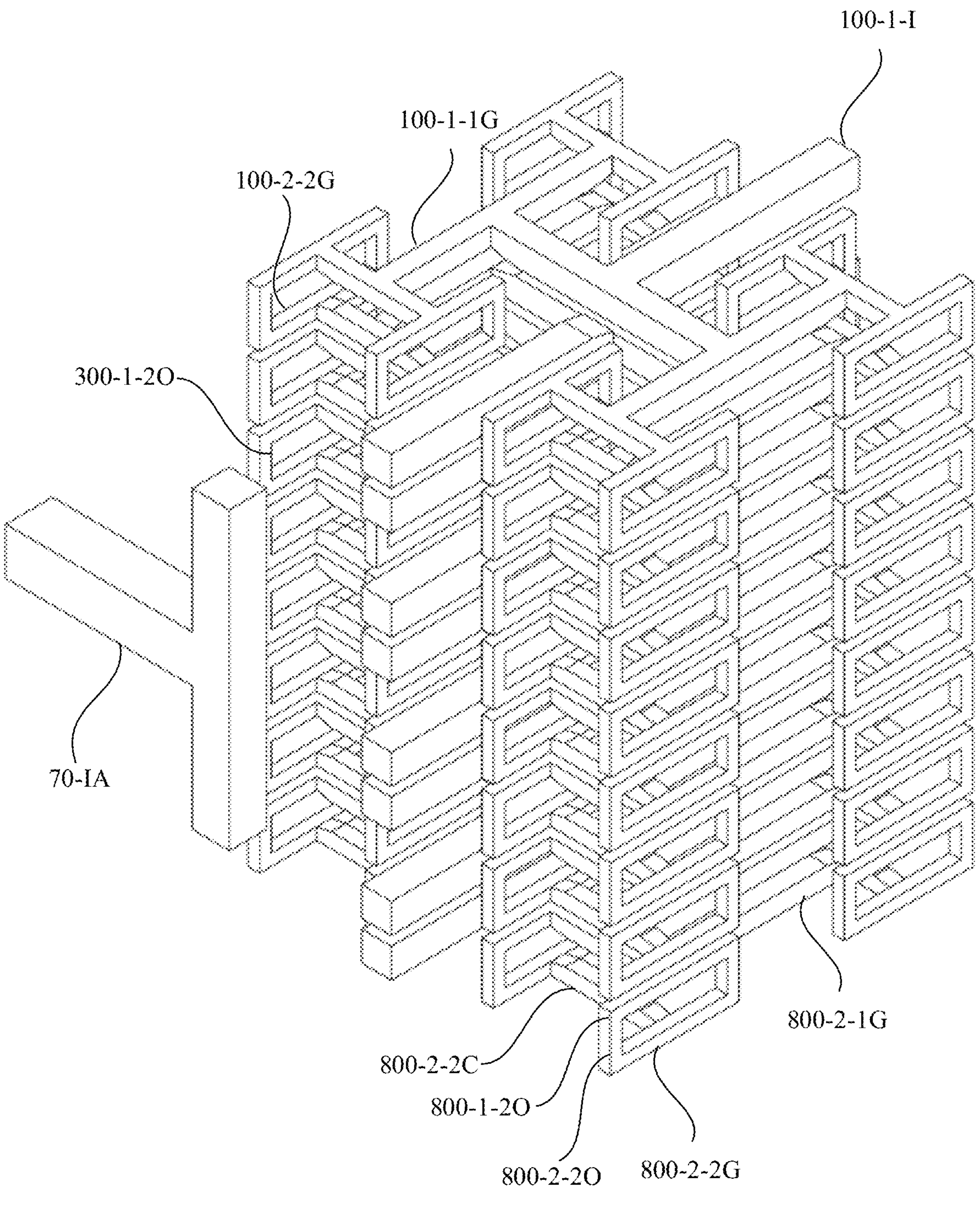
FIG. 22, FIG. 23, FIG. 24, FIG. 25, FIG. 26, FIG. 27, and FIG. 28 collectively illustrate an exemplary process for generating a stacked dual paired channel network layers scaffold device including master inlets and master outlets in accordance with embodiments of the present disclosure.
Figure 23:
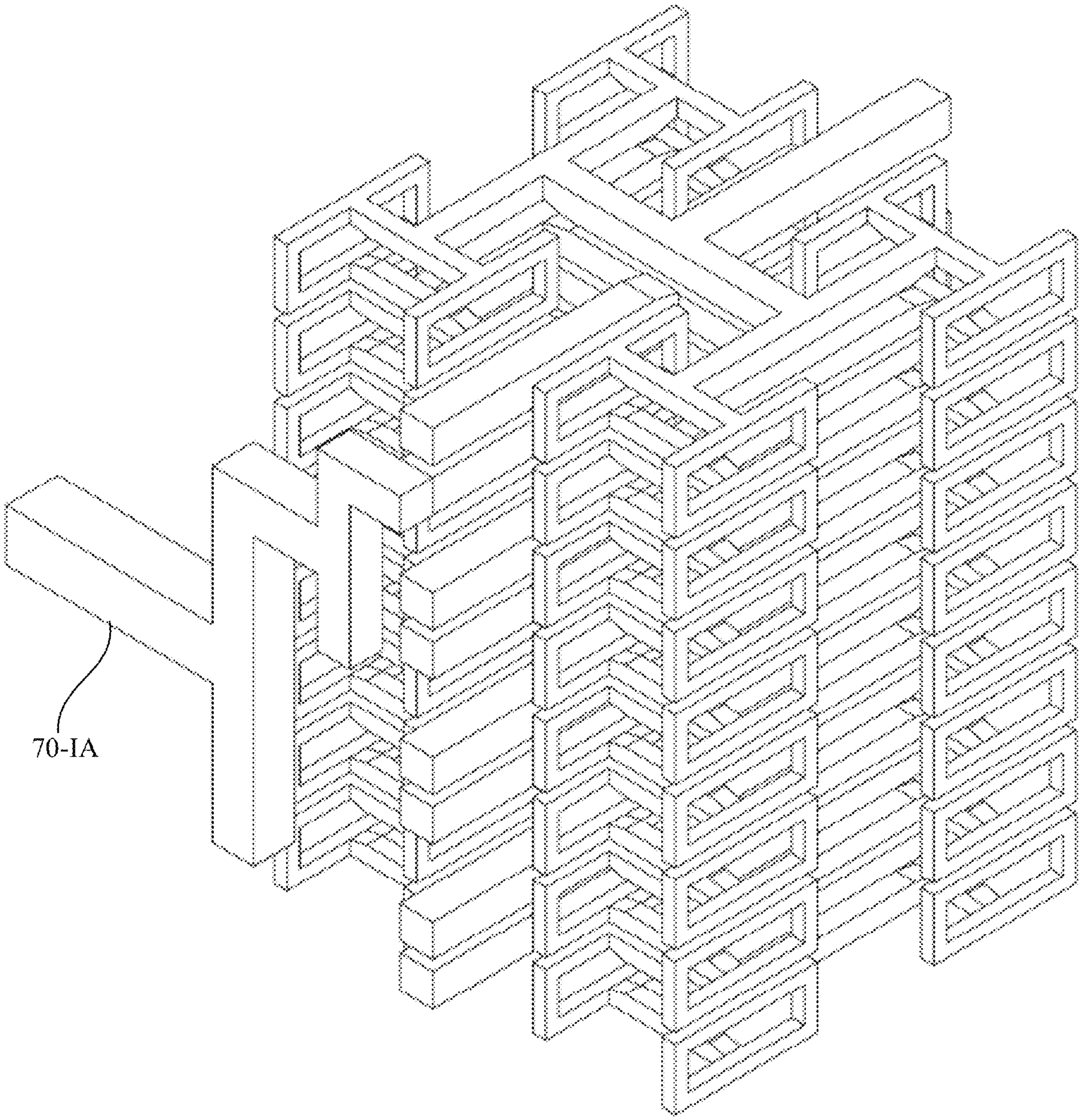
Figure 24:
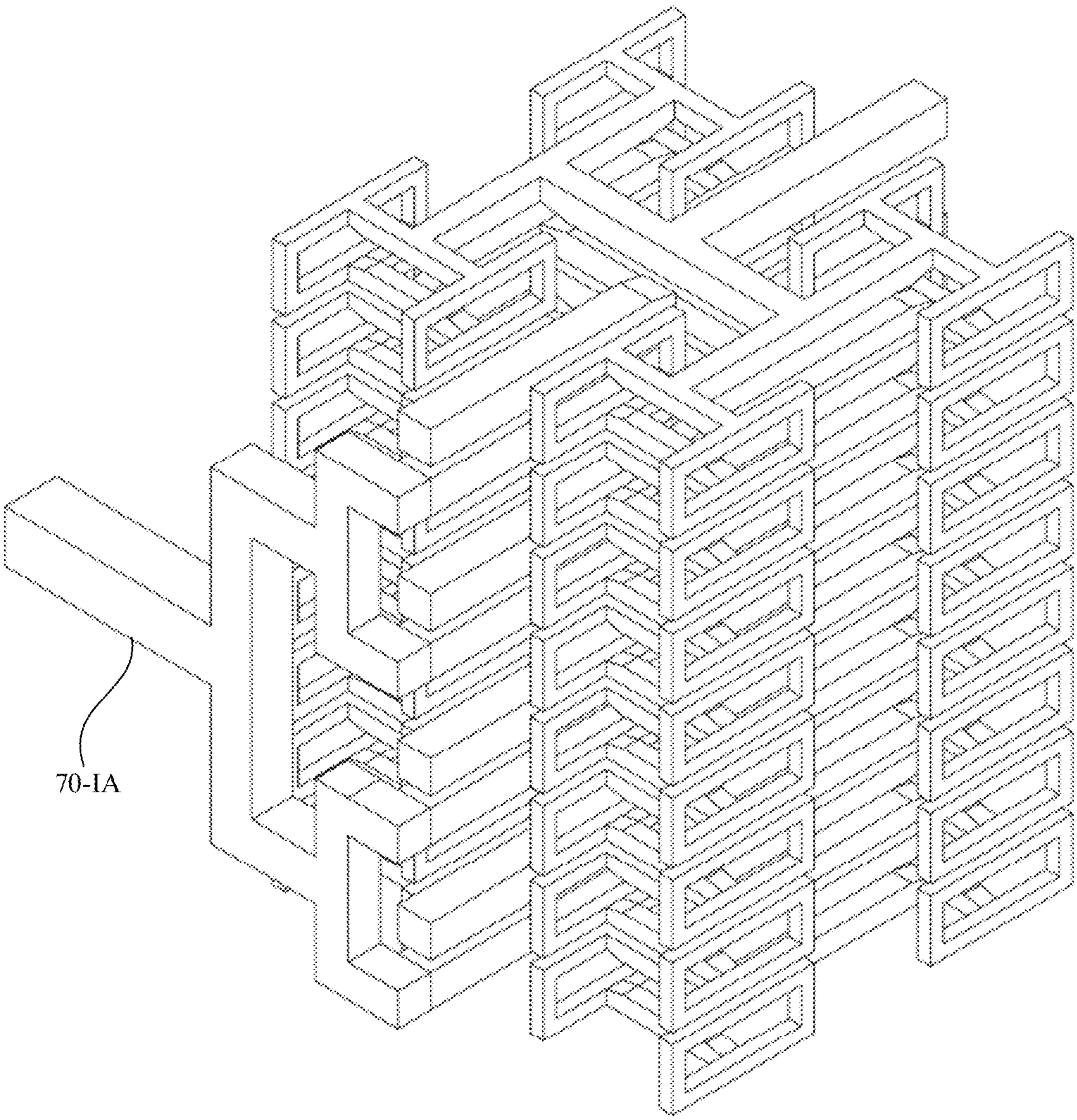
Figure 25:
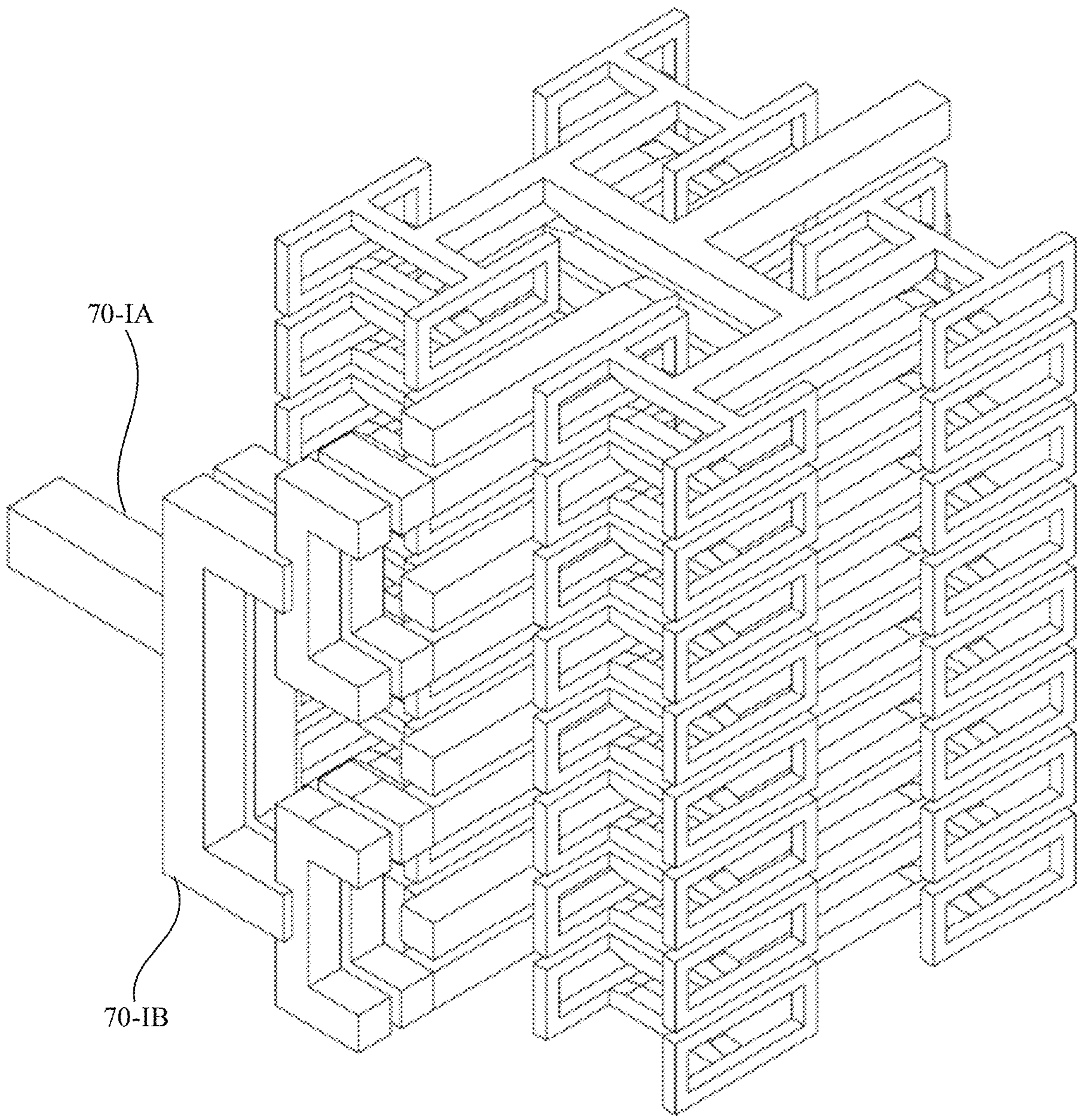
Figure 26:
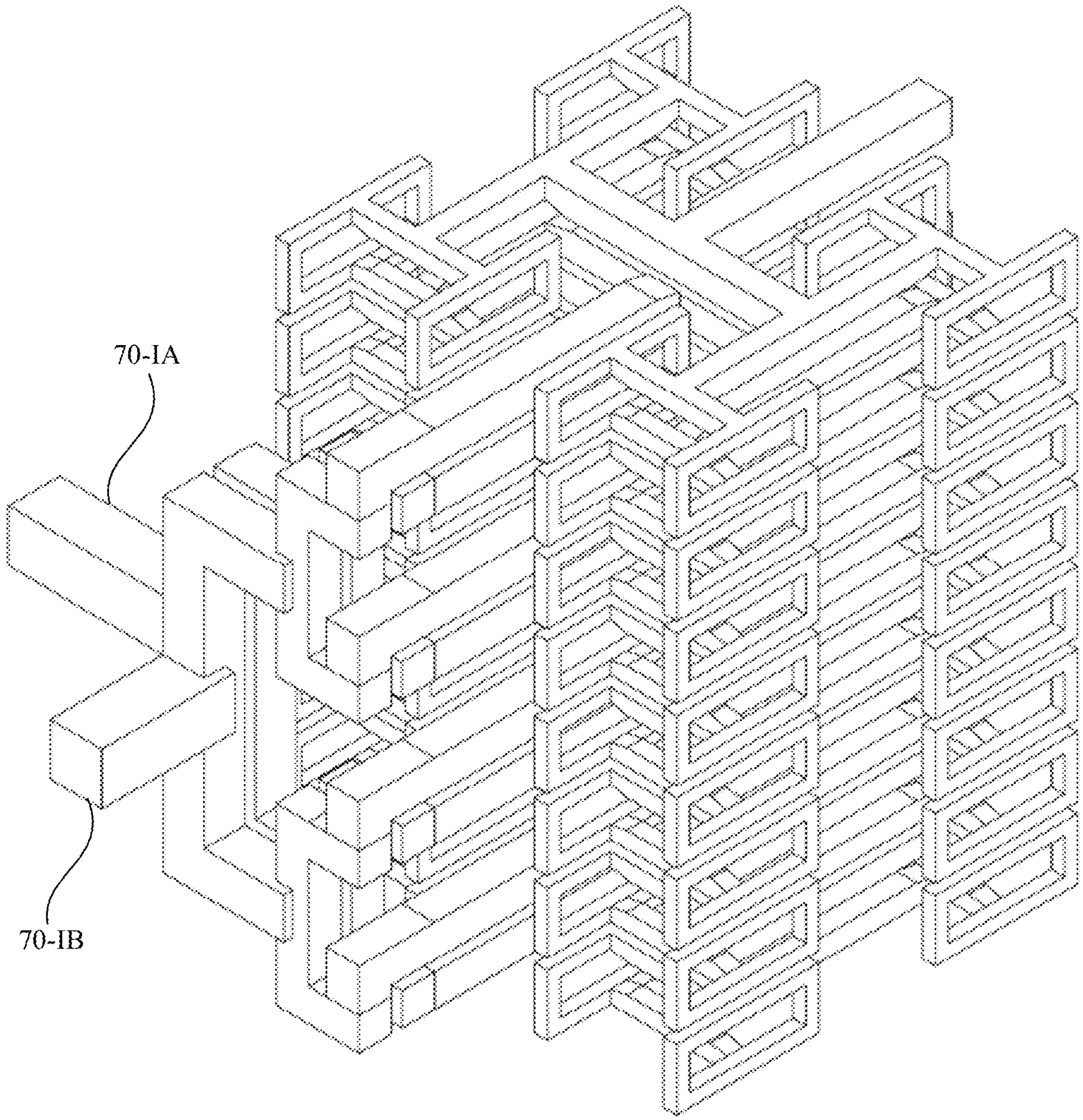
Figure 27:
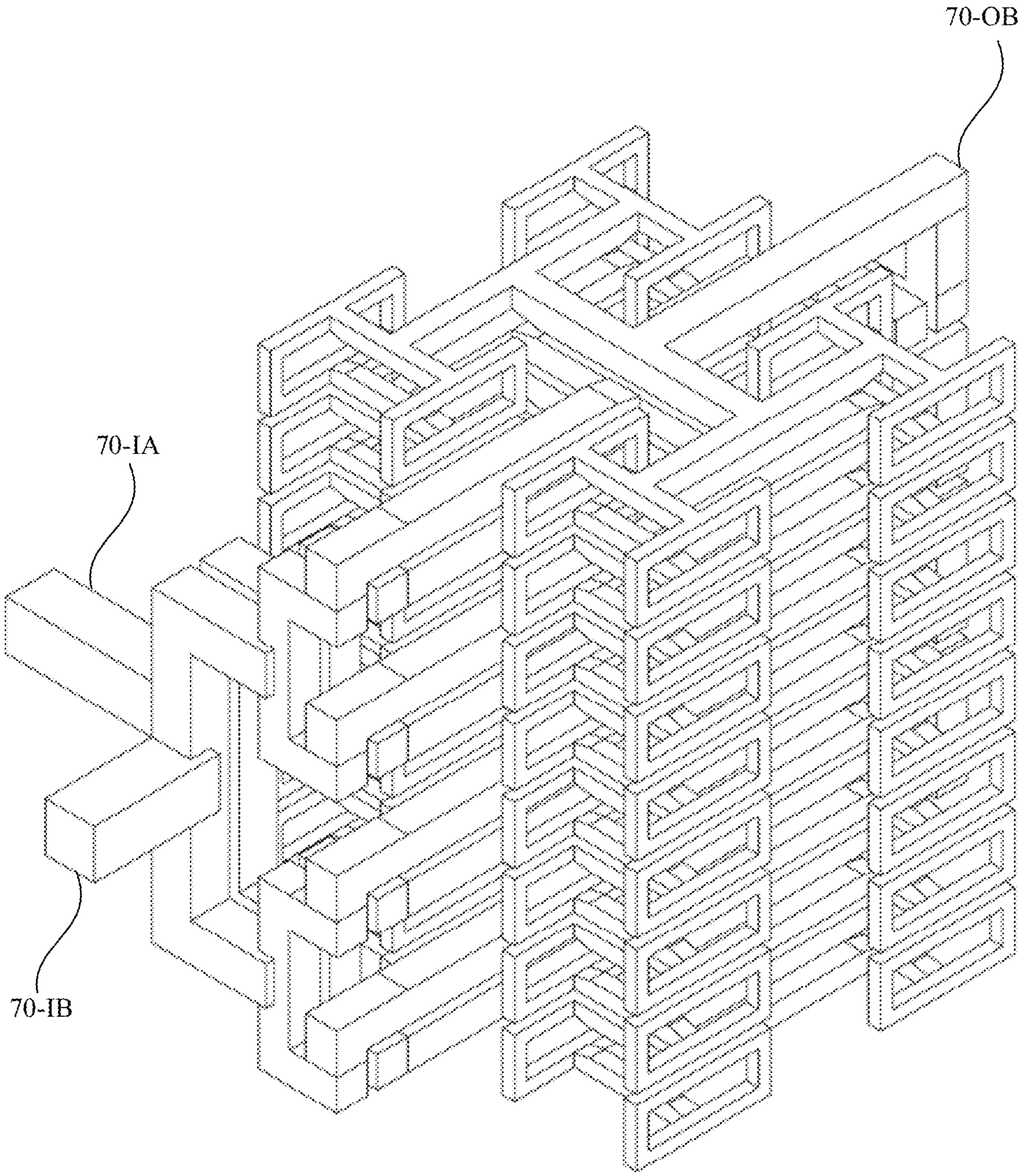
Figure 28:
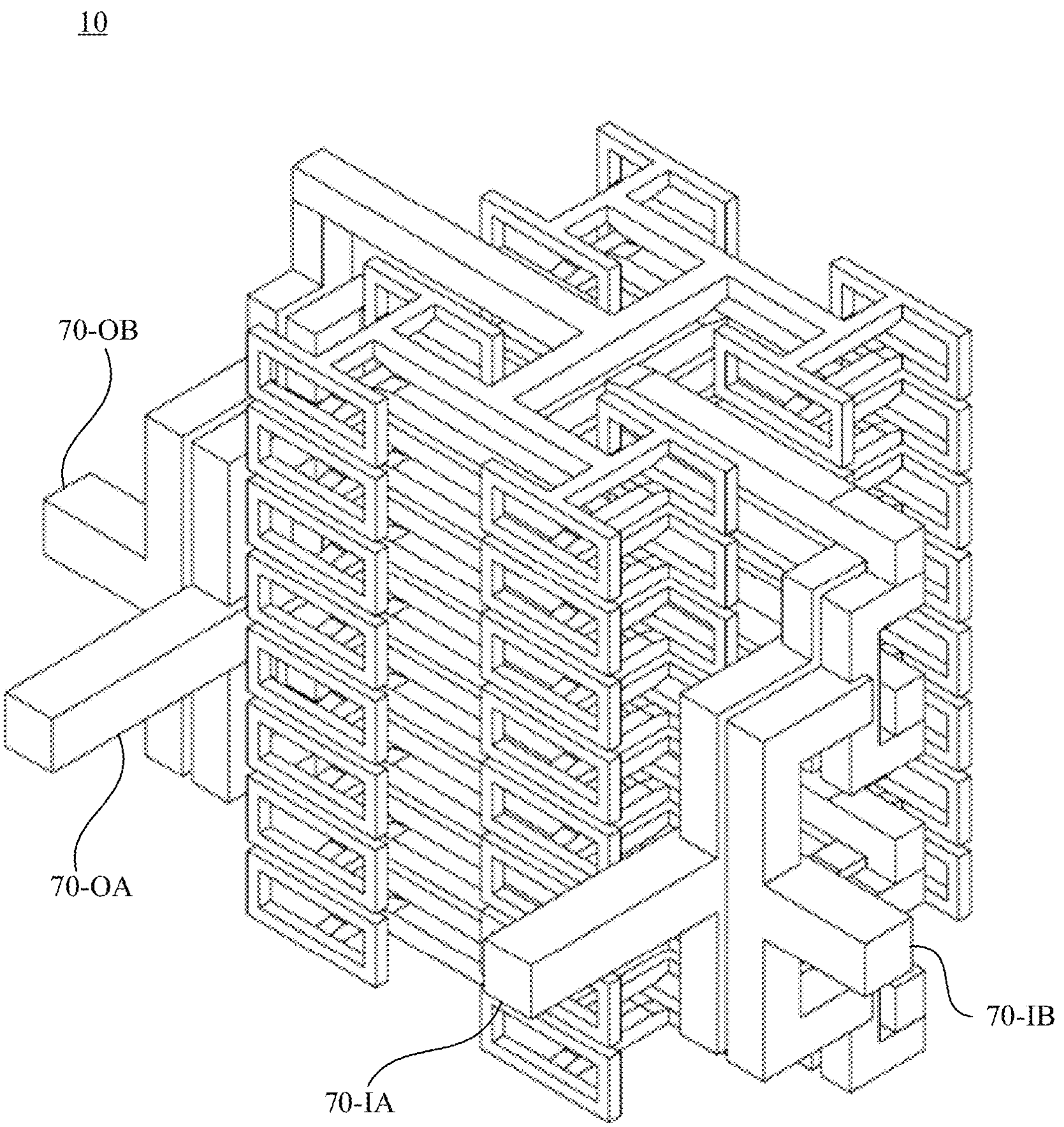
Figure 35:
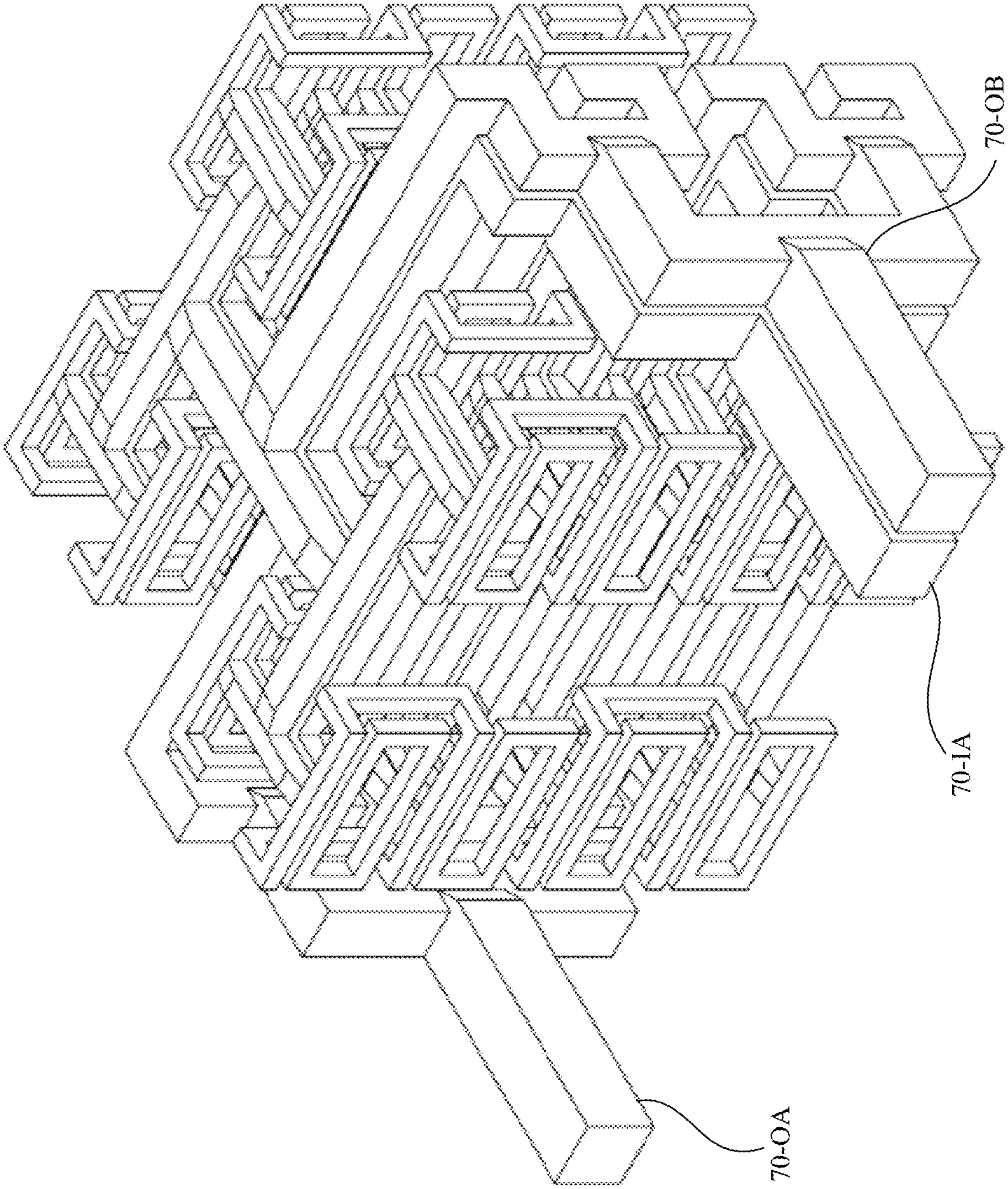
FIG. 35 illustrates an isometric schematic view of an exemplary stacked bypass channel network layers scaffold device including master inlets and master outlets in accordance with embodiments of the present disclosure.

Referring to FIG. 11 through FIG. 27, an exemplary embodiment for fabricating a device according to the present invention will now be described. In the present exemplary embodiment, an inlet of each parent channel is formed as a portion of a master inlet (e.g., inlet 70-IA FIG. 35). Once the above parameters have been determined, verified, and input, fabrication of device 10 may commence. From an active endpoint of a parent channel (e.g., parent channel 100-1-1P), child channels (e.g., child channels 100-1-1C) branch off in plane and perpendicular to the parent channel with a diameter reduced by the first predetermined ratio. Branching (e.g., bifurcating) is recursively repeated for each child channel (e.g., child channel 100-1-2C), and subsequently repeated until a specified number of generations is achieved. Once the specified number of generations is achieved (e.g., grand-child channel 100-1-2G), the smallest diameter channels are redirected (e.g., reoriented) to form a plurality of outlets (e.g., outlets 100-1-2O). FIG. 14 depicts completed channel network layer 100-1. In some embodiments, the completed network layer delivers a fluid or substance to cover a planar area.

In some embodiments, including the present embodiment, the fluid or substance (e.g., medium) is output to a single outlet. Therefore, a similarly designed (e.g., looking) layer (e.g., layer 100-2) of branching channels is formed to collect fluid and output to a single channel (e.g., outlet 100-2-O of FIG. 15 and FIG. 16, etc.). Once the recursive branching completes second level 100-2, the outlets of the first layer and the second layer are combined (e.g., coupled together), allowing fluidic communication between the layers. This fluidic communication forms a paired channel network layer (PCNL) 100.

In some embodiments, a plurality of PCNLs is stacked (e.g., stacked in a vertical orientation) to form a dual paired network. FIG. 17 through FIG. 21 depict various embodiments of device 10 including various numbers of stacked PCNLs. In the present embodiments, a maximum of eight PCNLs are illustrated. However, in some embodiments there exists any number k of PCNLs (e.g., PCNL {100, 200, i00, . . . , k00}) with k being an integer greater than or equal to 1.

As described above, in some embodiments, combining the inlets and the outlets of the device into at least one master inlet and at least one master outlet is advantageous to allow for a simple system for the supply and collection of medium. Some such embodiments are depicted in FIG. 22 through FIG. 28. By way of example, FIG. 22 through FIG. 28 demonstrate a process for forming a first master inlet (e.g., master inlet 70-IA), a second master inlet (e.g., master inlet 70-IB), a first master outlet (e.g., master outlet 70-OA), and a second master outlet (e.g., master outlet 70-OB) of device 10. In some embodiments, the forming of the master inlet and/or the master outlet utilizes the bifurcating as described in the present disclosure. Shapes, layouts, configurations, and orientations are not restricted by the exemplary embodiments and may be fabricated according to an end goal of a design for a scaffold device.

In some embodiments, a first layer circumvents (e.g., bypasses) a second layer of a channel network. In some embodiments, the first channel network circumvents the second channel network. In such embodiments, the first channel network is formed with a single level (e.g., layer) whose outlets are in communication with a single level of a third channel network. The present embodiment is known as a bypass embodiment, as the first channel network bypasses the second channel network to communicate with the third channel network.

Figure 29:
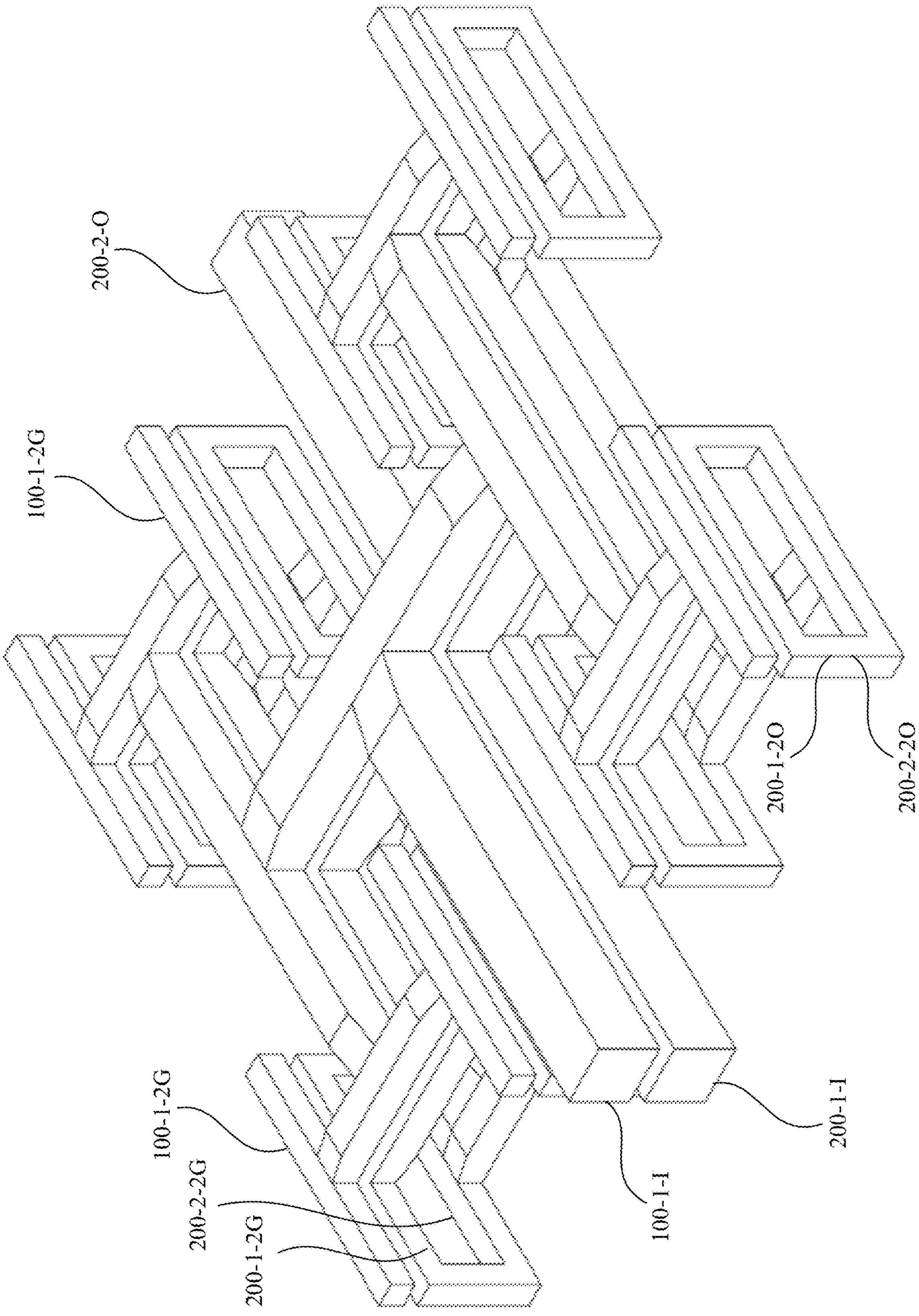
FIG. 29, FIG. 30, FIG. 31, FIG. 32, and FIG. 33 collectively illustrate an exemplary process for generating a stacked bypass channel network layer scaffold device in accordance with embodiments of the present disclosure.
Figure 30:
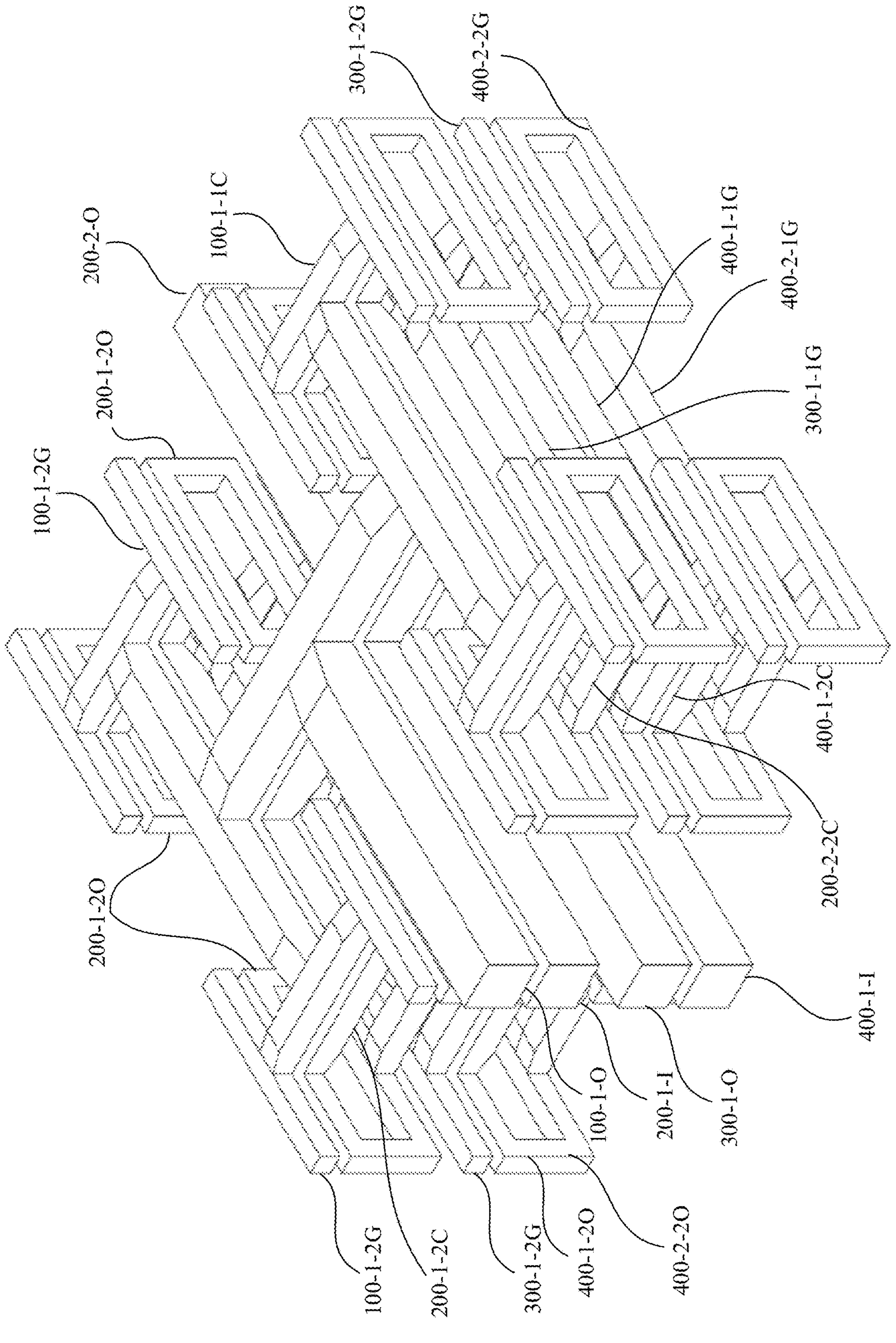
Figure 34:
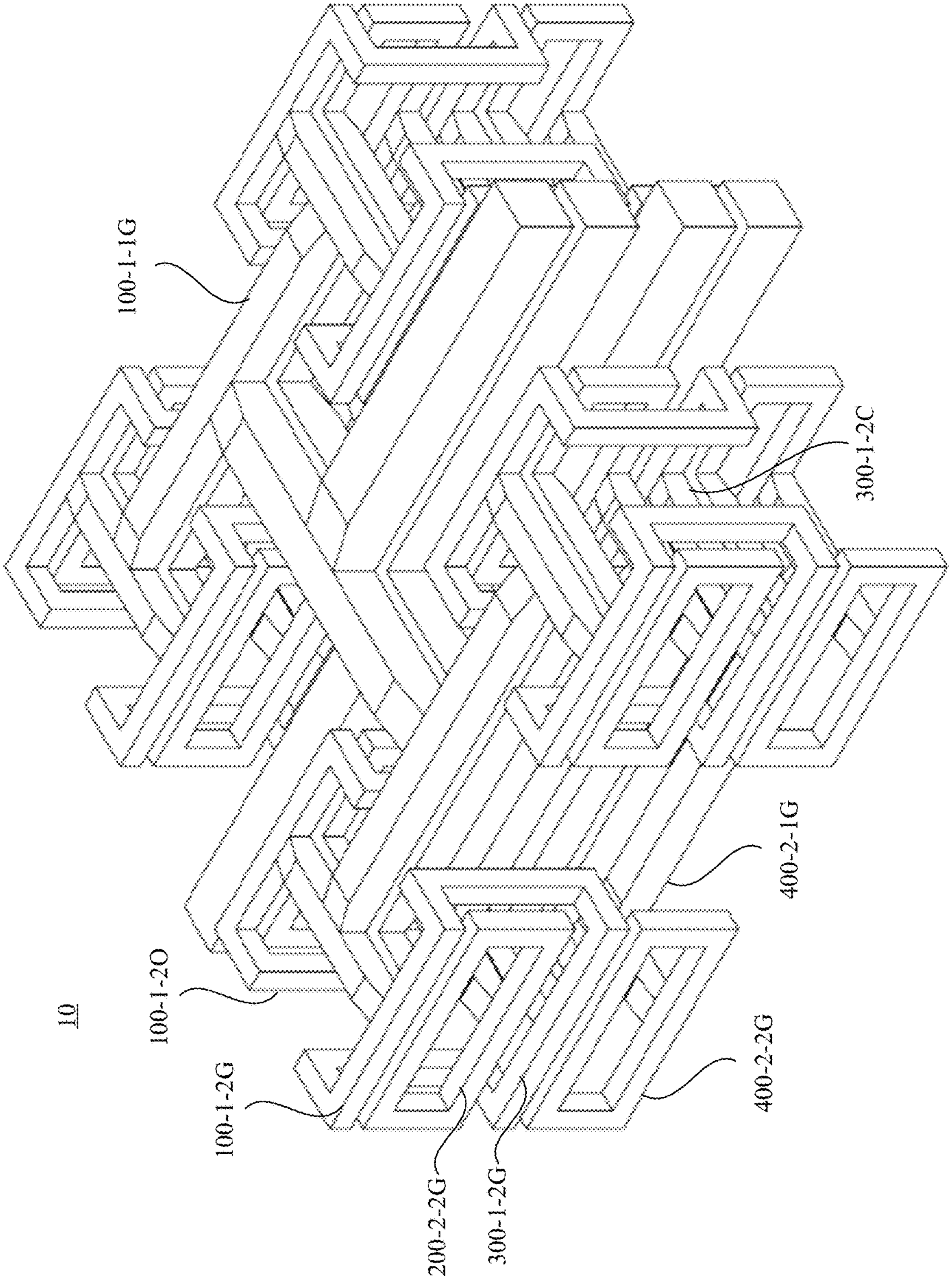
FIG. 34 illustrates an isometric schematic view of the stacked bypass channel network layer scaffold device of FIG. 33.

FIG. 29 through FIG. 35 depict another exemplary embodiment of the scaffold device, in particular a bypass embodiment. As shown in FIG. 29, second channel network layer 200 is formed in the same recursive manner (e.g., looped channel segment 2900) as shown in FIG. 12 through FIG. 16. However, first channel network layer 100 is only partially formed, as shown in FIG. 29 with the first layer omitting reoriented outlets. FIG. 34 depicts an additional stack of the first and second channel networks, forming third channel network 300 and fourth channel network 400. Final generations (e.g., smallest diameter channels) of first channel network 100-1-2G and final generations of third channel network 300-1-2G are connected while bypassing second channel network 200, as shown in FIG. 31 through FIG. 34. As further illustrated in FIG. 34, plane 3400 represents a mirror plane extending through the scaffold device. In some embodiments, the third channel network 300 (e.g., final generations of third channel network 300-1-2G) is arranged as a mirror image of the first channel network 100 (e.g., final generations of first channel network 100-1-2G) across plane 3400. In accordance with the previous exemplary embodiment, the inlets and the outlets of each channel network combine to form master inlets 70-I1 and 70-I2 as well as master outlets 70-IO and 70-IO.

Figure 36:
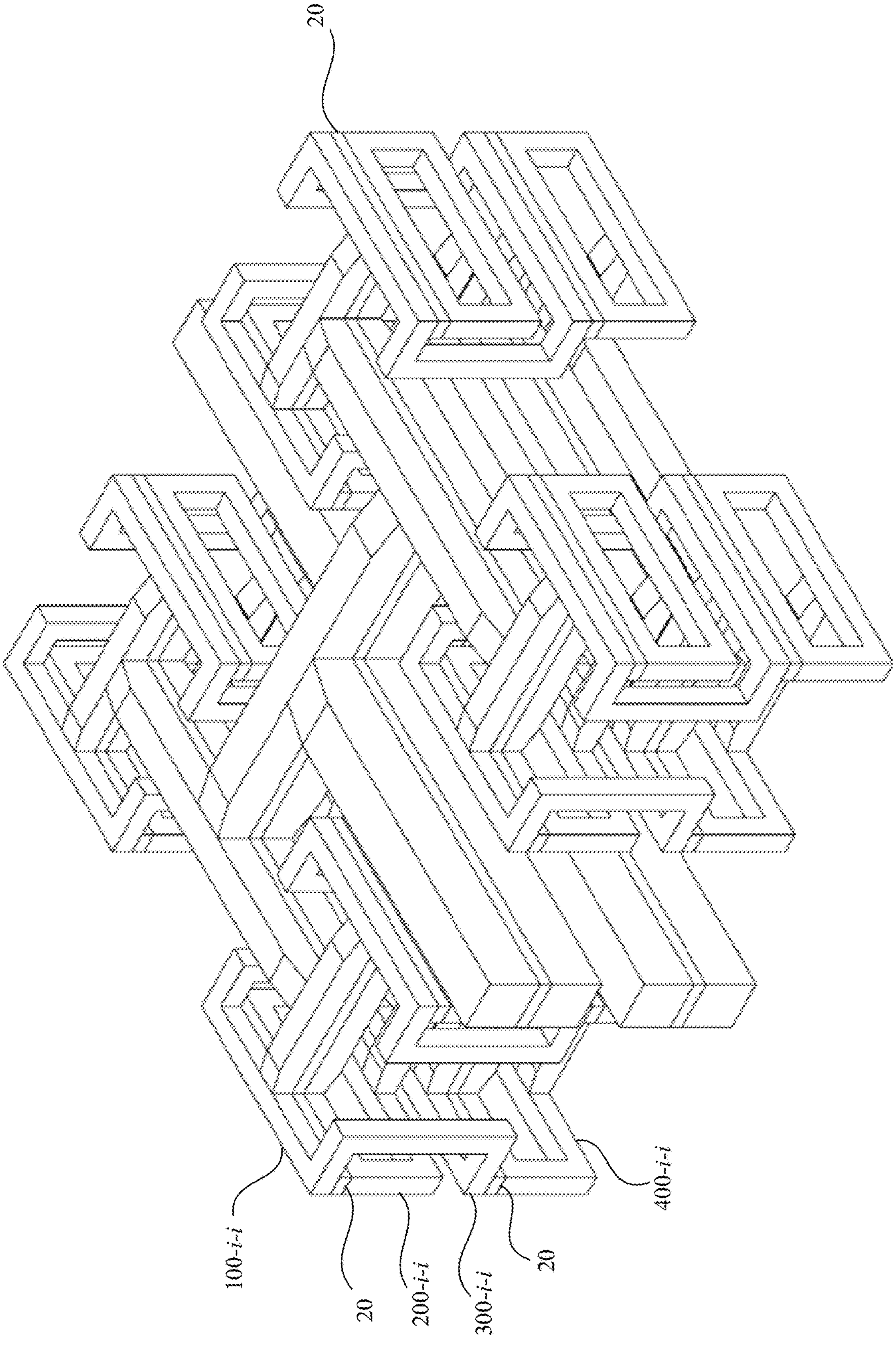
FIG. 36 illustrates an isometric schematic view of an exemplary stacked bypass channel network layer scaffold device including an exchange mechanism in accordance with embodiments of the present disclosure.
Figure 37:
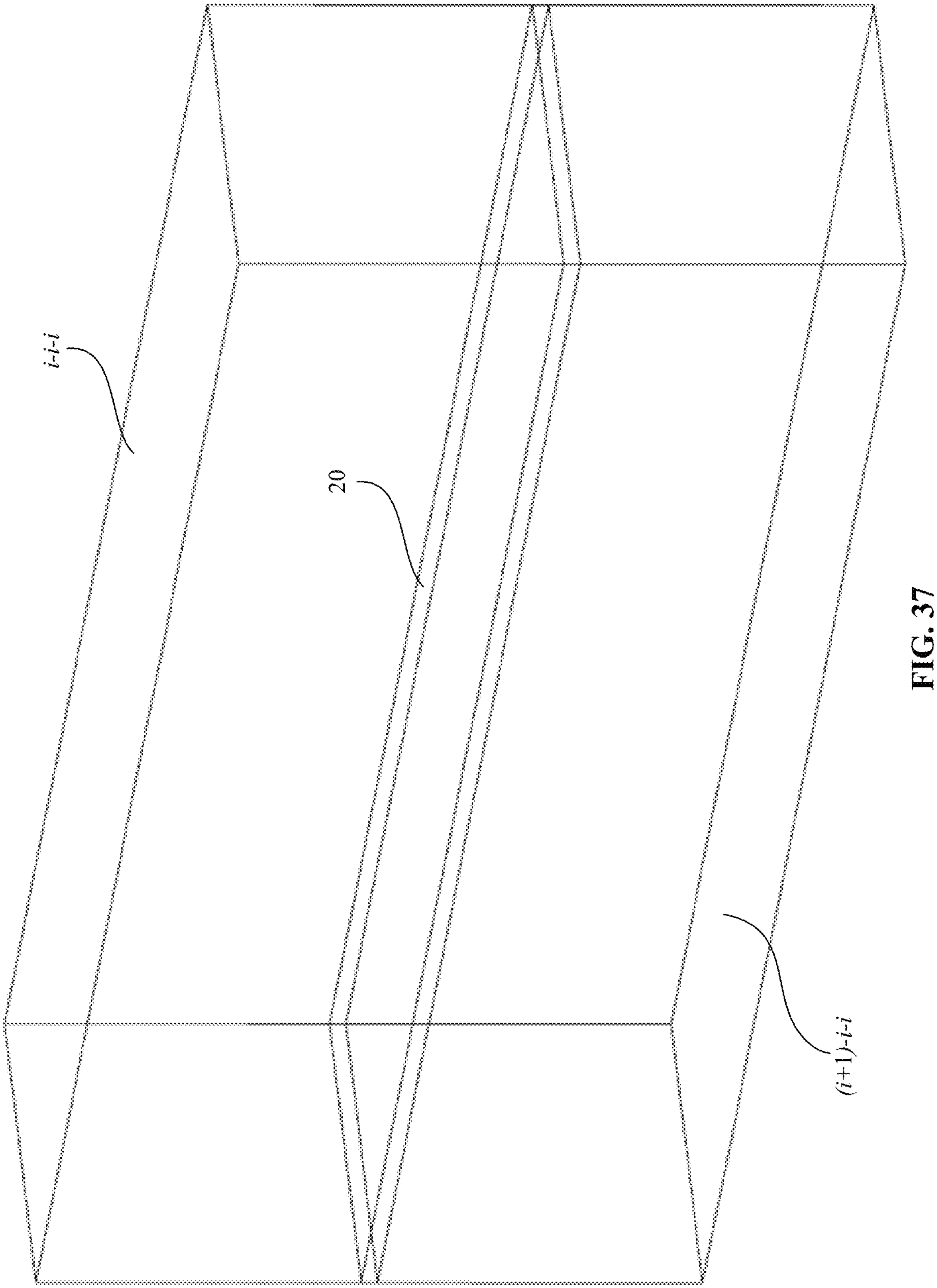
FIG. 37 illustrates an exemplary exchange mechanism in accordance with embodiments of the present disclosure.
Figure 38:
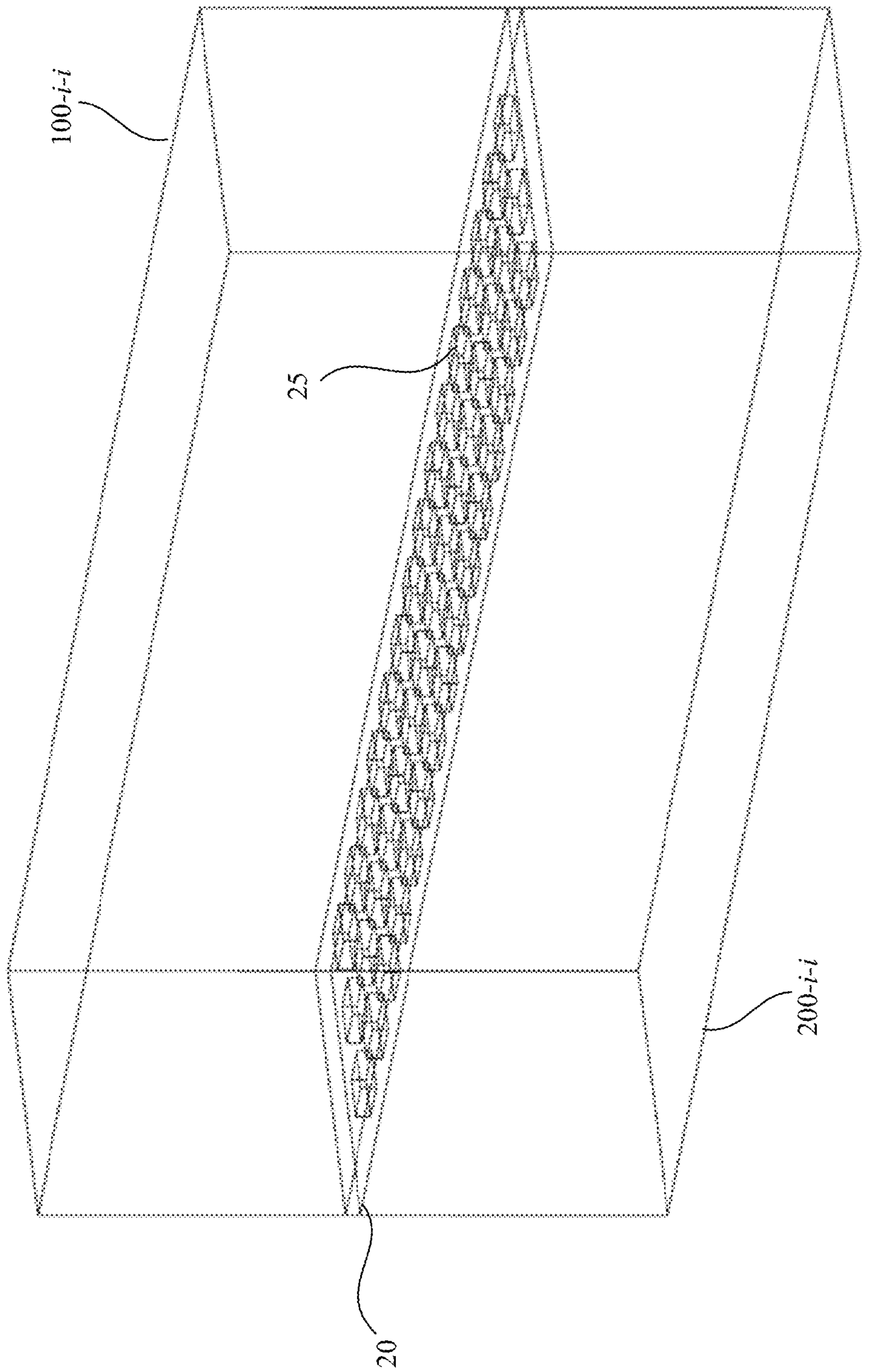
FIG. 38 illustrates an exemplary exchange mechanism in accordance with embodiments of the present disclosure.
Figure 39:
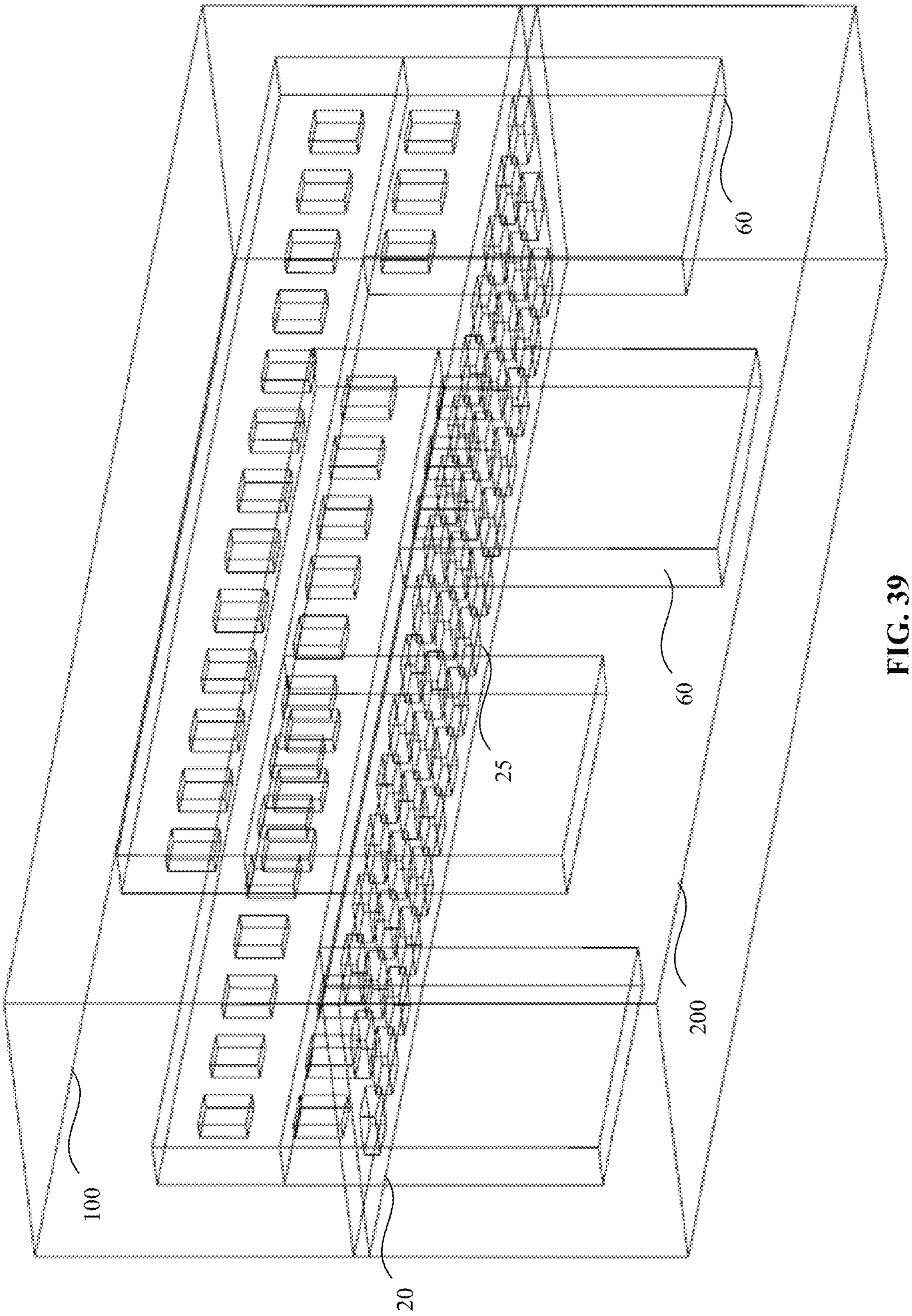
FIG. 39 illustrates an exemplary exchange mechanism and side channels in accordance with embodiments of the present disclosure.

In some embodiments, an exchange mechanism is disposed interposing between adjacent channel networks. FIG. 36 depicts an embodiment of the present disclosure including exchange mechanism 20 disposed interposing between networks 100 and 200 as well as 300 and 400. The exchange mechanism is configured to selectively allow a flow of material from the second channel network to the first channel network and/or from the first channel network to the second channel network. In the present embodiment, exchange mechanism 20 is a membrane. Exemplary membranes include but are not limited to a track-etch membrane, a fibrous membrane, and a membrane formed through additive manufacturing (e.g., a membraned formed through three-dimensional printing). Track-etch membranes typically include cylindrical through-holes in a dense polymer matrix. These track-etch membranes are typically made by ion-etching. Fibrous membranes are made by a variety of deposition techniques of polymeric fibers. While these fibrous membranes do not have a well-defined pore topology, production methods have been sufficiently refined so that fibrous membranes have specific molecular weight cut-offs. In some embodiments, track-etch type membranes are preferred, as they limit the fluid motion in one direction. In some embodiments, a membrane forms through additive manufacturing (e.g., 3D printing). This includes forming (e.g., printing) the membrane simultaneously to one or more channels of the scaffold device (e.g., as a portion of a monolithic device). In some embodiments, a motion of a medium (e.g., flow) is in a vertical direction (e.g., opposite a force of gravity). Fibrous membranes permit fluid motion both laterally and vertically. Moreover, a membrane formed through additive manufacturing (e.g., 3D printing) is configurable to control flow paths within and/or surrounding the device. In some embodiments, the exchange mechanism has a thickness in a range of from 5 μm to 10,000 μm, from 5 μm to 5,000 μm, from 10 μm to 5,000 μm, or from 10 μm to 4,000 μm. In some embodiments, the exchange mechanism includes a plurality of pores (e.g., exchange mechanism 20 including pores 25 of FIG. 38 through FIG. 40). In some embodiments, a pore size of the membrane is smaller than a diameter of a cell. Accordingly, cells will not be able to pass through the membrane (i.e. a low permeability for animal cells), while low molecular weight nutrients and fluids can pass through (i.e. a high permeability for nutrients), providing adequate cell-to-cell signaling. Cell sizes vary, and in general are in a range of microns. For example, a red blood cell has a diameter of approximately 8 μm. Preferably, the average membrane pore size is on a submicron-scale to ensure effective screening of the cells. In some embodiments, a permeability of the membrane is determined by a number of parameters including a property of the membrane (e.g., a pore size and/or a porosity), an interaction and/or an affinity between the membrane and a material, a size of a cell species, a concentration gradient of a material, an elasticity of a material, and/or a combination thereof. In some embodiments, a distance from a center of a first pore to a center of an adjacent pore is in a range of from 5 μm to 150 μm, from 5 μm to 100 μm, or from 5 μm to 50 μm. In some embodiments, a diameter of each pore is in a range of from 5 μm to 150 μm, from 5 μm to 100 μm, or from 5 μm to 50 μm. Furthermore, In some embodiments, the depth of each pore is in a range of from 5 μm to 5,000 μm, from 10 μm to 5,000 μm, from 10 μm to 4,000 m, or from 10 μm to 1,000 μm. In some embodiments, a pore has a rectangular shape (e.g., a rectangular opening and/or cross-section), a square shape, a cylindrical shape, a conical shape, a cup shape, an hourglass, or the like. In some embodiments, an exchange mechanism includes a material with a non-zero solubility to a predetermined solution or chemical. In some embodiments, the exchange mechanism includes a polymer with a high permeability for a predetermined solution or chemical. In some embodiments, the exchange mechanism includes polydimethylsiloxane, which has a high permeability to fluids such as oxygen and carbon dioxide.

Figure 40B:
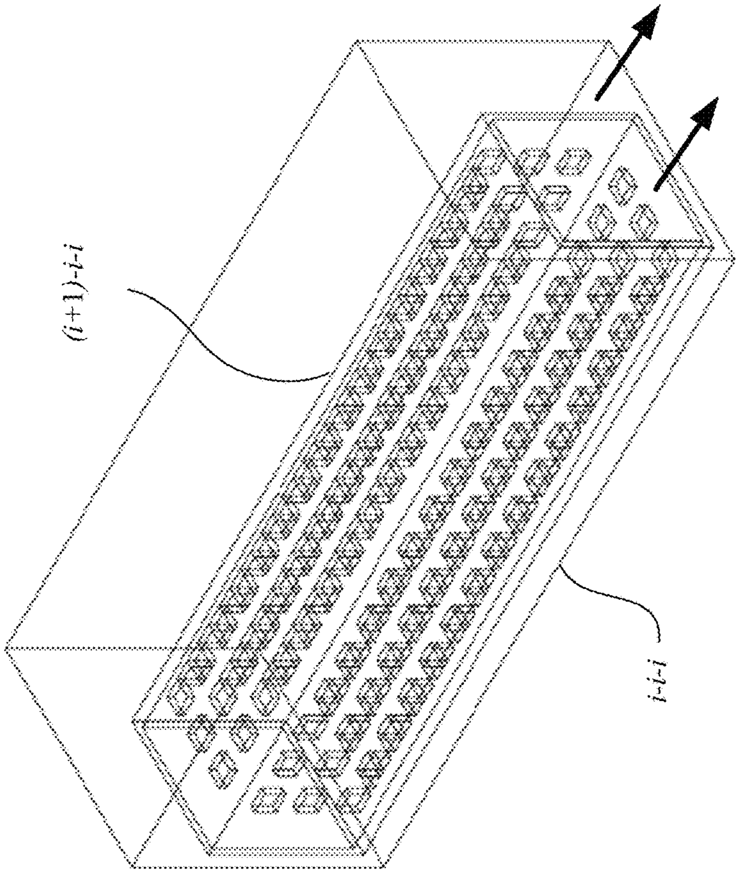
FIG. 40A and FIG. 40B illustrate exemplary layouts of a first channel network, a second channel network, and an exchange mechanism in accordance with embodiments of the present disclosure.
Figure 40A:
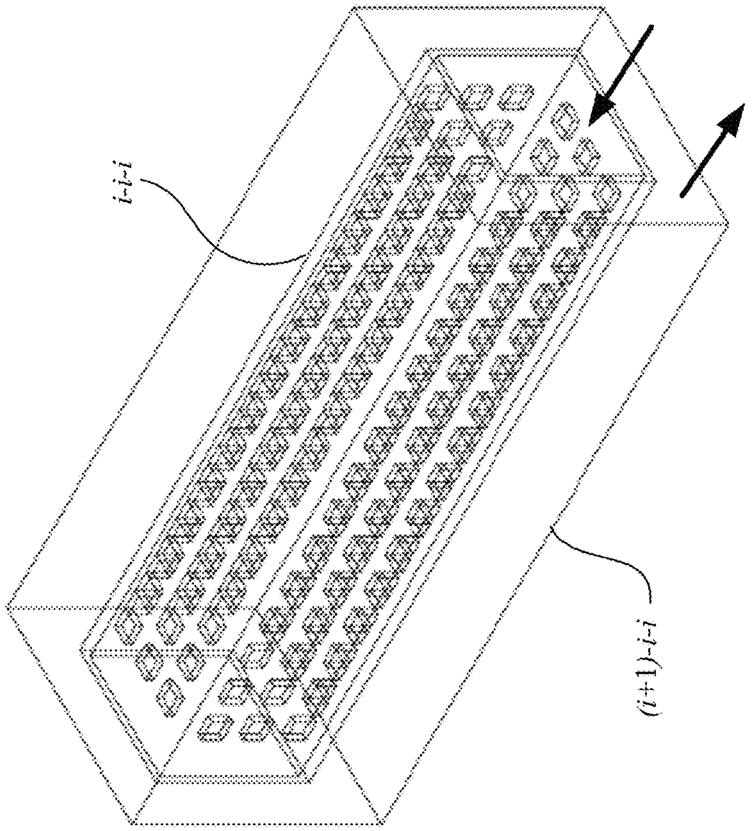

In some embodiments, to facilitate additional flow and/or exchange of material between channels, at least one side channel is formed in at least one channel network of the device. In some embodiments, the side channel extends from at least a first surface (e.g., a first internal surface) of the first channel network to at least a first surface of a second channel network. In some embodiments, the exchange mechanism is further disposed interposing between the side channel each of the channel networks. By way of example, FIG. 40 depicts side channels 60 with exchange mechanism 20 including pores 25 disposed interposing the side channels and first layer 100 and second layer 200. Sizes and shapes of the side channels and the pores are not limited to the sizes and shapes depicted in the present exemplary embodiment. In some embodiments, the exchange mechanism is disposed on a portion of all sides of either the first channel network or the second channel network, but never both channel networks. FIG. 40A and FIG. 40B depict such an embodiment. In some embodiments, the second channel network is embedded internally in the first channel network, or similarly the first channel network can be embedded internally in the second channel network. In some embodiments, the internally embedded channel is disposed in a different position and/or orientations, including but not limited to a centered orientation of FIG. 40A or an offset orientation of FIG. 40B. Furthermore, in some embodiments a flow of material in the internally embedded channel opposes a direction of flow in the other channel (e.g., as indicated by the arrows in FIG. 40A). However, the present disclosure is not limited thereto.

Figure 41:
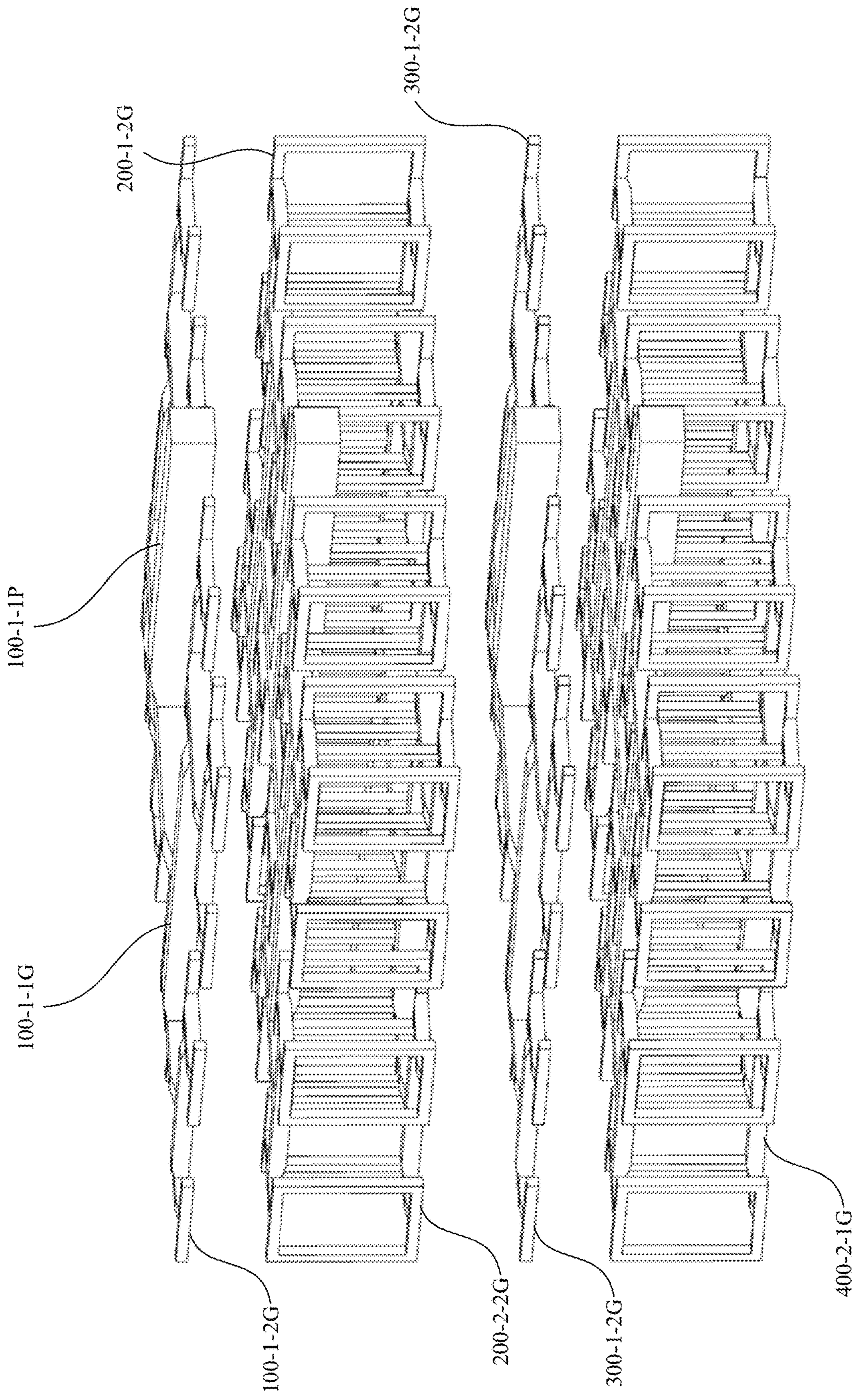
FIG. 41 illustrates an exemplary scaffold device in accordance with embodiments of the present disclosure.
Figure 42:
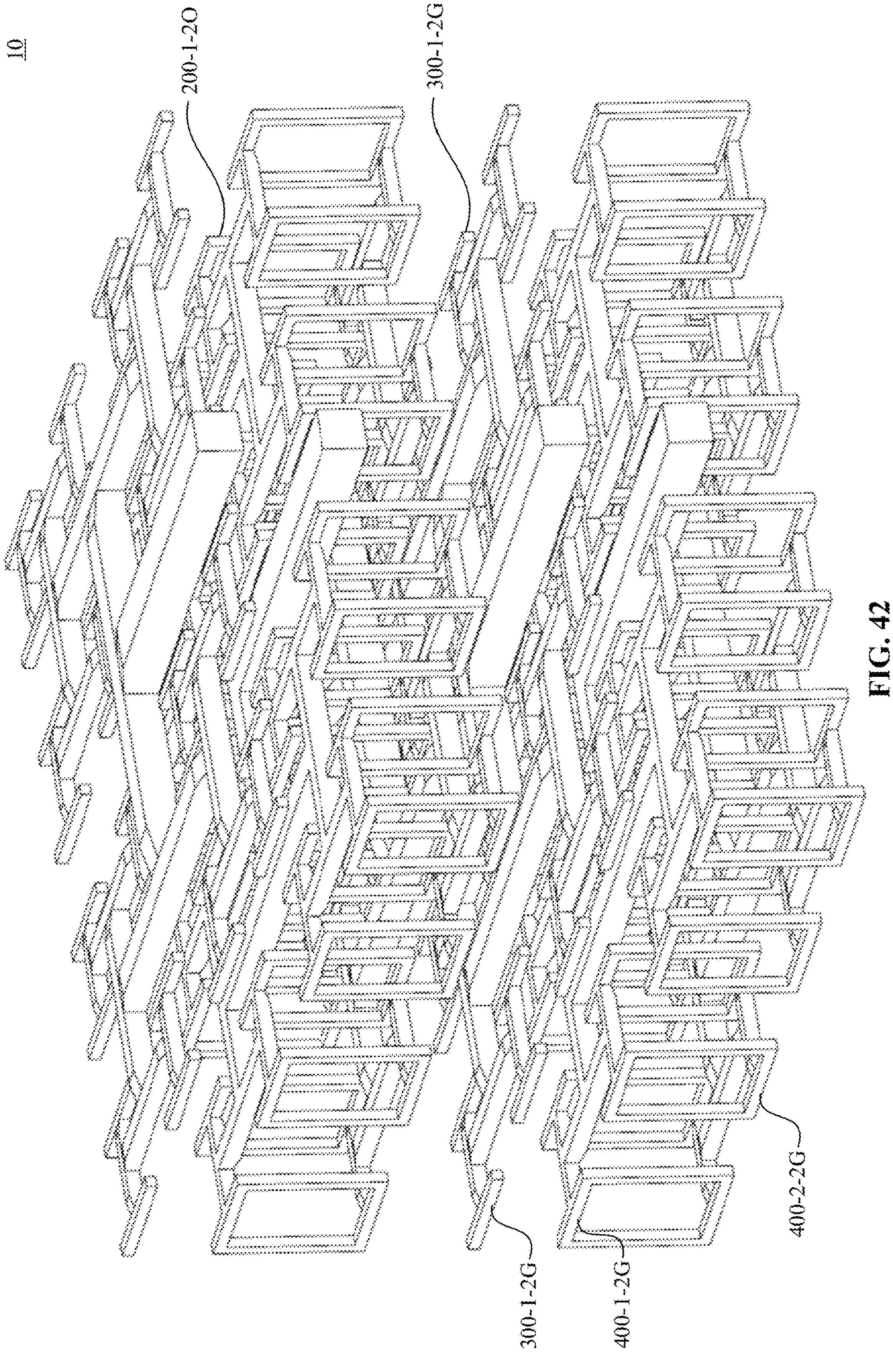
FIG. 42 illustrates another view of the scaffold device of FIG. 41.

FIG. 41 and FIG. 42 depict a bypass embodiment of the present invention where the first channel network and the third channel network are not in fluidic communication.

Figure 43:
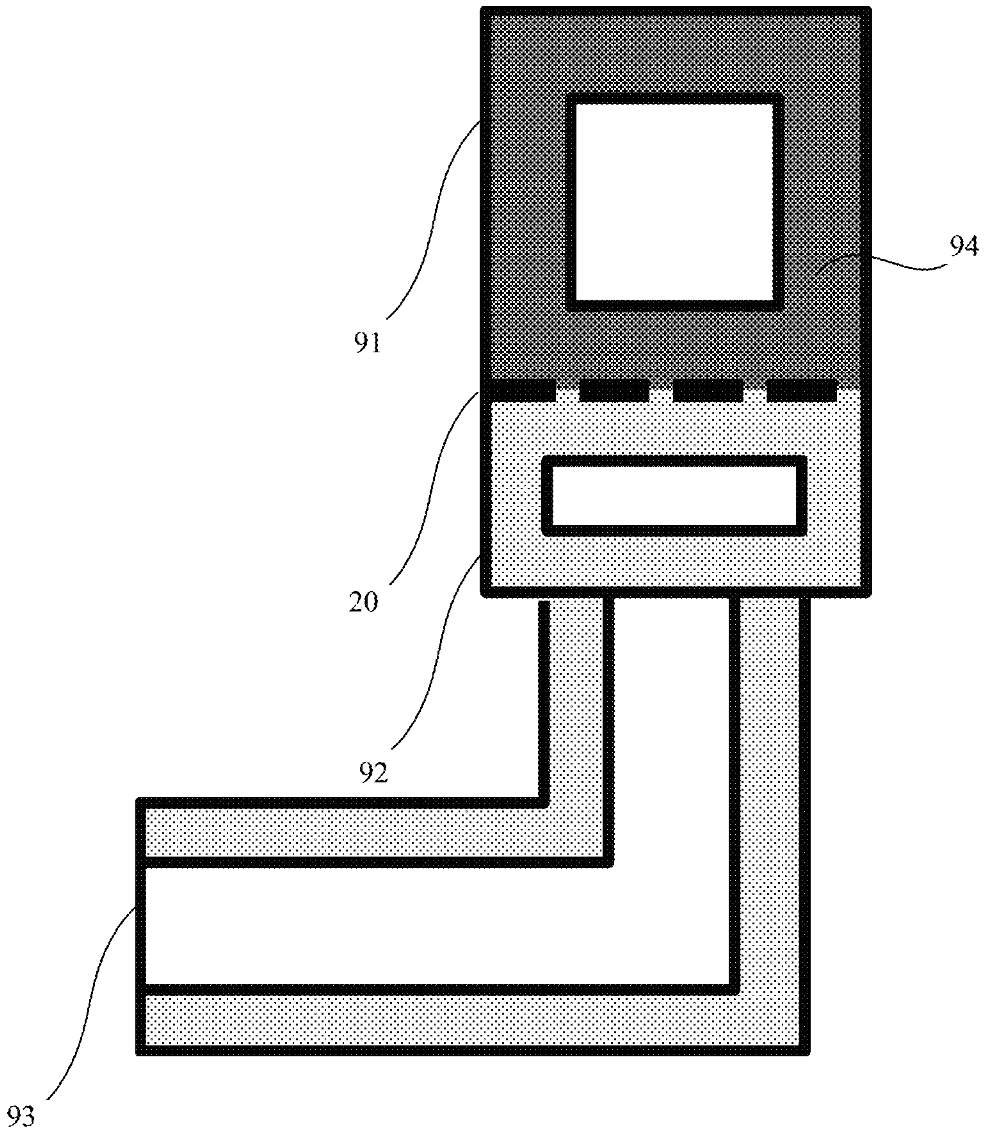
FIG. 43 illustrates an exemplary vascularized tissue layer with drainage in accordance with embodiments of the present disclosure.

FIG. 43 illustrates an exemplary schematic of a vascularized tissue layer with drainage embodiment of the present disclosure. The vascularized tissue layer supplies nutrients and oxygen to tissues of interest through an exchange mechanism (e.g., a fenestrated or a porous membrane). Nutrients and oxygen are exchanged to and from channel 91 lined with cells of interest 94 and tissue of interest 92 including drainage 93 with outflow. In some embodiments of the present disclosure (e.g., those that are configured for livers), nutrients and oxygen are exchanged to and from channel 91 lined with endothelial cells 94 and hepatic cells 92 including drainage 93 with outflow of bile.

Figure 44:
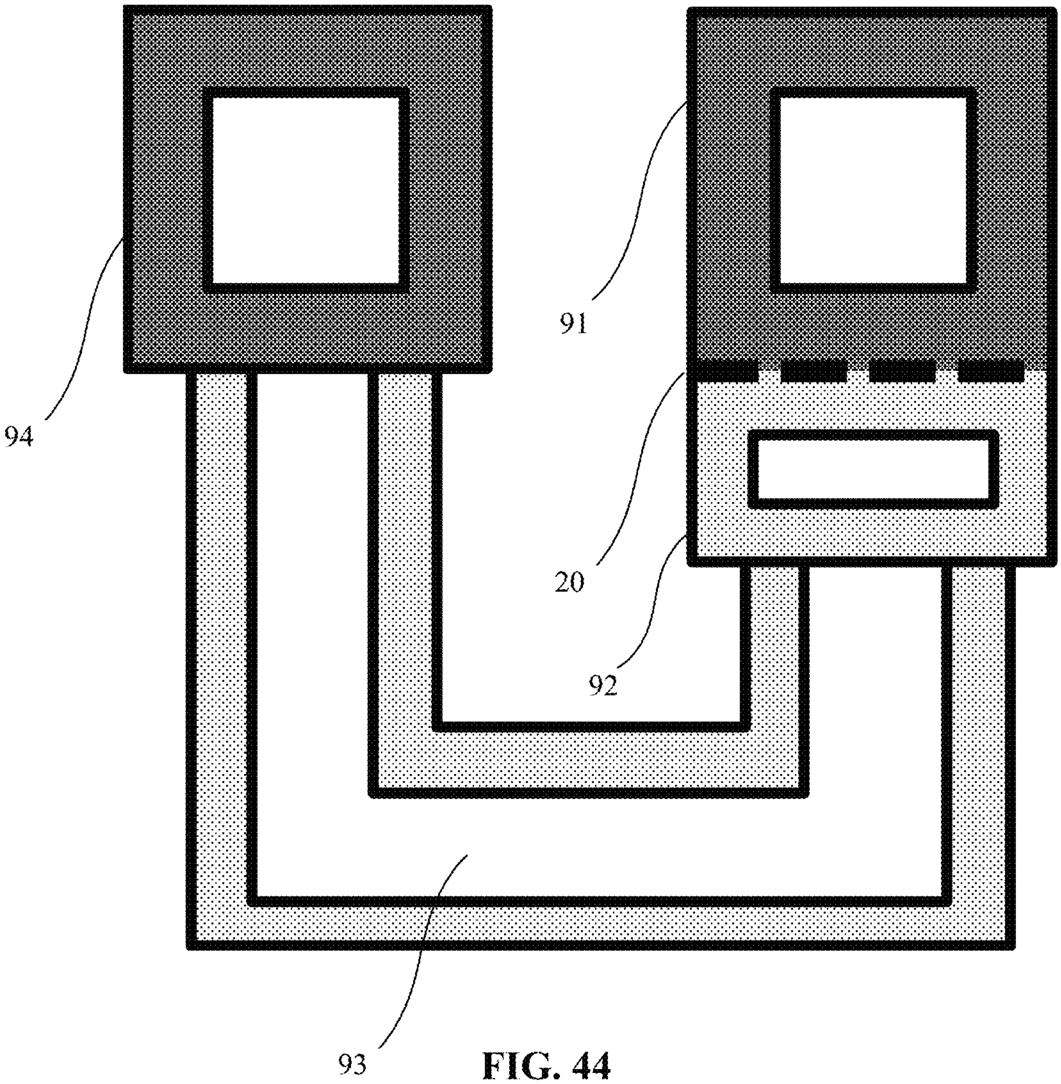
FIG. 44 illustrates an exemplary vascularized tissue layer with drainage in accordance with embodiments of the present disclosure.
Figure 45:
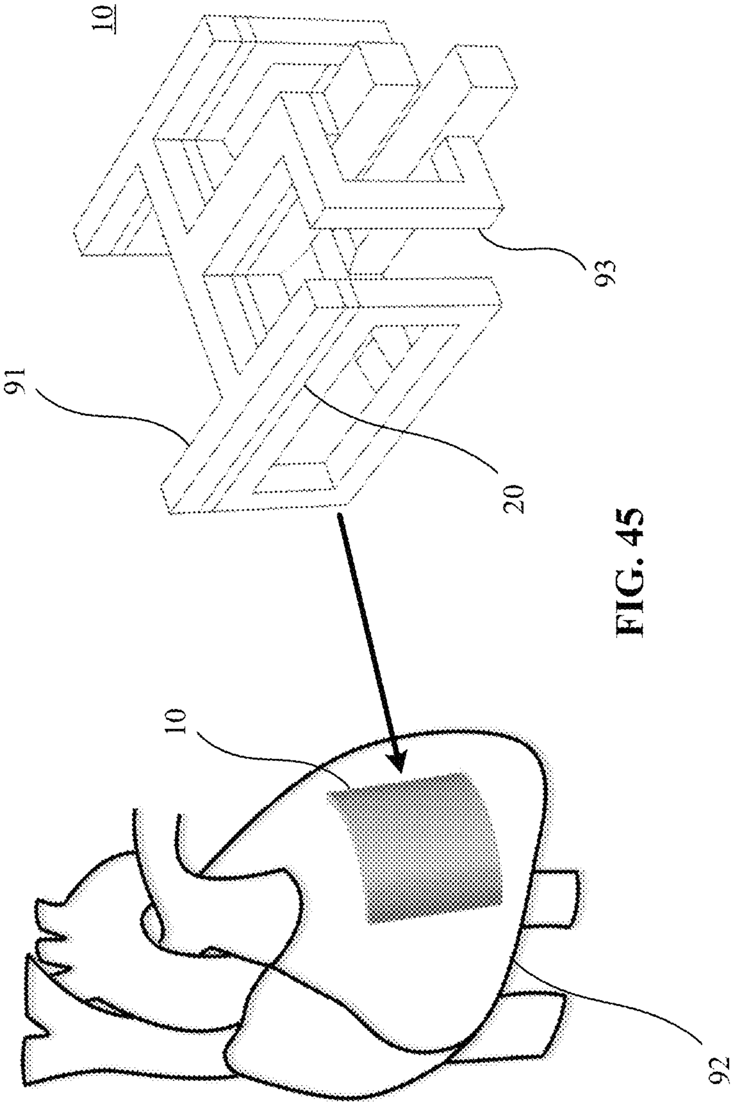
FIG. 45 illustrates an exemplary vascularized heart muscle patch in accordance with embodiments of the present disclosure.

FIG. 44 illustrates a schematic of a vascularized tissue layer with drainage embodiment that is similar to the embodiment depicted by FIG. 43. However, in the present embodiment, drainage 93 outflow is connected to channel 94 (e.g., parent channel) configured for outflow. In some embodiments, this configuration is utilized for a heart muscle tissue patch to strengthen, for instance, the left ventricle of the heart, as shown in FIG. 45.

Figure 46:
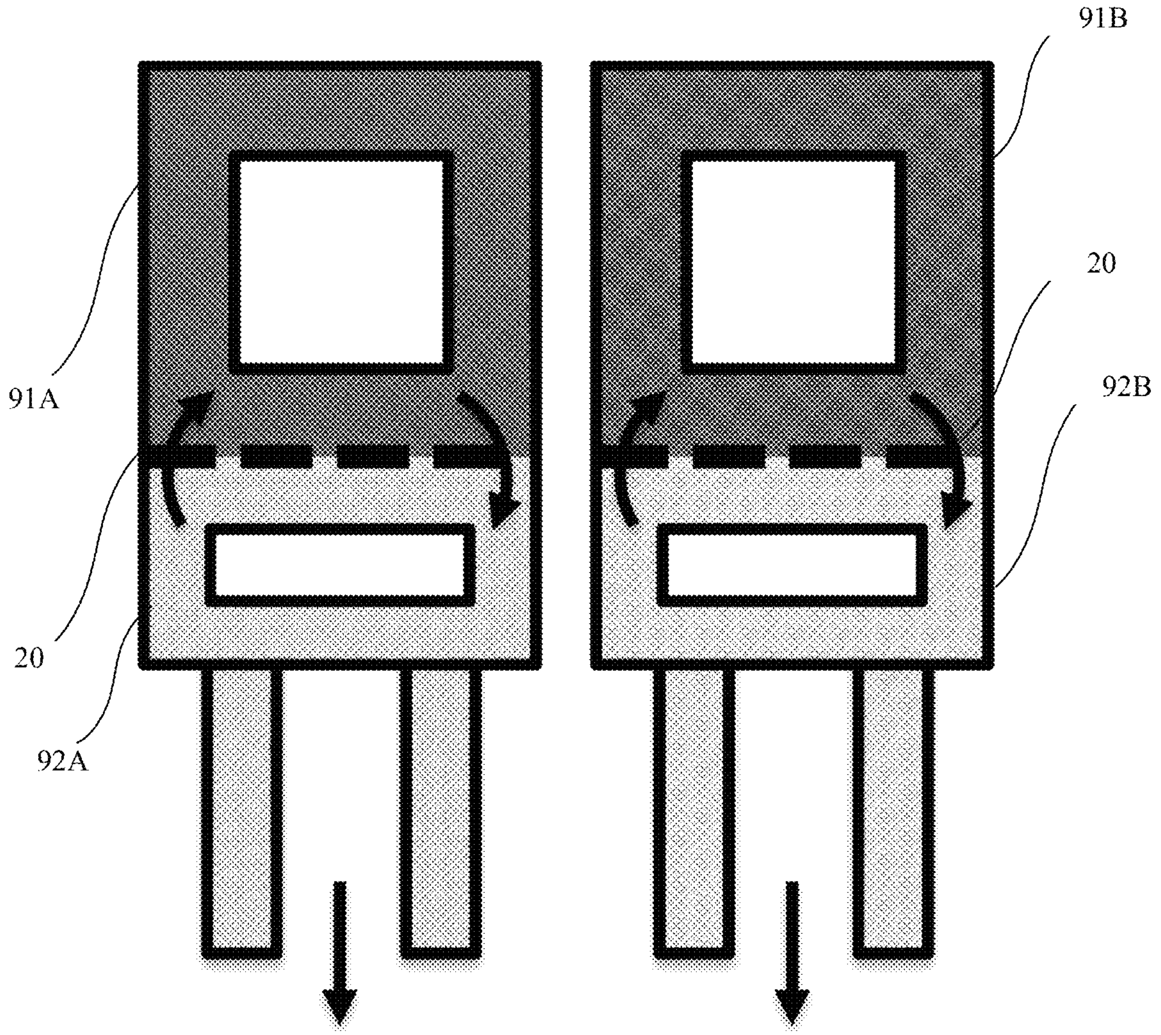
FIG. 46 illustrates an exemplary cross-section of multiple channels including a vascularized tissue layer with drainage in accordance with embodiments of the present disclosure.
Figure 47:
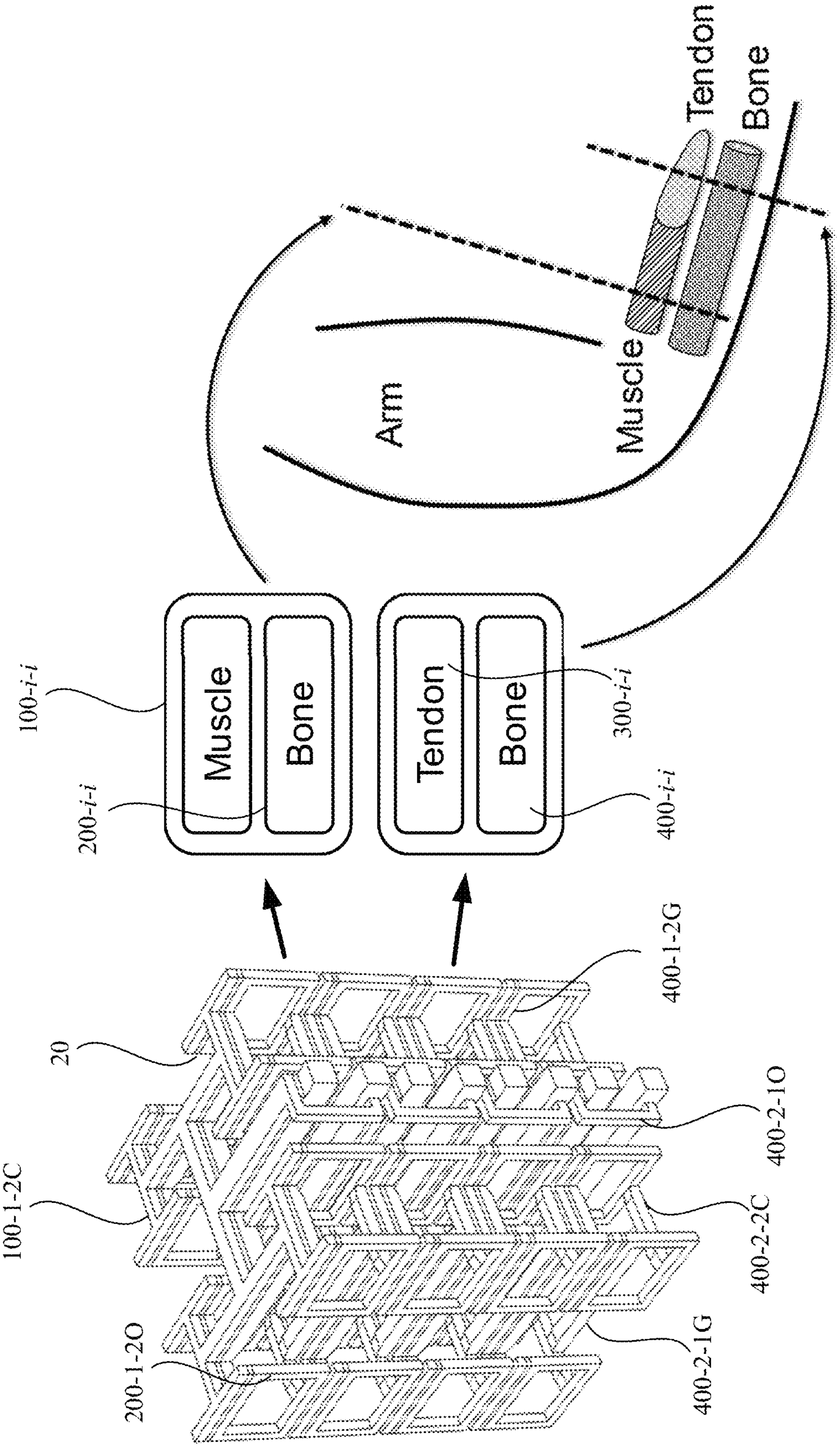
FIG. 47 illustrates an exemplary complex tissue construct including multiple units for implantation in an arm in accordance with embodiments of the present disclosure.

Referring to FIG. 46 and FIG. 47, an embodiment of the present disclosure is depicted including a plurality of layers with drainage. In the present embodiment, nutrients and oxygen are exchanged to and from a first channel layer 91A lined with first cells of interest 94A and first tissue of interest 92A as well as separately being exchanged to and from a second channel layer 91B lined with second cells of interest 94B and second tissue of interest 92B.

Figure 48A:
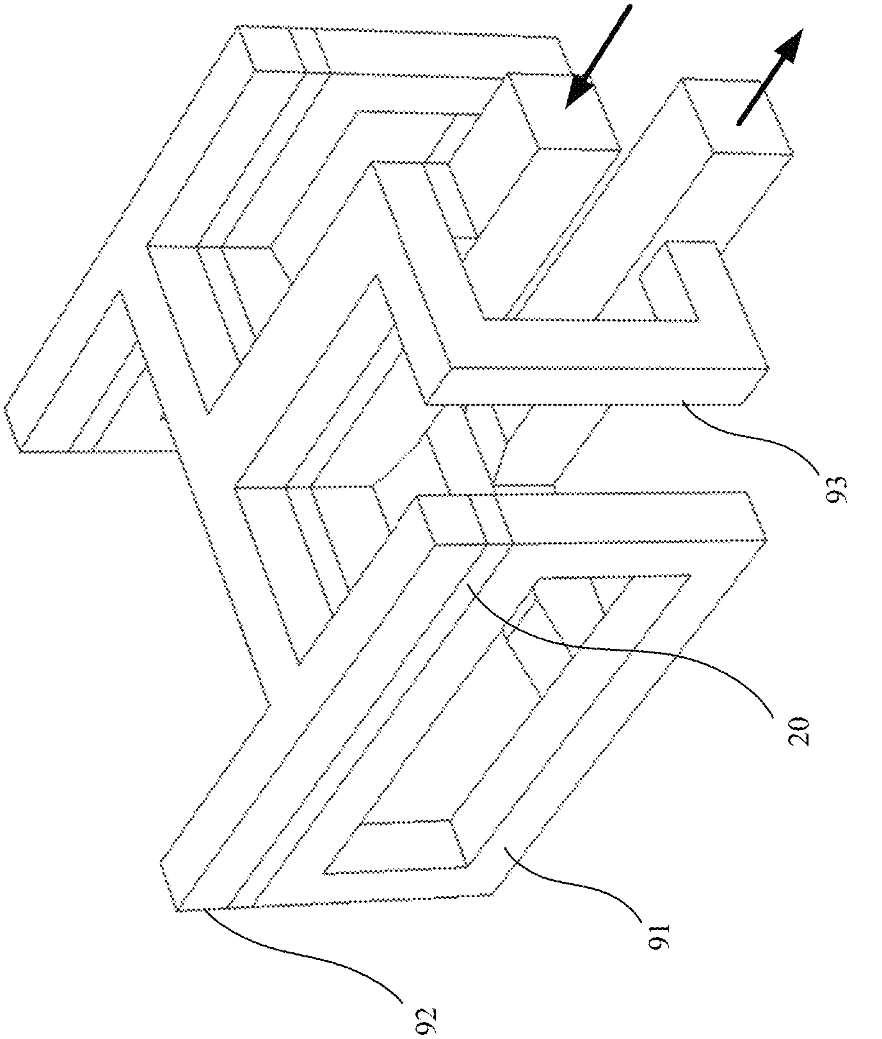
FIG. 48A and FIG. 48B illustrate an exemplary two generation vascularized tissue layer with drainage in accordance with embodiments of the present disclosure.
Figure 48B:
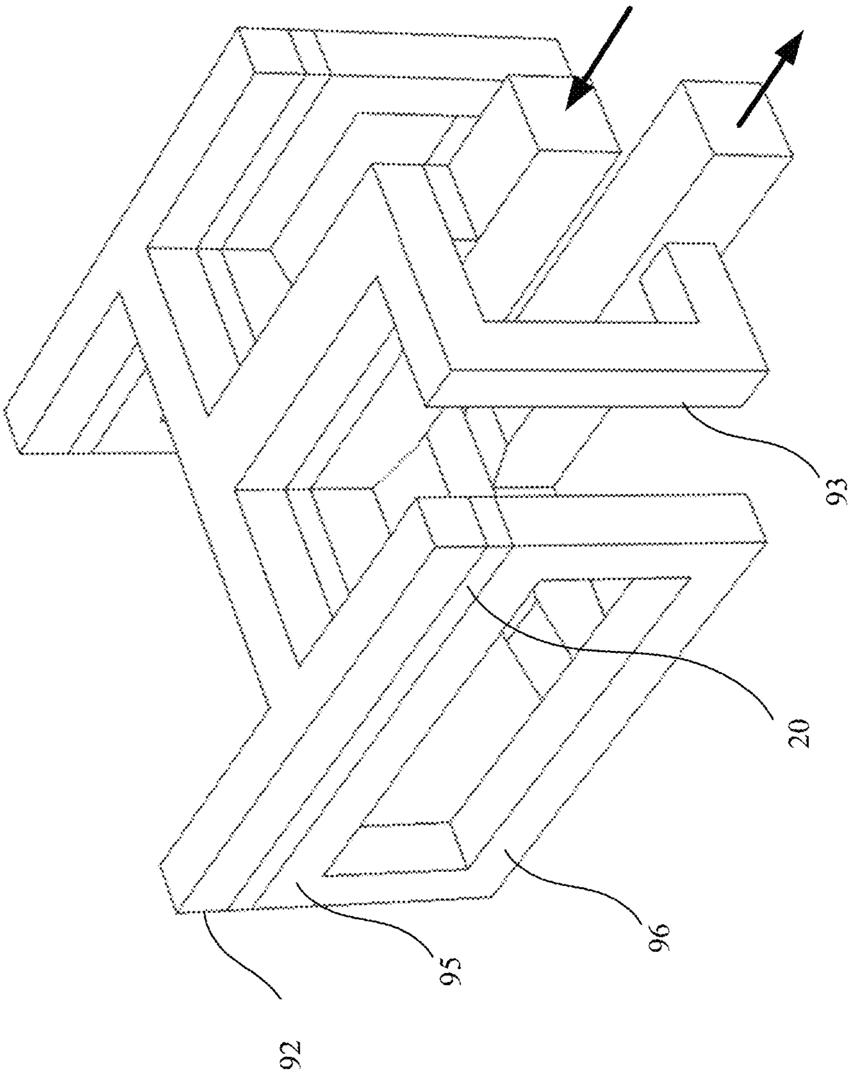

Referring to FIG. 48A, a two generation vascularized tissue layer embodiment of the present disclosure is illustrated. This embodiment is configured to allow nutrients, oxygen, and/or drugs to be supplied to the tissue layer from the other vascular layer. Return of waste and metabolites from tissue layer 92 to vascular layer 91 is provided by the previously described pressure drop, or gradient. Similarly, referring to FIG. 48B, in some embodiments the vascular layer include a distributor network mirrored to a collector network (e.g., distributor network 95 mirrored to collector network 96). In some embodiments, there is a tissue layer disposed between the distributor and collector networks. This configuration allows new blood vessels to grow and nourish additional portions of the tissue layer, allowing cells of interest to further proliferate throughout the device.

Figure 49A:
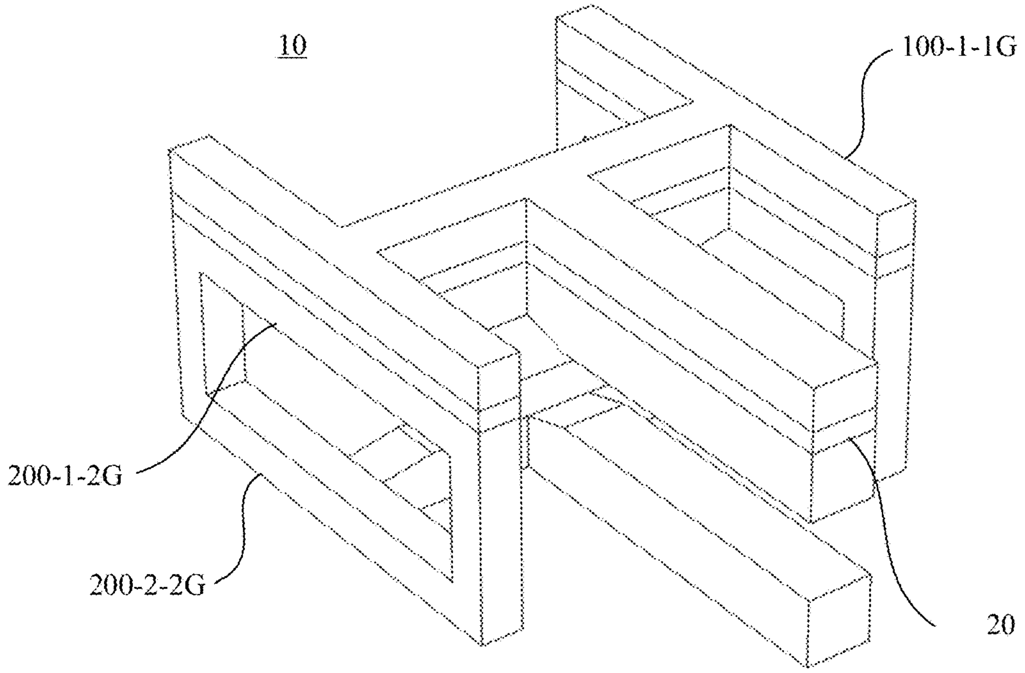
FIG. 49A, FIG. 49B, and FIG. 49C collectively illustrate an exemplary process for generating a four tissue hierarchical design in accordance with embodiments of the present disclosure.
Figure 49B:
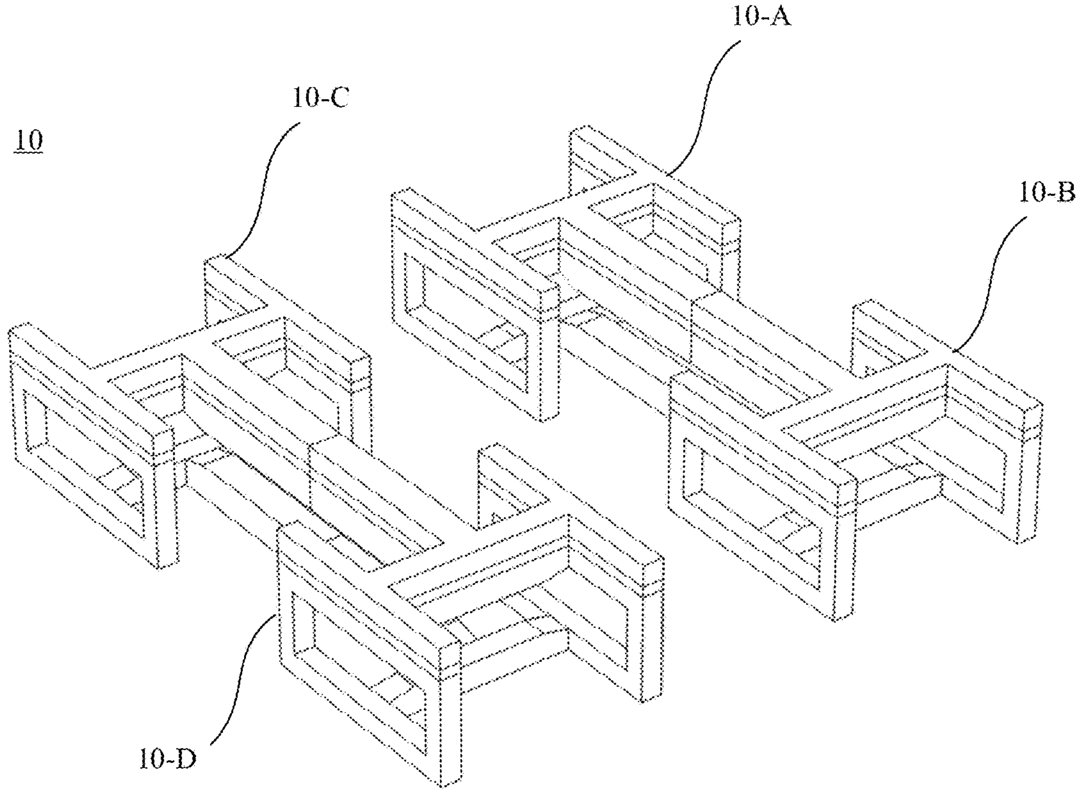
Figure 49C:
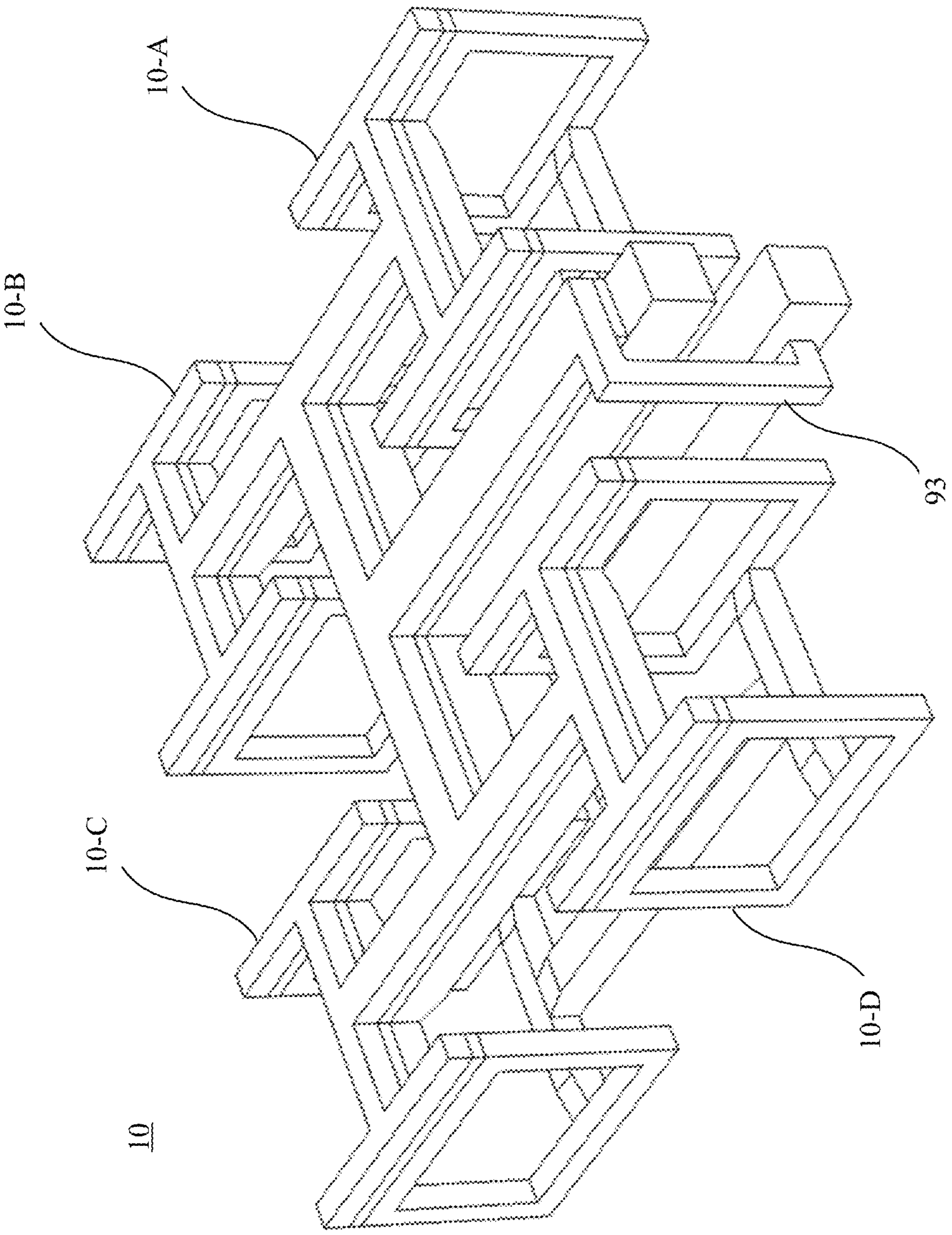
Figure 50D:
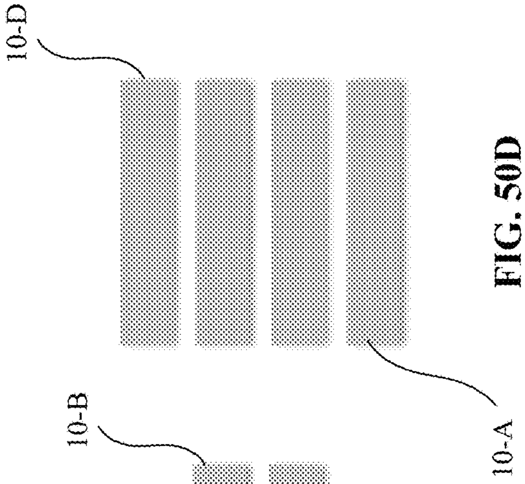
FIG. 50A, FIG. 50B, FIG. 50C, and FIG. 50D illustrate exemplary arrays and stacking configurations of a scaffold device in accordance with embodiments of the present disclosure.
Figure 50C:
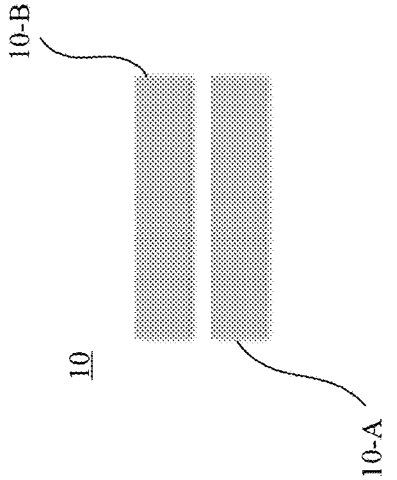
Figure 50B:
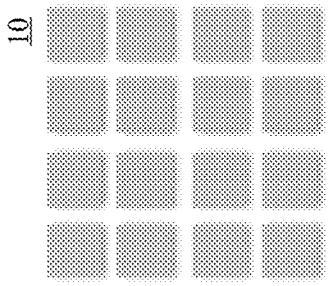
Figure 50A:
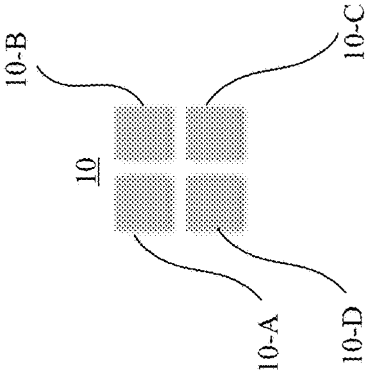

FIG. 49A through FIG. 49C collectively illustrate an exemplary progression from a single unit one generation vascularized tissue layer device embodiment to a four unit two generation vascularized tissue layer device embodiment. The hierarchical nature of the present disclosure allows for symmetry and recursion to iteratively build upon larger tissue constructs from simple micro tissue unit devices (e.g., device 10 includes micro devices 10-A, 10-B, 10-C, . . . , 10-*i*). In some embodiments, a scaffold device includes a plurality of microscale unit devices coupled together. For instance, as shown in FIG. 49C and FIG. 50A through FIG. 50D a variety of arrays and stacks are plausible in a design of a scaffold device of the present disclosure. For instance, the embodiments shown in FIG. 50A and FIG. 50B depict larger tissue constructs including arrays of connected units. FIG. 50C and FIG. 50D depict larger tissue constructs including stacks of connected units.

Figure 51:
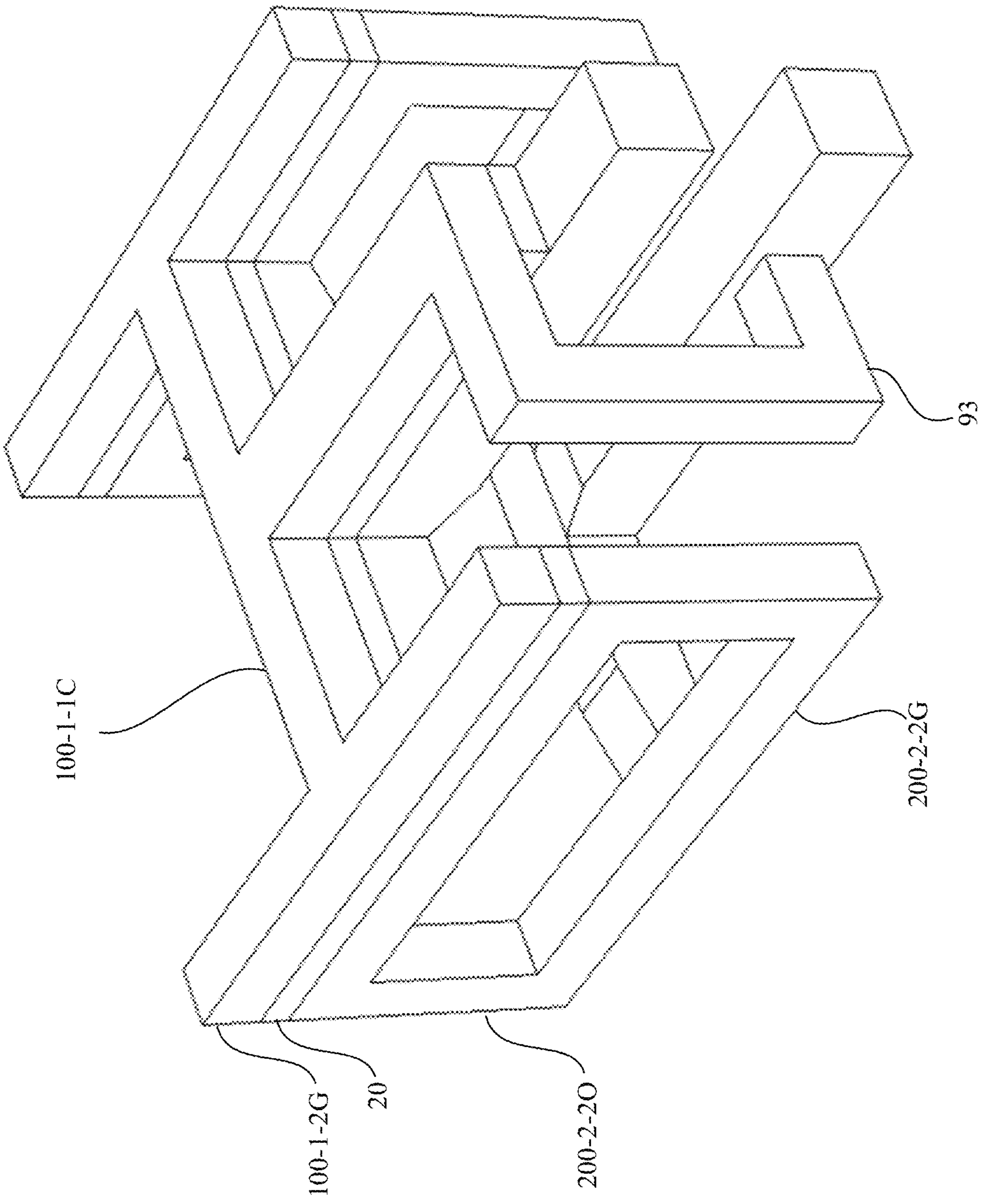
FIG. 51 illustrates an exemplary four by four scaffold device in accordance with embodiments of the present disclosure.
Figure 52:
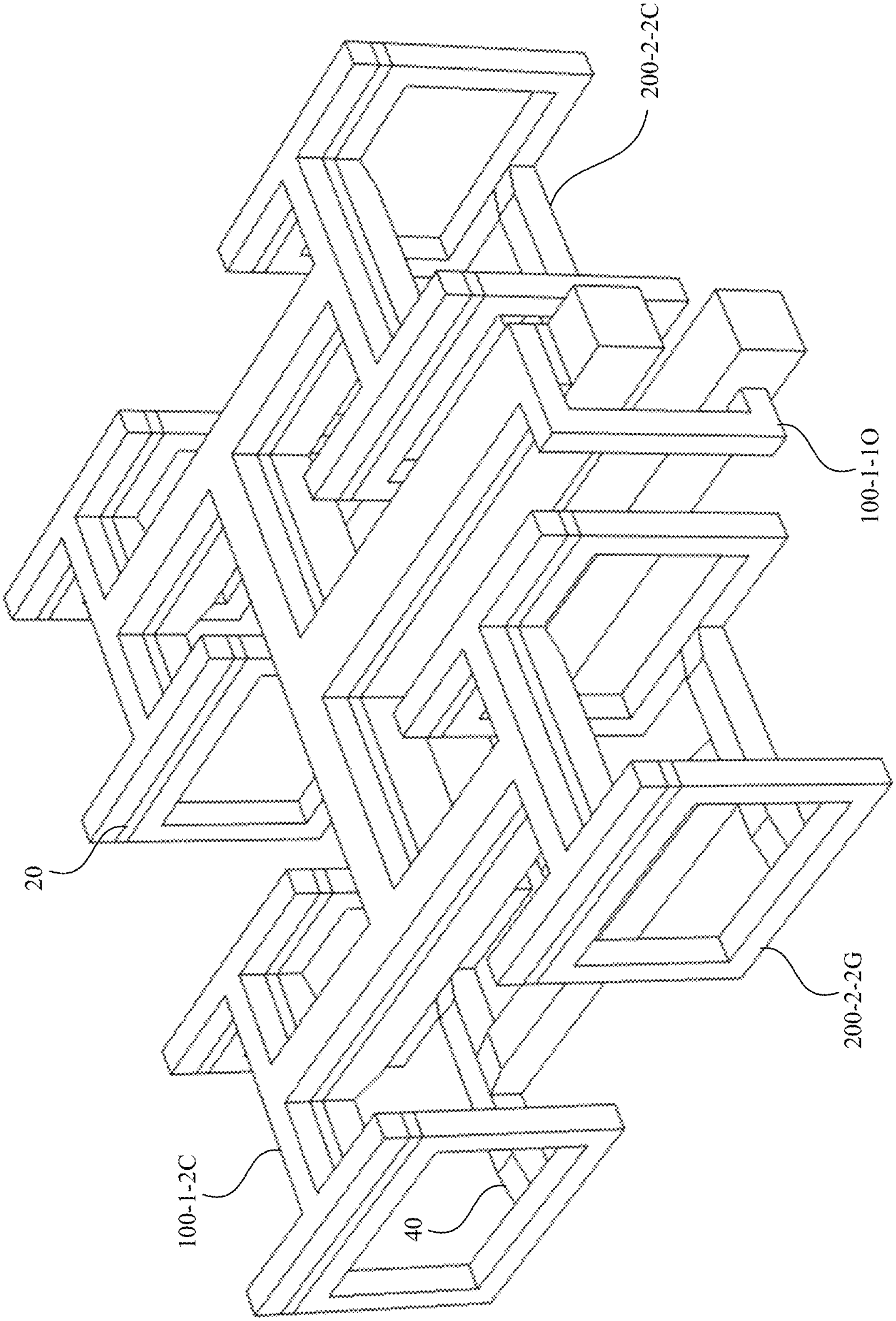
FIG. 52 illustrates an exemplary two generation vascularized tissue layer with drainage in accordance with embodiments of the present disclosure.
Figure 53:
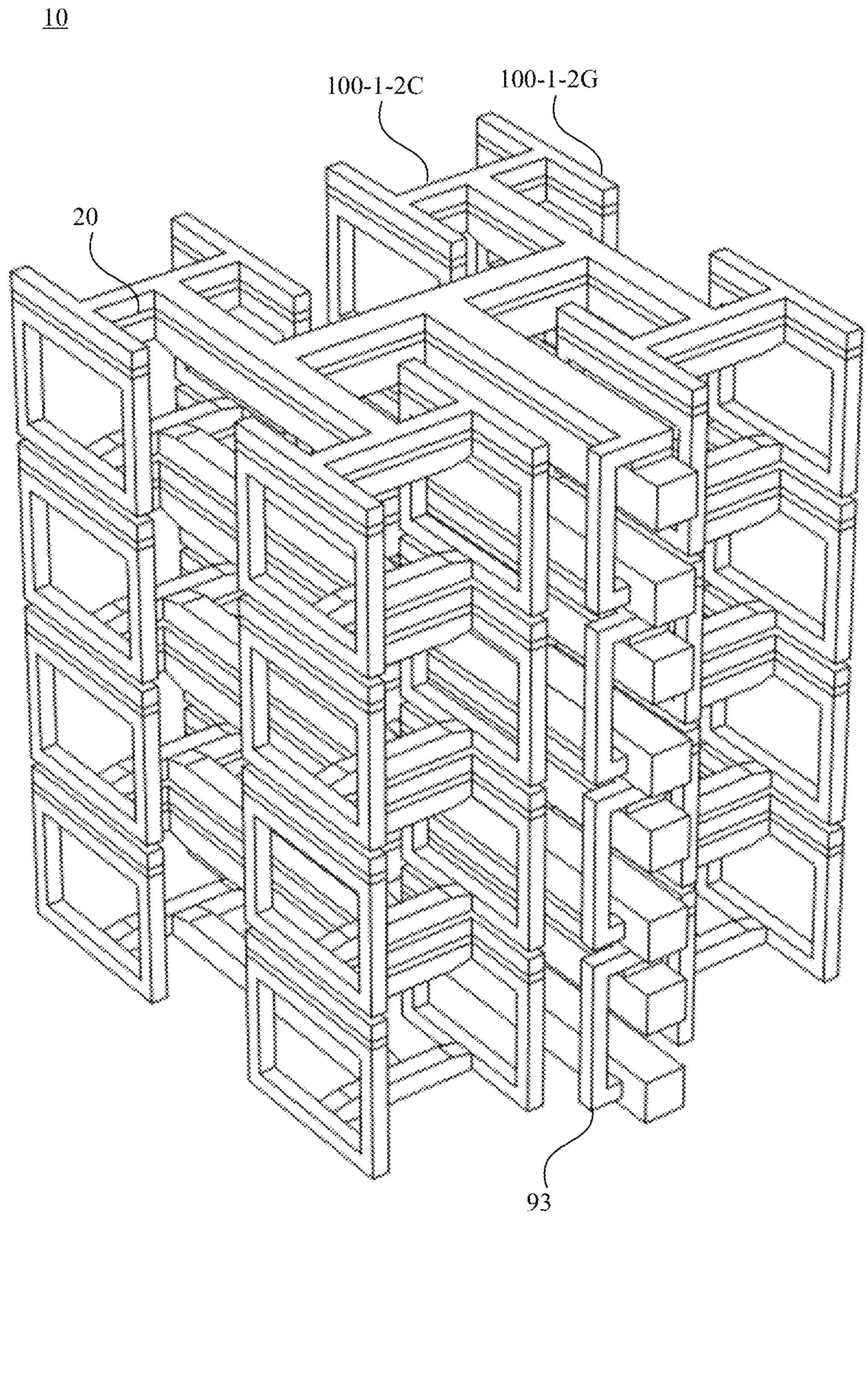
FIG. 53 illustrates an exemplary four generation vascularized tissue layer with drainage in accordance with embodiments of the present disclosure.

FIG. 51, FIG. 52, and FIG. 53 illustrate a unit, a four-unit network, and four stacks of four-unit networks, respectively. In some embodiments, the inflows and outflows of each stack are connected via a master inflow and a master outflow, respectively.

Figure 54:
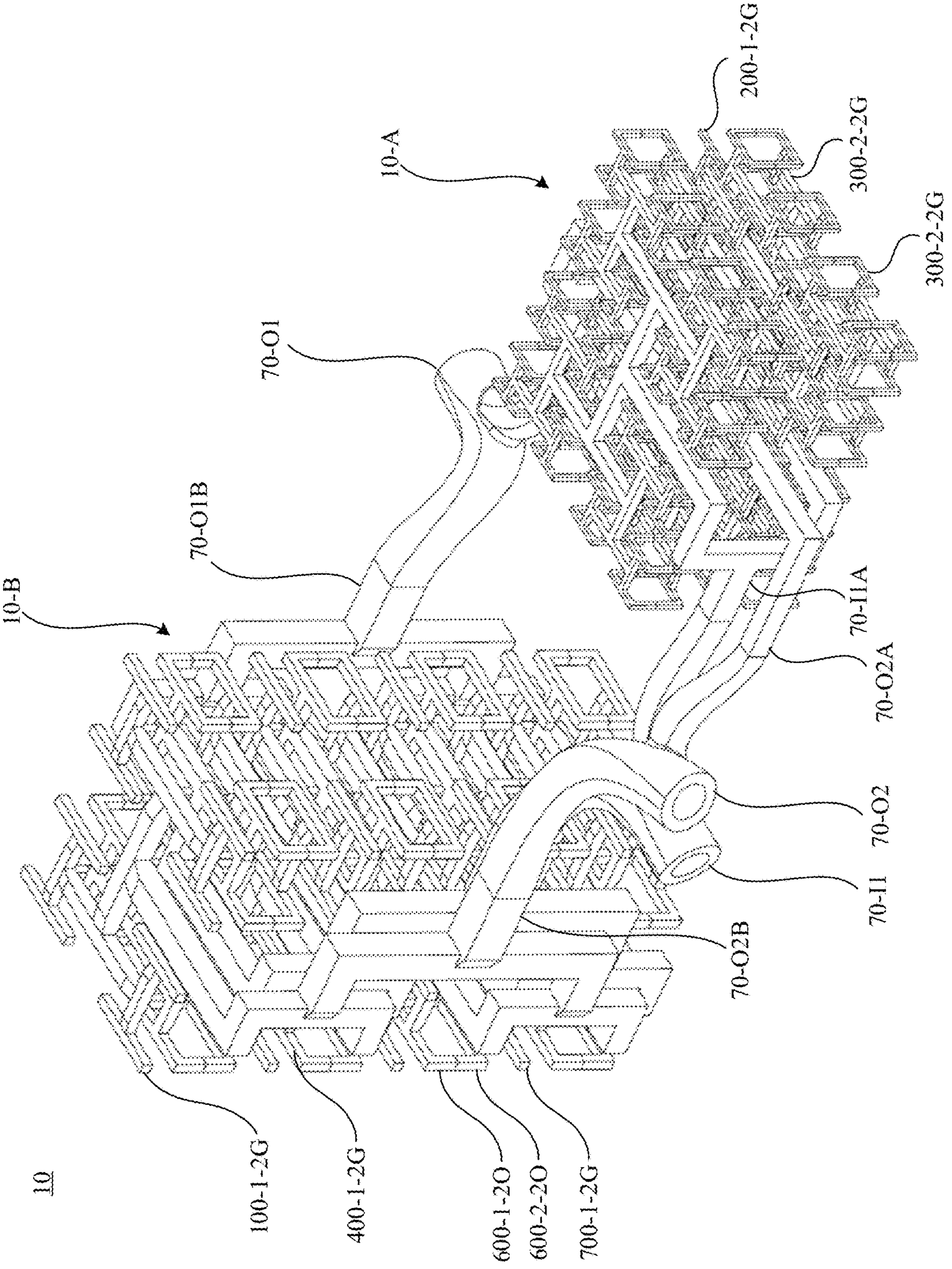
FIG. 54 illustrates an exemplary scaffold device including a first scaffold device and a second scaffold device in accordance with embodiments of the present disclosure.

FIG. 54 depicts an exemplary embodiment of a scaffold device including a first scaffold device and a second scaffold device with shared master inlet 70-11 and shared master outlets 70-O1 and 70-O2. Such an embodiment can be utilized in a liver device (e.g., a liver implant) which includes two lobes. In addition to the embodiment including a plurality of scaffolding networks, FIG. 54 illustrates various configurations of the channel networks with variations in number of generations, variations in network configuration (e.g., bypass device 10-B and stacked PCLN 10-A), and the like. In some embodiments, a parent channel of a first channel network layer is in communication with a parent channel of a second channel network. In some embodiments, this communication is facilitated by a bypass channel (e.g., bypass channel 93 of FIG. 49C and/or 100-1-10 of FIG. 52)

Figure 55B:
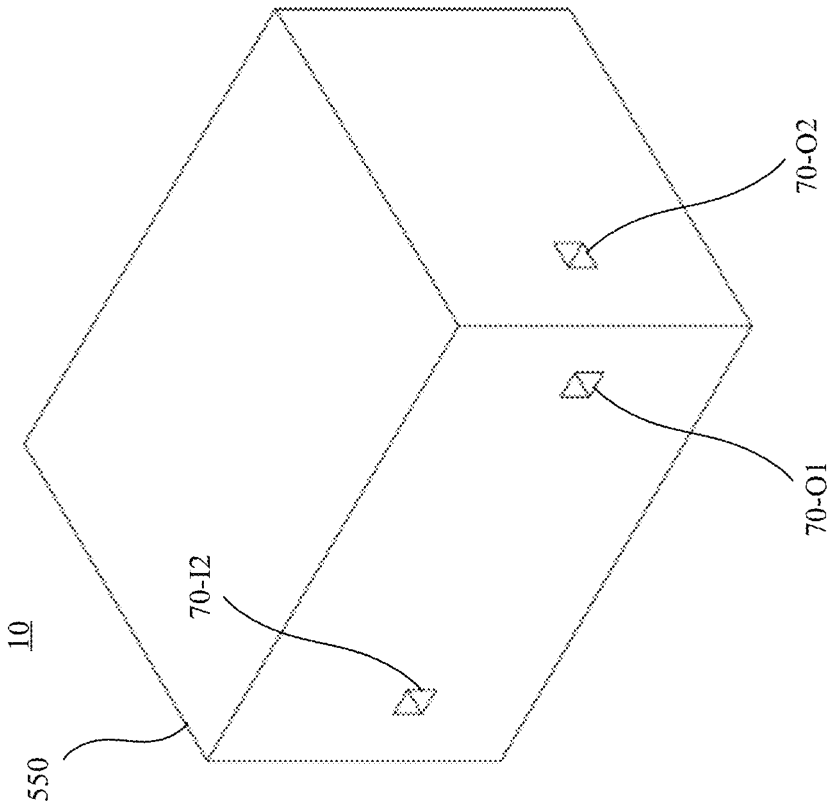
FIG. 55A, FIG. 55B, FIG. 55C, and FIG. 55D illustrate an exemplary scaffold device in accordance with embodiments of the present disclosure.
Figure 55A:
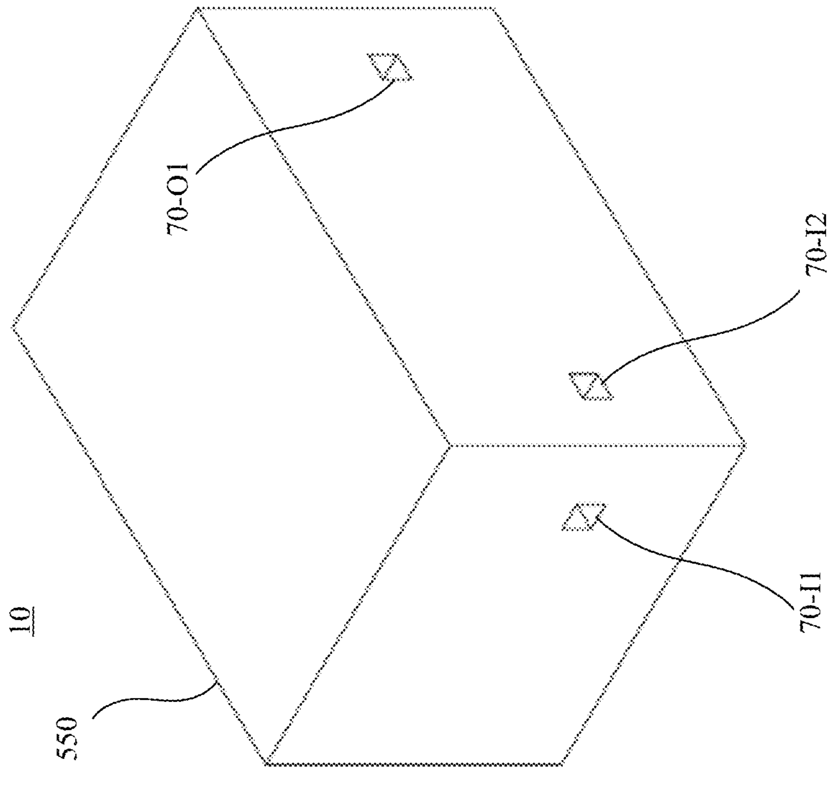
Figure 55C:
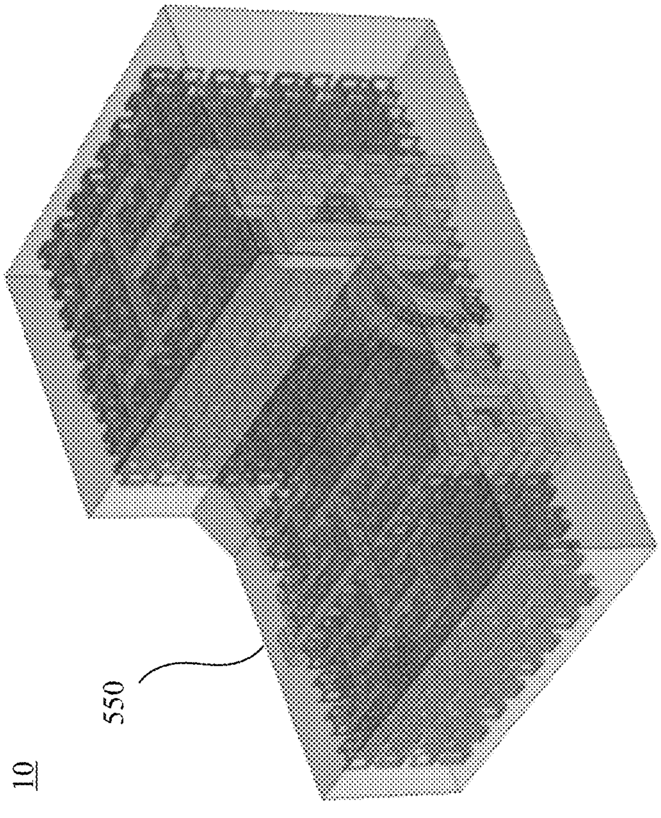
Figure 55D:
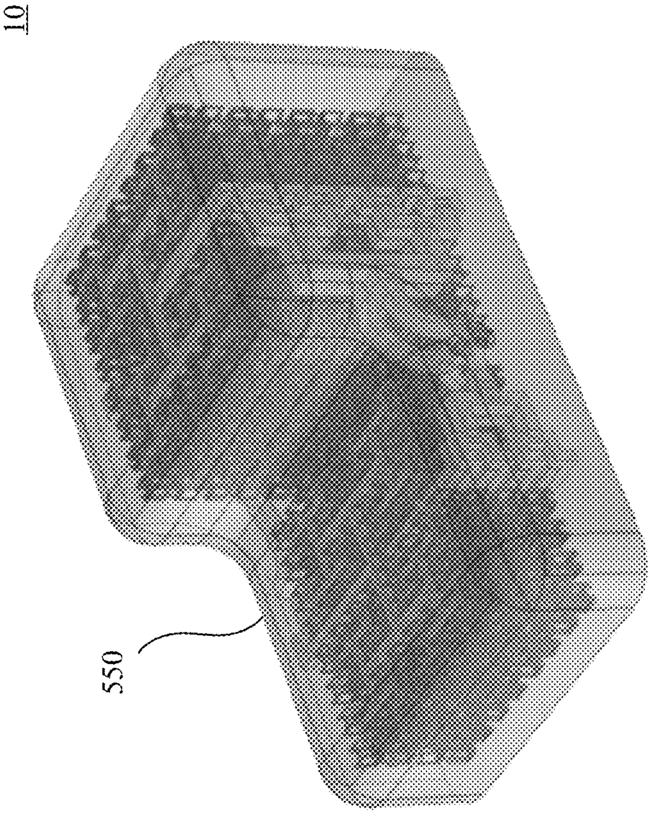

FIG. 55A through FIG. 55D depict an exemplary embodiment of a scaffold device encased in a closed structure (e.g., shell 550). In some embodiments, the shell is formed in a rectangular (e.g., shell 550 of FIG. 55A and FIG. 55B). In some embodiments, the shell is formed to minimize free space (e.g., voids) within the device (e.g., shell 550 of FIG. 55A and FIG. 55B). Furthermore, in some embodiments the shell includes rounded edge portions, which allows for easier insertion if the scaffold device is implanted in a subject. In some embodiments, device 10 is manufactured in a single fabrication process (e.g., as a monolithic device) such that internal channels and components are only accessible through master inlets 70-I1 and 70-I2 as well as master outlets 70-O1 and 70-O2. As illustrated in FIG. 55A and FIG. 55B, the device 10 may define a monolithic portion 551, within which the plurality of branching channel networks are integrally formed as a single continuous structure of the cell scaffold device. As further illustrated in FIG. 55B, device 10 includes a length 552, which may be defined as the distance extending between a first end portion of the inlet of the first channel (e.g., first end portion 554 of inlet 70-I2) and a first end portion of the inlet of the second channel (e.g., first end portion 555), wherein the first end portion of the inlet of the second channel is located on the opposite side (e.g., opposite side portion 553) of device 10 relative to the first end portion of the inlet of the first channel. However, the present disclosure is not limited thereto. For instance, in some embodiments a scaffold device is manufactured in a plurality of steps. For instance, in some embodiments, a first step manufactures a first channel network and a second step manufactures a second channel network. Likewise, in some embodiments a first step manufactures a first channel network and a second channel network, while a second step manufactures a shell of the device.

Figure 56B:
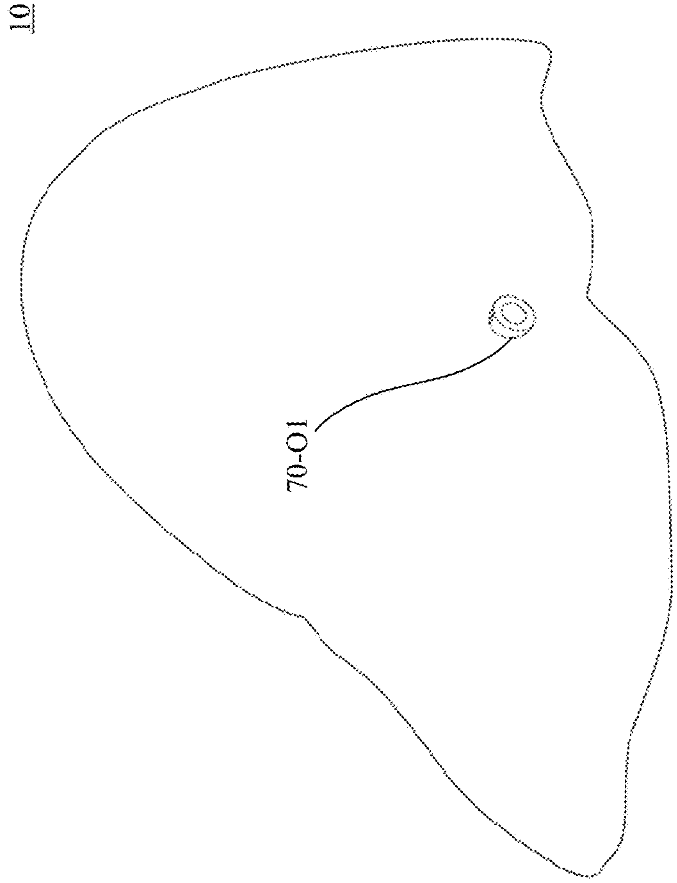
FIG. 56A, FIG. 56B, and FIG. 56C illustrate an exemplary scaffold device in accordance with embodiments of the present disclosure.
Figure 56A:
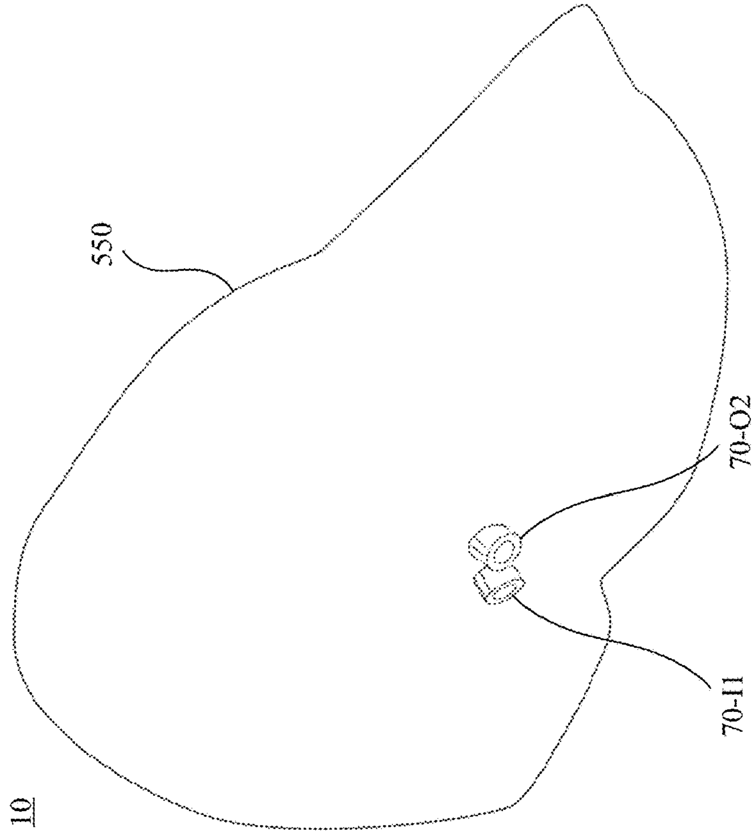
Figure 56C:
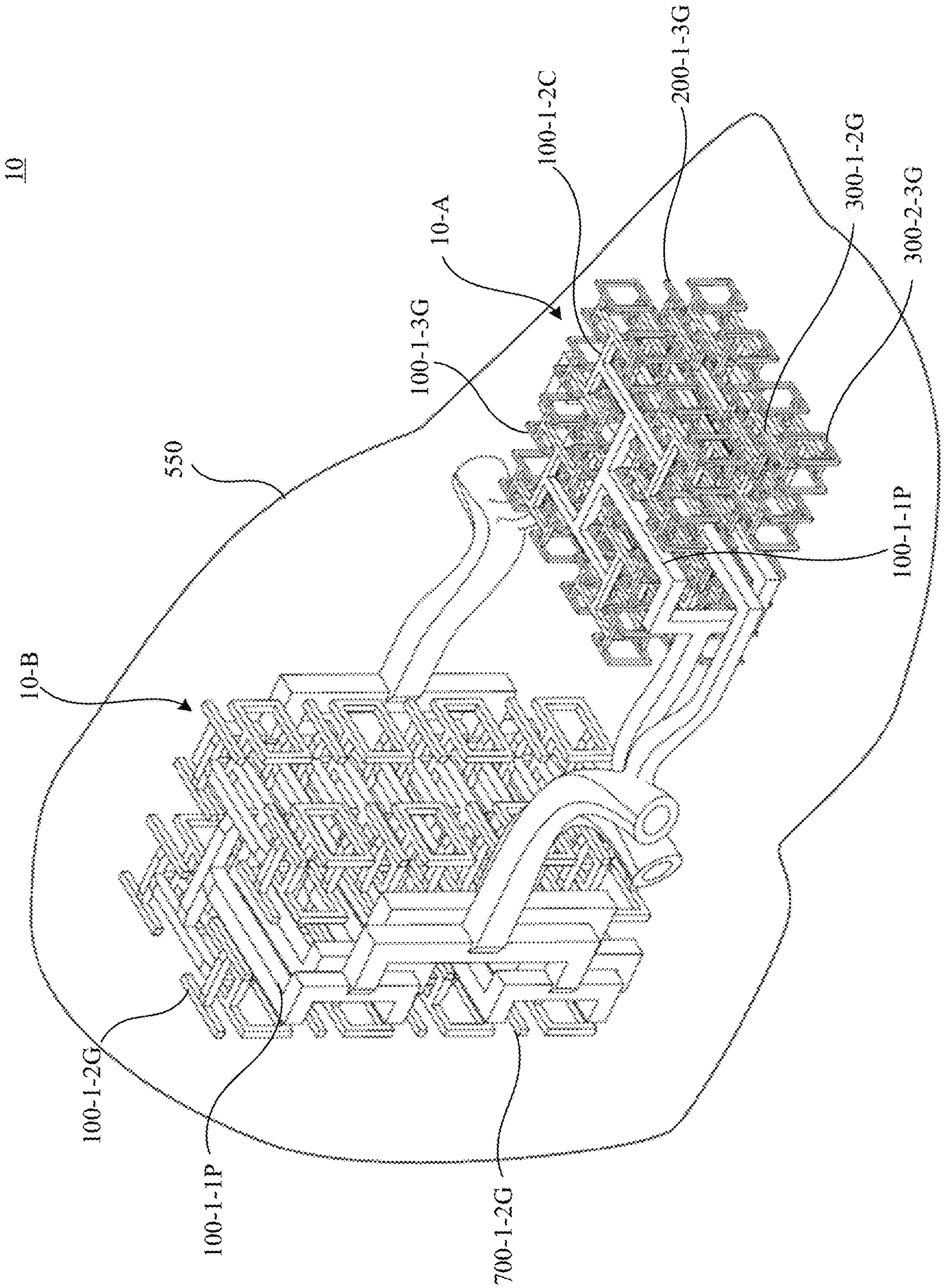
Figure 57A:
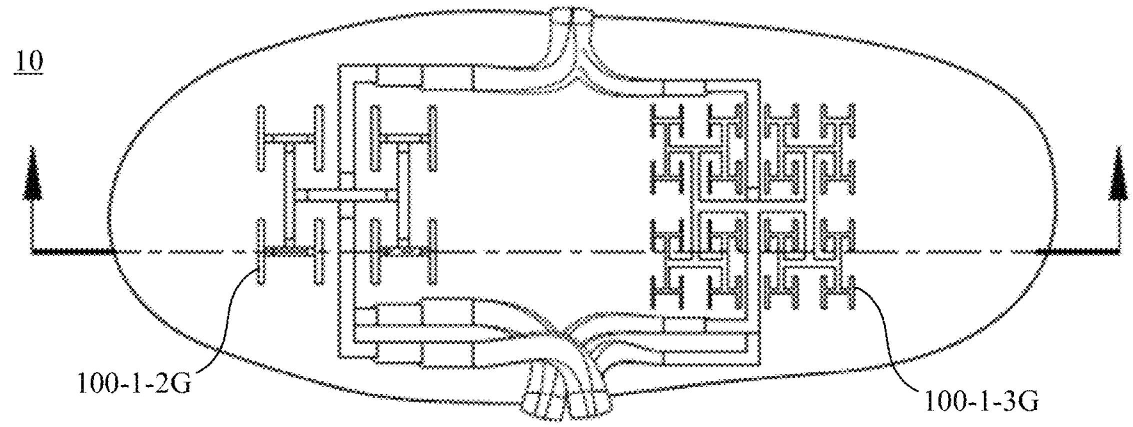
FIG. 57A, FIG. 57B, FIG. 58A, FIG. 58B, FIG. 59, FIG. 60, FIG. 61A, FIG. 61B, FIG. 62A, FIG. 62B, FIG. 63A, FIG. 63B, FIG. 64A, FIG. 64B, FIG. 65A, and FIG. 65B collectively illustrate a progressive cross-section splicing of the scaffold device of FIG. 56A, FIG. 56B, and FIG. 56C.
Figure 57B:
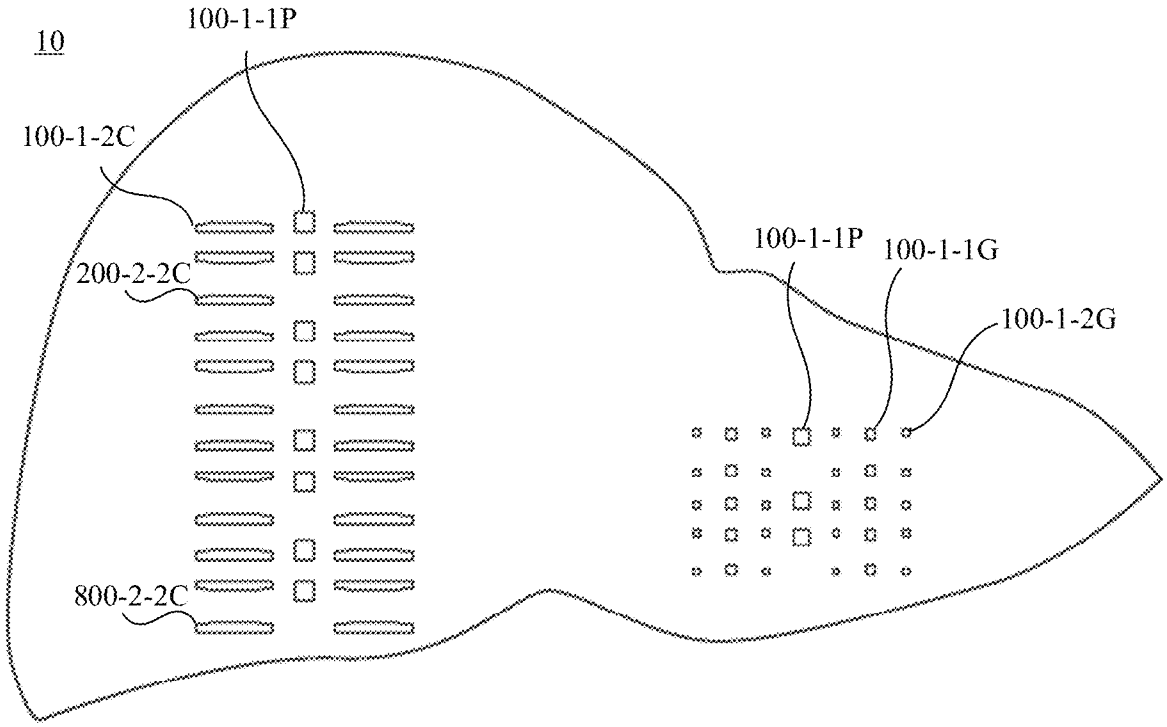
Figure 58A:
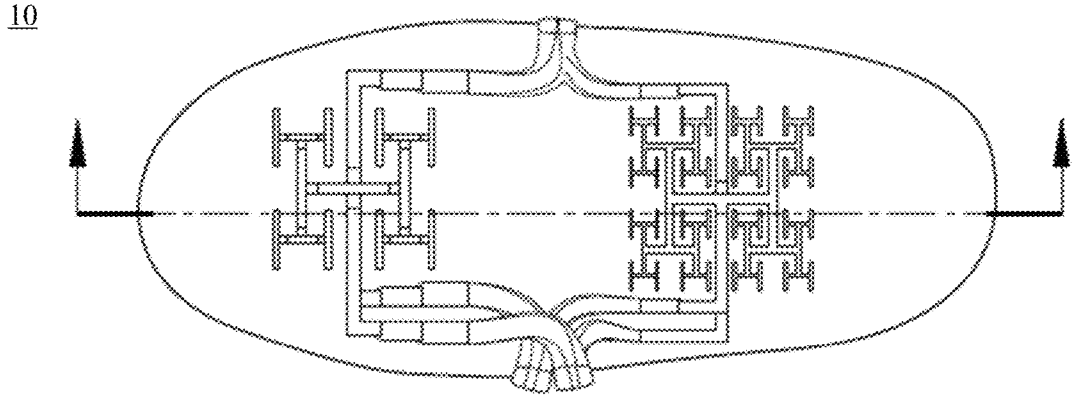
Figure 58B:
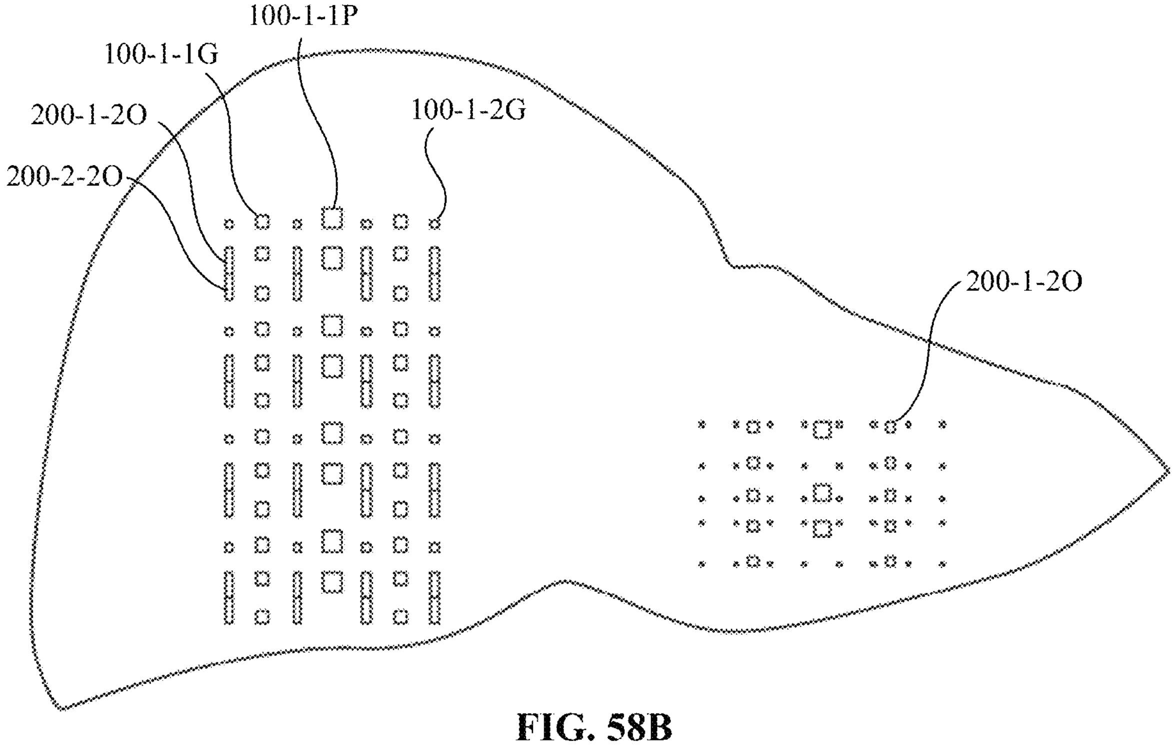
Figure 59:
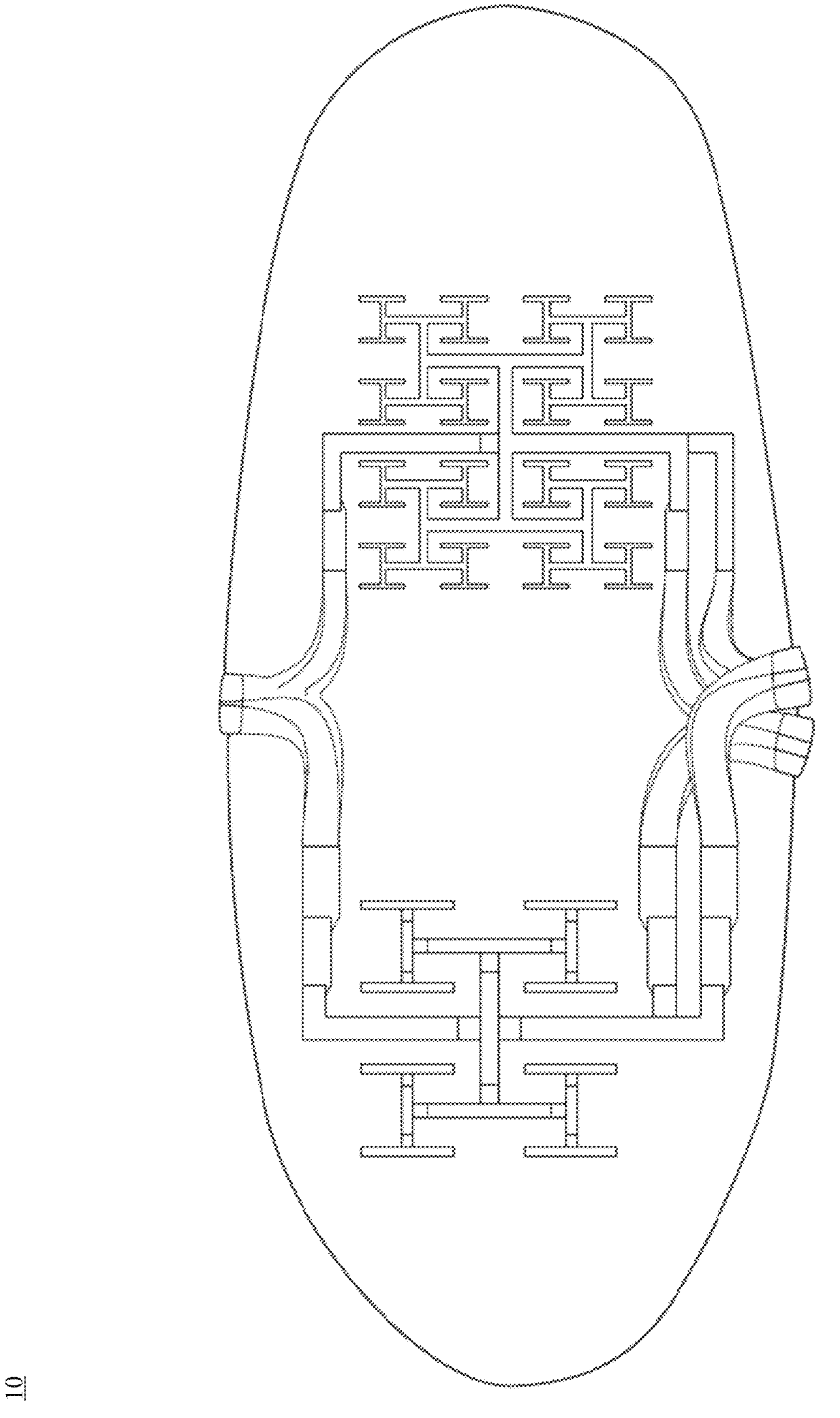
Figure 60:
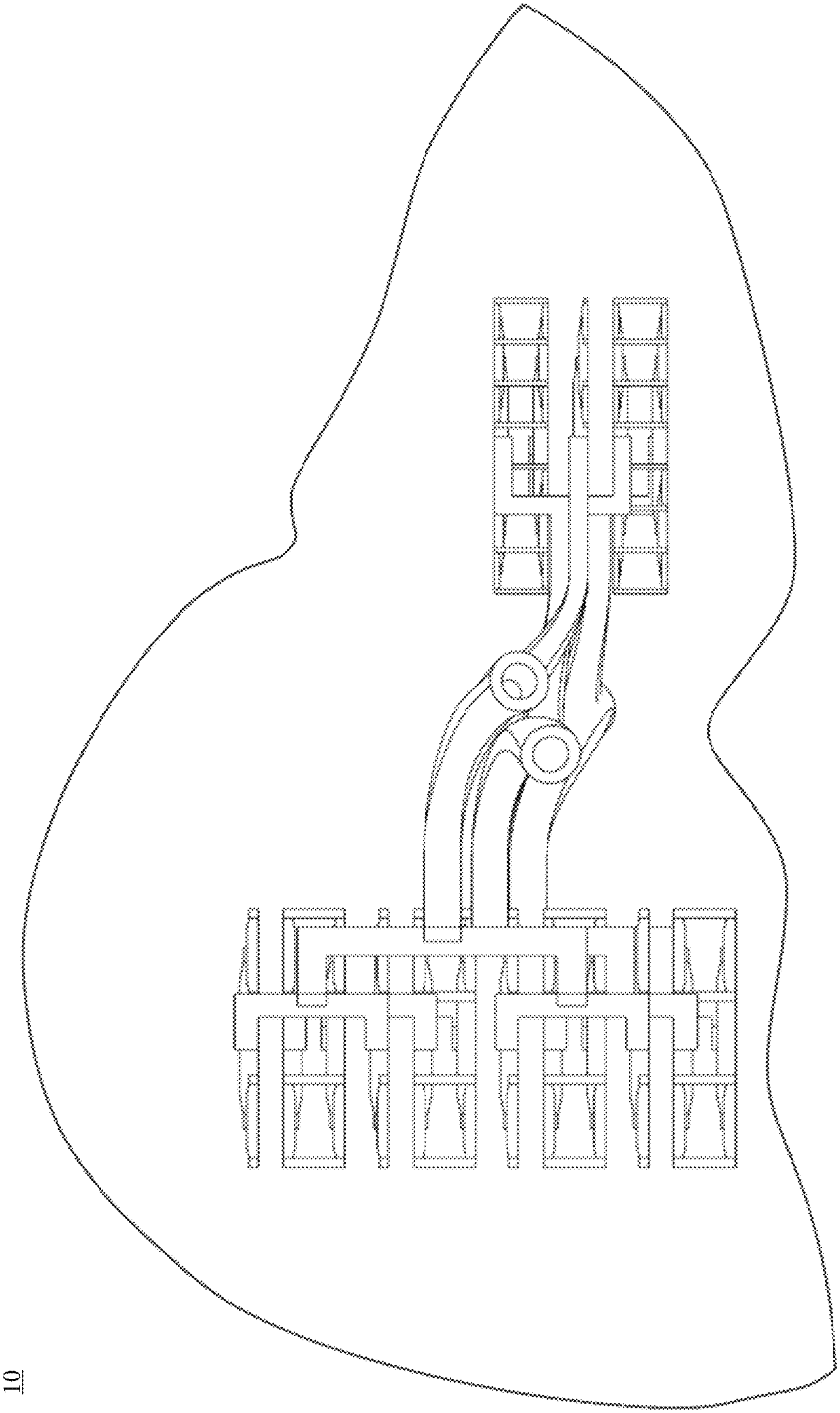
Figure 61A:
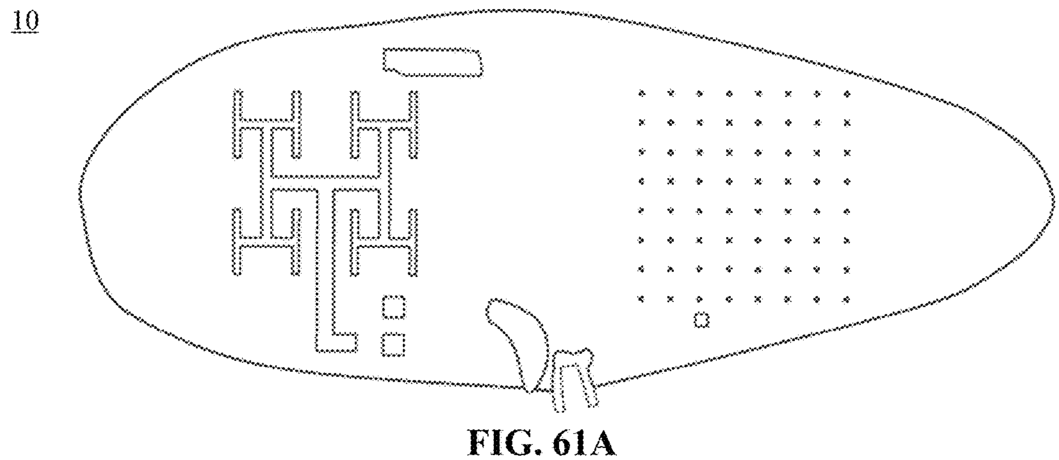
Figure 61B:
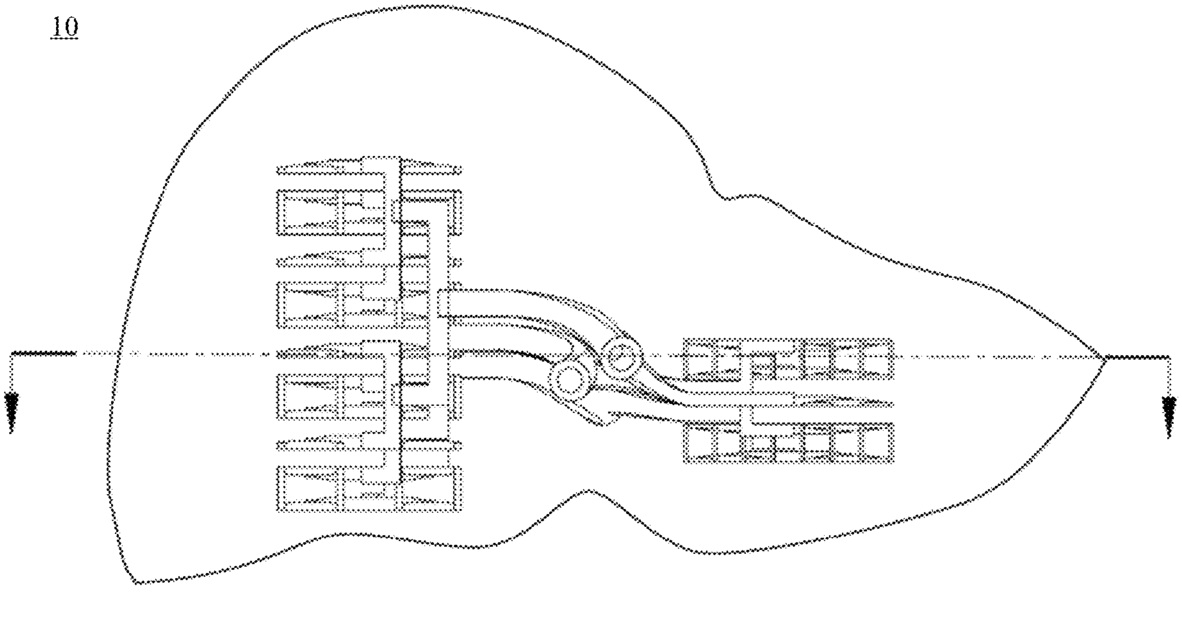
Figure 62A:
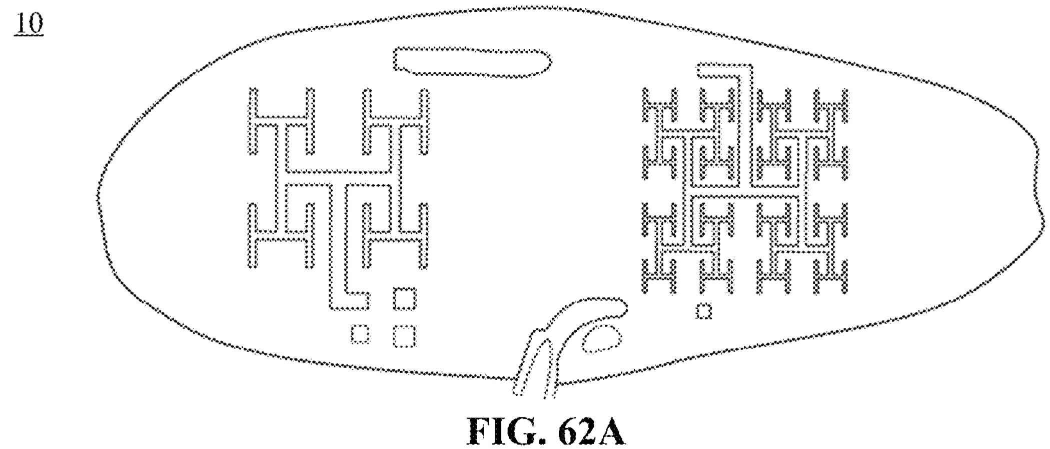
Figure 62B:
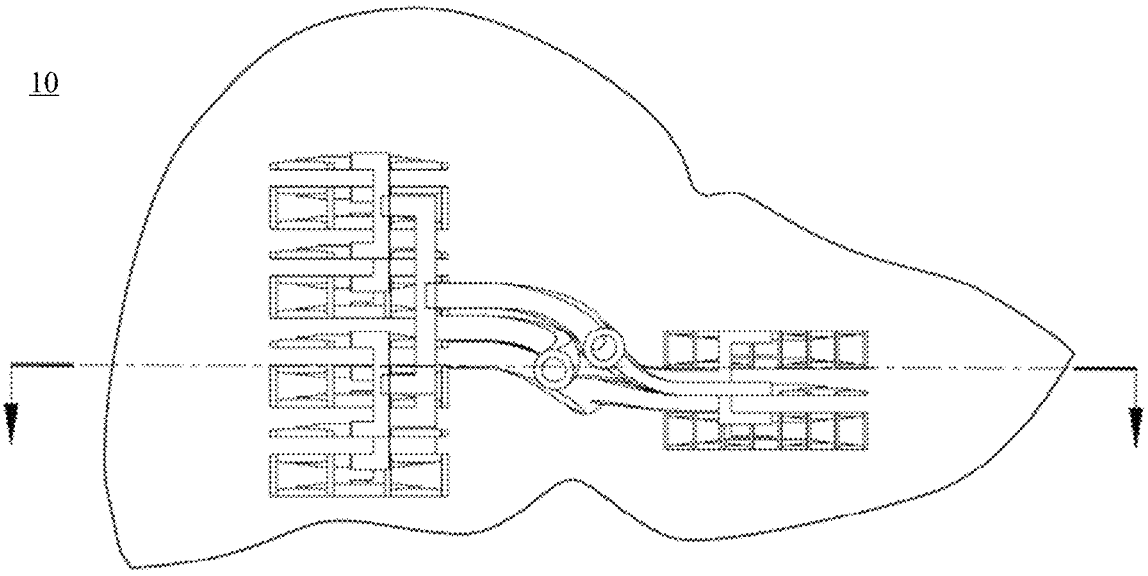
Figure 63A:
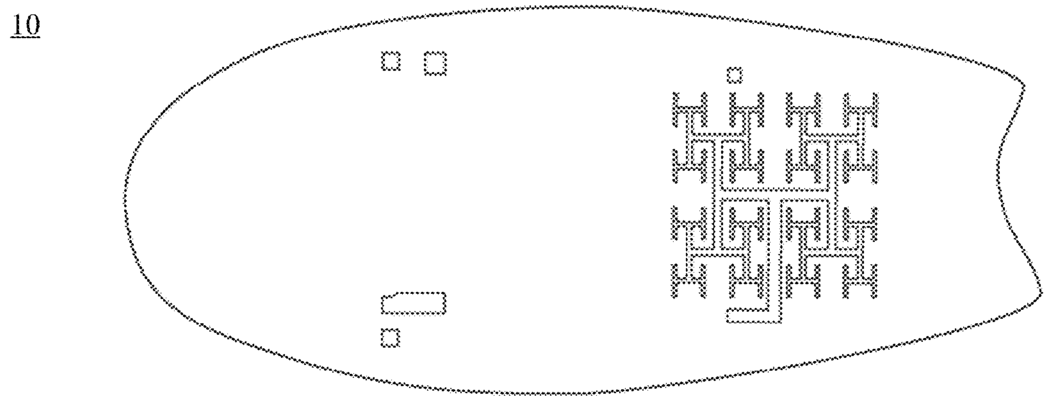
Figure 63B:
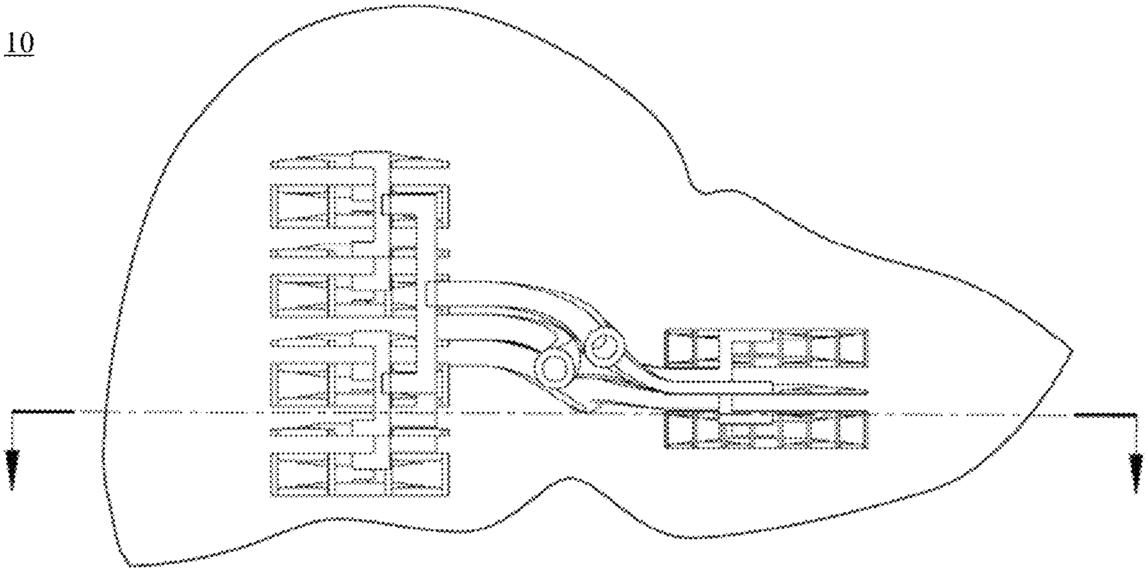
Figure 64A:
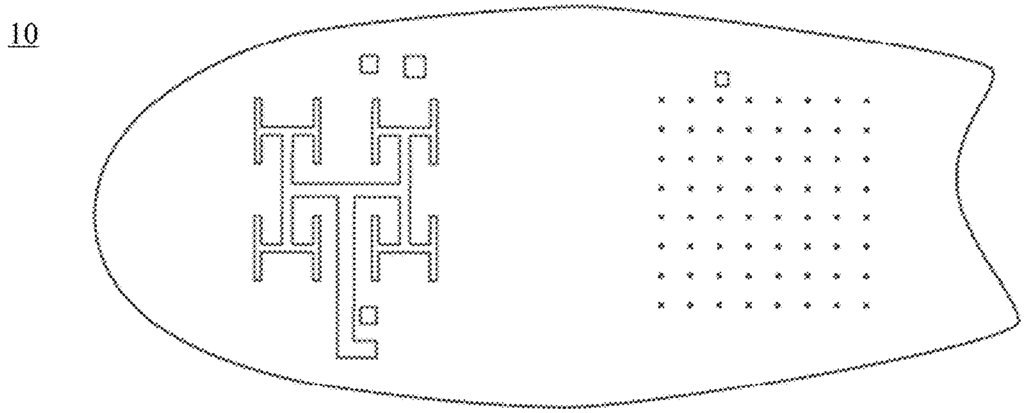
Figure 64B:
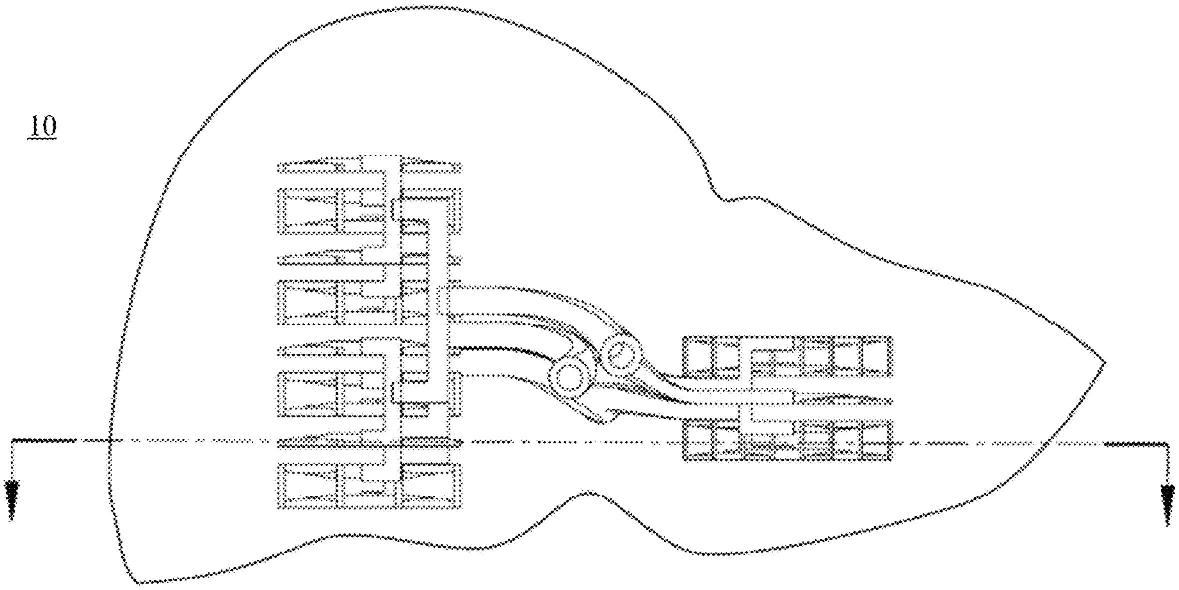
Figure 65A:
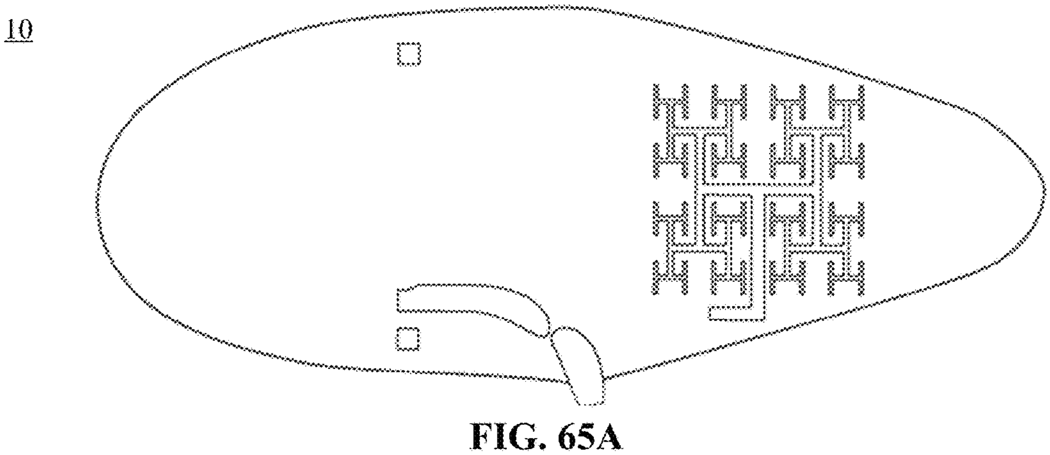
Figure 65B:
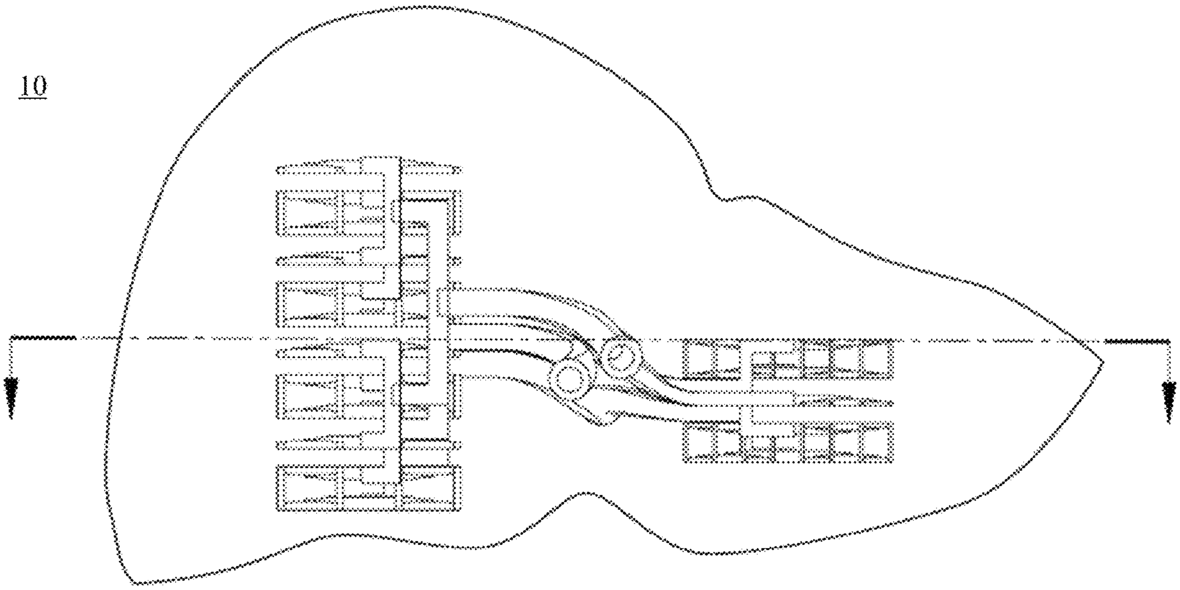

Similar to the device depicted in FIG. 55, FIG. 56 depicts an exemplary embodiment of a scaffold device encased in a liver structure (e.g., shell 550 formed in the shape of a liver). Accordingly, FIG. 57 through FIG. 65 illustrate a progressive slicing of a cross-section of the device depicted in FIG. 56.

In the present embodiment, the outlet is located on an opposite side of the device to a corresponding inlet. However, the present disclosure is not limited thereto. In some embodiments, an outlet is disposed above (e.g., a higher elevation), below (e.g., a lower elevation), or lateral to (e.g., even with) an inlet. In some embodiments, an outlet is disposed on a face of the device other than a face including an inlet. Additionally, in some embodiments, layers and stacks are reoriented, or flipped, such that corresponding channels in adjacent layers align and have a fixed vertical distance there between. In some embodiments, the present flipped configuration facilitates adding the exchange mechanism between the layers.

In some embodiments, a first channel network (e.g., a portal venous network) includes an inlet and an outlet, and a second channel network (e.g., a hepatobiliary network) includes an outlet but lacks an inlet. In some embodiments, a second channel network (e.g., a lung airway network) allows an inflow and an outflow of medium through a single port (designated as an outlet herein), but does not allow through flow.

In some embodiments, a lattice structure provides mechanical support to one or more channel networks of a scaffold device. For instance, in some embodiments the lattice structure interposes between various portions of a first channel network (e.g., a portal venous network) and a second channel network (e.g., a hepatobiliary network), to provide structural integrity to the channel networks. Further, the lattice structure allows an external medium to flow around the channel networks and transport material to and/or from the channel networks. Accordingly, in some embodiments a design of a scaffold device considers a number of bifurcations, a thickness of a channel wall, and a size of the lattice structure (e.g., a thickness) to provide desired structural integrity to the device while also providing external medium flow and material transport. Furthermore, in some embodiments the lattice structure is formed in an array of rectangles, with each rectangle being at least partially intercepted by a channel of the device. In some embodiments, the lattice structure varies spatially depending on a geometry of the device. For instance, in some embodiments a density of beams of the lattice structure and a diameter of the lattice structure vary according to a desired material transport and structural integrity (e.g., as a channel diameter decreases a density of a lattice structure increases, as a channel diameter decreases both a density and a diameter of a lattice structure decrease, etc.).

Figure 66:
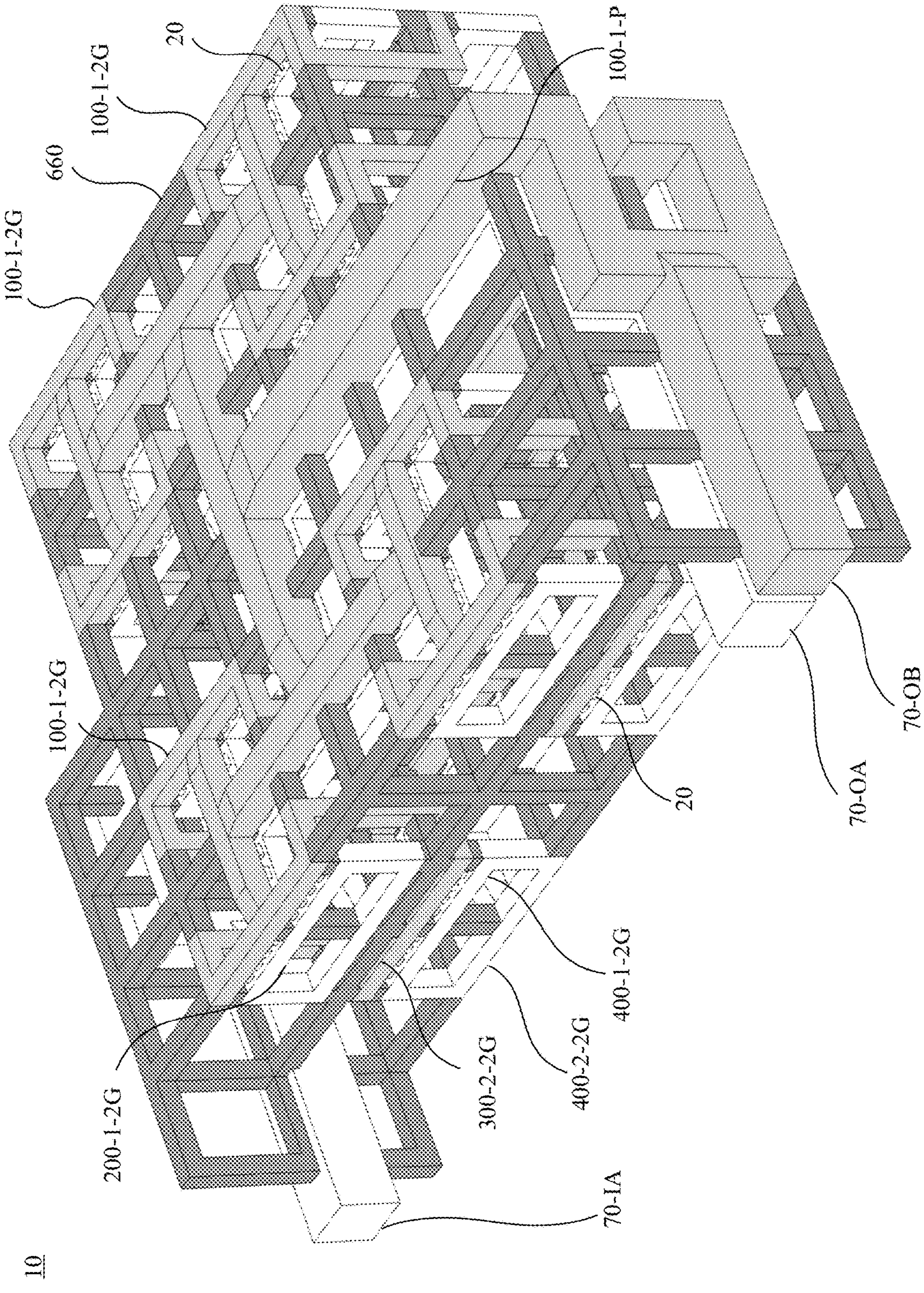
FIG. 66, FIG. 67, FIG. 68, FIG. 69, FIG. 70, and FIG. 71 illustrate an exemplary scaffold device including a lattice structure in accordance with embodiments of the present disclosure.
Figure 67:
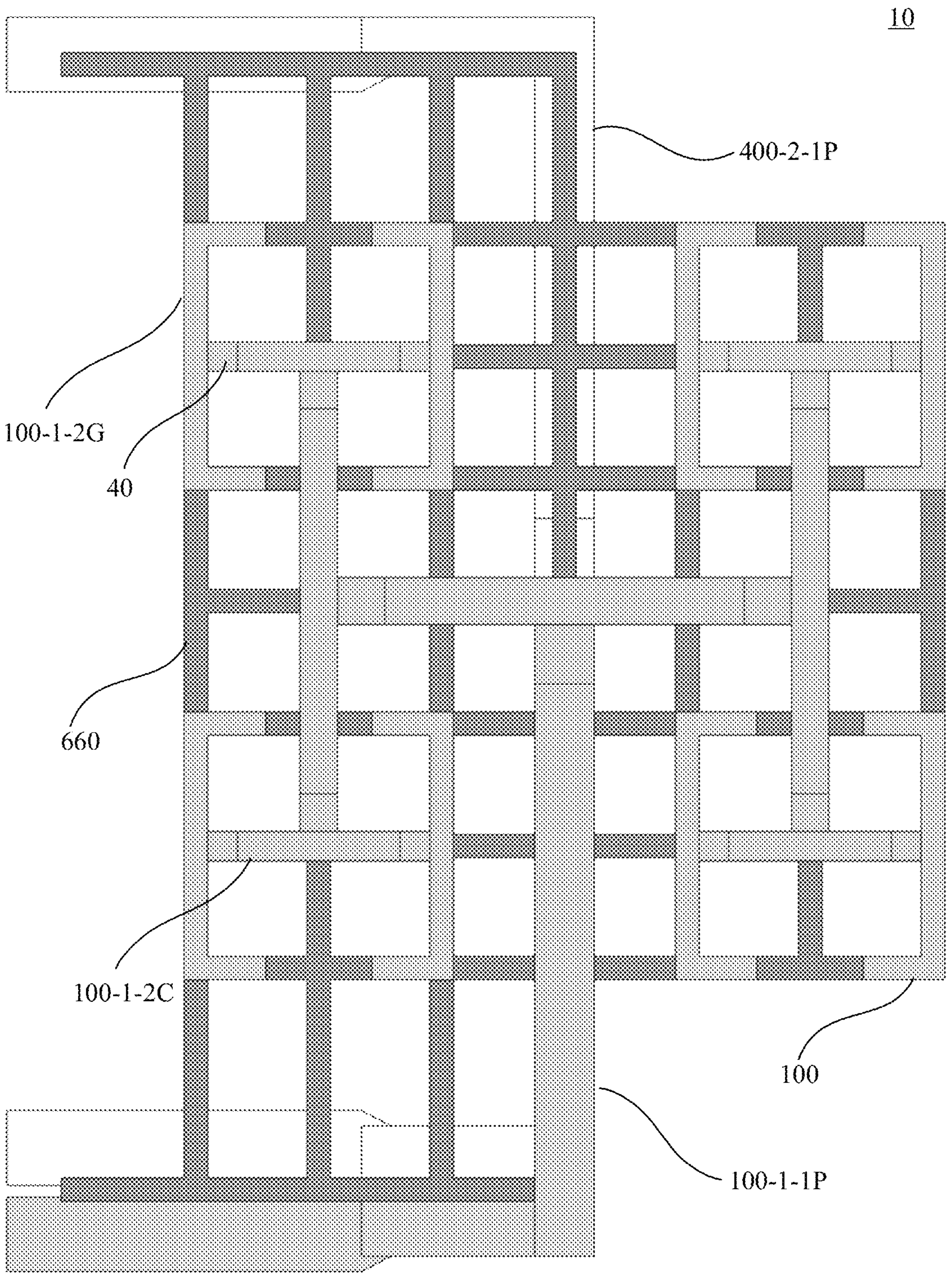
Figure 68:
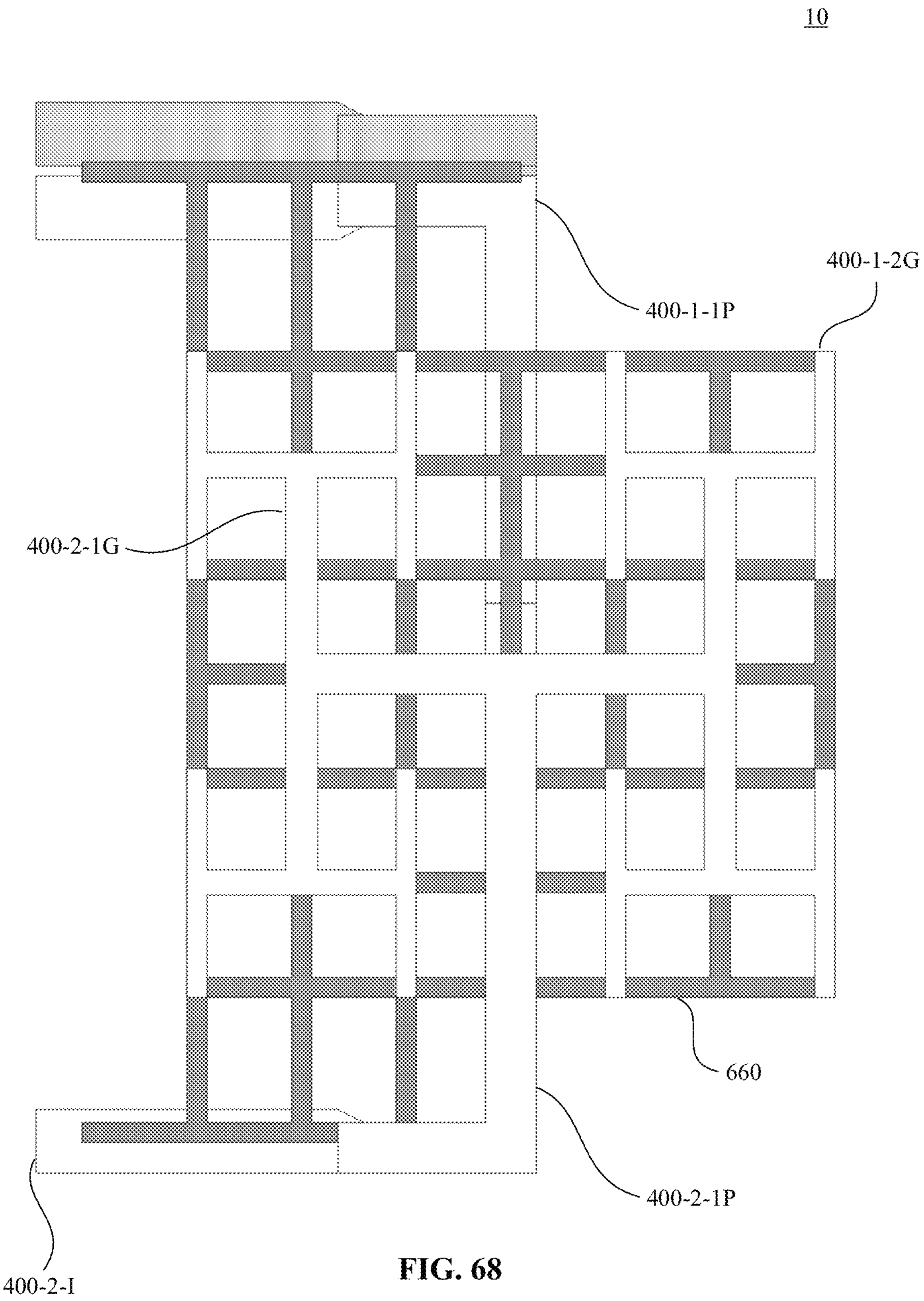
Figure 69:
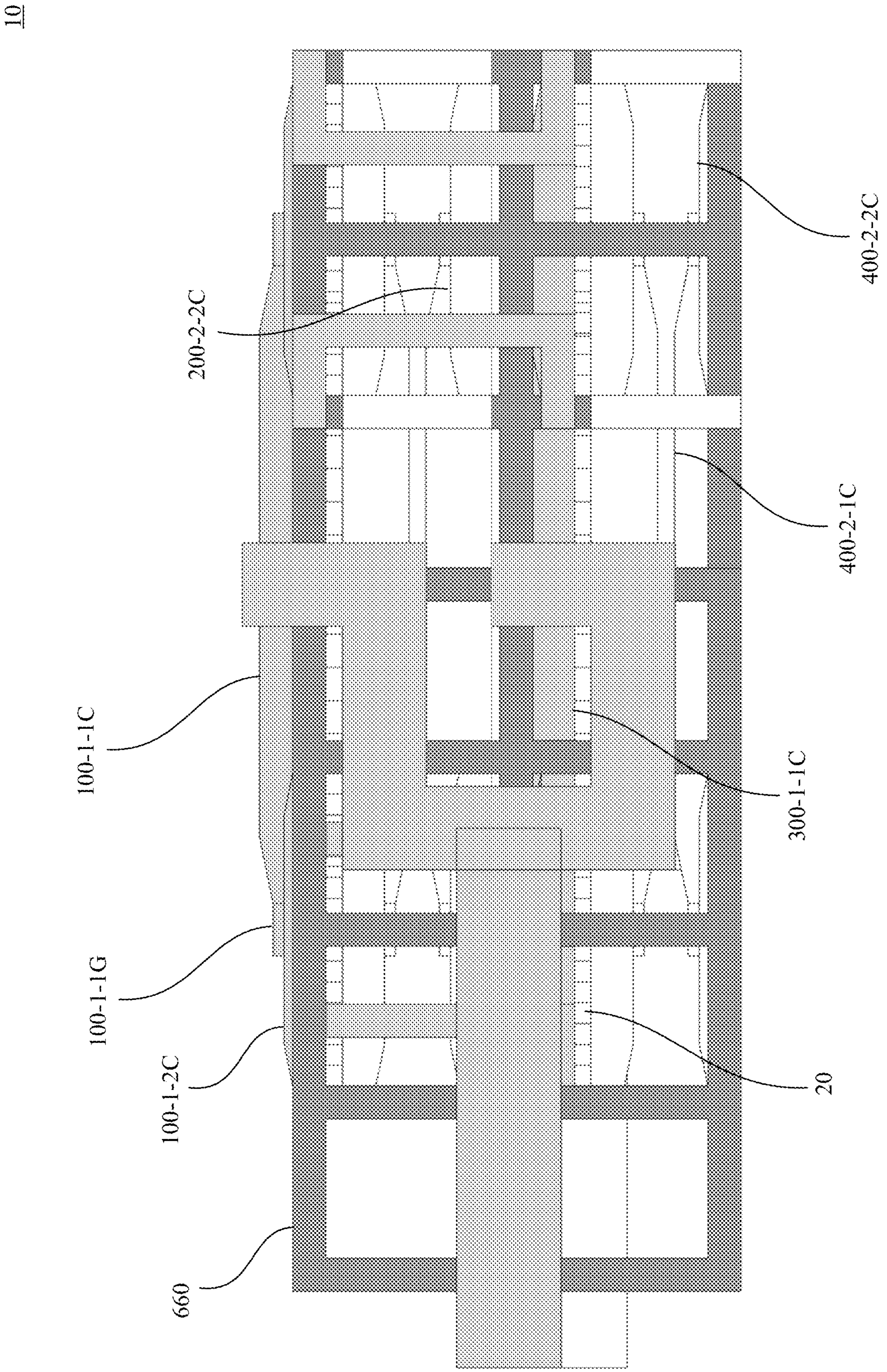
Figure 70:
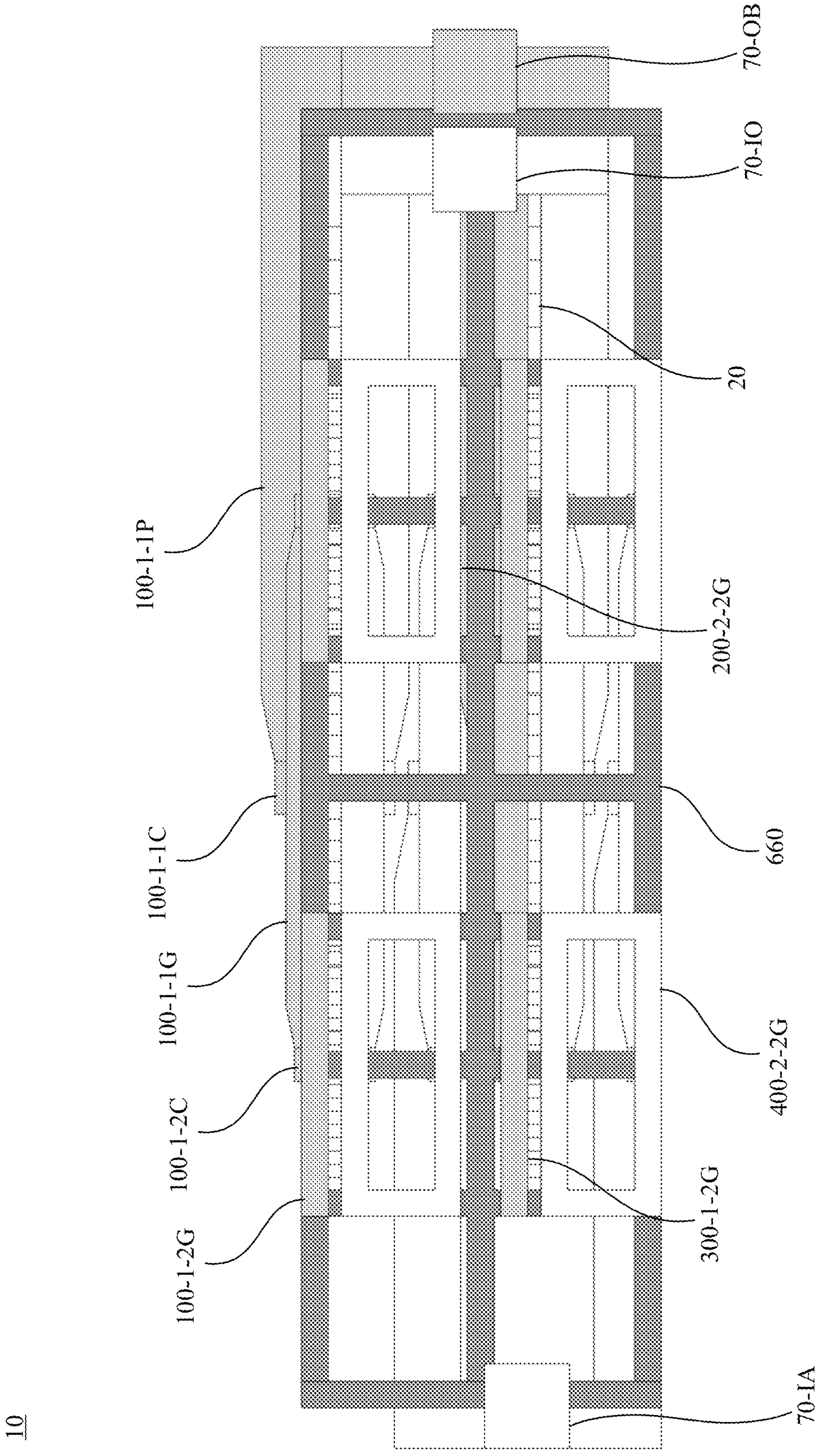
Figure 71:
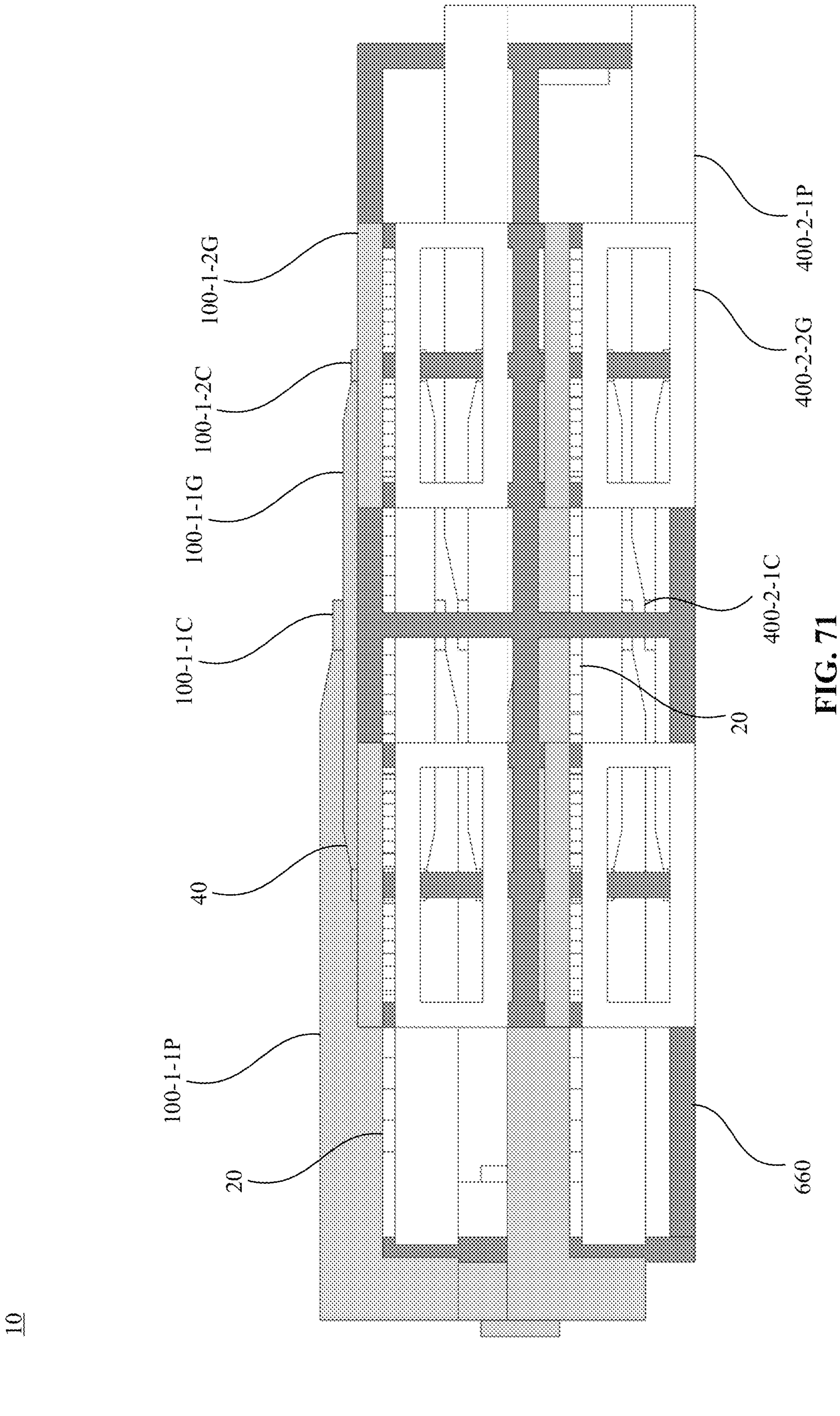
Figure 72:
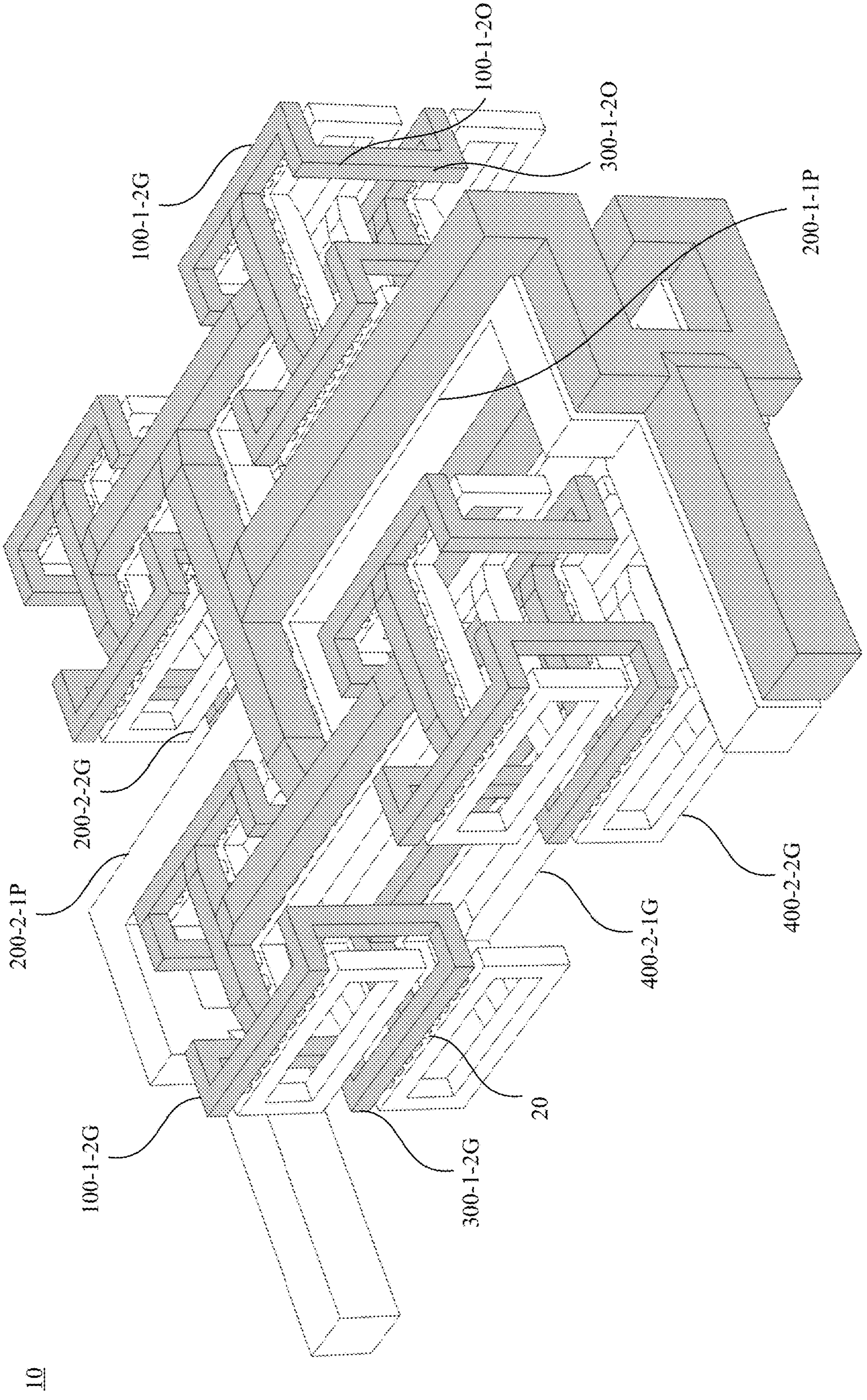
FIG. 72 illustrates the scaffold device of FIG. 66 without the lattice structure.

Referring to FIG. 66 through FIG. 71, scaffold device 10 is illustrated including first channel network 100 (e.g., portal venous network), second channel network 200 (e.g., hepatobiliary network), membrane 20 interposing between the first channel network and the second channel network, and lattice structure 660 providing structural integrity to the device. For visual clarity, in FIG. 66 through FIG. 72, first channel network 100 and membrane 20 are unshaded, second channel network 200 is shaded a light gray, and lattice structure 660 is shaded a dark gray. FIG. 66 illustrates an isometric view of scaffold device 10, FIG. 67 illustrates a top view of scaffold device 10, FIG. 68 illustrates a bottom view of scaffold device 10, FIG. 69 illustrates a first side view (e.g., facing an HB outlet) of scaffold device 10, FIG. 70 illustrates a second side view (e.g., facing a PV inlet) of scaffold device 10, and FIG. 71 illustrates a front view of scaffold device 10. Both first channel network 100 and second channel network 200 includes two generations of channels (e.g., channel 100-1-2G). Furthermore, first channel network 100 provides nutrients and waste removal for second channel network 200, which in turn cultures cells while collecting and draining (e.g., outflowing) waste. Membrane 20 provides oxygen, nutrient, and waste exchange between first channel network 100 and second channel network 200. Referring to FIG. 72, scaffold device 10 of FIG. 66 through FIG. 71 illustrated without lattice structure 660.

Cells can be incorporated into and/or onto the device of the present disclosure in various manners and methods. For instance, in some embodiments cells populate an exterior of the device in a naturally occurring manner (e.g., suspended in a solution that encompasses the device). In some embodiments, cells are bio-printed concurrently with the fabrication of the device. In some embodiments, the device is encapsulated and/or submerged in hydrogel or encapsulated therein. In some embodiments, the cells are encapsulated in at least two dimensions (e.g., three dimensions) within the device. In some embodiments, the cells are encapsulated within a hydrogel that is introduced (e.g., flows within) the device. An exemplary hydrogel includes totipotent cells (iTC), pluripotent cells (iPSC), progenitor cells (iMSC), or combinations thereof. Additionally, in some embodiments thin films of collagen are disposed on the device including in and/or on the exchange mechanism of the device. In some embodiments, a dense suspension of cells is seeded into at least one channel network and at least one channel network inlet is blocked once seeding is completed, allowing only an outflow of medium. In such embodiments, the dense suspension of cells is nourished by a flow of medium through at least a second channel network.

The scaffold device of the present invention is exceptionally diverse in design freedom, applicability, functionality, and size. Additionally, devices of the present disclosure can grow complex cells and tissues in three dimensions for a prolonged duration. As disclosed herein, a scaffold device of the present invention includes an inlet and a plurality of channels. The plurality of channels branch in series to form at least one channel network. Furthermore, the channel network(s) replicate various natural physiological systems and internal material flow conditions while also optimizing cell density within the device.

For convenience in explanation and accurate definition in the appended claims, the terms "upper," "lower," "up," "down," "upwards," "downwards," "inner," "outer," "inside," "outside," "inwardly," "outwardly," "interior," "exterior," "front," "rear," "back," "forwards," "backwards," "above," and "over" are used to describe features of the exemplary embodiments with reference to the positions of such features as displayed in the figures.

As used in the description of the implementations and the appended claims, the singular forms "a," "an," and "the" are intended to include the plural forms as well, unless the context clearly indicates otherwise.

The foregoing descriptions of specific exemplary embodiments of the present invention have been presented for purposes of illustration and description. They are not intended to be exhaustive or to limit the invention to the precise forms disclosed, and many modifications and variations are possible in light of the above teachings. The exemplified embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A cell scaffold device comprising:

a plurality of branching channel networks comprising a first branching channel network configured to distribute a first fluid at a first height of the cell scaffold device, a second branching channel network configured to distribute a second fluid, different from the first fluid, at a second height of the cell scaffold device, the second height interposing between the first height of the scaffold device and a third height of the scaffold device, and a third branching channel network configured to collect the first fluid at a fourth height of the cell scaffold device, wherein:

the first branching channel network comprises a plurality of first channels formed by at least three generations of branching, the plurality of first channels comprising a first-generation first channel and a plurality of final-generation first channels, wherein each respective channel in the plurality of first channels comprises a coplanar surface at the first height of the cell scaffold device;

the second branching channel network comprises a plurality of second channels formed by branching and recursive recombination, the plurality of second channels comprising an inlet second channel, an outlet second channel and a plurality of intermediate second channels branched from the inlet second channel and recursively recombined to the outlet second channel, wherein one or more second channels in the plurality of second channels comprises a coplanar surface at the second height of the cell scaffold device and one or more other second channels in the plurality of second channels comprises a coplanar surface at the third height of the cell scaffold device;

the third branching channel network comprises a plurality of third channels formed by at least three generations of branching, the plurality of third channels comprising a first-generation third channel and a plurality of final-generation third channels, wherein each respective channel in the plurality of third channels comprises a coplanar surface at the fourth height of the cell scaffold device; and the plurality of final-generation first channels of the first branching channel network is disposed adjacent to the second height of the second branching channel network, the plurality of final-generation third channels of the third branching channel network is disposed adjacent to the third height of the second branching channel network, each respective final-generation first channel in the plurality of final-generation first channels of the first branching channel network is in direct fluid communication with a corresponding final-generation third channel in the plurality of final-generation third channels by a corresponding bypass channel in a plurality of bypass channels, and each respective bypass channel of the plurality of bypass channels extends from the first height to the fourth height of the cell scaffold device, bypasses direct fluid communication with the second branching channel network, thereby producing a compact three-dimensional structure with channels.

2. The cell scaffold device of claim 1, wherein a lower end portion of one or more first channels of the first branching channel network are disposed adjacent to an upper end portion of the one or more second channels located at the second height of the second branching channel network.

3. The cell scaffold device of claim 1, further comprising:

a first master inlet configured to distribute the first fluid by direct fluid communication to the first-generation first channel;

a first master outlet configured to collect the first fluid by direct fluid communication from the first-generation third channel;

a second master inlet configured to distribute the second fluid by direct fluid communication to the inlet second channel; and a second master outlet configured to collect the second fluid by direct fluid communication to the outlet second channel.

4. The cell scaffold device of claim 3, wherein the plurality of branching channel networks further comprises a fourth branching channel network connected to the second master inlet and second master outlet and in indirect fluid communication with the third branching channel network.

5. The cell scaffold device of claim 1, wherein diameters of channels in the plurality of first, second or third channels formed by branching obey Murray's Law.

6. The cell scaffold device of claim 1, wherein for a respective channel in the plurality of first, second or third channels, a ratio of a diameter to a length of the respective channel is fixed along the length of the respective channel.

7. The cell scaffold device of claim 1, wherein a film of collagen is disposed on the cell scaffold device.

8. The cell scaffold device of claim 1, wherein the plurality of branching channel networks comprises an even number of branching channel networks greater than or equal to four.

9. The cell scaffold device of claim 1, wherein each channel of a respective branching channel network in the plurality of branching channel networks comprises a cross-sectional aspect ratio of one.

10. The cell scaffold device of claim 1, further comprising a polyhedron exterior surface configured to encompass the plurality of branching channel networks.

11. The cell scaffold device of claim 1, wherein the plurality of branching channel networks form a monolithic portion of the cell scaffold device.

12. The cell scaffold device of claim 1, wherein each branch of a respective branching channel network in the plurality of branching channel networks is in plane with a corresponding height of the respective branching channel.

13. The cell scaffold device of claim 1, wherein a first centerline of at least one channel in the plurality of first channels is oriented at an angle of greater than or equal to 90 degrees relative to a second centerline of the first-generation first channel.

14. The cell scaffold device of claim 1, wherein a first surface of each channel in the plurality of first channels is coplanar at the first height of the cell scaffold device and a second surface, opposite the first surface, of each channel in the plurality of first channels comprising a linear ramp extending from a fifth height of the cell scaffold device to a sixth height of the cell scaffold device.

15. The cell scaffold device of claim 1, wherein the third branching channel network is a mirror image of the first branching channel network across a plane extending through the cell scaffold device.

16. The cell scaffold device of claim 1, wherein a length of the cell scaffold device is a distance extending between a first end portion of an inlet of the first-generation first channel and a first end portion of the inlet of the second channel, and wherein the first end portion of the inlet of the first-generation first channel and the first end portion of the inlet of the second channel are on opposite side portions of the cell scaffold device.

17. The cell scaffold device of claim 1, wherein the second branching channel network forms a looped channel segment for distributing and collecting the second fluid.

* * * * *